(12) United States Patent
Dresdner, Jr. et al.

(10) Patent No.: US 12,295,916 B2
(45) Date of Patent: May 13, 2025

(54) PROCESS FOR MAKING AQUEOUS THERAPEUTIC PARTICLE HAVING STABLE EXTERIOR WATER CLUSTERING WITH NANOSIZED THICKNESS

(71) Applicants: Karl P. Dresdner, Jr., Haddonfield, NJ (US); Michael Raymond Cary, Lexington, SC (US); Chase Hudson, Provo, UT (US); Nathan A. Beckham, Provo, UT (US)

(72) Inventors: Karl P. Dresdner, Jr., Haddonfield, NJ (US); Michael Raymond Cary, Lexington, SC (US); Chase Hudson, Provo, UT (US); Nathan A. Beckham, Provo, UT (US)

( * ) Notice: Subject to any disclaimer, the term of this patent is extended or adjusted under 35 U.S.C. 154(b) by 385 days.

(21) Appl. No.: 16/873,552

(22) Filed: Apr. 30, 2020

(65) Prior Publication Data
US 2020/0345585 A1    Nov. 5, 2020

Related U.S. Application Data

(60) Provisional application No. 62/921,280, filed on Jun. 8, 2019, provisional application No. 62/920,747, filed on May 13, 2019, provisional application No. 62/920,450, filed on Apr. 30, 2019.

(51) Int. Cl.
| | |
|---|---|
| *A61K 9/00* | (2006.01) |
| *A23L 2/52* | (2006.01) |
| *A61J 3/07* | (2006.01) |
| *A61K 9/51* | (2006.01) |
| *A61K 31/05* | (2006.01) |
| *C02F 9/00* | (2023.01) |
| *C02F 1/00* | (2023.01) |
| *C02F 1/32* | (2023.01) |
| *C02F 1/44* | (2023.01) |
| *C02F 1/469* | (2023.01) |
| *C02F 103/04* | (2006.01) |

(52) U.S. Cl.
CPC . *A61J 3/07* (2013.01); *A23L 2/52* (2013.01); *A61K 9/0095* (2013.01); *A61K 9/5115* (2013.01); *A61K 9/5192* (2013.01); *A61K 31/05* (2013.01); *C02F 9/00* (2013.01); *A23V 2002/00* (2013.01); *C02F 1/001* (2013.01); *C02F 1/32* (2013.01); *C02F 1/441* (2013.01); *C02F 1/4691* (2013.01); *C02F 2103/04* (2013.01)

(58) Field of Classification Search
None
See application file for complete search history.

(56) References Cited

U.S. PATENT DOCUMENTS

| | | |
|---|---|---|
| 4,592,909 A | 6/1986 | Winer et al. |
| 4,876,014 A | 10/1989 | Malson |
| 5,435,913 A | 7/1995 | Ashbrook |
| 6,521,248 B1 | 2/2003 | Holloway et al. |
| 7,198,254 B2 | 4/2007 | Holloway et al. |
| 7,531,515 B2 | 5/2009 | Pincus |
| 7,745,405 B2 | 6/2010 | Pincus |
| 7,832,920 B2 | 11/2010 | Wood et al. |
| 8,193,251 B2 | 6/2012 | Lo et al. |
| 8,623,212 B2* | 1/2014 | Irvin, Sr. ................. C02F 1/005 210/512.3 |
| 9,334,200 B2 | 5/2016 | Kaiser |
| 9,474,991 B2 | 10/2016 | Irvin, Sr. et al. |
| 10,508,061 B2 | 12/2019 | Bunderson |
| 11,198,654 B2 | 12/2021 | Bunderson |
| 11,344,572 B2* | 5/2022 | Bishop ...................... A23L 2/52 |
| 11,779,645 B2* | 10/2023 | Bishop .................... C02F 1/005 424/455 |

(Continued)

FOREIGN PATENT DOCUMENTS

WO    WO 2018179495 A1    10/2018

OTHER PUBLICATIONS

The Declaration of Michael Raymond Cary Regarding Public Use and Public Availability of Inventions Claimed in U.S. Appl. No. 16/350,259, Oct. 2020.*

Keutish, Frank N., Saykally, Richard J. Water clusters: untangling the mysteries of the liquid, one molecule at a time, PNAS Sep. 1, 2001, pp. 10533-10540, vol. 98(19).

(Continued)

*Primary Examiner* — H. Sarah Park
(74) *Attorney, Agent, or Firm* — CALYX LAW; Graham Pechenik

(57) ABSTRACT

The invention relates to processes for making pharmaceutical aqueous therapeutic particles (AQTP) having stable exterior water clustering with nanosized thickness less than 300 nanometers, wherein the AQTP has an improved bioavailability when administered to a mammal compared to conventional pharmaceutical drug particles administered to the mammal. The invention relates to an improved process apparatus which is computer controlled, capable of continuous operation with high efficiency so as to make a more consistently acceptable AQTP compared to an previous prototype process apparatus of the Inventors. The invention provides compositions comprising of AQTP which comprise a substance selected from the group consisting of a cannabinoid such as CBD, a cell membrane pore-forming peptide such as PNC-27, a psychoactive drug, a pharmaceutical, a nutraceuticals, a mineral, an anion, a cation, a protein, a peptide, an amino acid, a polymer, a vitamins, an antioxidants, a fertilizer, a chemical, a medical use product, a medical kit use product, a personal consumer use product, a manufacturing use product, a energy use product such as a battery, and any combination thereof.

14 Claims, 28 Drawing Sheets

Specification includes a Sequence Listing.

(56) References Cited

U.S. PATENT DOCUMENTS

| | | |
|---|---|---|
| 2005/0031657 A1 | 2/2005 | Gilson |
| 2006/0146644 A1 | 7/2006 | Holloway et al. |
| 2007/0186367 A1 | 8/2007 | Field |
| 2009/0017167 A1 | 1/2009 | Krumhar et al. |
| 2011/0218251 A1 | 9/2011 | Lo et al. |
| 2012/0039951 A1 | 2/2012 | Watson |
| 2017/0233303 A1 | 8/2017 | Bunderson |
| 2017/0290854 A1 | 10/2017 | Matlick |
| 2019/0358169 A1* | 11/2019 | Bishop .................. A61K 33/00 |
| 2020/0121715 A1* | 4/2020 | Bishop .................. A61L 2/0047 |
| 2020/0223765 A1 | 7/2020 | Bunderson |
| 2020/0345585 A1 | 11/2020 | Dresdner, Jr. et al. |
| 2021/0353667 A1* | 11/2021 | Bishop .................. A61K 33/00 |

OTHER PUBLICATIONS

Plumridge, I.H., Waigh, H.D. Water structure theory and some implicaitons for drug design. JPP, 2002, pp. 1155-1179, vol. 54.

Stoyanov, Evgenii S. et al., The structure of the hydrogen ion (Haq+) in water. J. Am. Chem. Soc. , Feb. 10, 2010, pp. 1484-14, vol. 132(5).

Mechoulam, R.Hanus, L. Cannabidiol: an overview of some chemical and pharmacological aspects. Part 1: chemical aspects. Chemistry and Physics of Lipids, 2002,vol. 121,pp. 35-43.

Stukelj, Roman, et al. Synthesis of Stable Cannabidiol (CBD) Nanoparticles in Suspension. Materials & Technology 53 (2019) 4, 543-549.

Declaration of Michael Raymond Cary regarding Public Use and Public Availability of Inventions claimed in U.S. Appl. No. 16/350,259, signed Oct. 15, 2020, 33 pages.

Declaration of Michael Raymond Cary regarding Public Use and Public Availability of Inventions claimed in U.S. Appl. No. 16/421,163, signed Oct. 15, 2020, 33 pages.

U.S. Appl. No. 62/675,248, filed May 23, 2018; titled "Methods for Making, Compositions, and Uses of Nano-Sized Particles for Improved Biological Transport".

Mike Cary 2013 OSML Farm Data Sheet Form 100 for Contracts 2 pages.

Mike Cary On-Site-Mobile-Laboratories Presentation—fertilizer Humic Acid nanoparticulation from 5 micron down to 6 nanometer particle based on Malvern test (24 pages).

Shirreffs et al. 2011 Fluid and Electrolyte needs for training, competition and recovery. Journal of Sports Sciences pp. S39-S46, vol. 29(S1).

Smith, Jared, D et al. 2005 Unified description of temperature-dependent hydrogen bond arrangements in liquid water. PNAS vol. 102 (40) pp. 14171-14174.

Aquaporin, 2018, from Wikipedia the free encyclopedia, 12 pages.

Dehydration 2018, from Wikipedia the free encyclopedia, 5 pages.

Larson, Rita, 2015, What is the real difference between Energy Drinks and Sports Drinks? Elite Sports Clubs, WordPress.

Chaplin, Martin 2018, Nanobubbles (ultrafine Bubbles) Water and Structure Science from http://www1.isbu.ac.uk/water/nanobubble.html, 13 pages.

Rozanska, S. & Rozanski, J, Extensional flow of Carboxymethylcellulose sodium salt measured on the opposed-nozzle device, Soft Materials:15(4):302-314, 2017.

Purified Water, Wikipedia, last updated by contributors on May 9, 2022.

"What is Potable Water?" NPL is a written document published at https://Bjus.com/Chemistry/Potable-Water, and retrieved on May 31, 2022.

U.S. Appl. No. 62/675,248, Bishop, Patrick, C. and 5 others.

Declaration of Michael R. Cary Regarding Public Use and Public Availability of Inventions Claimed in U.S. Appl. No. 16/350,259 mailed Oct. 15, 2020 (33 pages).

Declaration of Michael R. Cary Regarding Public Use and Public Availability of Inventions Claimed in U.S. Appl. No. 16/421,163 mailed Oct. 15, 2020 (33 pages).

Second Declaration of Michael R Cary Regarding Public Use and Public Availability of Inventions Claimed in U.S. Appl. No. 16/421,163 mailed Apr. 16, 2021 (36 pages).

Third Declaration of Michael R Cary Regarding Public Use and Public.Availability of Inventions Claimed in U.S. Appl. No. 16/421,163 mailed Jun. 7, 2021 (40 pages).

Bishop, Methods for Making Compositions and Uses of Nano-Sized Particles for Improved Biological Transport. U.S. Appl. No. 62/675,248, filed May 23, 18 (93pgs, 12 Figs).

Nestle Pure Life Bottled Water Quality Report, Nestle Waters North America, Inc., 2015 (14 pages).

Gravelle, S et al. "Optimizing water permeability through hourglass shape of aquaporins." Proceedings National Academy Sciences vol. 10,No. 41,pp. 16367-16372, Oct. 8, 2013.

Mike Cary, 2013 On-Site Mobil Laboratories (OSML) 2 page Advertising Flyer with Warren Bell Testimonial 2 pages, Fertilizer particles reduced from 5 microns to 6 nanometer.

Mike Cary, 2013 Marketing Plan - Executive Summary—On-Site Mobil Laboratories (OSML's wet nano based technology for manipulating fertilizer to a nanoparticulate. 6 pages.

Mike Cary, 2013 OSML Marketing Plan Addendum No. 1 The process of wet nano manipulating and blending fertilizer was developed by Dr. James Kaiser 8 years ago. 2 pages.

Schieving, Aaron 2017. Understanding USP <1231> Water for Pharmaceutical Use from http://www.pharmatech.com/understanding-usp-water-pharmaceutical-use. 2 pgs.

Purified Water, 2018, from Wikipedia the free encyclopedia, 10 pages.

Tomaszewska, Emilia et al., 2013, Detection Limits of DLS and UV-Vis Spectroscopy in Characterization of Polydisperse Nanparticles Colloids. J Nanomaterials, ID 313081, 10pgs.

Trace Minerals, Ogden, Utah, Aug. 28, 2014, Kelly Jones, Certificate of Analysis, www.traceminerals.com, Trace Minerals Research, 2 pages.

Chaplin, Martin, 2007, Water's Hydrogen Bond Strengthpp. 1-20, Cornell University Library, https//arxiv.org<condmat>arXiv:0706.1355.

Krishan, Awtar, 1975, Rapid flow cytofluorometric analysis of mammalian cell cycle by propidium iodide staining. The Journal of Cell Biology vol. 66, pp. 188-193.

Eaves, J.D. et al. 2005. Hydrogen bonds in liquid water are broken only fleetingly. PNAS vol. 102(37): pp. 13019-13022.

Boughbina-Portoles, Aaron et al. 2021. Study. of the stability of citrate capped AgNPs in several environmental water matrices . . . Nanomaterials vol. 11, pp. 1-16.

NanoNutrients Avian LLC 2007-2009 Study and Field Trial Summaries, Lehi, Utah www.nanoavian.com 16 pages.

Shu, Li et al., 2013 Directly observe sodium chloride aggregates waltzing through dilute solutions pp. 213-223, Online Source: http://hdl.handle.net/10536/DRO/DU:30055194.

Mike Cary May 14, 2013 Quote to Gary Teague Farms in Fort Morgan, CO for OSML to optimize 5000 gallons of Gary Teague Farm's 32-0-0 $32/acre commercial proposal offer. 1 page.

Mike Cary Oct. 30, 2012 Memo—State by State Dept. Agriculture Registration Process re Commercial Fertilizer—Varys from State to State. Humic Fertilizer. 1 page.

\* cited by examiner

Zeta Potential of Colloid Charged Particle in Ionic Medium

EZ Water Interface Model of Charged Colloid in Bulk Ionic Medium

Cross Section A - Hollow Cylinder 1218

Graph of CBD Blood level Versus Time After Oral Administration Comparing Prophetic Example Improved Bioavailability of a Present Invention Embodiment Beverage Comprising Nano-Water Clusters of 80 mg Cannabidiol (CBD) Versus a Prior Art CBD Oral Tablet

FIG. 20

| | | |
|---|---|---|
| Order No.: | 705235 | 705236 |
| Batch No.: | 1 | 2 |
| Report Date: | 09/16/2019 | 09/16/2019 |
| Net Volume: | 510 ml | 510 ml |
| | | |
| Potency: | | |
| CBD Total: | 25.934 mg | 24.975 mg |
| THC Total: | not detectable | not detectable |
| CBG Total: | not detectable | not detectable |
| CBN Total: | not detectable | not detectable |
| Other Cannabinoids Total: | not detectable | not detectable |
| | | |
| Total detected Cannabinoids: | 25.934 mg | 24.975 mg |

FIG. 24
Cross Section View of Static Blending Pipe 1228
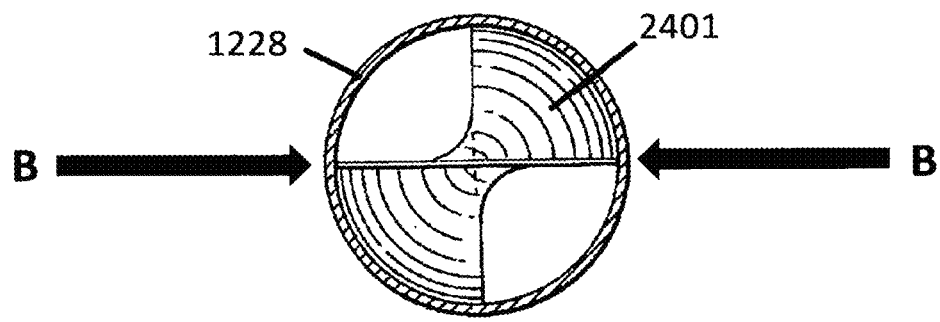
Longitudinal Sections of Static Blending Pipe 1228
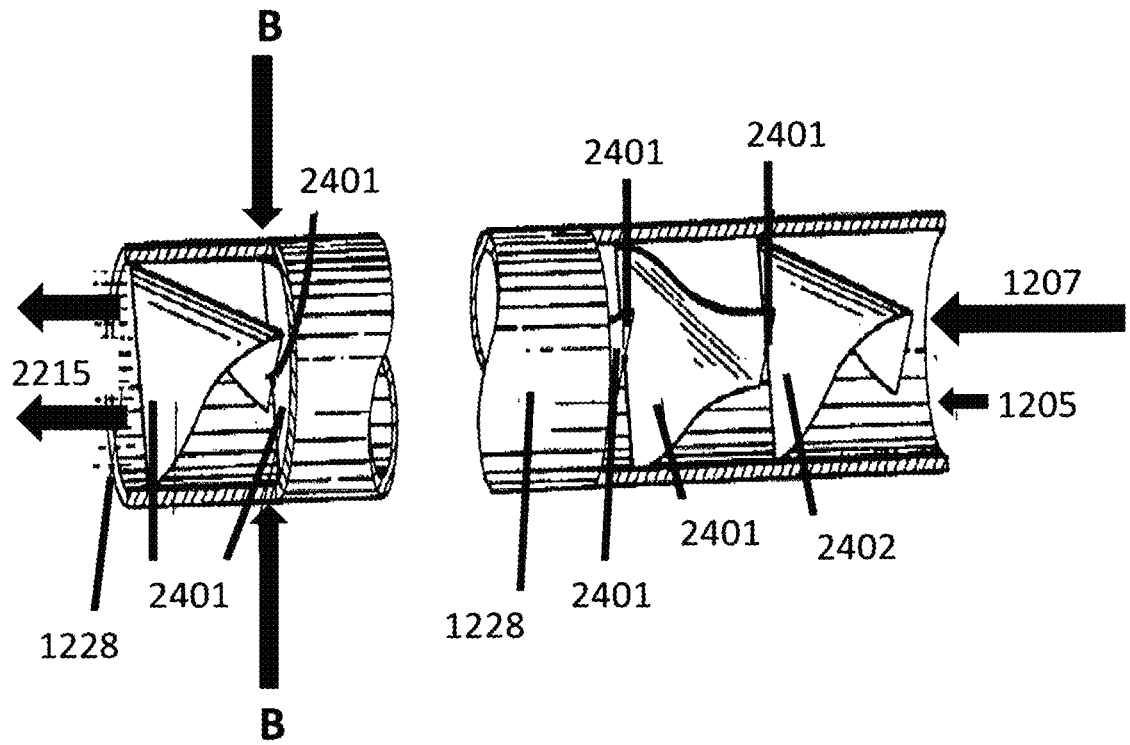

FIG. 25 Sensor Controlled Process for Ultrapure Water

| Process Steps 1-2: Purifying Water Source Using Charcoal |
|---|

Pressure Sensor 2501  Using a Source Water Pressure 45-55
Flow Sensor 2502  psi and a Flow rate of 16 gallons/min.
Chloride Sensor 2503  Keeping Chloride level under 1 ppm.
Resistivity Sensor 2504  Using a Resistivity of 4-5 meg-ohms.

| Process Step 3: Reverse Osmosing (RO) Charcoal-Purified Water |
|---|

Pressure Sensor 2505  Computer Adjusting Pressure to 23.5 psi
Flow Sensor 2506  and Flow to 14.5 gallons /min.
Resistivity Sensor 2507  Computer Requiring RO Resistivity to
Water Level Sensor 2508  be between 14-19 meg-ohms.
 Computer Controlling RO Sent to Tank.

| Process Step 4: Storing RO Water in a Holding Tank |
|---|

| Process Step 5: Electro-Deionizing (EDI) the RO Water |
|---|

Pressure Sensor 2509  Computer Adjusting Pressure to 23.5 psi
Flow Sensor 2510  and Flow to 14.5 gallons/min.
Resistivity Sensor 2511  Computer Requiring EDI Resistivity to
 be between 4-19 meg-ohms.

| Process Step 6: Purifying EDI Water with Mixed-Bed Resin Beads |
|---|

Pressure Sensor 2512  Computer Adjusting Pressure to 23.5
Flow Sensor 2513  psi and Flow to 14.5 gallons /min.
Resistivity Sensor 2514  Computer Requiring Resistivity after
 Beads to be between 14-19 meg-ohms.

| Process Step 7: Ultraviolet Light Sterilizing Purified EDI Water |
|---|

| Process Step 8: Optional Filtering thru 0.1 and 5 Micron Filter(s). Using the Ultrapure Water immediately or Storing for Using Later. |
|---|

Size Distribution Report by Intensity                                    Malvern

Sample Name:              20 Aug Immune 1
General Notes:            1 gal makes 300 gal, Post IP, 40K Trace minerals
Measurement Date:         August 20, 2019

<u>System</u>
Temperature (°C):                 25.0
Duration used (s):                460
Count Rate (kcps):                1.5
Measurement Position (mm):        4.65
Cell Description:                 Disposable sizing cuvette
Attenuator:                       11

| <u>Results</u> | Size (d.nm): | % Intensity: | St. Dev. (d.nm) |
|---|---|---|---|
| Peak 1: | 157.5 | 89.0 | 34.14 |
| Peak 2: | 1.611 | 11.0 | .1183 |

Size Distribution Report by Intensity — Malvern

Sample Name: 9 Sept 2019 1500 gal run 8:22 am 3rd Malvern 1
General Notes: 5 gal, All ingredients, An extra 95 Gal Pre Solution
Measurement Date: September 9, 2019

System

Temperature (°C): 25.0
Duration used (s): 150
Count Rate (kcps): 1.9
Measurement Position (mm): 4.65
Cell Description: Disposable sizing cuvette
Attenuator: 11

Results

| | Size (d.nm): | % Intensity: | St. Dev. (d.nm) |
|---|---|---|---|
| Peak 1: | 164.2 | 100 | 1.907 E-6 |

PROCESS FOR MAKING AQUEOUS THERAPEUTIC PARTICLE HAVING STABLE EXTERIOR WATER CLUSTERING WITH NANOSIZED THICKNESS

CROSS REFERENCE TO RELATED APPLICATION

The present US Non-Provisional patent application claims the benefit of the filing date of U.S. Provisional patent application with Ser. No. 62/920,450 filed Apr. 30, 2019, the entirety of which is hereby incorporated by reference herein. Also, the present US Non-Provisional patent application claims the benefit of the filing date of U.S. Provisional patent application with Ser. No. 62/920,747 filed May 13, 2019, the entirety of which is hereby incorporated by reference herein. Furthermore, the present US Non-Provisional patent application claims the benefit of the filing date of U.S. Provisional patent application with Ser. No. 62/921,280 filed Jun. 8, 2019, the entirety of which is hereby incorporated by reference herein.

FIELD OF THE INVENTION

The present invention generally relates to a process for making aqueous therapeutic particles having stable exterior water clustering with nanosized thickness. The present invention also relates to compositions and uses of the aqueous therapeutic particles having stable exterior water clustering of a selected nanosized thickness.

BACKGROUND OF THE INVENTION

The present invention generally relates to continuous manufacturing processes for making nanowater-based, improved-bioavailability, aqueous cannabinoid compositions for more effectively administering cannabinoids to an individual.

Molecules which bind reversibly to cannabinoid biological receptors include 3 classes: endocannabinoids produced naturally in the body by animals, phytocannabinoids found in cannabis and some other plants, and synthetic cannabinoids. There are more than 100 phytocannabinoids in cannabis plants. The phytocannabinoid THC (Tetrahydrocannabinol) produced in the Cannabis plant is a well-known hallucinogen. Cannabidiol (CBD) which is also produced in the cannabis plant is a chemical considered to have a non-psychotropic effect on individuals. CBD counteracts cognitive impairment associated with the use of cannabis. Cannabinoids are a class of chemical compounds being studied with great interest because of their many actions upon biological proteins, enzymes, and lipids in various parts of individuals, Cannabidiol (CBD) is an another medically-important chemical molecule and is a cannabinoid. Three classes of cannabinoids are known: (1) a small endocannabinoid class of molecules endogenously made and acting in mammals, (2) a large synthetic cannabinoid class of molecules with various improvements in pharmacological selectivity and potency, and (3) a phytocannabinoid class of about 100 molecules detectable in mainly cannabis plants but just of these molecules predominate, namely CBDA (Cannabidiolic acid) and THCA (Δ9-tetrahydro-cannabinolic acid). Heating Cannabis plant material de-acidifies the CBDA to CBD which is a non-psychotropic, and de-acidifies the THCA to THC (Tetrahydrocannabinol), a hallucinogen. There are Cannabis hybrid plants such as the YP5 hybrid plant grown by the company YP5 Plants, Colorado which have high CBDA and nil THCA content. The YP5 Company is an important legal source of pure CBD bulk powder with less than 0.2% THC. Many synthetic cannabinoids structurally related to THC have been discovered. The synthetic cannabinoids class molecules are also known as cannabimimetics and have been sub-classified according to their molecule's core structure. There are at least 5 sub-classes: aminoalkylindoles, quinolones, 1,5-diarylpyrazoles, arylsulfonamides and eicosanoids. Eicosanoids are like endocannabinoids.

Cannabinoids affect conscious and subconscious function, endocrine functions, inflammation, healing, and the immune system. CBD promotes sleep and suppresses arousal. CBD is used over the counter as a treatment for chronic pain, inflammation, and short-term memory loss. CBD counteracts cognitive impairment associated with the use of cannabis. CBD has low direct binding affinity for CB1 and CB2 biological cell membrane receptors but can indirectly to antagonize cannabinoids which can bind to CB1 or CB2 receptors. Also, CBD can directly antagonize CNS caudate and putamen cannabinoid receptor GPR55, and does serve as a 5-HT1A receptor agonist.

Due to the availability of THC-free CBD, there is a growing legal acceptance of CBD use by governments and consumers who are interested that CBD might help treat some of their medical problems without causing them to suffer hallucinogenic side effects. So many CBD formulations are being marketed as drinks, edibles, vapes, and topical balms or lotions. However, for aqueous CBD drinks there is a formulation problem because CBD is water-insoluble. Currently, this problem is overcome only by adding surfactant to the aqueous CBD drink to form a CBD emulsion. The problem with using a surfactant in an aqueous CBD drink is that the drink looks hazy and unhealthy unless it is made as a colored drink like a fruit juice. Also, CBD drink products have a low CBD content, generally below 10 milligrams per bottle. Needed is clear, attractive, healthy-looking CBD drink with above 10 milligrams CBD per bottle.

Water molecules are a common small chemical molecule which everyone must drink to stay alive. The most common 2D view of $H_2O$ is illustrated in FIG. 1 where two (2) hydrogen atoms 101, 104 are chemically bonded to one (1) oxygen atom 102 at a 106° angle to makes make a polar molecule with an electronic size (dashed line) of 0.28 by 0.32 nanometers. $H_2O$ is known to ionize to hydronium cations and hydroxonium anions ($OH^-$). The most common depiction of the hydronium ion is ($H^+$) and is illustrated in FIG. 4. Its most common name is the proton. The hydronium ion is also frequently given the empirical molecular formula $H_3O^+$ and depicted in 2D in FIG. 4 as an oxygen atom 400 bonded to three hydrogen atoms 401, 402, and 403 with the dashed line 404 defining its 2D electronic size (see FIG. 4). The hydroxonium ion (traditionally called hydroxide ion with molecular formula $OH^-$) is depicted in FIG. 3 as an oxygen atom 301 and a hydrogen atom 302.

Each $H_2O$ molecule can form up to four hydrogen bonds in liquid water. FIG. 2 illustrates a hydrogen bond between two (2) water molecules. Oxygen atom 202 is hydrogen bonded to water molecule hydrogen atom 201. Most models for intermolecular water H-bonding would suggest that hydrogen atoms 203 and 204 would be also have formed hydrogen bonds with other $H_2O$ molecules at the same time. The hydrogen bond is generally considered to be a partial electrostatic attraction between a hydrogen which is bound to a more electronegative atom (the hydrogen atom donor)

such a nitrogen, oxygen, or fluorine, and another atom bearing a lone pair of electrons (the hydrogen atom acceptor). The hydrogen bond's energy can vary greatly (between 1 and 40 kcal/mole) depending upon the donor atom donating the hydrogen atom and acceptor atom receiving the hydrogen atom to make the H-bond. Also the energy of an H-bond varies for the same type hydrogen bond as a function of the relative size of the water cluster of $H_2O$ molecules, a particular H-bond's conformation, geometry and needs for resonance delocalization of neighboring charges and radical free electrons, steric effects, electronic induction effects, and other H-bond network attraction, dipole, and opposition forces.

The H-bond has some features ascribed to covalent bonding such as the H-bond being a directional bond, can be a strong bond, and can produce interatomic distances shorter than the sum of the van der Waals radii. Note van der Waals radius is used to define half of the distance between the closest approach of two non-bonded atoms of a given element. Covalent characteristics of H-bonds are more substantial when acceptors bind hydrogens from more electronegative donors. For example, the acceptor atoms in the $H_2O$ molecule and in the $H_2S$ (hydrogen sulfide) molecule are oxygen and sulfur atoms respectively. $H_2O$ forms stronger intermolecular hydrogen bonds due to the higher electronegativity of the oxygen atom (in $H_2O$) compared to the lower electronegativity of the sulfur atom in hydrogen sulfide ($H_2S$) which forms weaker intermolecular hydrogen bonds. Consequently $H_2O$ has a higher melting temperature and a higher boiling temperature than $H_2S$ because $H_2O$ forms stronger intermolecular H-bonds. Thus at room temperature $H_2O$ is a liquid whereas $H_2S$ is a gas. H-bonds readily form between molecules of water, ice, ammonia, hydrogen sulfide ($H_2S$), and many functionalized organic molecules for example where the functional group has a hydrogen atom bonded to a nitrogen or oxygen. Hydrogen bonds also can form between atoms in a single molecule are termed intramolecular hydrogen bonds. Many polynucleotides, proteins, drugs, and polymers form intramolecular hydrogen bonds and these bonds critically define or restrict secondary and tertiary structure conformations of these molecules. Below depicted in a simple way are five types of hydrogen bonds and their H-bond enthalpies (energy) which range in strength about 3.5 fold.

In the H-bond depictions below the H donor atom is on the left; the H-Bond is the dashed line, and the acceptor atom is depicted on the right.

| H-Bond Enthalpy (kJ/mole) or (kcal/mole) units | |
|---|---|
| O—H . . . :N | 29 kJ/mole (= 6.9 kcal/mole), as for example with a hydrogen bond between a water molecule and an amine group molecule. |
| O—H . . . :O | 21 kJ/mole (= 5.0 kcal/mole), as for example with a hydrogen bond between two water molecules. |
| HO—H . . . :OH$^+_3$ | 18 kJ/mole (= 4.3 kcal/mole) as for example with a hydrogen bond between a water molecule and a hydronium ion |
| N—H . . . :N | 13 kJ/mole (= 3.1 kcal/mole), as for example with a hydrogen bond between two amine group molecules. |
| N—H . . . :O | 8 kJ/mole (= 1.9 kcal/mole), as for example with a hydrogen bond between a water molecule and an amine group molecule. |

Stoyanov Model for Hydrogen Ion Indicates Water Cluster Formation about a Proton A model for a hydrogen ion by Stoyanov (2010) proposes that the hydrogen ion in water is a proton 502 clustered by six water molecules as depicted in FIG. 5 within circular dashed line 501. Structure inside the circular dashed line 501 for the hydronium ion has a molecular formula $H_{13}O_6^+$. Next to proton 502 is a water molecule that is hydrogen bonded to it by an oxygen atom 503 of another water molecule. Depicted hydrogen atom 504 which is of the same water molecule as oxygen atom 503, is itself hydrogen bonded to oxygen atom 507. Depicted hydrogen atom 505 which is of the same water molecule as oxygen atom 507, is itself hydrogen bonded to oxygen atom 506 of a water molecule which is depicted just on the perimeter of circular dashed line 501.

Some prior art teaches a Uniform Continuum model for liquid water. When X-ray (Morgan & Warren, 1938) and infrared studies (Magat, 1936) on liquid water were first carried out, these studies suggested a liquid water structure model to Bernal& Fowler (1933) which called a uniform continuum model for liquid water. In this model, all oxygen atoms retain their four-coordination, but the hydrogen bonds are bent to such an extent that an instantaneous view from the central oxygen would see no order beyond the nearest neighbors. A random network model with soft hydrogen bonds suggested a water network with apex-linked polygons in rings of 4-membered rings, 5-membered rings, 6-membered rings or more complex rings, similar to ices and clathrates, but randomly arranged (from Plumridge & Waigh, 2002).

Some prior art teaches a Mixture model for liquid water. Frank & Evans in 1945 introduced "the concept of icebergs induced in water by solute molecules or the mixture model of water." Using volume and entropy measurements to study effects of non-polar molecules dissolved in water (noble gases, CO, methane), they found that the non-polar molecules affected the water around them, making the water around them less dense, at a lower entropy, and less mobile than the bulk water. In other words, they found that the dissolution of small non-polar molecules in water made the water more structured. They postulated that perhaps some molecules could be added to water to make it act in the opposite way, namely to act less structured and to act more dense than bulk water.

Some prior art teaches a model of Flickering Clusters of Hydrogen-Bonded Water Molecules. In 1957, Frank & Wen postulated that the existence of long-lived structures in liquid water was not likely. They thought a more useful model might involve flickering clusters of hydrogen-bonded water molecules. Frank & Wen also classified ions that could behave in liquid water as either being structure makers or structure breakers. They suggested a mechanism for this which assumed the ion is surrounded by three concentric regions: an innermost ice-like region nearest the ion where all water molecules are immobilized by H-bonds; a second region in which water molecules are less ice-like; and the third region in which the influence of the ion on water molecules is weak (from Plumridge & Waigh, 2002).

The classification of ions and some polar molecules as a water structure-maker or a water structure-breaker was furthered by the observation that some ions/polar molecules stabilized (kosmotropic) whereas some ions/polar molecules destabilized (chaotropic) the native conformations of proteins, as assessed by enzyme activity, denaturation, temperature and solubility (Collins & Washabaugh 1985). These effects had additivity, for example a strongly denaturing (structure breaking) solute such as urea could be offset by adding a strongly stabilizing (structure making) solute such as trimethylamine oxide. Also two structure-breaking solutes would destabilize a protein structure more so than either one alone. The structure-making or structure-breaking action of solutes was quantifiable in aqueous solution by measuring either the change in aqueous medium viscosity (structure breakers lower it), or the rate of exchange of water molecules (structure breakers lower energy of activation), or the longitudinal relaxation rate of water molecules as measured by NMR (structure breakers increase the rate).

In 1986 Marcus proposed that the entropy of hydration was affected by the structure-making and structure solutes based on individual entropy contributions of 50 ions to causing compression, immobilization and electrostatic effects upon water structure. The Hofmeister ion series (1988) ranked ions based on their ability to precipitate hen egg-white proteins and Collins in 1997 demonstrated that the Hofmeister ions destabilizes the structure of other biological macromolecules in the same order. The Hofmeister ion series shows opposite correlations for anions and cations with their degree of hydration. It turns out that structure-breaking ions destroy the hydrogen-bonded water network in a manner similar to increased temperature or pressure (Leberman & Soper 1995). It has been noticed that anions hydrate more strongly than cations of the same ionic radius and this is believed due to the fact that the partial-positive hydrogen atom of a water molecule can approach anions about 0.8 Å more closely than the partial negative oxygen atom of a water molecule. Note 10 Å (angstrom) is the same distance as 1 nanometer (nm). The hypothesis is (A) that small ions are strongly hydrated with small or negative hydration entropies creating local order, and (B) that large singly charged ions have larger positive entropies of hydration, and so act like hydrophobic molecules with their binding being dependent on van der Waals forces and their ion charge. The product of the measured viscosity and the measured conductivity at infinite dilution of a solution, has been used as a measure of a solute's water-structuring activity and is called the Walden product. This has been used to quantify structure-making and structure-breaking effects of amino acids, in conjunction with spectroscopic studies. Most anion forms of amino acids exhibit some structure-breaking activity. For example, 1-lysine, 1-glutamic acid, 1-aspartic acid and their salts show strong structure-breaking activity. Dextrose, however, behaves as a classic structure maker and reverses the structure-breaking action of 1-lysine (Lutz et al 1994) (from Plumridge & Waigh, 2002).

Some prior art teaches there is a Positive Cooperativity of Hydrogen Bonding in Tetrahedral $H_2O$ Networks. Positive cooperativity effects of hydrogen bonding in water are found and promote large tetrahedral networks of hydrogen-bonded water to form. Cooperative patterns were found in the first systematic studies of hydrogen bonding in carbohydrates (Jeffrey et al 1977). The water molecule acting as acceptor in a particular hydrogen bond will strengthen the other hydrogen bonds of the water molecule acting as a donor (Tombari et al., 1999). In 1998, Luck reported that in liquid water, hydrogen bonding cooperativity strengthens hydrogen bonds by up to 25 times the strength of the individual hydrogen bond in the water dimer (from Plumridge & Waigh, 2002).

Some prior art teaches there is a shortening of Hydrogen Bond Lengths in $H_2O$ Larger Tertiary Confirmations. Keutsch (2001) compiled data on hydrogen bond lengths in $H_2O$ dimers, trimers, tetramers, pentamers and hexamers using terahertz laser vibration-rotation-tunneling (VRT) spectra and mid-IR laser spectra. The obvious limitation of the Keutsch study is probably that he studied only UPW which is never the state of biological water. Keutsch hypothesized that the hydrogen bond (H-bond) in bulk water should be dominated by electrostatic interactions. Coulomb force, also called "electrostatic force" or Coulomb interaction, attraction or repulsion of particles or objects because of their electric charge. Two like electric charges which can be either two positive charges or two negative charges are known to repel each other along a straight line between their centers.

Keutsch also hypothesized that the hydrogen bond (H-bond) in bulk water should be balanced by the repulsive electron exchange. The consequence of the Pauli principle here is that electrons of the same spin are kept apart by a "repulsive electron exchange" interaction, which is a short-range effect, acting simultaneously with the long-range electrostatic or Coulombic force.

Keutsch further hypothesized that the hydrogen bond (H-bond) in bulk water should result in the dispersion force having a detectable effect. The London "dispersion force" is the weakest intermolecular force. The London dispersion force is a temporary attractive force that results when the electrons in two adjacent atoms occupy positions that make the atoms form temporary dipoles. This force is sometimes called an induced dipole-induced dipole attraction.

In addition, Keutsch hypothesized that the hydrogen bond (H-bond) in bulk water should cause induction (polarization) acting as the dominant many-body effect. Induction is a general phenomenon where charges are 'induced'(redistribution) in a body when another charged body is brought near it. Polarization is a vector quantity defined as the dipole moment per unit volume.

Keutsch measured the H-bond in the water dimer in terms of the oxygen-oxygen distance between the two water molecules to be 2.952 Å (0.295 nanometers). Note 10 Å (angstrom) is 1 nanometer (nm). Keutsch found that the water trimer is a much more rigid structure than the dimer, as the former has three strained H-bonds. The oxygen-oxygen distance of the H bond in the trimer is 2.85 Å, which is shorter than the H bond in the dimer, a result of the increased hydrogen bond strength caused by the cooperative effect of three-body forces. He found that the H-bonding motif of the water tetramer is similar to that of the trimer, with each monomer acting as a single donor and acceptor, and having one free and one bound H. He found that the average oxygen-oxygen distance in the tetramer is further shortened to 2.79 Å. The water pentamer was found to be similar to the trimer in both structure and dynamics. However, he found the pentamer ring is puckered with an oxygen-oxygen distance further shortened to 2.76 Å and having hydrogen bonds nearly linear in the axis of the two opposing oxygen atoms.

Keutsch reported that five-membered water molecule hydrogen bonded rings are a dominant topology in liquid water after running computer simulations of their molecular dynamics. He reported that the water hexamer represents a transition of a H-bond network from being two-dimensional to being most stably as a three-dimensional octahedral cage structure in which four of the water molecules are triple H-bonded, and two apical water molecules are double H-bonded. Thus Keutsch reported that $H_2O$ molecules in bulk liquid water are hydrogen bonded together to form $H_2O$ dimers, $H_2O$ trimers, $H_2O$ tetramers, $H_2O$ pentamers, $H_2O$ hexamers and larger poly-$H_2O$ molecular structures. It is unclear how to relate a pure water structure model to a biological water structure model which contains a myriad of biological molecules other than to point out that small water molecule clustering occurs even in pure water.

Some prior art teaches evidence for what are called water clathrates. There is evidence from studies of the ices, from water clathrates and other solid solutions, as well as from liquid solutions, that certain motifs (designs, patterns) occur very frequently and have relatively high stability, such as the $(H_2O)_{20}$ cavity-forming structure known from studies on clathrates. The implications of recent models of water structure for an understanding of biological events, including the interactions of drugs with receptors, are profound. It is becoming clear that modeling of aqueous solutions of any molecule must consider the explicit interactions with water molecules and that water structures are simply not a continuum. As Keutsch shows water itself is not a continuum. Solute molecules which possess hydrogen-bonding groups will provoke the formation of further hydrogen-bonding chains of water molecules: if these can form rings, such rings will tend to persist longer than chains, giving the solute a secondary identity of associated water which may play a role in molecular recognition. Solutes that do not have hydrogen-bonding capability, or regions of solutes which are non-polar, may also produce partial cage-like water structures that are characteristic of the solute (from Plumridge & Waigh, 2002, Water structure theory and some implications for drug design, J. Pharmacy & Pharmacology vol 54, 1155-1179).

Some prior art teaches properties of $H_2O$ in Confined Conditions. High-resolution neutron diffraction and spectroscopic techniques have investigated pure water in confined conditions. Confined $H_2O$ molecules to 40 Å pores in Vycor glass show orientational preferences that are very different from those of bulk water (Bruni et al 1998). These $H_2O$ molecules have very slow relaxation times indicative of longer-lived cavity structures encaging other $H_2O$ molecules (Starr et al 1999). $H_2O$ dielectric relaxation times of water molecules confined by ultrafast laser spectroscopy are bimodal with a fast sub-picosecond response component as expected from bulk water and a slow response component of hundreds to thousands of picoseconds. This slow response component is 10%-40% of the total relaxation response and it is absent in pure water (Bhattacharyya & Bagchi 2000). The confined environments in these studies included molecular assemblies: reverse micelles, microemulsions (Riter et al., 1998), cyclodextrin (Vajda et al., 1995), micelles (Telgmann & Kaatze, 2000), lipids (Datta et al., 1998), proteins (Jordanides et al 1999) and DNA (Halle & Denisov 1998), and macroscopic solids which can trap water such as hydrogels (Datta et al 1997)). In all cases, the slow response component was detected and the researcher believe its origin lies in the dynamic exchange between free and bound water. A comprehensive understanding of the mechanism and implications of this phenomenon is not yet available. Overall, it is apparent that water in contact with regular hydrogen-bonding surfaces can adopt the pattern expressed at the surface and extend that pattern out into the bulk water, at least to several hundred molecular diameters (taken from Plumridge & Waigh, 2002).

The prior art often give measurements either absolute values or ranges of values for the estimated sizes of molecules and larger objects without considering that they may cluster with same molecules or objects or with other molecules or objects. For example, FIG. 6 depicts a horizontal bar graph of sorts which provides the ranges of sizes of small known objects and particulates to illustrate their sizes relative to the lengths of 0.0001 to 1000 microns. This is the same range as 0.1 nanometer to 1,000,000 nanometers. Also, named are at the bottom of FIG. 6 are several well-known processes: reverse osmosis, nanofiltration, ultrafiltration, microfiltration, and conventional particulate filtration that have been used to trap or to exclude particulates of certain ranges of size.

The prior art teaches that the three-dimensional structures of all biological macromolecules are intimately associated with water. The solid-state hydration structures of small biological molecules (carbohydrates, purines, pyrimidines, nucleosides and nucleotides) are determined mainly by packing forces, and hydrogen bonding between the functional groups of the organic molecules. Water plays a secondary role in these structures, occupying the space between the organics, and adding to the hydrogen bond energy of the lattice while in competition with the molecular packing in the absence of water. If biological molecules aggregate, or if a substrate enters the active site of an enzyme, the water molecules have to move from the contact surface of the biological molecule in a coordinated manner with the least expenditure of energy. Hydrogen bonding must play an important role in this substitution process (Jeffeey & Saenger, 1991). However, the structural information regarding aqueous solutions in the liquid state that can be obtained from diffraction studies on liquid species is limited because of the continual translational and rotational movement of the molecules (taken from Plumridge & Waigh, 2002).

The prior art teaches a Model for a Potential Role of Radial Electrostatic Charge Dispersement. In regard to current hypotheses for the structure of water at an interface with a charged particle or surface note that FIG. 8 depicts a prior art diagram of a model for a radial electrostatic charge distance 813 (mv) neutralization 812 of the static charge on the surface of a colloidal charged particle 802 at an interface 807 with an ionic aqueous medium 800 containing anions and cations 801. In this aqueous radial electrostatic charge neutralization model there are three regions with the potential 809, 810, and 811. This model predicts 2 layers of aqueous ions. There is a measurable Zeta potential 811 but potentials 809 and 810 are theoretical. FIG. 8 presents this model using a negative surface charge on a colloid particle. The fundamental model depicted in FIG. 8 is that there is a millivolt (mv) negative charge on the colloid particle surface 812 which becomes electrically neutralized over a distance 813 from the charged particle surface due to the neutralizing cations 807 in a Stern layer 805 which further out from the charged particle surface becomes accompanied by anions 806, 807 in a second neutralizing layer that is a Slipping plane 808. In FIG. 8 there is a graph depicting the neutralization of the charged particle surface in millivolts on the Y-axis 812 as a function of the distance out from charged particle surface indicated on the X-axis 813. The layers of charge neutralizing ions 804, 806, and 807 eventually become the bulk ionic medium 800 composition of cation and anions 801. In other words, in FIG. 8 the charged particle 802 has a negative charge surface 803 which causes a surface potential 809 and there is a Stern layer 805 of positive counter-ions (cations) 804 and peripheral to the Stern layer is a concentrated mixture of cations 807 and anions 806 which has a finite thickness and then further out from the colloid charged particle is a demarcation point known as the slipping plane 808. In addition, the voltage at the slipping plane 808 is called the Zeta potential 811. The Zeta potential is an experimentally measurable characteristic of stable colloidal particle dispersions in aqueous media, which is very sensitive to the ionic constituents of the medium and its colloidal particle's charge.

The prior art also teaches a model called the EZ Water Interface Model of a Charged Colloid in a Bulk Ionic Medium which is depicted in FIG. 9. The ionic medium at the interface of a positively charged surface 905, 903 in the EZ Water Interface Model of a Charged Colloid with ionic core material 902 is a relatively thick layer of "EZ Water". There is a thick layer of an aqueous medium having only anions 906, 907 and 908 in the EZ Water Interface Model of a Charged Colloid. The EZ Water model markedly contrasts with the with the thin counter ion layers of the Charged Colloid model depicted in FIG. 8 where there is more of a mixing of anions 806 and cations 804 so that the layer of this mixing appears to be thinner. In contrast for the EZ Water layer model as shown in FIG. 9 the concentration of anions decreases radially from the charged surface 905. There is a sudden change at 904 where the EZ Water layer and the bulk ionic medium come into contact. At this contact location 904 the EZ Water Interface Model predicts that the bulk ionic medium has become concentrated in cations 909. Further and further out in the bulk ionic medium from interface 904 the concentration of cations decreases as depicted by 909, 910 and 911. The basis for the thickness of the EZ Water layer is hypothesized as due to the tendency of water molecules to form complex large networks (arrays, clusters, aggregates) of water molecules that can be stabilized in unpredictable ways by various formations of variable strength H-bonds and numbers of H-bonds.

The prior art teaches gaseous water can form stable water clusters. Structured water in the gaseous state has provided some evidence for long lasting stable water cluster species. Very generally speaking a cluster is a chemical description of aggregates of atoms or molecules that can be weakly bound together to create a larger structure than its individual atoms or molecules. In the mass spectra of polymeric compounds or complexes the appearance of prominent peaks in an otherwise continuous distribution of signals is called a magic number cluster, and may indicate the existence of species with enhanced stability. In water systems, it is well known that the cluster corresponding to $(H_2O)_{21}H+$ always exhibits a pronounced magic number under different experimental conditions (e.g. expansion of ionized vapor (Beuhler & Friedman 1982), ion bombardment of ice surfaces (Haberland 1984); electron impact ionization (Echt et al 1989) and vacuum photoionization of neutral clusters (Shinohara et al 1985)). Shinohara et al (1985) employed a neutral supersonic nozzle linked to a molecular-beam mass spectrometer supplied with premixed water±ammonia gas, to investigate the formation of mixed binary water±ammonium clusters. Evidence was found for exceptional structural stability of protonated clusters corresponding to $(H_2O)_{20}(NH_3)mH+(m^{-1\pm6})$ and $(H_2O)_{27}NH^{+4}$. A parallel Monte Carlo simulation yielded larger binding energies for these structures compared with their close neighbors, in agreement with the mass spectrometry results, and a deformed pentagonal dodecahedron enclosing an $NH^{+4}$ ion was proposed, with the stability due to strong coulombic interactions (ionic hydrogen bonding) between the $NH^{+4}$ and the 20 waters, as well as the inherent stability of pentagonal rings and the pentagonal dodecahedron (taken from Plumridge & Waigh, 2002).

The prior art teaches Hydration of Molecules Influences their Molecular Conformations.

Hydration of nucleic acids is important for the conformation of DNA. This has been demonstrated by the alteration of water activity by the addition of salts. If the DNA is fully hydrated, there are appears to be about twenty water molecules of hydration per nucleotide. If the hydration is reduced, the minimum number of waters per nucleotide approaches 3 to 6. The hydration of DNA has been described as existing with two hydration shells (Cohen & Eisenberg 1968), based on DNA sedimentation equilibrium studies. The first hydration shell is viewed as impermeable to ions and does not freeze into an ice-like state. Of the twenty waters per DNA nucleotide, it appears that 11 to 12 waters would be are directly bound in the first hydration shell to the DNA. In hydrated DNA crystal structure analyses, the first hydration shell waters are hydrogen bonded to DNA oxygen and nitrogen atoms. The second hydration shell is permeable to cations, freezes to ice I structure, and is subtly different from bulk water far away from the DNA. In considering the hydration of A-DNA, B-DNA, and Z-DNA, there are characteristic hydration patterns which are DNA sequence-dependent and DNA sequence-independent motifs (taken from Plumridge & Waigh, 2002).

Plumridge and Waigh propose there are at least four ways in which water can alter the structure of a biological macromolecule. (1) An $H_2O$ molecule can bridge two hydrogen-bonding substituents. (2) By hydrophobic bonding, two or more non-polar regions can come together and release the water molecule(s) structured about the two or more non-polar regions. (3) A polar residue that is geometrically incompatible with structured water may be transmitted by water molecules to neighboring groups and lead to a disruption of hydrophobic bonding. (4) The connecting of two domains of structured water which are geometrically compatible could occur over a relatively long distance. They propose that water domains of structured water between non-polar groups could be promoted by phosphorylation of hydrocarbons. This occurs in living cells by protein kinases and such phosphorylation is known to have a profound effects on the protein conformation which greatly modify, increase or decrease key protein functions.

Water has high adhesion properties because of its polar nature. On glass, water may form a thin film when molecular adhesive forces between glass molecules and water molecules are stronger than the cohesive forces between the water molecules. In biological cells and organelles, water is in contact with various cellular membranes and protein surfaces that are hydrophilic (water attracting).

The prior art teaches that the entropy of Liquid Water Clusters is due to the Brief Nature of Hydrogen Bonding. Overall there is in any given time period in liquid water a clustering of a large portion of the $H_2O$ molecules by many H-bonds of varying strengths and steady state lifetimes. Water molecules stay close to each other (cohesion), due to the collective action of hydrogen bonds between water molecules. However, when an additional non-water substance is present or water is confined, then the hydrogen bonding should no longer be randomized and merely tetrahedral. There is ample biological evidence of this critical and essential role of water structures in the functioning of biological molecules. The strength of hydrogen bonding between water molecules is hypothesized to explain why liquid water has a high surface tension of 72 mN/m at 25° C. Another piece of evidence for the strong cohesive forces between water molecules and the strong adhesive forces between water molecules and various hydrophilic surfaces is the observation that liquid water can be transported in the trunk of a tree to a height of more than 300 feet above ground. The solvent ability of liquid water is related to its high dielectric constant (88–55 at 0-100° C.). Thus the higher the dielectric constant of the substance the higher an electric field can exist between two coulombic point charges in the substance before there is an electric discharge current flow between the two coulombic point charges. Substances that mix well and dissolve in water are described as hydrophilic, whereas substances that do not mix well with water are described as hydrophobic. The ability of a substance to dissolve in water is depends on whether or not the substance can match or better the strong cohesive forces between water molecules. If a substance has properties that do not allow it to overcome the cohesive forces between the water molecules, then the substance appears to be insoluble. Put another way, it is not that water and insoluble (hydrophobic) substances "repel" each other; it is the cohesiveness of water molecules.

The prior art teaches that the hydration of Hydrophobic Interactions is Energetically Favorable. The hydration of insoluble (hydrophobic) substances are actually energetically favorable but not entropically favorable. Entropy is a thermodynamic concept in which it is tendency of the universe to go towards a state of greater disorder. Many non-polar substances such as fats and oils are often poorly soluble (insoluble or immiscible) in water.

The prior art teaches that Hydration of Ions in Liquid Water is Due to Adhesive Forces of Ions to Water. In the case when an ionic compounds or a polar compound is placed in liquid water, the compound is surrounded by water molecules and is thus hydrated because the adhesive forces of the water molecules to the hydrophilic substance are greater than the cohesive forces between the liquid water molecules. Many water molecules may surround one molecule of solute. Many ionic and polar substances such as acids, alcohols, and salts are highly soluble or miscible (soluble in each other in any proportion) in water. Water solubility of a substance may depend as well on the presence of other species dissolved in the solvent, for example, complex-forming anions (ligands) in liquids may facilitate the solubility of poorly soluble molecules.

The prior art has a definition for a Water Cluster. According to the prior art, a water cluster of $H_2O$ molecules is defined to be a discrete hydrogen bonded assembly of $H_2O$ molecules of water. Water clusters have been found experimentally or predicted in silico in various forms of water; in ice, in crystal lattices and in bulk liquid water. The realization that water manifests itself as clusters rather than an isotropic collection may help explain many anomalous water characteristics such as its highly unusual density temperature dependence. Water clusters are also implicated in the stabilization of certain supramolecular structures. So little is understood about water clusters in bulk water that it is considered one of the unsolved problems in chemistry that hydrogen bonds in water break and reform at similar rates (Water Clusters, Wikivisually).

The prior art has In-silico Water Models which are Cyclic Water Clusters. In-silico water models have been discovered which are cyclic water clusters $(H_2O)_n$ are found with n=3 to 60. Structures of water molecules with the highest resolution have been demonstrated in the studies of Saykally of Univ. Cal. At Berkeley. With increasing cluster size the oxygen to oxygen distance is found to decrease which is attributed to so-called cooperative many-body interactions: due to a change in charge distribution the H-acceptor molecule becomes a better H-donor molecule with each expansion of the water assembly. Many isomeric forms seem to exist for the hexamer: from ring, book, bag, cage, to prism shape with nearly identical energy. Two cage-like isomers exist for heptamers, and octamers are found either cyclic or in the shape of a cube. Even larger clusters are predicted: the fullerene-like cluster $(H_2O)_{28}$ is called the water buckyball and even for a 280 water molecule monster icosahedral network (with each water molecule coordinate to 4 others) there is found a local energy minimum. The 280 molecule icosahedral structure, which is 3 nm in diameter, consists of icosahedral shells with 280, 100 and 320 molecules (the 100 molecule structure is shown the figure above). There is increased stability with the addition of each shell. There are theoretical models of water clusters of more than 700 water molecules by Chaplin and Zenin.

The prior art has measured Life Spans of Hydrogen Bonds to be about 10 Picoseconds. In the prior art, it is assumed that the hydrogen bonds (H-bonds) between water molecules all have an average lifetime of 10 picoseconds, but this is unlikely. The great variability of the energy in H-bonds means that the strength of H-bonds must be highly variable and this means that the average half life time of an H-bond is going to be highly variable (some H-bonds with a half-life as brief as 10 picoseconds and some H-bonds (as in DNA chains) that has a half-life which for all purposes lasts the lifetime of the molecule. The life time of a molecule may be many years and be more affected by sudden changes in the chemical environment of the H-bond rather than the kinetic rate constants of its inherent H-bond forming and retention (adhesion and cohesion) forces. Important to note is that quantum chemical calculations of the relevant inter-residue potential constants (compliance constants) predict there should be significant differences between individual hydrogen bonds of the same type in a molecule which is a member of a population of molecules. These significant differences may result in separate or various degrees of aggregation or clustering of molecules having intermolecular H-bonds. For example, the central inter-residue N—H . . . N hydrogen bond between guanine and cytosine is much stronger in comparison to the N—H . . . N bond between the adenine-thymine pair. Accordingly within arrays of hydrogen bonds in poly water arrangements, there is no need to assume the hydrogen bonds have an equal hydrogen bond strength (Hydrogen Bond, Wikipedia, 2018).

In conclusion, the prior art teaches that there are a large number of variables and relationships between chemical molecular, atomic and electronic and physical forces in settings of $H_2O$ molecules which take place between $H_2O$ molecules, and between water cluster populations of $H_2O$ molecules. The assessment of these forces and their relative roles in water remains controversial study (Plumridge & Waigh, 2002; Eaves et al., 2005; Smith et al., 2005; Chaplin, 2007; Del Guidice, 2015). The two water structure models: the uniform continuum model for liquid water versus the mixture models for liquid water are considered more than research models by most scientists. However, contemporary science regardless of its area: chemistry, physics, pharmacology, physiology, biophysics, biochemistry, or biology try to side-step the clustering phenomena occurring between $H_2O$ molecules. Some scientists prefer to perform mathematical model computer simulations and spectroscopy experiments and extrapolate data from them to an aqueous settings in biology, but they have performed artificial studies of $H_2O$ molecular phenomena which may not be the actual case. The bottom line is that many prior art water studies are not directly applicable to settings occurring inside a human or animal, a drink, an aqueous formulation (containing minerals, a protein, a food, a pharmaceutical, a nutraceutical), or for a use such as animal farming, medical practice, medical treatments, and agriculture. Water compositions prepared for human use and consumption even spring water always contain some minerals and other non-$H_2O$ substances. The prior art suggests $H_2O$ molecules and non-$H_2O$ substances do interact in very complex ways in some cases. There has always been the need for improved water compositions for more rapid consumption to hydrate humans, animals, and plants (Dehydration-Wikipedia, 2018; Shirreefs & Sawka, 2011; Gravelle et al., 2013), however, the prior art does not teach how to change the bioavailability of water to hydrate a human, an animal, or a plant more rapidly and more completely.

SUMMARY OF THE INVENTION

Generally, embodiments of the present invention relate to improved bioavailability compositions comprising nanosized clusters of water molecules carrying nanosized, non-$H_2O$ substance(s), wherein the water molecules are obtained from an ultrapure water source. The present invention embodiments include processes and apparatus for manufacturing these nanosized compositions as well as methods for effectively using these nanosized compositions.

Some embodiments of the present invention specifically relate to improved bioavailability compositions comprising nanosized clusters of water molecules carrying nanosized cannabidiol (CBD) particles or other cannabinoid particles, wherein the water molecules are obtained from an ultrapure water source or anther highly purified water. The present invention embodiments include processes and apparatus for manufacturing these nanosized clusters of water molecules carrying the nanosized cannabidiol (CBD) particle compositions or other cannabinoid particle compostions as well as methods for using these compositions for more effectively treating medical conditions in a human or animal including anxiety, inflammation, and drug addiction.

Some embodiments of the present invention specifically relate to improved bioavailability compositions comprising nanosized clusters of water molecules carrying nanosized mineral ions or nutrient particulates, wherein the water molecules are obtained from an ultrapure water source. The present invention embodiments include processes and apparatus for manufacturing these nanosized mineral ions or nutrient particulate compositions as well as methods for using these compositions for more effectively treating medical conditions in a human or animal including preventing and treating various dehydration conditions in a human or an animal.

Some embodiments of the present invention specifically relate to improved bioavailability compositions comprising nanosized clusters of water molecules carrying a nanosized cancer cell membrane pore-forming peptide (CCMPFP) which may be a PNC family peptide such as PNC-27 or an SLH family peptide such as SLH-1, wherein the water molecules are obtained from an ultrapure water source or another highly purified water. The present invention embodiments include processes and apparatus for manufacturing these nanosized clusters of water molecules carrying the nanosized cancer cell membrane pore-forming peptide compositions as well as methods for using these compositions for more effectively preventing and treating a cancer, or preventing a cancer reoccurrence in a human or in an animal. A particularly effective cancer cell membrane pore-forming peptide is PNC-27.

Some embodiments of the present invention specifically relate to improved bioavailability compositions comprising nanosized clusters of water molecules carrying a nanosized pharmaceutical chemical compound, wherein the water molecules are obtained from an ultrapure water source. The present invention embodiments include processes and apparatus for manufacturing these nanosized clusters of water molecules carrying a nanosized pharmaceutical chemical compound, as well as methods for using these compositions to more effectively administering a therapeutically effective drug treatment to a human or to an animal in need.

Some embodiments of the present invention specifically relate to an improved manual control apparatus for manufacturing product embodiments, further comprising: an inline mixing pipe and one or more additional hollow cylinder devices each with an internal nozzle with jets for nanosizing clusters of water molecules to carry nanosized, non-$H_2O$ substance(s).

A particularly preferred apparatus for manufacturing product embodiments of the present invention comprises a computer controlled apparatus for manufacturing product embodiments of the invention which are nanosized clusters of water molecules carrying nanosized, non-$H_2O$ substance(s), the apparatus comprising:
   using process stream sensors situated in the apparatus for measuring process stream flow rates, process stream pressure, initial process stream chlorine ppm, and process stream megohm resistivity;
   sending sensor information from the process stream sensors to the computer processor;
   using the computer processor to compare the sensor information received from the sensors in the process streams to selected process stream parameters
   using the computer processor to identify if any of the process stream sensor measurements deviates significantly from the selected process stream parameters; and
   using the computer processor to sends commands to the apparatus manufacturing control pints to make adjustments in process stream parameters to control the manufacturing of the product embodiments which are nanosized clusters of water molecules carrying nanosized, non-$H_2O$ substance(s).

Some embodiments of the present invention specifically relate to compositions for improving farming of animals and growing of plants, the compositions comprising nanosized clusters of water molecules carrying a nanosized non-$H_2O$ substance(s), wherein the water molecules are obtained from an ultrapure water source. The present invention embodiments include processes and apparatus for manufacturing these improved compositions for improving farming of animals and growing of plants.

Some embodiments of the present invention specifically relate to improved bioavailability compositions comprising nanosized clusters of water molecules carrying nanoparticles of cerium oxide and nanoparticles of manganese dioxide, wherein the water molecules are obtained from an ultrapure water source. Effective nanoparticles of cerium oxide (individually $CeO_2$ NPs, $Ce_2O_3$ NPs, and in some cases in combinations as nanocrystals) typically have a size between 1 to 20 nanometers and can catalytically protect normal cells from superoxide anion free radical and other reactive oxygen species (ROS) formations in normal cells provided the normal cells have what is considered to conventionally be a non-acidic intracellular pH. of about 6.8-7.2. On the other hand, CeONPs promote the formation of free radicals in cancer cells due to their lower pH environment of less than pH 6.8.

Nanoparticles of manganese dioxide, ($MnO_2$NPs) typically are between 1 to 20 nanometers in size, can effectively break down hydrogen peroxide ($H_2O_2$) in cancer cells and in normal cells to form oxygen and water molecules. Hydrogen peroxide levels are elevated in cancer cells because of derangements of cellular metabolism. Hydrogen peroxide functions as a paracrine second messenger in cancer cells because $H_2O_2$ has a long life span comparted to most free radicals and being a small molecule can diffuse rapidly and is effectively membrane permeable as it can travel thru Aquaporin water channels as easily as water molecules.

Hydrogen peroxide is important as it can reversibly oxidize thiol groups of cysteine amino acids in cell proteins to reversibly form disulfide bonds which are bonds that can bridge different amino acid chains of proteins to cause major functional changes in protein conformations in regulatory pathways in cells. Cancer cells use $H_2O_2$ to stimulate the cancer cells ability to proliferate while inhibiting the cell from programmed cell death signaling (apoptosis). The present invention embodiments include processes and apparatus for manufacturing individually or collectively nanoparticles of cerium oxide and nanoparticles of manganese dioxide these nanosized clusters of water molecules carrying nanoparticles of cerium oxide and nanoparticles of manganese dioxide, as well as methods for using these compositions for decreasing levels of hydrogen peroxide and other cellular free radicals in the body of a human or an animal as a method which comprises: (1) preventing cancer cell formation occurrence, (2) slowing the development of cancer clonal populations, (3) de-stimulating proliferation of cancer cells, (4) slowing factors promoting cancer tumor metastases and (5) lessening cancer reoccurrence.

The terms nanowater, nanowater clusters, nano-sizing, and nano-sized are all related terminology which refer to nanometer measurements of the median size of the water clusters surrounding a nano-sized particle of a non-$H_2O$ substance in a bulk phase that was originally ultrapure water (UPW). The term non-$H_2O$ substance means the same thing as the non-$H_2O$ ingredients.

Process embodiments of the present invention produce highly useful composition embodiments of the invention which are stable nano sized water clusters about the non-$H_2O$ non-$H_2O$ substance. The combination of the water cluster around the non-$H_2O$ substance is detected by a laser beam and its reflections from the particle. The temporal patterns of water-clustered particle reflections can be analyzed by a Malvern Zetasizer instrument by principals of DLS (direct light scattering). The Zetasizer collects DLS (dynamic light scattering) data and uses computer algorithms to generate a histogram graph of the distribution in nanometers of the water-clustered particle sizes, which are an important factor for present invention product embodiments. Typical embodiments of the invention have a single mode distribution of the water-clustered particle sizes of particle sizes for the water cluster size encapsulating the non-$H_2O$ substance. The term non-$H_2O$ substance simply is used to mean a substance other than water.

Preferred embodiments of the present invention comprise computer-controlled manufacturing processes for making nanowater CBD drinks for treating inflammation, hastening recovery from addiction, and alleviating anxiety in a human or animal and needing a single, repeated, or continuous dosing of that pharmaceutical by a route of administration. It is prophetically depicted by the dashed line 1901 in FIG. 19, that some embodiments of the invention will provide a superior 80 mg CBD oral formulation drug blood level 1901 compared to the drug blood level 1902 of a prior art 80 mg CBD oral table of Hurd (2015). The drug blood level over time following drug administration is subjected to pharmacokinetic descriptor terms. Tmax is a term meaning the time to maximum blood level of a drug following the drug administration to the person. Cmax is a term meaning the maximum drug blood level achieved in the patient after one or more drug administrations to the person. AUC is a term meaning the area calculated under the drug blood level curve versus time in a graph such as the one depicted in FIG. 19. T½ elimination is a term meaning the half-time for drug elimination measured beginning in some cases from peak drug level as the drug is eliminated from the blood by person in various ways. s of its pharmacokinetics and net bioavailabily. Invention embodiments which are liquid formulations of nanosized water clusters of drugs or non-$H_2O$ substances made using ultrapure water (UPW) are expected to have a lower Tmax, higher Cmax, larger AUC, and perhaps a longer T½. This is illustrated in FIG. 19 where curve 1901 reflects the lower Tmax, higher Cmax, larger AUC, and longer T½ elimination than curve 1902 for the prior art 80 mg CBD oral table of Hurd (2015).

Preferred embodiments of the present invention comprise computer controlled manufacturing processes for making nanowater hypotonic mineral drinks for a human or an animal needing rapid hydration for routine exercise or for rapidly reversing their dehydration.

Preferred embodiments of the present invention comprise computer controlled manufacturing processes for making nanowater PNC-27 aqueous pharmaceutical formulations for treating a human or an animal at risk of or suffering a cancer and needing a single, repeated, or continuous dosing of that pharmaceutical by a route of administration.

Preferred embodiments of the present invention comprise computer controlled manufacturing processes for making improved bioavailability nanowater formulations of approved pharmaceutical for treating a medical condition of a human or an animal needing a single, repeated, or continuous dosing of that pharmaceutical by a route of administration.

Preferred embodiments of the present invention comprise computer controlled manufacturing processes for making nanowater-based, improved-bioavailability compositions for growing vineyard grapes, crops, trees, fruits, grains, fruit, and grasses on land and also hydroponically, as well as for improving farm chicken and beef production, as well as for improving fish farming of depleted stocks of ocean fish, and as well improving crustacean and mollusk farming.

Preferred composition embodiments of the invention are nanosized to have non-$H_2O$ substances encapsulated by water clusters which have a less than 150 nanometer median size, more preferably less than 100 nanometer median size, most preferably a less than 50 nanometer size.

FIG. 10 presents a highly schematic depiction of a relatively large clustering 1001 of hydrogen-bonded water molecules covering a CBD particle 1002 so that the large water clustered CBD particle has a diameter depicted as 1003. This example names CBD as the non-$H_2O$ core particle but any non-$H_2O$ substance which is clustered by water can be nanosized by using present invention embodiment processes and apparatus. FIG. 10 process arrow 1004 is intended to symbolize a present invention process and apparatus as taught by the Specification here. FIG. 12 depicts a relatively simple process and apparatus for nanosizing water clustered non-$H_2O$ particles 1001. FIG. 12 process and apparatus comprise blending a concentrate of the large water clustered non-$H_2O$ substance 1001 with a quantity of ultrapure water (UPW) using a recirculation tank 1206 process for slowly mixing the large non-$H_2O$ particles 1001 in UPW to create a mixture; and nanosizing the mixture of the large water clustered non-$H_2O$ particles 1001 in the UPW water by passing the mixture of the large non-$H_2O$ particles 1001 in UPW through a single hollow cylinder device 1218. The FIG. 12 process apparatus is poorly regulated in terms of its process stream flow and pressure through the hollow cylinder 1218 and this can interfere with the effectiveness of the hollow cylinder 1218 nanosizing process. Compare FIG. 15 and FIG. 16 where the particle size reduction was significant and the particles had single mode particle size distributions based on Malvern Zetasizer DLS instrument measurements of process stream sample A before hollow cylinder and process stream sample B after hollow cylinder 1218. FIG. 15 Malvern report for Sample A indicate it had a median particle size of 358 nanometers. FIG. 16 Malvern report for Sample B indicate it had a median particle size of 8 nanometers which represents a surprisingly large (45-fold) reduction in the particle size. This indicates the therapeutic substance(s) particles may have a very thick layer of water clusters around the therapeutic particles that was removed by the process of the hollow cylinder device. Clumping of the therapeutic substance may also have been present that was reduced by the nanosizing process of the invention. Depicted in FIG. 22 is another invention process and apparatus which comprises blending a concentrate of the large water clustered non-$H_2O$ substance 1001 with a quantity of ultrapure water (UPW) using a rapid flow one-pass static blending pipe 1228 to create an instant mixture of the large water clustered non-$H_2O$ particles 1001 in the ultrapure water; and nanosizing particles 1001 without a delay by pumping the instant mixture through two hollow cylinders devices 1218 and 2222 arranged in series. Computerized Malvern Instruments Direct Laser Scanning (DLS) technology was used to quantify the nanosizing effectiveness of the FIG. 22 process and apparatus.

FIG. 21 and FIG. 23 depict additional example process and apparatus embodiments of the present invention for nanosizing a quantity of large water clustered non-$H_2O$ particles. The process and apparatus of FIG. 21 uses two hollow cylinder devices 1218 and 2122 instead of one hollow cylinder device 1218 but otherwise is the same process and apparatus depicted in FIG. 12. Depicted in FIG. 23 is another invention process and apparatus which comprises blending a concentrate of the large water clustered non-$H_2O$ substance particles 1001 in the ultrapure water (UPW) or another purified water using a rapid flow one-pass static blending pipe 1228 to create an instant mixture of the particles 1001 in the purified water; pumping the instant mixture for further blending in a blending tank 2330; and nanosizing the aqueous particles 1001 which comprises a thickness of clustering hydrogen-bonded water molecules 1008 covering a non-$H_2O$ substance 1002 by pumping the instant mixture through two hollow cylinder devices 1218 and 2322 arranged in series.

In some embodiments, the present invention is a process wherein more specifically the reduced size water clusters containing a soluble non-$H_2O$ substance in the aqueous medium may have a median water cluster size selected from the group consisting of between about 2 to 10 nanometers, about 10 to 25 nanometers, about 25 to 40 nanometers, about 40 to 60 nano-meters, about 60 to 100 nanometers, about 3 to 300 nanometers, and a combination thereof.

In some embodiments, the present invention is a process wherein more specifically the reduced size water clusters containing an insoluble non-$H_2O$ substance in the aqueous medium may have a median water cluster size selected from the group consisting of about 25 to 50 nanometers, about 50 to 75 nanometers, about 75 to 100 nanometers, about 100 to 150 nanometers, about 150 to 200 nanometers, and a combination thereof.

It is contemplated that some product embodiments of the present invention comprise an aqueous composition comprising a number of gallons of UPW and a weight amount of an chemical compound per gallon of the UPW, wherein the weight amount of the chemical compound is selected from the group consisting of between about 10 micrograms to 50 micrograms, about 50 micrograms to 100 micrograms, about 100 micrograms to 200 micrograms, about 200 micrograms to 400 micrograms, about 400 micrograms to 800 micrograms, about 800 micrograms to 1.6 milligrams, about 1.6 milligrams to 3.2 milligrams, about 3.2 milligrams to 6.4 milligrams, about 6.4 milligrams to 30 milligrams, 30 milligrams to 60 milligrams, about 60 milligrams to 120 milligrams, about 120 milligrams to 240 milligrams, 240 milligrams to 480 milligrams, about 480 milligrams to 1 gram, about 1 gram to 2 grams, about 2 grams to 4 grams, about 4 grams to 8 grams, about 8 grams to 16 grams, about 16 grams to 30 grams, about 30 grams to 60 grams, about 60 grams to 120 grams, about 120 grams to 250 grams, about 250 grams to 500 grams, about 500 grams to 1000 grams, and a combination thereof.

For some invention embodiments the term chemical compound includes a substance which can be selected from the group consisting of a of a salt, an acid, a base, a non-ionizable salt, a soluble salt, a partially-soluble salt, a sugar, a fat, an organic liquid, an organic solvent, an organic solid, a pharmaceutical excipient, an amino acid, an organic acid, an organic base, an alcohol, a ketone, an aldehyde, a carboxylic acid, an ether, an amine, an amide, an ester, an alkyl halide, an aromatic compound, a cyclic compound, a heterocyclic compound, a polypeptide, an oligosaccharide, a carbohydrate, an oxide, a peroxide, a carbonyl, an alkene, an alkyne, a lipid, an enzyme, a protein, a nucleic acid, a combination of a cation(s) and an anion(s) so that the combination is electrically neutral, a hydrocarbon, an oil, a wax, a starch, a chelator, a pH buffer, a reducing agent, an oxidizing agent, a surfactant, a catalyst, and an inorganic chemical nanoparticle, and any combination thereof.

Some product embodiments of the present invention comprise an aqueous composition comprising an aqueous medium with cations and with anions, wherein the cation is selected from the group consisting of aluminum ion, ammonium ion, antimony ion, barium ion, bismuth ion, boron ion, calcium ion, cerium ion, cesium cation, chromium ion, cobalt ion, copper ion, dysprosium ion, erbium ion, europium ion, gadolinium ion, gallium ion, germanium ion, gold ion, hafnium ion, holmium ion, indium ion, iridium ion, iron ion, lanthanum ion, lithium ion, lutetium ion, magnesium ion, manganese ion, molybdenum ion, neodymium ion, nickel ion, niobium ion, osmium ion, palladium ion, phosphorus ion, platinum ion, potassium ion, praseodymium ion, rhenium ion, rhodium ion, rubidium ion, ruthenium ion, samarium ion, scandium ion, selenium ion, silicon ion, silver ion, sodium ion, strontium ion, sulfate ion, tantalum ion, tellurium ion, terbium ion, thulium ion, tin ion, titanium ion, tungsten ion, vanadium ion, ytterbium ion, yttrium ion, zinc ion, zirconium ion, and a combination of thereof, and wherein the anion is selected from the group consisting of a bromide, a chloride, a fluoride, an iodide, a nitrate, a nitrite, a sulfate, a sulfite, a phosphate, a hydrogen phosphate, a dihydrogen phosphate, a Good's buffer anion, a carbonate, a bicarbonate, an EDTA anion, a citrate, a carboxylic acid anion, an inorganic anion, an organic anion, and a combination thereof.

Some embodiments of the invention are processes of manufacturing for producing a product or an intermediate product and there is a process step with a flow rate which can be selected. For the invention embodiment process depicted in FIG. 12, the flow rate in gallons per minute of the blended aqueous formulation 1213 through a transfer pipe 1217 and through a hollow cylinder 1218 can have a controlled flow rate in gallons per minute optionally selected from the group consisting of about consisting of about 5 to 6, about 6 to 7, about 7 to 8, about 8 to 9, about 9 to 10, about 10 to 11, about 11 to 12, about 12 to 13, about 13 to 14, about 14 to 15, about 15 to 16, about 16 to 17, about 17 to 18, about 18 to 19, about 19 to 20, about 20 to 21, about 21 to 22, about 22 to 23, about 23 to 24, about 24, to 25, about 1 to 30, about 1 to 40, about 1 to 50, and any combination thereof.

FIG. 12, FIG. 21, FIG. 22, and FIG. 23 all depict various processes and various apparatuses of the invention which include a storage tank 1206 containing UPW (ultra-purified water) 1207. Some alternative embodiments of the invention are processes of manufacturing which are not using a ultra-purified water (UPW) storage tank 1206 for storing UPW 1207 during the process of manufacturing, but instead, the process of manufacturing is receiving UPW 1207 directly from a source of UPW as soon as the UPW is made by the source.

For the invention embodiment process depicted in FIG. 21, the flow of the blended aqueous formulation 1213 through the transfer pipe 1217 enters top 1219 of first hollow cylinder 1218 and exits from the first hollow cylinder 1218, through the exit pipe 2121 as a nanosized intermediate product 2120 flows through a second hollow cylinder 2122 and exits the second hollow cylinder 2122 as a more completely nanosized product 2124 via pipe 2123. The process stream flowing through the first hollow cylinder 1218 and then through the second hollow cylinder 2122 is a controlled flow rate in gallons per minute selected from the group consisting of about 0.5 to about 5, about 5 to 5.5, about 5.5 to 6, about 6 to 6.5, about 6.5 to 7, about 7 to 7.5, about 7.5 to 8, about 8 to 8.5, about 8.5 to 9, about 9 to 9.5, about 9.5 to 10, about 10 to 10.5, about 10.5 to 11, about 11 to 11.5, about 11.5 to 12, about 12 to 12.5, about 12.5 to 13, about 13 to 13.5, about 13.5 to 14, about 14 to 14.5, about 14.5 to 15, about 15 to 15.5, about 15.5 to 16, about 16.5 to 17, about 17 to 17.5, about 17.5 to 18, about 18 to 18.5, about 18.5 to 19, about 19 to 19.5, about 19.5 to 20, about 20 to 20.5, about 20.5 to 21, about 21 to 21.5, about 21.5 to 22, about 22 to 22.5, about 22.5 to 23, about 23 to 23.5, about 23.5 to 24, about 24 to 24.5, about 24.5 to 25, about 25 to 30, about 30 to 35, about 35 to 40, about 40 to 45, about 45 to 50, about 50 to 60, about 60 to 70, about 70 to 80, about 80 to 90, about 90 to 100, about 100 to 150, about 150 to 300, and any combination thereof.

For the invention embodiment process depicted in FIG. 22, there is a pump 1216 pumping to move ultrapure water 1207 from UPW tank 1206 through the transfer pipe 1217 to junction 2225 of transfer pipe 1217 and transfer pipe 1200. There is a pump 1212 pumping concentrate 1205 through transfer pipe 1200 to junction 2225. The mixture of UPW 1207 and concentrate 1205 occurring at junction 2225 then flows through pipe 2227. The flowing mixture is then blended in static blending pipe 1228, and then flows as blended flowing mixture 2215 through the transfer pipe 2229, and into the top 1219 of first hollow cylinder 1218, and then flows out as a nanosized intermediate product 1220 through the exit pipe 2221 and next the nanosized intermediate product 1220 flows via transfer pipe 2221 into top 2229 of the second hollow cylinder 2222 and exits the second hollow cylinder 2222 as a more completely nanosized product 2230 via pipe 2223. The process stream flowing through the first hollow cylinder 1218 and then through the second hollow cylinder 2222 has a controlled flow rate in gallons per minute which is selected from the group consisting of about 0.5 to about 5, about 5 to 5.5, about 5.5 to 6, about 6 to 6.5, about 6.5 to 7, about 7 to 7.5, about 7.5 to 8, about 8 to 8.5, about 8.5 to 9, about 9 to 9.5, about 9.5 to 10, about 10 to 10.5, about 10.5 to 11, about 11 to 11.5, about 11.5 to 12, about 12 to 12.5, about 12.5 to 13, about 13 to 13.5, about 13.5 to 14, about 14 to 14.5, about 14.5 to 15, about 15 to 15.5, about 15.5 to 16, about 16.5 to 17, about 17 to 17.5, about 17.5 to 18, about 18 to 18.5, about 18.5 to 19, about 19 to 19.5, about 19.5 to 20, about 20 to 20.5, about 20.5 to 21, about 21 to 21.5, about 21.5 to 22, about 22 to 22.5, about 22.5 to 23, about 23 to 23.5, about 23.5 to 24, about 24 to 24.5, about 24.5 to 25, about 25 to 30, about 30 to 35, about 35 to 40, about 40 to 45, about 45 to 50, about 50 to 60, about 60 to 70, about 70 to 80, about 80 to 90, about 90 to 100, about 100 to 150, about 150 to 300 and any combination thereof.

For the invention embodiment process depicted in FIG. 23, there is a pump 1216 pumping to move ultrapure water 1207 from UPW tank 1206 through the transfer pipe 1217 to junction 2325 of transfer pipe 1217 and transfer pipe 1200. There is a pump 1212 pumping concentrate 1205 through transfer pipe 1200 to junction 2325. The mixture of UPW 1207 and concentrate 1205 occurring at junction 2325 then flows through pipe 2327 where it flows to the then blended in static blending pipe 1228, and then flows through the transfer pipe 2315 into blending tank 2330 from which pump 2331 pumps the blend via pipe 2332 and then pipe 2333 into the first hollow cylinder 1218, and then flows out as a nanosized intermediate product through the exit pipe 2326 and then the nanosized intermediate product flows via transfer pipe 2326 and pipe 1221 into top 1229 of second hollow cylinder 2322 and the twice-nanosized intermediate product exits the second hollow cylinder 2322 as a significantly smaller nanosized product 2350 via pipe 2340.

The process stream flowing through the first hollow cylinder 1218 and then through the second hollow cylinder 2322 has a controlled flow rate in gallons per minute optionally selected from the group consisting of about 0.5 to about 5, about 5 to 5.5, about 5.5 to 6, about 6 to 6.5, about 6.5 to 7, about 7 to 7.5, about 7.5 to 8, about 8 to 8.5, about 8.5 to 9, about 9 to 9.5, about 9.5 to 10, about 10 to 10.5, about 10.5 to 11, about 11 to 11.5, about 11.5 to 12, about 12 to 12.5, about 12.5 to 13, about 13 to 13.5, about 13.5 to 14, about 14 to 14.5, about 14.5 to 15, about 15 to 15.5, about 15.5 to 16, about 16.5 to 17, about 17 to 17.5, about 17.5 to 18, about 18 to 18.5, about 18.5 to 19, about 19 to 19.5, about 19.5 to 20, about 20 to 20.5, about 20.5 to 21, about 21 to 21.5, about 21.5 to 22, about 22 to 22.5, about 22.5 to 23, about 23 to 23.5, about 23.5 to 24, about 24 to 24.5, about 24.5 to 25, about 25 to 30, about 30 to 35, about 35 to 40, about 40 to 45, about 45 to 50, about 50 to 60, about 60 to 70, about 70 to 80, about 80 to 90, about 90 to 100, about 100 to 150, about 150 to 300, and any combination thereof.

The selected flow rate per minute is a multiple of the volume of the hollow cylinder cavity 1424 which depicted in cross-section in FIG. 14. The multiple of flow rate per minute over volume of hollow cylinder volume is a multiple selected from the group consisting of about 1 to 2, about 2 to 3, about 3 to 4, about 4 to 5, about 5 to 6, about 6 to 7, about 7 to 8, about 8 to 9, about 9 to 10, about 10 to 11, about 11 to 12, about 12 to 13, about 13 to 14, about 14 to 15, about 15 to 16, about 16 to 17, about 17 to 18, about 18 to 19, about 19 to 20, about 20 to 21, about 21 to 22, about 22 to 23, about 23 to 24, about 24 to 25, about 25 to 26, about 26 to 27, about 27 to 28, about 28 to 29, about 29 to 30.

Some preferred embodiments of the present invention are processes, wherein the apparatus of the process is using one hollow cylinder 1218 or is using a plurality of hollow cylinders, wherein the number of hollow cylinders in use in the process is selected from the group consisting of 1, 2, 3, 4, 5, 6, 7, 8, 9, 10, 11, 12, 13, 14, 15, 16, 17, 18, 19, and 20.

Note that FIGS. 21, 22, and 23 depict invention apparatus embodiments with two hollow cylinders. A preferred number of hollow cylinders is 2, 3, or 4 hollow cylinders of the kind depicted in FIG. 13 and FIG. 14 as used in process apparatus depicted in FIG. 22.

In some embodiments, the present invention is a process, wherein the apparatus of the process has a hollow cylinder with an inner width 1429. The hollow cylinder 1218 is depicted in cross-section A in FIG. 14 with the location of cross-section A indicated in a longitudinal depiction of hollow cylinder 1218 in FIG. 13. The inner width 1429 in inches may be selected from the group consisting of between about 1 to 2 inches, about 2 to 3 inches, about 3 to 4 inches, about 4 to 5 inches, about 5 to 6 inches, about 6 to 7 inches, about 7 to 8 inches, about 8 to 9 inches, about 9 to 10 inches, about 10 to 11 inches, about 11 to 12 inches, about 12 to 13 inches, about 13 to 14 inches, about 14 to 15 inches, about 15 to 16 inches, about 16 to 17 inches, about 17 to 18 inches, about 18 to 19 inches, about 19 to 20 inches, and a combination thereof.

In some embodiments, the present invention is a process, wherein the apparatus of the process has a hollow cylinder (s). See FIGS. 12, 21, 22, and 23 for examples of hollow cylinders. The inner length 1228 is depicted in FIG. 13. Inner length 1228 of a hollow cylinder may be selected from the group consisting of between about 2 to 4 inches, about 4 to 6 inches, about 6 to 8 inches, about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, about 26 to 28 inches, about 28 to 30 inches, about 32 to 34 inches, about 34 to 36 inches, about 36 to 38 inches, about 38 to 40 inches, about 40 to 42 inches, about 42 to 44 inches, about 44 to 46 inches, about 46 to 48 inches, about 48 to 50, about 50 to 52, about 52 to 54, about 54 to 56, about 56 to 58, about 58 to 60, about 60 to 62, about 62 to 64, about 64 to 66, about 66 to 68, about 68 to 70, about 70 to 72, about 72 to 74, about 74 to 76, about 76 to 78, about 78 to 80 and a combination thereof.

In some embodiments, the present invention is a process, wherein the apparatus of the process has a ratio of the inches of nozzle outer (width) diameter 1430 (see FIG. 14) to the inches of the hollow cylinder inner width 1429 (see FIG. 14.) which may be selected from the group consisting of about a ratio of 1:1.15 to about 1:1.25, a ratio of 1:1.25 to about 1:1.33, a ratio of about 1:1.33 to about 1:1.50, a ratio of about 1:1.50 to about 1:1.75, a ratio of about 1:1.75 to about 1:2.0, a ratio of about 1:2.0 to about 1:2.35, a ratio of about 1:2.35 to about 1:2.70, a ratio of about 1:2.70 to about 1:3.0, a ratio of about 1:3.0 to about 1:3.40, a ratio of about 1:3.40 to about 1:3.70, a ratio of about 1:3.70 to about 1:4.0, a ratio of about 1:4.0 to about 1:4.30, a ratio of about 1:4.30 to about 1:4.60, a ratio of about 1:4.60 to about 1:4.80, a ratio of about 1:4.80 to about 1:5.10, a ratio of about 1:5.10 to about 1:5.50, a ratio of about 1:5.50 to about 1:5.90, a ratio of about 1.5.90 to about 1:6.50, a ratio of about 1:6.50 to about 1:7.50, and about a ratio of 1:7.50 to about 1:12.0, and a combination thereof.

In some embodiments, the present invention is a process, wherein the apparatus of the process has a nozzle 1422. See cross-section of nozzle 1422 in FIG. 14. The nozzle 1422 may have the one or a plurality of jet openings 1423 selected from the group consisting of 1, 2, 3, 4, 5, 6, 7, 8, 9, 10, 11, 12, 13, 14, 15, 16, 17, 18, 19, and any combination thereof. Preferred embodiments of the invention are an apparatus which has two or more hollow cylinders with each of the hollow cylinders having a nozzle 1422 with four (4) jet openings 1423 on the nozzle 1422. FIG. 14 depicts a longitudinal depiction of the example hollow cylinder 1218 with four jet openings 1423. Note in FIG. 13 that the nozzle is numbered 1222 and the jet openings are numbered 1223. FIG. 13 suggests one flow pattern for the blended aqueous formulation exit6ing jet openings 1223 by the spiral dashed line.

In some embodiments, the present invention is a process, wherein the apparatus of the process has a one or more hollow cylinders with each of the cylinders having one or more nozzles 1422 wherein for each nozzle 1422 the ratio of the sum total area of jet openings 1423 on nozzle 1422 outer side to the area of nozzle inner diameter 1450 is a ratio that can be selected from the group consisting of the ratio of about 0.01 to 0.05, a ratio of about 0.05 to 0.10, a ratio of about 0.10 to 0.15, a ratio of about 0.15 to 0.20, a ratio of about 0.20 to 0.25, a ratio of about 0.25 to 0.30, a ratio of about 0.30 to 0.35, a ratio of about 0.35 to 0.40, a ratio of about 0.40 to 0.45, a ratio of about 0.45 to 0.50, a ratio of about 0.50 to 0.55, a ratio of about 0.55 to 0.60, a ratio of about 0.60 to 0.65, a ratio of about 0.65 to 0.70, a ratio of about 0.70 to 0.75, a ratio of about 0.75 to 0.80, a ratio of about 0.80 to 0.85, a ratio of about 0.85 to 0.90, a ratio of about 0.90-1.0, a ratio of about 1.0 to 1.2, a ratio of about 1.2 to 1.5, a ratio of about 1.5 to 1.7, and a combination thereof.

In some embodiments, the present invention is a process, wherein the apparatus of the process has one or more hollow cylinders with one or more nozzles 1422, wherein each nozzle has jet openings 1423. FIG. 14 depicts schematically a view of "Cross Section A—Hollow Cylinder 1218" from a vantage point of looking down from hollow cylinder 1218 top 1219 (See FIG. 13) towards hollow cylinder bottom 1233, As depicted schematically in FIG. 14, each nozzle 1422 has at least one jet opening 1423 with a jet bore hole 1427. In some embodiments a nozzle has a plurality of jet openings 1423 each with a jet bore hole 1427. See FIG. 14 the depicted example hollow cylinder 1218 with four jet openings 1423. Four jet openings 1423 per nozzle are a preferred embodiment. In some embodiments, the present invention is a process using an apparatus wherein each of the one or more hollow cylinders has one or more nozzles 1422 with each nozzle 1422 having one or more jet hole openings, wherein the number of nozzles in each hollow cylinder selected from the group consisting of 1, 2, 3, 4, 5, 6, 7, 8, 9, 10, 11, 12, 13, 14, 15, 16, 17, 18, 19, and any combination thereof.

When viewed from a vantage point radially out from the nozzle surface a jet opening 1423, the jet nozzle appears to have an opening which is a shape between a round and an oval shape. The nozzle 1222 jet opening 1223 is oval in FIG. 13. Also when viewed from the vantage point at a distance radially out from a single jet opening 1423, the jet opening 1423 is "normal to" (at 90 degrees) the nozzle outer surface. Drawn in FIG. 14, is a short straight line pointer arrow (headless) which is "normal to" nozzle 1422 outer surface and which points to each of the four jet openings in FIG. 14. In FIG. 14, each jet bore hole 1427 exits the outer surface of nozzle 1422 at an angle 1428 relative to the normal angle of outer nozzle 1422 surface. Note arc angle 1428 drawn in FIG. 14. For the hollow cylinder embodiments of the present invention, the arc angle 1428 is selected from the group consisting of 0, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, and 90 degrees. In FIG. 14, the arc angle 1428 is depicted as deflecting the direction of the jet nozzle outflow in a counterclockwise direction. However it is imagined that any hollow cylinder of the present invention may have the arc angle deflecting the jet nozzle outflow either clockwise or counterclockwise. Keeping in mind that FIG. 14 depicts schematically a view of a "Cross Section A of a Hollow Cylinder 1218" from the vantage point of looking down from hollow cylinder from its top 1219 towards hollow cylinder bottom 1233. The top 1219 and bottom 1233 details of the hollow cylinder 1218 are also schematically depicted in FIG. 13. In FIG. 14, the arc angle 1428 is depicted as going counterclockwise. In FIG. 13, looking down from nozzle 1222 to hollow cylinder bottom 1233 process stream flow pattern suggested by the dotted spiral line is running from the jet openings 1223 in a counterclockwise direction. However any hollow cylinder of the present invention may have an arch angle as running either clockwise or counterclockwise.

In some embodiments, the present invention is a process for nano-sizing water cluster sizes in an aqueous composition containing a non-$H_2O$ substance in order to improve bioavailability of the aqueous composition, the process comprising the steps of: choosing an amount of a non-$H_2O$ substance to be added to a large volume of ultrapure water; blending all of the non-$H_2O$ substance in a small volume of the ultrapure water to make a small volume concentrate of the non-$H_2O$ substance in the ultrapure water, wherein the small volume concentrate of the non-$H_2O$ substance which is blended with the ultrapure water is a percent of the large volume of the ultrapure wherein percent is selected from the group consisting of a 0.01 to 0.05 percent, a 0.05 to 0.1 percentage, a 0.1 to 0.2 percentage, a 0.2 to 0.3 percent, a 0.3 to 0.4 percent, a 0.4 to 0.5 percent, a 0.5 to 0.6 percent, a 0.6 to 0.7 percent, a 0.7 to 0.8 percent, a 0.8 to 0.9 percent, a 0.9 to 1.0 percent, a 1.0 to 2.0 percent, a 2.0 to 3.0 percent, a 3.0 to 4.0 percent, a 4.0 to 5.0 percent, a 5.0 to 10.0 percent, a 10.0 to 20.0 percent, and a combination thereof;

filtering optionally, the small volume concentrate of the non-$H_2O$ substance in the ultrapure water using a clean filter to remove micron-sized particulates from the small volume concentrate, wherein the minimum particle sizes removed by an inline process filter may be selected from the group consisting of about 0.1 to 1 micron, 1 to 2 microns, 2.5 microns, 3 microns, 4 to 7 microns, 6 microns, 8-10 microns, 11 microns, and 12-25 microns, and a combination thereof;

recirculating the large volume of the ultrapure water in a mixing tank and slowly adding the small volume concentrate of the non-$H_2O$ substance in the ultrapure water to the mixing tank to form a blended aqueous formulation containing the non-$H_2O$ substance in an aqueous medium;

wherein the large volume amount of the ultrapure water may be selected from the group consisting of about 10 to 20 gallons, about 20 to 50 gallons, about 50 to 100 gallons, about 100-300 gallons, about 300 to 600 gallons, about 600 gallons to about 1000 gallons, about 1000 gallons to about 2500 gallons, and a combination thereof, and wherein the adding of the small volume concentrate volume of the non-$H_2O$ substance in the ultrapure water to the mixing tank to form a blended aqueous formulation containing the non-$H_2O$ substance in the aqueous medium may be accomplished over a time period selected from the group consisting of about 1 to 5 minutes, about 5 to 10 minutes, about 10 to 15 minutes, about 15 to 20 minutes, about 20 to 25 minutes, about 25 to 30 minutes, about 30 to 35 minutes, about 35 to 40 minutes, and a combination thereof;

pumping the blended aqueous formulation at a selected flow rate from the mixing tank to a nozzle with a jet opening inside a hollow cylinder;

using the jet opening in the nozzle to jet the blended aqueous formulation at a higher flow rate into the hollow cylinder;

using the higher flow rate of the blended aqueous formulation from the jet opening inside the hollow cylinder for nanosizing the water clusters in the blended aqueous formulation of the non-$H_2O$ substance in the ultrapure water;

removing the aqueous composition with the nanosized water clusters containing the non-$H_2O$ substance at the selected flow rate from inside the hollow cylinder; and using the nanosized water clusters containing the non-$H_2O$ substance in the aqueous medium to improve the bioavailability of the aqueous composition.

A particularly preferred apparatus for manufacturing product embodiments of the present invention comprises a computer controlled apparatus for manufacturing product embodiments, comprising:

using process stream sensors situated in the apparatus for measuring process stream flow rates, process stream pressure, initial process stream chlorine ppm, and process stream meg-ohm resistivity;

sending sensor information from the process stream sensors to the computer processor; using the computer processor to compare the sensor information received from the sensors in the process streams to selected process stream parameters using the computer processor to identify if any of the process stream sensor measurements deviates significantly from the selected process stream parameters;

using the computer processor to sends commands to the apparatus manufacturing control pints to make adjustments in process stream parameters to control the manufacturing of the product embodiments by the apparatus.

In some embodiments, the present invention as depicted in FIG. 25, uses an eight step sensor controlled process for preparing an ultrapure water comprising the steps of: treating a water supply with a charcoal to make a charcoal purified water supply; testing a chlorine level in the charcoal purified water supply and discarding any charcoal purified water having a water chlorine level above about one part per million; measuring the water flow rate, water pressure, and water resistivity in the charcoal purified water and controlling the water flow rate to between about 14 to about 17 gallons per minute and maintaining water pressure between about 45 to about 55 psi using sensors;

performing reverse osmosis process on the charcoal purified water for osmotically removing ions and molecules from the charcoal purified water and for making a reverse osmosis purified water having a water resistivity between about 14 to about 19 megohms;

adjusting the water exiting from the reverse osmosis to have a flow rate of about 14.5 gallons per minute at a water pressure of about 23.5 psi;

performing an electro-deionizing process on the reverse osmosis purified water to remove ions so as to produce an ultrapure water having a water resistivity of between about 17 to about 19 meg-ohm cm;

performing optionally a step for purifying the ultrapurified water further using a mixed bed of resin beads for performing molecular sieve chromatography to remove any large remaining non-$H_2O$ molecules;

irradiating the ultrapure water with ultraviolet light to make a sterilized ultrapure water; and storing the sterilized ultrapure water in a stainless steel container.

In some embodiments, the present invention is a process, wherein more specifically the non-$H_2O$ substance comprises a ionizable salt, wherein the amount of the ionizable salt added per gallon of the ultrapure water may be selected from the group consisting of between about 20 micrograms to 100 micrograms, about 100 micrograms to 500 micrograms, about 500 micrograms to 2.5 milligrams, about 2.5 milligrams to 5 milligrams, about 5 milligrams to 10 milligrams, wherein the ionizable salt is comprised of ions selected from the group consisting of boron ion, bromide ion, calcium ion, cerium ion, cesium cation, chloride ion, chromium ion, cobalt ion, copper ion, fluoride ion, gold ion, indium ion, iodine ion, iridium ion, iron ion, lanthanum ion, lithium ion, lutetium ion, magnesium ion, manganese ion, molybdenum ion, neodymium ion, niobium ion, osmium ion, palladium ion, phosphorus ion, platinum ion, potassium ion, rhenium ion, rhodium ion, rubidium ion, ruthenium ion, scandium ion, selenium ion, silicon ion, silver ion, sodium ion, strontium ion, sulfate ion, tantalum ion, tin ion, titanium ion, tungsten ion, vanadium ion, zinc ion, zirconium ion, and a combination of thereof.

In some embodiments, the present invention is a process, wherein more specifically the non-$H_2O$ substance comprises a ionizable salt, wherein the amount of the ionizable salt added per gallon of the ultrapure water may be selected from the group consisting of between about 20 micrograms to 100 micrograms, about 100 micrograms to 500 micrograms, about 500 micrograms to 2.5 milligrams, about 2.5 milligrams to 5 milligrams, about 5 milligrams to 10 milligrams, wherein the ionizable salt is comprised of ions selected from the group consisting of boron ion, bromide ion, calcium ion, cerium ion, cesium cation, chloride ion, chromium ion, cobalt ion, copper ion, fluoride ion, gold ion, indium ion, iodine ion, iridium ion, iron ion, lanthanum ion, lithium ion, lutetium ion, magnesium ion, manganese ion, molybdenum ion, neodymium ion, niobium ion, osmium ion, palladium ion, phosphorus ion, platinum ion, potassium ion, rhenium ion, rhodium ion, rubidium ion, ruthenium ion, scandium ion, selenium ion, silicon ion, silver ion, sodium ion, strontium ion, sulfate ion, tantalum ion, tin ion, titanium ion, tungsten ion, vanadium ion, zinc ion, zirconium ion, and a combination of thereof.

In some embodiments, the present invention is a process, wherein more specifically the hollow cylinder 1218 has an inner width 1429 (see FIG. 14) in inches which may be selected from the group consisting of between about 3 to 4 inches, about 4 to 5 inches, about 5 to 6 inches, about 6 to 7 inches, about 7 to 8 inches, and a combination thereof, and wherein the hollow cylinder has an inner length in inches selected from the group consisting of between about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, and a combination thereof.

In some embodiments, the present invention is a process, wherein more specifically the selected flow rate out from nozzle 1223 (see FIG. 13) a flow rate per minute which is a multiple of the hollow cylinder cavity 1424 volume (see FIGS. 13 and 14), the multiple selected from the group consisting of about 12 to 13, about 13 to 14, about 14 to 15, about 15 to 16, about 16 to 17, about 17 to 18, about 18 to 19, and a combination thereof.

In general, the present invention is a nano sizing process using apparatus embodiments of the present invention for processing an amount of purified water and an amount of a non-$H_2O$ substance for manufacturing nano sized clusters of water surrounding a non-$H_2O$ substance, wherein the nano-sized clusters of water surrounding the non-$H_2O$ substance have a median water cluster size from between about 1 nanometers to about 400 nanometers according to dynamic light scattering (DLS) measurements using a Malvern Zetasizer DLS instrument.

DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 7 also depicts a graph A which plots a hypothetical relatively slow variation 707 in the intensity of scattered laser light reflections patterns. The variations 707 are slow but significant in magnitude over time and consistent with the slower diffusion rates of the large water clustered non-H₂O particle 703. FIG. 7 also depicts a graph B which plots hypothetical rapid variations 708 in the intensity of scattered laser light reflections patterns which would be expected for more rapidly diffusing smaller water clustered non-H₂O particle 704. These diffusion dependent scattered laser light speckle patterns are mathematically processed by Malvern laser processor 706 to determine distributions of particle sizes for the water-clustered particles.

FIG. 8 presents this model using a negative surface charge on a colloid particle 802. The concept of the FIG. 8 diagram is that the negative charge of the colloid particle 802 surface in this model will become electrically neutralized 812 over a radial distance 813 (see graph in lower portion of FIG. 8) away from the particle's negative charge surface 803 due to the charge neutralizing layers of cations 807 which accumulate and are gradually also accompanied by some anions 806, 807 in a second layer. These layers of particle charge neutralizing ions eventually become the bulk ionic medium 800 composition of cations 801 and anions 801. In FIG. 8 the charged particle 802 has a negative charge surface 803 which causes a surface potential 809 and there is a Stern layer 805 of positive counter-ions (cations) 804 and peripheral to the Stern layer is a concentrated mixture of cations 807 and anions 806 which has a finite thickness and then further out from the colloid charged particle is a demarcation point known as the Slipping plane 808. The voltage at the Slipping plane 808 is called the Zeta potential 811. The Zeta potential is an experimentally measurable characteristic of stable colloidal particle dispersions in aqueous media and its value is sensitive to constituents of the medium and its colloidal particle.

In FIG. 9 the ionic medium at the interface of a positively charged surface 905, 903 is a model called the EZ Water Interface Model of a Charged Colloid 902 in Bulk Ionic Medium in which there is a relatively thick layer of "EZ Water" which is an aqueous medium having only anions 906, 907 and 908. This markedly contrasts with the model depicted in FIG. 9 where there is more mixing of anions and cations and the layer of anion and cation mixing appears to be thinner. Notably, within the EZ Water layer, the concentration of anions decreases radially from the charged surface 905. There is then a sudden change at 904 where the EZ Water layer and the bulk ionic medium come into contact. At this contact location 904 the EZ Water Interface Model predicts that the bulk ionic medium is concentrated in cations 909. Further and further out in the bulk ionic medium from interface 904 the concentration of cations decreases as depicted by 909, 910 and 911. The basis for the thickness of the EZ Water layer is hypothesized to be due to the tendency of water molecules to form complex large networks (arrays, clusters, aggregates) of water molecules that can be stabilized in unpredictable ways by various formations of variable strength H-bonds and numbers of H-bonds.

FIG. 10 right side, presents highly schematic views of therapeutic particle 1005 which is a non-H₂O substance 1006 particle of size 1007 with nanosized water clusters 1009 of hydrogen bonded H₂O molecules that have been nanosized by process(s) 1004 to a size 1007 with a nanosized thickness of water clusters 1009 of hydrogen bonded H₂O molecules. CBD particles 1002 and 1006 remain the same size. The smaller sized therapeutic particle 1005 has a higher rate of aqueous diffusion and increased bioavailability relative to the larger sized therapeutic particle 1001.

FIG. 12 depicts the apparatus and process as entirely located within a single clean room 1208. Optionally, the concentrate 1205 is prepared in a separate clean room and then situated near tank 1206 containing the UPW 1207. Step 1107 is illustrated in the FIG. 12 process and begins with the use of pump 1212 to pump the concentrate 1205 slowly over a period of 10 to 30 minutes, into tank 1206 which already is holding about 300 gallons of UPW 1207. For blending the small volume of concentrate 1205 in with the large volume of UPW, the prototype FIG. 12 process is for using a tank recirculation line 1209 with a pump 1210 for taking tank fluid from the bottom of the tank 1206 and returning it back to the top surface of the fluid in the tank 1206. It was surprisingly found that submicron size CBD particles will stick to air bubbles and float in foamy clumps should the aqueous CBD suspension be pumped and allowed to free fall into a tank. This means the tank recirculation pipe 1209 is going to cause CBD floaters in tank 1206 and inventors witnessed this problem until the recirculating aqueous CBD suspension entered the tank from its bottom so it did not free fall into the tank. Note that the top of tank 1206 has an air filter 1211 for filtering out particles that might be entering tank 1206 when air needed to be vented as fluid is drained from this tank during the production process. Step 1108 of FIG. 11 is illustrated in the FIG. 12 process and begins with the pumping of the blended aqueous formulation 1213 by pump 1216 through transfer pipe 1217 into top 1219 of hollow cylinder device 1218, which contains a nozzle with jet openings for producing nanosized clusters of water carrying nanosized non-H$_2$O substance. The single hollow cylinder device 1218 is depicted in FIG. 12 has a cross sectional line A-A which is the location of a "Cross Section A" depiction of hollow cylinder 1218 that is provided in FIG. 14.

FIG. 13 depicts hollow cylinder cavity 1224 where blended aqueous formulation flows against inner surface 1222, hollow cylinder outside wall 1226, and hollow cylinder inner width 1229. Also note FIG. 13 depicts hollow cylinder length 1228, hollow cylinder bottom 1233, and hollow cylinder inner surface 1222.

In FIG. 14, the nozzle 1422 with bore holes 1427, and jet openings 1423 can be manufactured as needed by for example a 3-D printing system and machine or by a molding process. The nozzle material may be comprised of a plastic such as ABS, nylon, another hard plastic, a ceramic, a metal or some other hard material that is non-toxic and substantially not altered when exposed to an aqueous formulation.

It is an important object of the present invention to perform a process step comprising nanosizing clusters of water surrounding a non-$H_2O$ substance in the blended aqueous formulation so as to improve the bioavailability of the clusters of water surrounding a non-$H_2O$ substance in the blended aqueous formulation. It is contemplated that this important object of the present invention can be accomplished when the hollow cylinder 1218 is designed with various cross-sectional shapes. Thus the apparatus depicted in FIG. 14 is but one example of contemplated cross sectional shapes for a hollow cylinder embodiment of the present invention. It is contemplated a cross sectional shape for the hollow cylinder may be selected from the group consisting of an oval, an ellipse, a triangle, a square, a rectangle, a pentagon, a hexagon, a heptagon, an octagon, a polygon with any number of sides between 8 sides to 25 sides, and any combination thereof. The polygon with any number of sides between 8 sides to 25 sides has sides selected from the group consisting of flat sides, curved sides and a combination thereof.

To make compositions comprising high-bioavailability nanosized clusters of water surrounding a non-$H_2O$ substance, there are multiple factors which contribute to accomplishing this goal. The process for making the compositions requires blending an amount of ultrapure water with an amount of a non-$H_2O$ substance. The process requires an apparatus for practicing the invention process. Some example features of an apparatus needed for practicing the invention process are depicted in FIGS. 13 and 14. The hollow cylinder nozzle 1422, bore holes 1427, and jet openings 1423 are apparatus factors important and range of flow rates and pressures for the process stream inside the hollow cylinder 1218 are important process factors. In practicing the present invention, it is contemplated that the chemical and physical properties of the non-$H_2O$ substance (a) may require that special adjustments be made to practicing the invention process step embodiments of the present invention, (b) may alter the chemical and physical quality of composition embodiments of the present invention, and (c) may require that specialized apparatus embodiments of the invention be used. For example, the chemical stability of a non-$H_2O$ substance is an important factor needs to be taken into account known so that the apparatus and the processes of the invention will not destabilize or change the non-$H_2O$ substance during the making of an invention product that is intended to contain the non-$H_2O$ substance in a selected amount. Another example is that the degree of solubility and extent of dissolution of the non-$H_2O$ substance in the final blended aqueous formulation that is to enter the hollow cylinder 1218 have the potential to set a limit on the degree to which the invention processes may nanosize the clusters of water surrounding the nanosized non-$H_2O$ substance unless special measures are taken. For example, an amount of an insoluble non-$H_2O$ substances will be more difficult to nanosize than a water-soluble non-$H_2O$ substance. An as small as possible physical size for an-insoluble non-$H_2O$ substance may be required to make a useful product from a process embodiment of the present invention.

Figure 17:
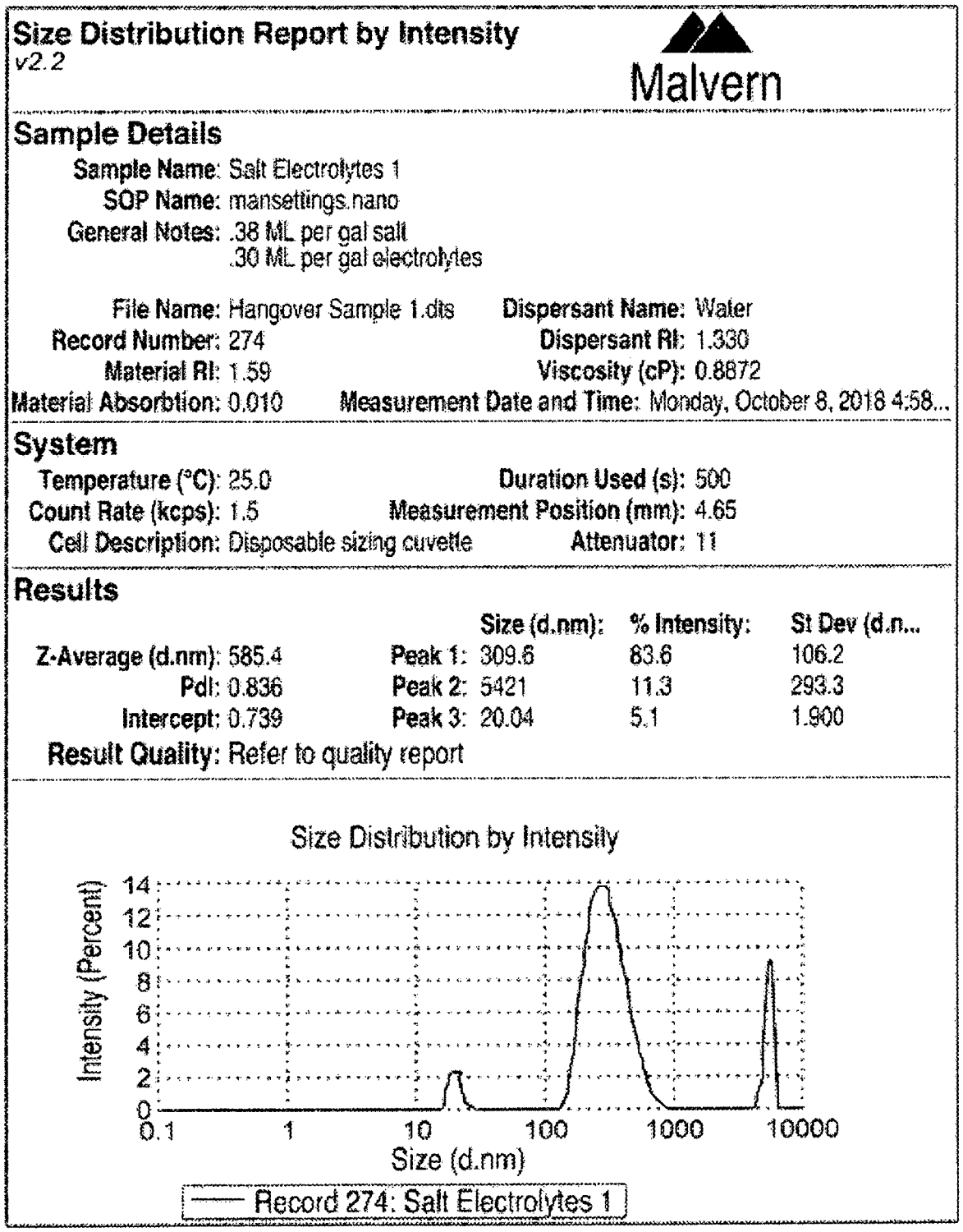
FIG. 17 and FIG. 18 present Malvern Zetasizer DLS instruments data reports "Size Distribution Reported by Intensity" which are measurements of water clustered trace mineral ions sizes in a first sample taken from the flowing blended aqueous formulation 1213 in the transfer pipe 1217 (see FIG. 12 for transfer pipe 1217 location) after the flowing blended aqueous formulation 1213 enters into hollow cylinder device 1218. The hollow cylinder device 1218 process causes a reduction in aqueous particle size measurement on in flowing blended aqueous formulation 1213. Process Apparatus depicted in FIG. 12 is the original-prototype process apparatus embodiment of the present invention. Improved process apparatus are depicted in FIGS. 21, 22, and 23. Michael Raymond Cary is the main inventor behind all of the four process apparatuses of the invention depicted in FIGS. 12, 21, 22, and 23. Karl P. Dresdner, Jr., PhD, MS conceived of chemical formulations and process apparatus parameter embodiments for the hollow cylinder, and the process and composition of the CBD Concentrate preparation used to make Nu Aqua™ hydration drink. Months before the Nu Aqua™ project started, Dr. Dresdner drafted/filed a U.S. Non-Provisional patent application Ser. No. 16/350,259 on Oct. 20, 2018 on behalf of its primary inventor Michael Cary and for other inventors. application Ser. No. 16/350,259 became the first teaching of the process apparatus of FIG. 12. The Oct. 20, 2018 filed application Ser. No. 16/350,259 published on Apr. 23, 2020 as US Published Patent Application No. US2020/0211715 A1. This US Published Patent Application US2020/0211715 is incorporated by reference in its entirety in the present patent application specification. The process apparatus depicted in FIG. 12 is a manually-controlled, prototype system. It taught the inventors that the process stream 1217 needs to enter hollow cylinder device 1218 at certain flow rates and pressures so as to allow the hollow cylinder 1218 to optimally function. Frequent manual adjustments by a human operator "on-hand" are required to operate the FIG. 12 process apparatus during a production run without errors occurring in the processing steps making the ultrapure water or blending steps or nanosizing steps. The operator also watches over other factors such as process stream conductivity to be sure that the conductivity of the process stream is in the proper range. The response of process apparatus of FIG. 12 is slow after manual adjustments are made to the process stream flow rate and pressure. It can take 20 to 60 seconds before process stream flow rate and flow pressure change completely to a new set point. A minute is a significant time delay given a 300 gallon production batch run occurs in 20 minutes.
Figure 18:
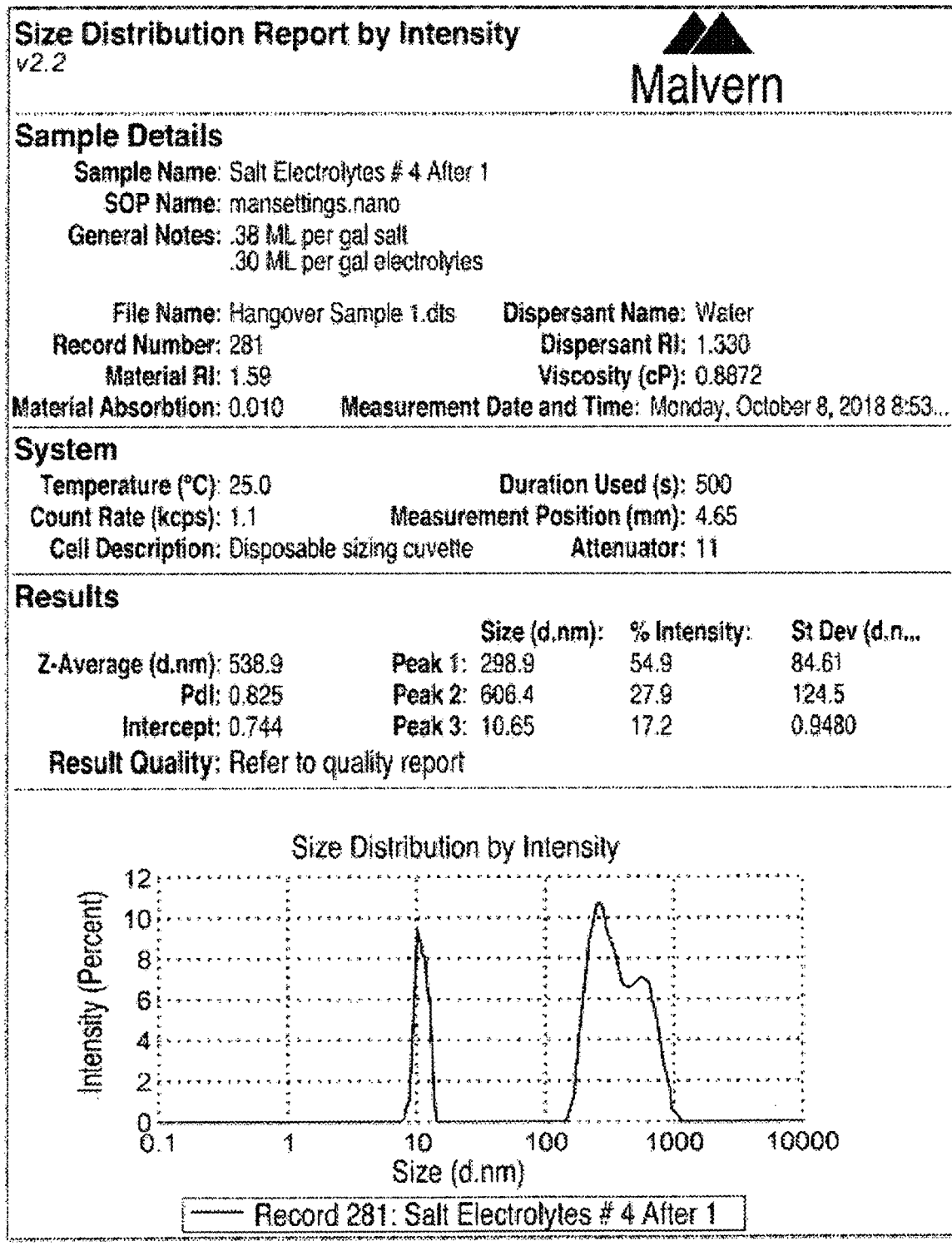

The effectiveness of the nano-sizing process occurring in the hollow cylinder 1218 is reduced when delays in process stream flow and pressure regulation occur. This was observed and confirmed by Malvern Zetasizer DLS measurements of aqueous product samples taken at various times during the experimental production runs when stream flow rate and pressure were below or above their optimal values. As shown in the data of FIG. 17 and FIG. 18 based on Malvern Zetasizer DLS data reports, sizes of the aqueous therapeutic water-clustered particles are multimodal distributions instead of single mode distribution, and the particle sizes are larger than normal. A "hangover product" formula was being nanosized. Before the process stream entered the hollow cylinder 1218, 84% of its water clustered therapeutic particles had a median size of 309 nanometers (see FIG. 17 Report). After the process stream had passed through the hollow cylinder 1218, 55% of the water clustered therapeutic particles had a median size of 309 nanometers and there was a new significant percentage (28%) population of larger water-clustered therapeutic particles which were 606 nm in size (see FIG. 18 Report). For the process apparatus of FIG. 12 process, a constant process stream flow rate of 14 gallons per minute through the hollow cylinder 1218 is preferred.

Figure 19:
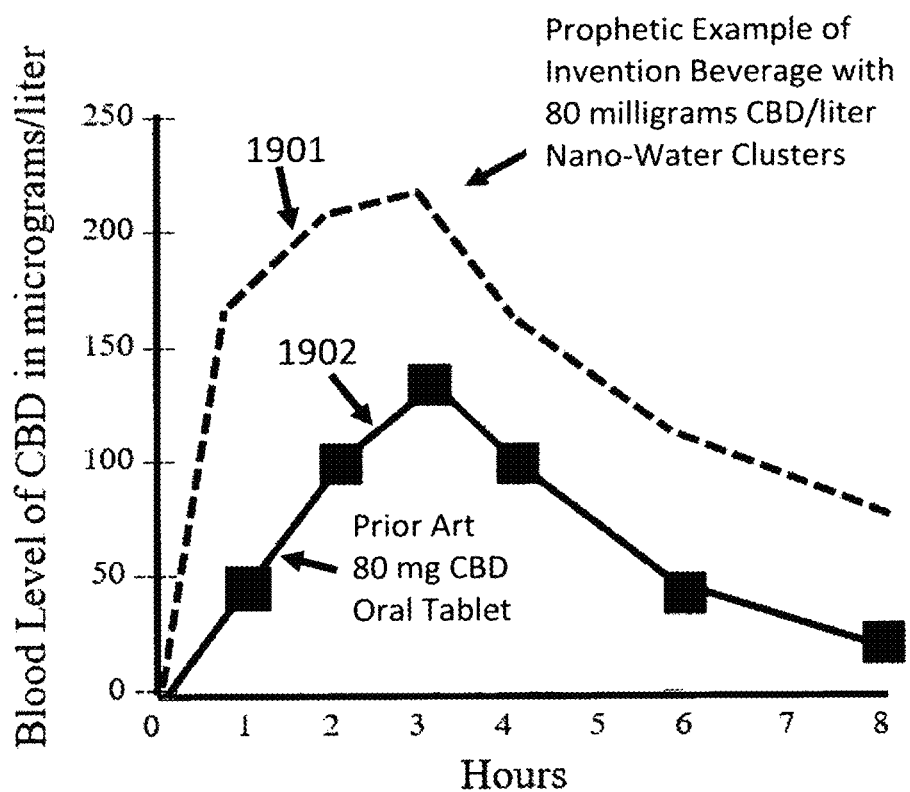

FIG. 19 depicts a simple CBD blood level pharmacokinetics graph. The dashed curve line 1901 is prophetic but quite likely what the CBD blood level pharmacokinetics of a single high bioavailability drink embodiment of the present invention containing 80 milligrams of CBD could achieve. The tablet data is a result of human ingestion of a 400 mg CBD oral tablet. The label for the graph X axis is Hours (namely hours after initial oral administration of a CBD Drink formulation of the present invention) and the label for the graph Y axis is Blood Level of CBD in micrograms/Liter (of blood plasma). Thus, oral ingestion of the CBD drink should result in quicker and higher blood levels of CBD in the drinker as depicted by graph line 1901. The lower solid line 1902 curve is based on published human data for CBD blood levels after oral administration of a single 400 milligram CBD (cannabidiol) tablet. CBD blood levels due to the 400 mg CBD tablet are plotted at hour time points 1, 2, 3, 4, 6, and 8 hours after the single oral tablet dose was taken (Hurd, 2015). The 400 mg tablet had about a 130 microgram CBD/liter blood plasma Cmax (maximum achieved blood plasma concentration of the CBD). The tablet CBD Tmax (Time to CBD Cmax) was 3 hours. Tablet use was associated with a CBD blood level at 8 hours of only about 20 micrograms CBD per liter blood plasma. It is well known that oral CBD tablets have a low bioavailability (6% to 9%), Millar et al., 2018 is a broad review; and Devinsky et al, 2014 at page 7 states that 6% is a typical CBD oral bioavailability. The prophetic CBD drink formula comprises 80 milligrams of CBD particles that are water clustered so their particle size is less than 200 nanometers, preferably less than 150 nanometers in size. The pharmacokinetics of oral ingestion of a 400 mg CBD tablet (see solid line 1902) is published (Hurd, 2015).

FIG. 20 presents CBD certified assay data from an outside third party who quantified the total CBD content in milligrams in two sample bottles of a half-liter plastic bottle aqueous CBD drink beverage Nu Aqua™ bottle. The Nu Aqua™ CBD drink was made by the inventors using the process apparatus depicted in FIG. 22 on Sep. 12, 2019. The advantage of the FIG. 22 process apparatus is that it can run non-stop and there is no need to store any intermediate product. As the beverage was made it was bottled. The CBD assay was conducted and reported within 4 days of the Nu Aqua™ production bottling run. The CBD content in two Nu Aqua™ bottles holding 510 ml (milliliters) beverage liquid was found to be 24.98 mg (milligrams) total CBD in one Nu Aqua™ bottle and 25.93 mg total CBD in a second Nu Aqua bottle. No other cannabinoids were detected in the Nu Aqua drink embodiment of the invention. The CBD drink beverage Nu Aqua™ appears as transparent and colorless as spring water because it contains no surfactant. It has a nice taste due to its trace minerals, sodium carbonate, and ultrapure water. The inventors' goal for the half-liter drink to contain between 20 to 25 mg CBD per bottle was accomplished.

Figure 12:
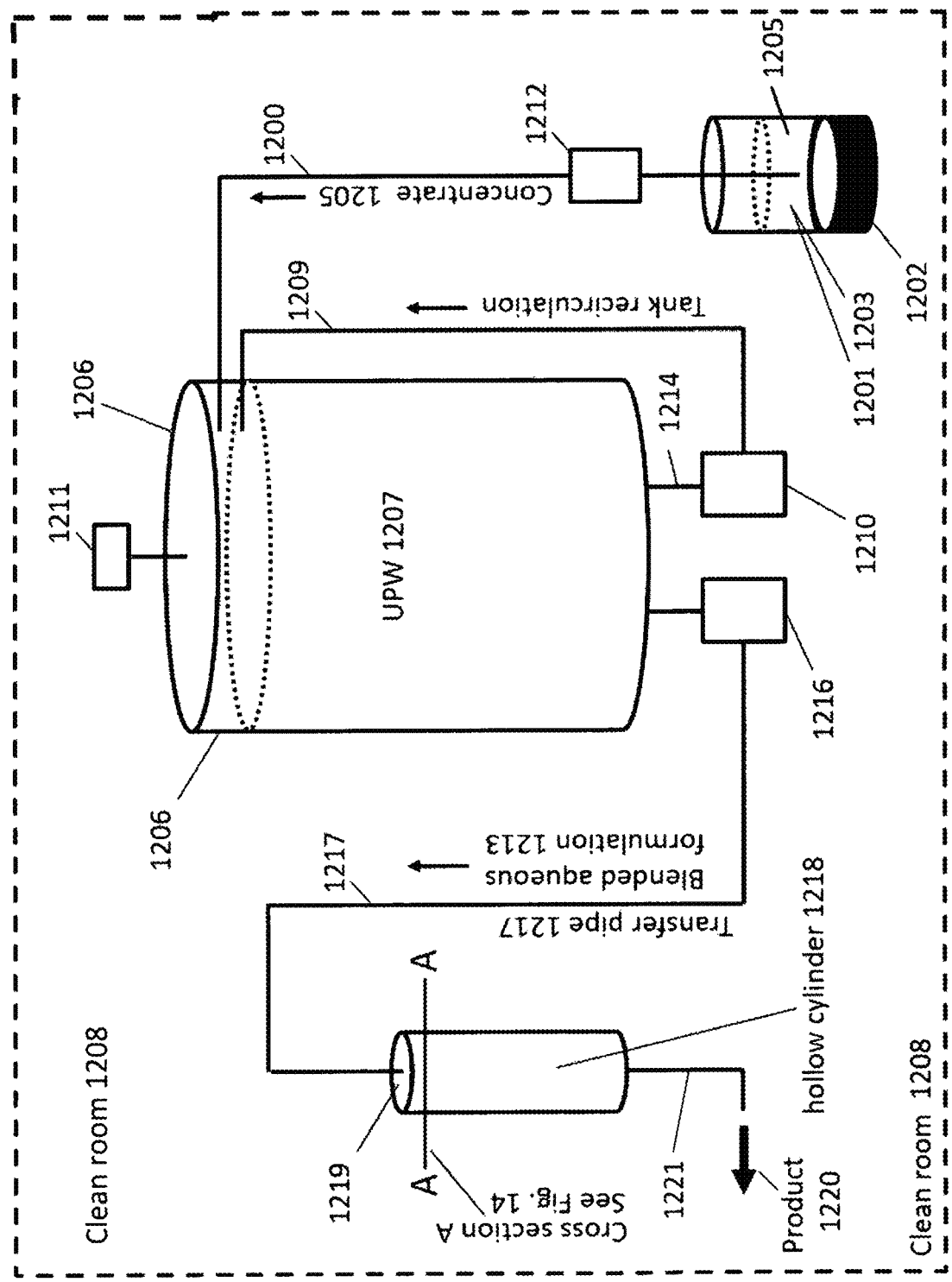
FIG. 12 depicts more details of the FIG. 11 process steps 1106-1108 charted out in the nine-step process depicted in the FIG. 11 flow chart. Step 1106 is performed before running the apparatus depicted in FIG. 12, about 300 gallons of ultrapure water (UPW) 1207 is prepared on site and is pumped for storage into tank 1206. Also, before running the apparatus depicted in FIG. 12, a gallon of a concentrate 1205 which comprises a mixture of a gallon 1201 of UPW and an amount of a non-H$_2$O substance(s) 1203 is prepared in a clean room 1208 using a container 1202 with a blender mixer.
Figure 21:
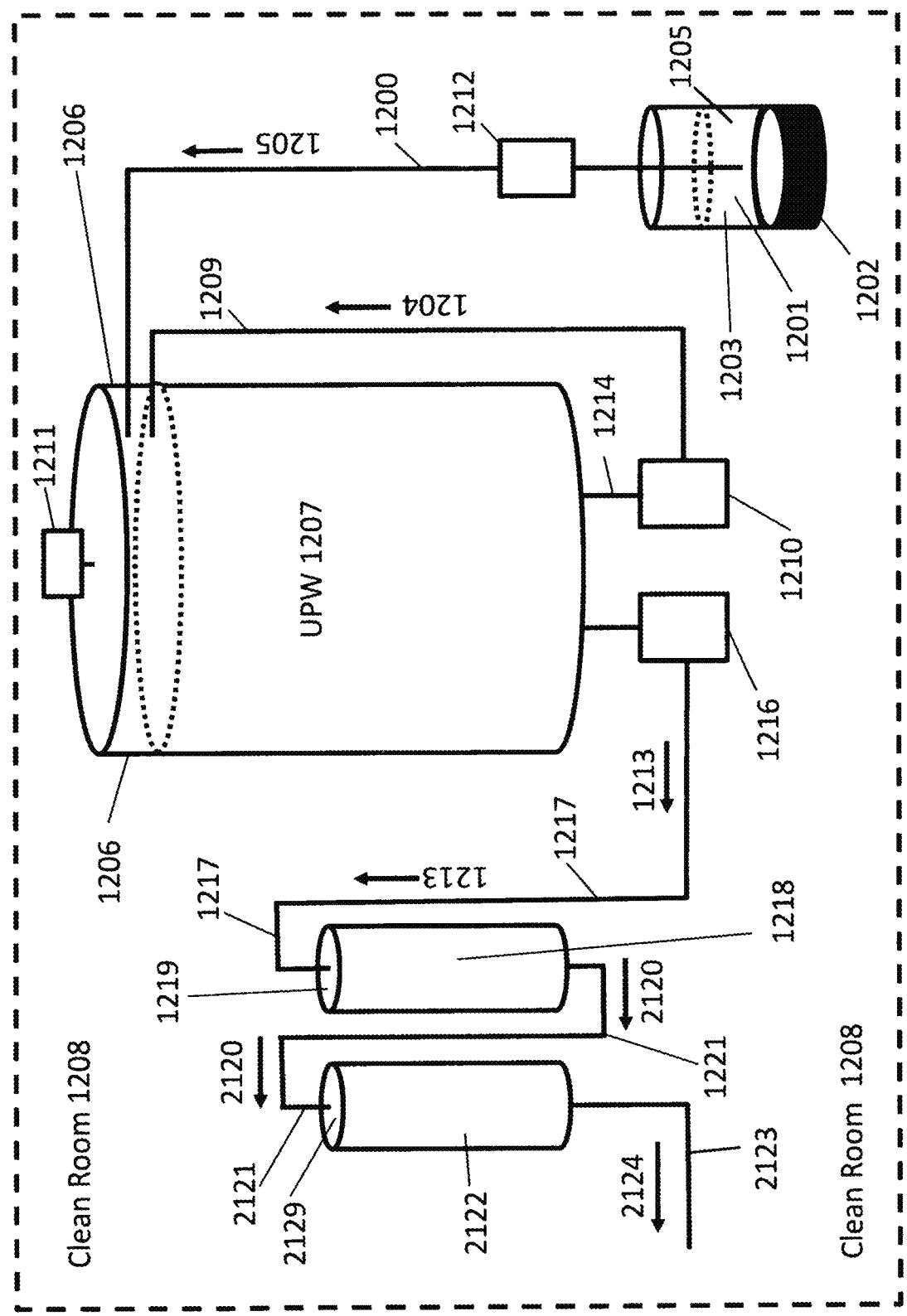

FIG. 21 is a schematic depiction of an inventive process for making some product embodiments of the present invention and comprises an improved process relative to the process depicted in FIG. 12. The process in FIG. 21 comprises a first hollow cylinder 2118 with an intermediate product 2120 exiting the first hollow cylinder 2118 via pipe 1221. Then the pipe 2121 sends the intermediate product 2120 into top 2129 of second hollow cylinder 2122 for nanosizing a second time. Then the final product exits from second hollow cylinder 2122 via pipe 2123 as product 2124. Note that the top of tank 1206 has an air filter 1211 for filtering out particles that might be entering tank 1206 when air needed to be vented as fluid is drained from this tank during the production process. The effect of adding 2 additional hollow cylinder devices to the process depicted in FIG. 21 significantly improves the process of nanosizing clusters of water surrounding the non-H$_2$O substance.

Figure 22:
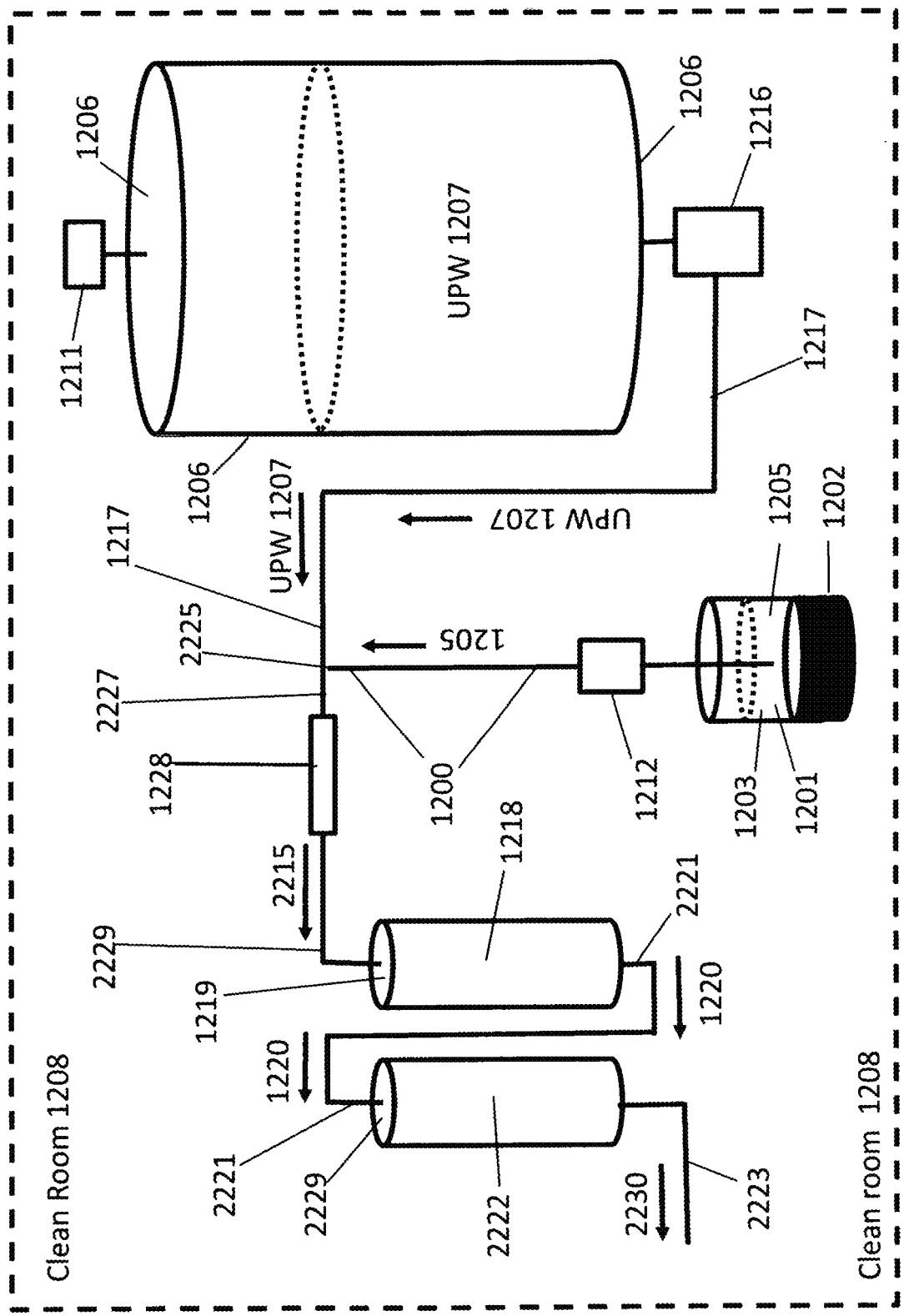

FIG. 22 is a schematic depiction of an improved invention process for making some product embodiments of the present invention relative to the process depicted in FIG. 12. The process in FIG. 22 eliminates the slow blending step involving having to blend the UPW 1207 in tank 1206 with the concentrate 1205 by using a slow recirculation process with tank 1206. The slow recirculation process is depicted in the processes in FIGS. 12 and 21. In the improved process depicted in FIG. 22, the UPW 1207 from tank 1206 is transferred by transfer pipe 1217 to a pipe junction 2225. From container 1202 the concentrate 1205 in transfer pipe 1200 is sent to the same pipe junction 1225. The UPW 1207 and the concentrate 1205 then flow down pipe 1221 from the pipe junction 2225 to a static blending pipe 1228. See FIG. 24 for a longitudinal section and a cross-section of an example static blending pipe taken from Armeniades U.S. Pat. No. 3,286,992. The disclosure of U.S. Pat. No. 3,286,992 is incorporated by reference herein in its entirety. Then from the static blending pipe 1228, the blend 2215 of the UPW 1207 and the concentrate 1205 is sent via transfer pipe 1215 to flow into top 1219 of a first hollow cylinder 1218. Transfer pipe 1229 pulls the intermediate nanosized product 1220 from the bottom of the first hollow cylinder 1218 and transfers it to the 2229 of the second hollow cylinder 2222 and then the final product 2230 exits using pipe 2223. Note that the top of tank 1206 has an air filter 1211 for filtering out particles that might be entering tank 1206 when air needed to be vented as fluid is drained from this tank during the production process.

The process depicted in FIG. 22 is much faster to accomplish than the processes depicted in FIGS. 12 and 21 where about 15 to 20 minutes were required to slowly pump the concentrate 1205 in with the UPW 1207 in tank 1206 while running pump 1210 and a recirculating pipe 1209 to tank 1206 to get the mixture of the concentrate 1205 and the large volume of UPW 1207 blended in tank 1206. The process depicted in FIG. 22 like the processes in FIG. 12 and FIG. 21 would be sensitive to flow and pressure disruption in transfer pipes 1217, 1200, 2227, and 2215 during a product production run. If there is a reduction in flow in the hollow cylinder(s) 1218, 2122, and 2222 then the Step 8 nanosizing process (See FIG. 11, Step 1108) is expected to be less effective and this will disrupt the uniformity of the size reduction in the water clustered therapeutic particle.

Figure 23:
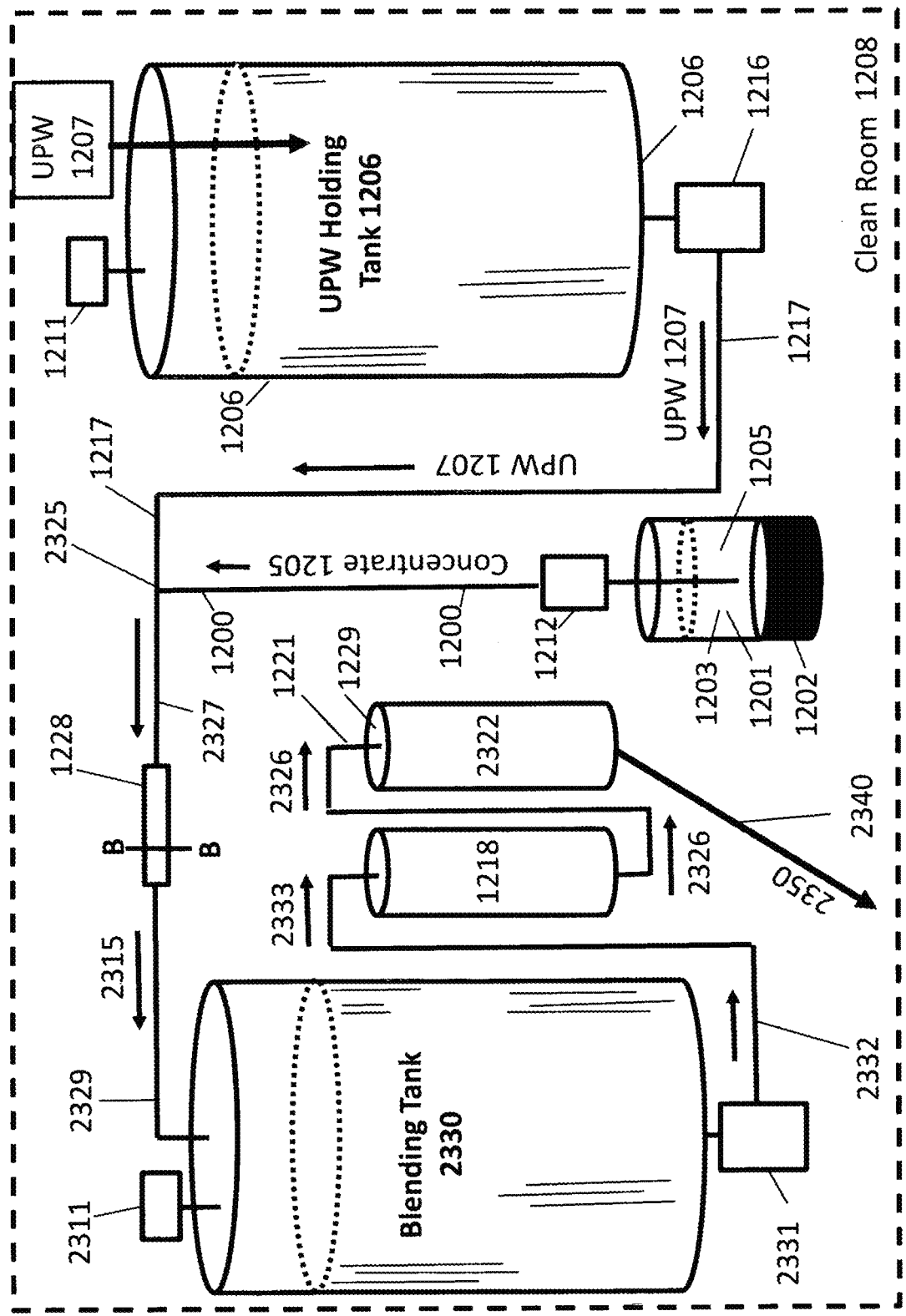

FIG. 23 is a schematic depiction of an inventive improved process for making some product embodiments of the present invention. The process comprises a process where UPW 1207 from tank 1206 is transferred by transfer pipe 1217 to a pipe junction 2325. From container 1202 the concentrate 1205 in transfer pipe 1200 is sent to the same pipe junction 2325. The combination of UPW 1207 and the concentrate 1205 after pipe junction 2325 flow together down pipe 2327 to a static blending pipe 1228. See FIG. 24 for a longitudinal section and a cross-section of an example static blending pipe taken from Armeniades U.S. Pat. No. 3,286,992. Then from the static blending pipe 1228, blend 2315 of the UPW 1207 and the concentrate 1205 is sent via transfer pipe 2329 for storage inside blending tank 2330. Note that the top of tanks 1206 and 2330 have air filters 1211, 1231 for filtering out particles that might be entering the tanks when air needed to be vented into these tanks as fluid was drained from the tanks during the production process. The blending tank 2330 has been added as a refinement which allows the blended aqueous formulation 2315 to continue to be prepared even if the production of product 1250 from second hollow cylinder 1222 is stopped. In addition, the blending tank 2330 serves as a reservoir so that the production of the product 2350 may continue even if the supply of blended aqueous formulation 2315 pauses. Then from blending tank 2330 the blend is called 2333 and is sent via transfer pipe 2332 to flow into top of first hollow cylinder 1218. A transfer pipe pulls the intermediate nanosized product 2326 from the bottom of the first hollow cylinder 1218 and transfers it to top of the second hollow cylinder 2322 and then the final product 2250 exits using pipe 2340.

FIG. 24, upper drawing is cross section view depicting a static blending pipe 1228 at position B. FIG. 24 lower drawing is a longitudinal section view depicting the static blending pipe 1228 and indicates the location of cross section B. Static mixing blade 2401 is shown in the cross-section of the pipe 1228. The blade 2401 is curved so as to radially deflect UPW 1207 to mix with the concentrate 1205 and this mixture forms a blended aqueous formulation 2215 inside the pipe 1228. Depicted in lower drawing of FIG. 24 are a plurality of sequentially positioned static mixing blades 2401 which are immobilized inside the pipe 1228. Most invention embodiments involve processes which need to mix a large volume of UPW 1207 with a small volume of concentrate 1205. The process depicted in FIG. 23 provides that the UPW 1207 and concentrate 1205 flow through separate pipes 1217, 1200 to a junction 2325 and then the combination of the large volume of UPW 1207 and small volume of concentrate 1205 flow together in pipe 2327 to the static blending pipe 1228. Inside static blending pipe 1228 the large volume of UPW 1207 and small volume of concentrate 1205 become well mixed as they flow through a plurality of sequentially positioned curved blades 2401 that are fixed in position inside the pipe 1228. In the FIG. 12 process, about one gallon of concentrate 1205 is typically added to 300 gallons of ultrapure water (UPW) 1207 and the process runs at about 15 gallons per minute. If 300 gallons of UPW 1207 and one gallon of concentrate 1205 were to be used in the FIG. 23 process, then the rate of flow of the concentrate 1205 would need to be about 0.05 gallons per minute and about 20 minutes would be needed for the large volume of UPW 1207 and small volume of concentrate 1205 to pass through the static blending pipe 1228.

FIG. 25 is a flow chart of an eight step process for making ultrapure water using several kinds of sensors whose measurements are fed to a computer which is programmed for using the sensor data to regulate the eight step process for making the ultra-purified water (UPW). The UPW making process uses an apparatus with computer-monitored flow rate sensors (2502, 2506, 2510, and 2513) for measuring flow rate in gallons per minute (gpm) are located before steps 3, 4, 6, and 7 in FIG. 25. The apparatus also has computer-monitored pressure sensors (2501, 2505, 2509, and 2512) for measuring pressure in pounds per square inch (psi) located before steps 3, 4, 6, and 7 in FIG. 25. The apparatus also has a computer-monitored chloride sensor (2503) before the reverse osmosis (RO) equipment in process step 3 to avoid saturating the RO with chloride anions.

In addition, there are computer-monitored resistivity or conductivity sensors (2504, 2507, 2511, and 2514) to measure resistivity in meg-ohms before and after reverse osmosis process step 3, after electro-deionization step 5, and after the step 6 mixed-bed resin, molecular-sieve chromatography-purification of the electro-deionized water. In addition, there are computer-monitored tank level sensors (2508), computer operated flow valves, and computer controlled pumps for controlling volume, flow rate, and pressure in the UPW production process steps. In the data from aforementioned sensor systems is displayed on a touch screen display so the operator of the UPW production apparatus may adjust the computer regulation of the process. The touch screen monitor also will prompt the operator by displaying red flags and sounding an audio alarm if the process sensors detect a deviation from their set point ranges. FIGS. 12, 20, 21, 22, and 23 drawings are depicted in the present patent application as without any computer and sensor technology. However, the inventors are currently experimenting with the process depicted in FIG. 23 so that it is being upgraded to have computer controls and uses sensors for measuring process stream flow rate (gallons per minute), process stream pressure (pounds per square inch, psi), process stream resistivity (meg-ohms) and tank fluid level sensors.

Figure 26:
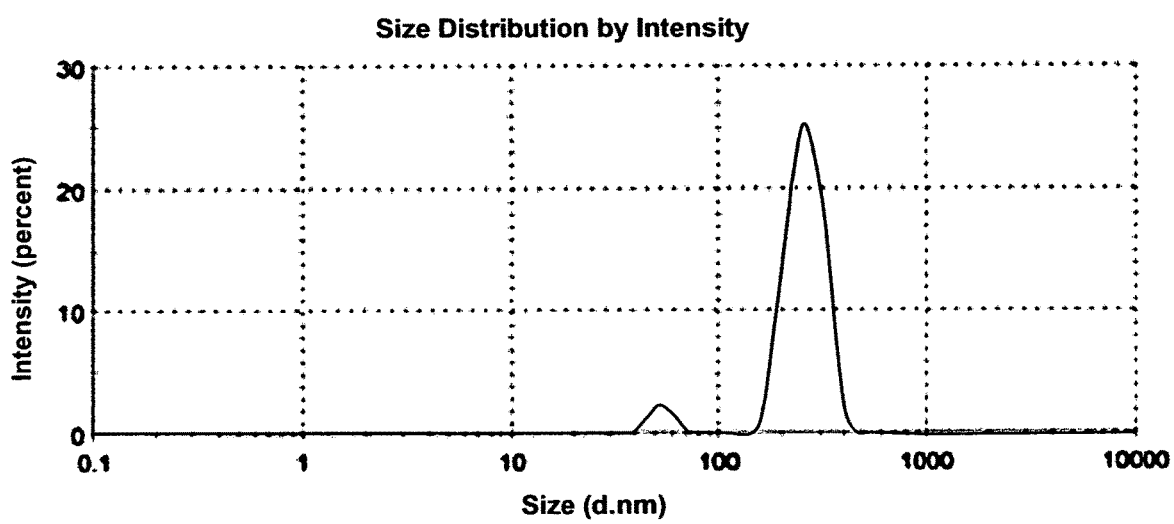

FIG. 26 presents measurements of water clustered CBD (Cannabidiol) therapeutic particle sizes in a "Pre IP" sample of a CBD drink embodiment of the present invention using a Malvern Zetasizer instrument "Size distribution. Reported by Volume" DLS measurements. The CBD drink Nu Aqua™ was produced in a 300 gallon experimental production batch using the process depicted in FIG. 22 with sensor and computer control refinements identified in FIG. 25. This sample was obtained from the flowing blended aqueous formulation 2215 in the transfer pipe 2229. See FIG. 22 for transfer pipe 2229 location. The "Pre IP" sample was taken BEFORE the flowing blended aqueous formulation 2215 had entered into the hollow cylinder 1218 and then flowed thru hollow cylinder 2222 for processing to make an aqueous therapeutic CBD particle having a stable exterior water clustering with nanosized (reduced) thickness. The "Pre IP" sample has two distinct median particle size distributions. The Malvern Report indicates that 94.3% of the "Pre IP" water-clustered CBD therapeutic particles had a median size of 260 nanometers and that 5.7% of the "Pre IP" water-clustered CBD therapeutic particles had a median size of 53 nanometers.

Figure 27:
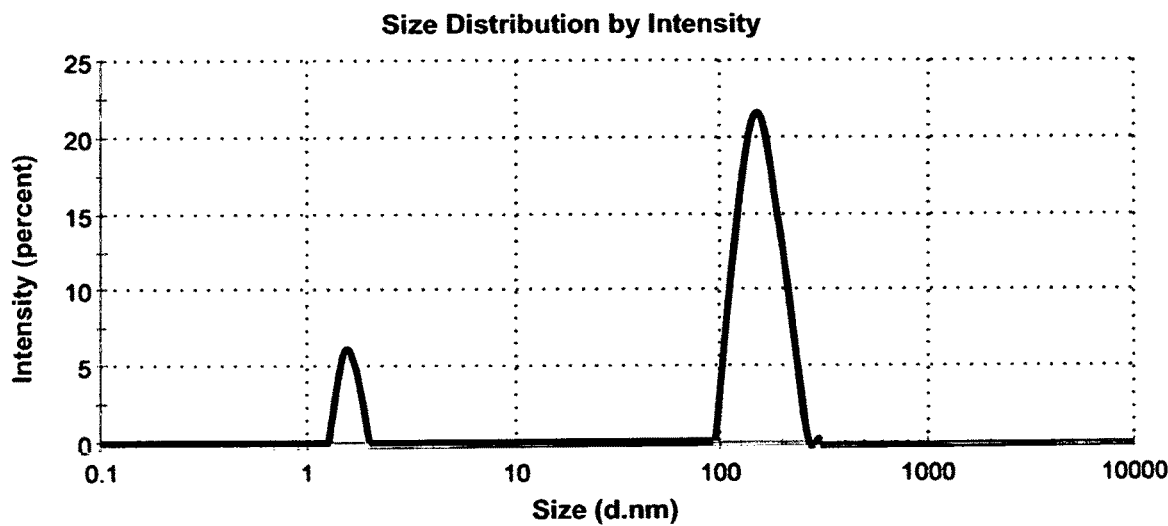

FIG. 27 measurements of water clustered CBD (Cannabidiol) therapeutic particle sizes in a "Post IP" sample of a CBD drink embodiment of the present invention using a Malvern Zetasizer instrument "Size distribution Reported by Volume" DLS measurements. This sample was obtained from the nanosized aqueous formulation 2230 in the transfer pipe 2223. See FIG. 22 for transfer pipe 2223 location. The "Post IP" sample was taken AFTER the flowing blended aqueous formulation 2215 had entered into the hollow cylinder 1218 and then flowed thru hollow cylinder 2222 for processing to make an aqueous therapeutic CBD particle having a stable exterior water clustering with nanosized (reduced) thickness. The "Post IP" sample has two different median distributions of particle sizes. The Malvern Report indicates that 89% of the "Post IP" water-clustered CBD therapeutic particles had a median size of 158 nanometers and 11% of the "Post IP" water-clustered CBD therapeutic particles had a median size of 1.6 nanometers.

Figure 28:
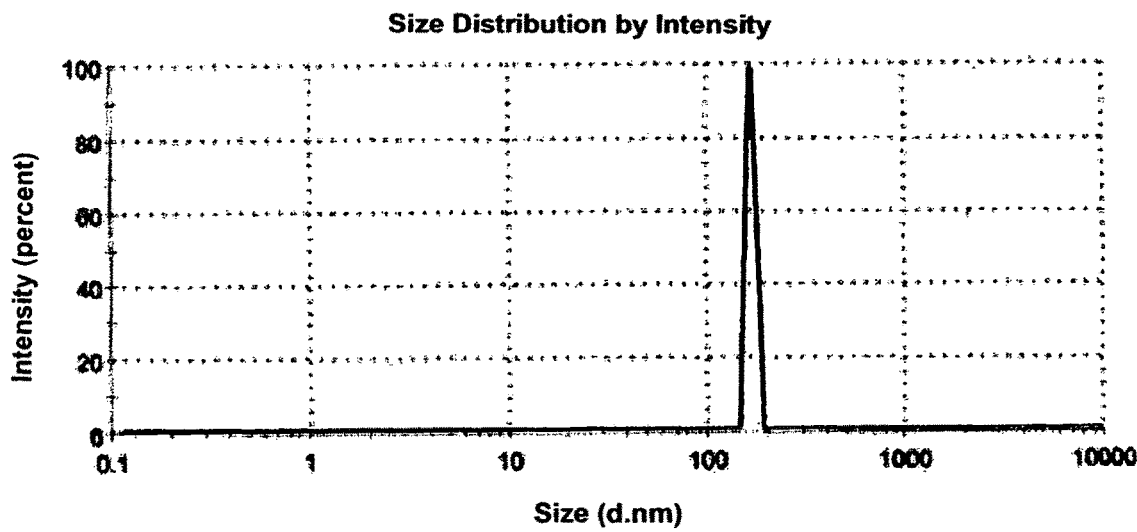

FIG. 28 presents Malvern Zetasizer instrument "Size distribution Reported by Volume" DLS measurements in nanometers of clusters of water containing nanosized CBD in a sample of a CBD drink embodiment of the present invention. The CBD drink contains 5 milligrams of CBD per liter drink. The CBD drink was produced in a 1500 gallon production batch run on Sep. 9, 2019 using the process depicted in FIG. 22 with sensor and computer control refinements identified in FIG. 25. As per FIG. 22 process, the FIG. 28 Sample was produced using a static mixing pipe 1228 and nanosized using a series of two hollow cylinders 1218 and 2222 (See FIGS. 13, 14 and 22). The FIG. 22 process apparatus enabled the making of an aqueous therapeutic CBD particle having a stable exterior water clustering with nanosized (reduced) thickness with a single median distributions of particle sizes. The Malvern Report indicates that 100% of the "Post IP" water-clustered CBD therapeutic particles had a median size of 164 nanometers

DETAILED DESCRIPTION OF THE INVENTION

The novel embodiments of the present invention generally relate to:

(1) Compositions of high bioavailability, nano-sized CBD (cannabidiol) in nanowater clusters for treating anxiety, inhibiting inflammation, for improving healing in a human or animal, and for facilitating recovery and craving from addiction in an addict;

(2) Compositions of high bioavailability nano-sized mineral nutrients in nanowater clusters for preventing and treating dehydration in a human or animal;

(3) Compositions of high bioavailability, nano-sized cancer cell membrane pore-forming peptides (CCMPFP) for example, PNC-27 in nanowater clusters for preventing and treating a cancer, or preventing a cancer reoccurrence in a human or in an animal;

(4) Compositions of high bioavailability, nano-sized pharmaceuticals in nanowater clusters for more rapidly and effectively providing a therapeutic drug treatment to a human or to an animal with a medical condition;

(5) Apparatuses and processes for making a composition of high bioavailability comprising a nano-sized non-$H_2O$ substance in nanowater clusters from a mixture of the nano-sized non-$H_2O$ substance in ultrapure water (UPW) and measuring the cluster sizes of the nano-sized non-$H_2O$ substance in nanowater clusters by using a laser-beam diffraction light scattering (DLS) process for detecting and treating the nanowater clusters of the nano-sized non-$H_2O$ substance as particles so as to use computer algorithms for calculating a distribution of the cluster sizes for obtaining the median cluster size from a graphed histogram;

(6) Improved manual control processes with an inline mixing pipe and a plurality of process stream cylinders with nozzle jets for nano-sizing a blended aqueous formulations of ultrapure water and a non-$H_2O$ substance for making nano-sized non-$H_2O$ substance in nanowater clusters;

(7) Computer-controlled apparatus and processes using sensor feedback with an inline mixing pipe and a plurality of process stream cylinders with nozzle jets for for nano-sizing a blended aqueous formulations of ultrapure water and a non-$H_2O$ substance for making a nano-sized non-$H_2O$ substance in nanowater clusters;

(8) Methods of using a high bioavailability aqueous composition of nano-sized non-$H_2O$ substance in nanowater clusters for improving farming of animals and growing of plants;

(9) Compositions of high bioavailability nanoparticles of cerium oxide and of high bioavailability nanoparticles of manganese dioxide in nanowater clusters useful for decreasing levels of hydrogen peroxide and other cellular oxidants as a method for slowing proliferation of cancer cells in the body of a human or an animal as methods for preventing cancer, for slowing cancer growth, and lessening cancer reoccurrence in a human or in an animal;

The terms nanowater, nanowater clusters, nanosized water clusters, nano sizing, and nano sized are all closely related terminology which essentially refer to nanometer measurements of the size of water clusters containing a nano sized particle of a non-$H_2O$ substance. are carried out using DLS technology of a Malvern Zetasizer DLS instrument on liquid test samples of invention product embodiments of the present invention. Various process embodiments of the present invention produce highly useful composition embodiments of the invention which are remarkably stable nano sized water clusters about the non-$H_2O$ substance and the composite of the water clusters surrounding the non-$H_2O$ substance is laser light detectable as an aqueous non-$H_2O$ substance particle which about its size measurement by a Malvern Zetasizer DLS instrument by principals of DLS (dynamic light scattering). The Malvern Zetasizer DLS instrument collects DLS (dynamic light scattering) data and uses computer algorithms to generate a histogram of the aqueous particle sizes of present invention product embodiments. Typical embodiments of the invention have a single mode distribution of sizes for the water cluster size encapsulating the non-$H_2O$ substance.

Preferred embodiments of the present invention comprise computer-controlled manufacturing processes for making nanowater CBD drinks for treating inflammation, hastening recovery from addiction, and alleviating anxiety in a human or animal and needing a single, repeated, or continuous dosing of that pharmaceutical by a route of administration. It is expected as prophetically depicted by the dashed line in FIG. 19, that some embodiments of the invention can provide a formulation of CBD which can provide a faster rapid onset (lower Tmax), a larger effect (higher Cmax), and a longer time period of effectiveness (longer T½ elimination) and an increased bioavailability (greater AUC) than prior art cannabinoid formulations such as the CBD table of Hurd (2015).

A preferred CBD drink embodiment is prepared according to a continuous computer controlled manufacturing process (see FIG. 22 for the process and apparatus) of the present invention. Another preferred CBD drink embodiment is prepared according to a continuous computer controlled manufacturing process (see FIG. 23 for the process and apparatus) of the present invention.

NuAqua™ CBD Drink Beverage Example

One CBD (cannabidiol) drink embodiment of the present invention comprises CBD, Sodium carbonate, and small amounts of other electrolytes as is detailed below made using ultrapure water. Below Example CBD Drink composition is for a 500 milliliter (ml) CBD Drink container contains ingredients a, b, c and d below.

(a) CBD: In a 500 ml (½ liter, 16.9 fluid ounces) CBD drink embodiments of the present invention, the CBD drink may contain an amount of CBD (in milligrams) which is selected from the group consisting of 1 mg, 2.5 mg, 5 mg, 10 mg, 15 mg, 20 mg, 25 mg, 30 mg, 40 mg, 60 mg, 70 mg, 80 mg, 90 mg, 100 mg, 150 mg and any combination thereof. Note than an ingestion of more than 1,500 mg CBD per day without the supervision of a medical doctor is reported to be unsafe (Devinsky, 2015). A preferred amount of CBD per 500 ml CBD drink embodiment of the present invention is between 10 mg to 30 mg CBD.

Preparation of a CBD Isolate from Cannabis Plants: The preferred physical state of the CBD is a crystalline powder isolated from young Cannabis plants harvested to have a low THCA so the amount of THC formed during processing is less than 0.3%, more preferably less than 0.1%. Preferably the low THC composition young Cannabis plants are grown without toxic fertilizers or chemical pesticides and are pathogen free. The plants are harvested as a food grade product, bagged, dried, pulverized, stored to avoid excessive heat.

Liquid Carbon Dioxide Extraction of CBD: The Cannabis plant material later is extracted with liquid carbon dioxide kept at a sufficient pressure so that the carbon dioxide ($CO_2$) is not simply a gas. There are three methods for using carbon dioxide as an extraction medium that are known as supercritical, subcritical and 'mid-critical' $CO_2$ methods. The supercritical $CO_2$ method is safe and provides a pure end product. The supercritical $CO_2$ is used as nontoxic solvent and the process sues freezing and compressor equipment to convert $CO_2$ gas into a supercritical cold liquid state. Carbon dioxide becomes liquefied below −69 degrees Fahrenheit at a pressure of more than 75 pounds per square inch (psi). Then both the temperature and the pressure are increased to make the liquid carbon dioxide 'supercritical'. This is when the $CO_2$ has properties between a gas and liquid. It fills container as if a gas while having a liquid's density. The supercritical carbon dioxide is mixed with the Cannabis plant material and supercritical the $CO_2$ extract the essential trichomes and terpene oils from the plant. The $CO_2$ liquid gets returned to a storage tank for using again.

Cold Ethanol Extraction of (the CBD Oil from the Liquid $CO_2$ Extraction): Left over carbon dioxide from the CBD oil from the liquid $CO_2$ extraction is allowed to dissipate. To the CBD oil is added ethanol cooled to a low temperature (for example between 0 to −50 centigrade). At such low temperatures in ethanol, waxes present in the CBD oil are a solid which floats on the top of the cold ethanol and the solid waxes can be filtered away. Then the ethanolic extract may be vacuum dried to yield a crystalline CBD isolate which actually contains the CBD as its carboxylic acid form which is the CBDH.

Decarboxylation of the CBDH to Produce CBD: CBDH is heated under vacuum to a temperature of between 110 to 145 degrees Centigrade, most preferably heated to about 115 degrees Centigrade which is close to 240 degrees Fahrenheit. This preferred temperature is Given in "Decarboxylation: The Best Guide You'll Ever Read—Cannabis 101 (See link https://www.marijuanabreak.com/decarboxylation) which states "The mystery of the decrabing [decarboxylating] temperature was somewhat solved thanks to the efforts of Marijuana Growers HQ. In 2012, they tested cannabis trim and kief at 240 degrees for 30 and 60 minutes. They chose 240 degrees because, during their research, they discovered that the vapor point of all major terpenes, flavonoids, and cannabinoids was over 246.2 degrees. As consumer grade ovens are not that reliable when reading temperatures, they played it safe by staying a few degrees below." In the process of decarboxylation of the CBDH (CBD acid) to CBD, there is a production of carbon dioxide gas which is removed by the decarboxylation reaction being conducted under vacuum. The remaining material should contain CBD and some of the aromatic terpenes. The CBD isolate has been found to have a particle size of between about 1500 to 300 nanometers prior to it being nanosized in Step 8 process by hollow cylinder 1218, (b) Sodium Carbonate: In a CBD drink embodiment of the present invention, the drink may have a pH between 8.5 to 11.5 due to the presence of sodium carbonate in the drink. If a lower drink pH is desired then the amount of sodium carbonate to CBD should be reduced.

(c) Trace Minerals™ 40,000 Volts Electrolyte Concentrate: In a 500 ml CBD drink embodiment of the present invention, the drink will contain some amounts of electrolytes using an electrolyte concentrate which is called "Trace Minerals™ 40,000 Volts Electrolyte Concentrate". This concentrate of electrolytes is used to supply each 500 ml. of the CBD drink the following amounts of electrolytes: between about 0.01 to about 1 mg. magnesium ion, 0.03 to about 1 mg. chloride ion, 0.008 to about 0.1 mg. potassium ion, 0.001 to about 0.1 mg. sulfate ion, 0.05 to about 1 microgram boron, and some other minor ions including citrate ion. In one preferred embodiment, the CBD drink per 500 ml. is made using Trace Minerals™ 40,000 Volts Electrolyte Concentrate to supply each 500 ml. drink effectively with 0.1 mg. magnesium ion, 0.3 mg. chloride ion, 0.08 mg. potassium ion, 0.01 mg. sulfate ion, 0.5 micrograms boron, and some other minor ions including citrate ion. Trace Minerals™ 40,000 Volts Electrolyte Concentrate is obtained from Trace Minerals Research, Roy, Utah. Note that an eight oz. fluid container of the Trace Minerals™ 40,000 Volts Electrolyte Concentrate contains magnesium 190 mg., chloride 600 mg., sodium 105 mg., potassium 150 mg., sulfate 20 mg., boron 950 micrograms, and some non-GMO citric acid. Note that in the preferred embodiment that 10 fluid oz. of Trace Minerals™ 40,000 Volts Electrolyte Concentrate is added to a 300 gallon batch to become the preferred embodiment CBD drink.

(d) ConcenTrace® Trace Mineral Drops: In a 500 ml CBD drink embodiment of the present invention, the drink will contain some amounts of electrolytes using an electrolyte concentrate ConcenTrace® Trace Mineral Drops. This concentrate of electrolytes is used to supply each 500 ml. of the CBD drink the following amounts of electrolytes: between about magnesium ion about 0.3 to 10 mg, chloride ion about 1 to 10 mg, sodium ion about 0.01 to 1 mg, potassium ion about 0.01 to 1 mg, sulfate ion about 0.05 to 1 mg, boron about 1 to 100 micrograms. ConcenTrace® Trace Mineral Drops, Trace Mineral Research, Roy, Utah. In one preferred embodiment, the CBD drink per 500 ml. is made using ConcenTrace® Trace Mineral Drops to supply each 500 ml. of the CBD drink the following amounts of electrolytes: magnesium ion 3.1 mg, chloride ion 8.1 mg, sodium ion 0.06 mg, potassium ion 0.04 mg, sulfate ion 0.5 mg, boron 0.01 mg. ConcenTrace® Trace Mineral Drops is obtained from Trace Mineral Research, Roy, Utah. A 6.4 oz. container of ConcenTrace® Trace Mineral Drops contains 96 servings wherein each serving contains magnesium ion 250 mg., chloride ion 650 mg., sodium ion 5 mg., potassium ion 3 mg., sulfate ion 40 mg., lithium ion 1.5 mg., and boron 1 mg. Note that in the preferred embodiment that 2 fluid oz. of ConcenTrace® Trace Mineral Drops is added to a 300 gallon batch to become the preferred embodiment CBD drink.

CBD Drink Example Formulation Examples

Basic Example 1—Formulation To Make 300 Gallons of CBD Drink Beverage

Note that 1 gallon of a CBD Concentrate is made for each 300 gallons of CBD drink beverage to be produced using one of the process apparatuses depicted in FIG. 12, 21, 22, or 23. To make 1 gallon of a CBD Concentrate, there are several important steps.

Step A is to slowly add 60 grams of food-grade sodium carbonate powder (anhydrous) into one half gallon of mixing freshly prepared ultrapure water (UPW). Allow the sodium carbonate to completely dissolve.

Step B is to then add 10 fluid ounces of 40K Volts Trace Minerals™ liquid into the mixing sodium carbonate solution. The solution will go milky due to magnesium carbonate formation.

Step C is to then add 2 fluid ounces of ConcenTrace™ trace minerals fluid into the mixing sodium carbonate solution. The solution will go milky due to magnesium carbonate formation.

Step D is to then add 48 grams of Cannabidiol (CBD) Isolate powder (99.8-100% pure) into the mixing sodium carbonate solution with trace minerals. The CBD will float and eventually sink into the liquid. If a blender is used the whipping in air from the blender will generate foam. Note—48 grams CBD diluted into 300 gallons of fluid (1,200 quarts) means each quart will contain 40 mg of CBD. Each NuAqua™ bottle holds 16.9 fluid ounces (500 ml) and thus about 21 mg CBD/16.9 ounce Nu Aqua™ bottle.

Step E is when the CBD has sunken below the liquid surface, then add ultrapure water to bring the total volume of the CBD Concentrate to 1 gallon. Now mix the ingredients at least ½ hour. None of the CBD should be floating and when mixing is stopped, it will be apparent that the CBD is present as a suspension of which some will slowly settle and some will remain suspended. If left overnight, all of the CBD will settle to the bottom like a fine silt.

Step F is to reduce the particle size of the CBD in the suspension by using a Ross Model HSM-703X-10 Ultra-High Shear Mixer, Hauppauge, New York at a rotor speed between 1,000-14,000 rpm. The Ross will heat the CBD Concentrate gradually. Preferably the CBD concentrate is allowed to flow by gravity through the Ross rotor spinning at 13,000 rpm. The passage of the CBD Concentrate through the Ross needs to be done between 3-6 times. However, foam is generated which make the CBD Concentrate a viscous foam and difficult to manage without spilling losses.

Step G is to use a single stage vacuum oil pump to create a sufficiently strong vacuum to the Ross-Sheared foamy CBD Concentrate that it can eventually boil gently at room temperature. To do the vacuum step, first pour all of the 1 gallon foamy CBD Concentrate in a 3-5 gallon strong glass-walled carboy jug leaving a lot of air space. During strong vacuum, the foam will expand and the CBD concentrate will slowly boil at room temperature due to the strong vacuum. The vacuum may be needed to continue for a few minutes after the CBD Concentrate has been boiling. When the vacuum is removed, the foam will completely disappear. Any shaking of the de-foamed CBD Concentrate will cause the very fine particles of the CBD suspension catch an air bubble and be air-lifted to float on the liquid top surface.

Step H is to keep the fine suspension of CBD in the CBD Concentrate gently mixing so the fine particulate suspension of CBD swims in a uniform state of suspension while it is being withdrawn using a titration pump (LMI Pump Model No. C771-26S Series C Chemical Metering Pump, Maximum Flow 10 Gallons per Hour @ 80 PSI, Maximum 100 strokes per minute, Maximum Viscosity 400 CPS, Pulse Input with Dual Manual Control, 4FV—Four Function Valve, Ivyland, PA) to blend the CBD Concentrate in a ratio of 1 part CBD Concentrate to 300 parts freshly-prepared Ultrapure Water during a Step I which is occurs when the CBD Concentrate is being added in a very metered fashion using one of the process apparatuses depicted in FIG. 12, 21, 22, or 23.

Basic Example 2—Formulation To Make 300 Gallons of CBD Drink Beverage

The amount of sodium carbonate can be varied to shift the pH and or the amount of CBD can be changed so that the beverage contains more or less CBD. The ratio of the mass of sodium carbonate used to the mass of CBD is a consideration. If insufficient sodium carbonate is used then the CBD may not wet sufficiently to become in suspension. If too much sodium carbonate is used then the drink will become salty and taste bad.

Since CBD has a double bond, it is sensitive to oxidation by ozone. It is preferable to simply sterilize all tanks, pumps, and piping to the bottling machine in advance with ozonated water.

CBD NanoParticles in Bottled NuAqua™ Beverage Drink Are Size Stable

Malvern Zetasizer DLS measurements on 12 bottles of NuAqua™ were conducted on Apr. 27, 2020 to measure the CBD therapeutic particle size so as to judge the stability of the exterior ultrapurewater clustering on the CBD particles. Also if the ultrapurewater-clustered CBD particles were agglomerating or crystallizing in some way then this would cause a detectable change in the ultrapurewater-cluster CBD particle size as well. For background control ultrapurewater-clustered CBD particle size data, two production batches are being used here for baseline size data. First, an experimental 300 gallon production batch of Nu Aqua™ was produced Aug. 20, 2019 which formed ultrapurewater-clustered CBD particles with a median particle size of 158 nanometers (report in FIG. 27). Secondly, a larger experimental 1500 gallon production batch of Nu Aqua™ made Sep. 9, 2019 had water-clustered CBD particles with a median particle size of 164 nanometers (See report in FIG. 28). Thus, the normal ultrapurewater-clustered CBD particle forming in NuAqua™ CBD drinks appears to be about 160 nanometers. Below is a Table listing data from 12 bottles of NuAqua™ CBD Drink based on the Malvern Zetasizer DLS measurement technology.

Nu Aqua™ CBD Drink Bottle's No. 1-3 produced Sep. 9, 2019.

| Particle Distributions (median values) | |
| --- | --- |
| Bottle No. 1 | 75% are 118 nm size and 25% are 473 nm size. |
| Bottle No. 2 | 77% are 122 nm size and 20% are 630 nm size. |
| Bottle No. 3 | 69% are 112 nm size and 31% are 501 nm size |
| Bottle No. 4 | 80% are 128 nm size and 15% are 560 nm size. |
| Average | 75% are 120 nm size and 23% are 541 nm size. |

Nu Aqua™ CBD Drink Bottle's No. 5-8 produced Oct. 11, 2019.

| Particle Distributions (median values) | |
| --- | --- |
| Bottle No. 5 | 98% are 211 nm |
| Bottle No. 6 | 95% are 220 nm |
| Bottle No. 7 | 100% are 174 nm. |
| Bottle No. 8 | 100% are 215 nm. |
| Average | 98% are 205 nm size and none are larger. |

Nu Aqua™ CBD Drink Bottle's No. 9-12 produced Nov. 14, 2019

| Particle Distributions (median values) | |
|---|---|
| Bottle No. 9 | 67% are 123 nm size and 33% are 582 nm size. |
| Bottle No. 10 | 50% are 107 nm size and 50% are 359 nm size. |
| Bottle No. 11 | 75% are 114 nm size and 25% are 427 nm size |
| Bottle No. 12 | 57% are 105 mu size and 43% are 387 nm size. |
| Average | 62% are 112 nm size and 38% are 439 nm size.m size. |

Conclusion:
1. Overall the median value for 78% of the Nu Aqua product ultrapurewater-clustered CBD particles is 146 nanometers in size and for 20% of the particles is 490 nanometers.
2. If fresh NuAqua™ ultrapurewater-clustered CBD particles are about 160 nanometer size, then the measurements on NuAqua™ that is 5-7 months old suggest that the majority (78% of the Nu Aqua™ ultrapurewater-clustered CBD particles does not change their size.
3. Perhaps 20% of the NuAqua™ ultrapurewater-clustered CBD particles increase but overall the Nu Aqua™ ultrapurewater-clustered CBD nanoparticles are surprisingly time stable in size compared with Stukelj et al., 2019 study.

Present inventors process employed (a) sodium carbonate with ultrapure water to create an aqueous CBD suspension, (b) Ross ultra-high speed shear-mixing to reduce the size of the suspended CBD particles, and (c) the hollow cylinder jet nozzle process to reduce the thickness of the ultrapurewater-clustering on the CBD particles.

Stukelj 2019 employed (a) antisolvent precipitation process to dissolve CBD particles in an organic solvent and then quickly precipitate the CBD amorphously using a large amount of water, and (b) ultrasonication to create 700 nanometer CBD suspension particles in di-ionized water The Stukelj CBD nanoparticles regardless of organic solvent conditions all double in size in 24 hours. Stukelj reports and promotes one to use a mixture of Span 80/Tween 80 surfactants to create very time stable 70 nanometer CBD nanoparticle. However, the Stukelj surfactants turns the solution so very cloudy, that a conventional surfactant is not an attractive viable answer. Thus the storage size stability of the Nu Aqua ultrapurewater-clustered CBD nanoparticles is surprisingly effective way to make time stable CBD nanoparticles.

Basic Example 3—Using Sodium Carbonate to Make Aqueous Suspension of CBD

According to the processes depicted in FIGS. 12, 21, 22 and 23, some embodiments of the present invention use an alkalinizing aqueous medium as a means for creating an aqueous suspension of CBD. In an early experiment testing processes and an apparatus embodiment of the invention, one method of preparing a concentrate of CBD and minerals in ultrapure water comprised using an alkalinizing aqueous medium as a means for creating an aqueous suspension of CBD, which comprised performing the steps of: adding firstly, 406 grams of anhydrous food grade (ACS) sodium carbonate (amounting to 3.83 moles of anhydrous sodium carbonate (molecular weight of 106.0 grams per mole, see Wikipedia, 2019) to seven gallons of ultra-pure water; adding secondly, and slowly with stirring 336 grams (amounting to 1.07 moles of at least 99 percent purity crystalline CBD isolate (CBD is Cannabidiol) having a molecular weight of 314.5 grams per mole, see Wikipedia, 2019) (Concentrate at this stage had a pH of about 11.35 based on an earlier 1 gallon pilot experiment); adding thirdly, 14 fluid ounces (pH 5.81) of ConcenTrace™ trace minerals; adding fourthly 70 fluid ounces (pH 2.96) of trace minerals 40,000K Electrolyte™ (Concentrate at this stage had a pH of about 11.35 based on an earlier 1 gallon pilot experiment). When the Concentrate was diluted 300-fold (pH was then about 10.32. In the 7 gallon Concentrate the pH was slightly lower (pH=9.9) after the CBD and the minerals had been added to the 7 gallons of the ultrapure water. This pH 9.9 seven gallon Concentrate was used for making an experimental large production batch of 2000 gallons of a CBD drink product.

To make the 2000 gallon experimental batch of the drink product, the 7 gallons of the concentrate of the CBD and the minerals were blended with 2000 gallons of ultra-pure water using a static mixing tube 1228 as the blending device. The rate of introduction of the Concentrate was set so that the 7 gallons of Concentrate blended into the 200 gallons of UPW at a flow rate which was $\frac{1}{300}^{th}$ of the bulk UPW flow rate thru the static mixing tube 1228. The static mixing tube 1228 is depicted in the apparatus depicted in FIG. 23. In this early large batch experiment, following the blending process step, the next step in the process comprised pumping the aqueous blended composition of the CBD and minerals in 2000 gallons of UPW at a flow rate of 14.5 gallons per minute through the hollow cylinders 1218 and 2322 as a means for making an aqueous alkaline pH mixture of nanosized clusters of water containing CBD and nanosized clusters of water containing minerals. In some embodiments of the invention, the mixture of nanosized clusters of water containing CBD and nanosized clusters of water containing minerals may be filtered using a 5, 10, or 20 micron filter to stop 5, 10, or 20 micron CBD particles from becoming a part of the drink product. In this experimental batch a 20 micron filter was used prior to ozonating the batch and subsequent piping leading it bottling of the CBD-trace minerals drink product in 500 milliliter bottles which would contain about 20 mg of CBD. Bottle samples were sent for assay of CBD.

The experimental batch was sampled three times during its production to make the drink product, which comprises a mixture of nanosized clusters of water containing CBD and nanosized clusters of water containing trace minerals. The production process ran 137 minutes in this experiment to blend 7 gallons of the Concentrate into 200 gallons of UPW. The total volume of 2007 gallons was sent to a holding tank. The process of pumping of the blend through the Hollow Cylinders 1218 and 2322 which are in a series configuration as depicted in FIG. 23 took 137 minutes. Drink product samples for Malvern Zetasizer Instrument particle sizing determinations: Sample No. 1 was taken 10 minutes after the start of the pumping of the blend through the Hollow Cylinders; Sample No. 2 was taken 81 minutes after the start of the pumping of the blend through the Hollow Cylinders; and Sample No. 3 was taken about 105 minutes after the start of the pumping of the blend through the Hollow Cylinders. The Malvern Zetasizer instrument testing of Sample No. 1, determined that the clusters of water containing CBD and minerals in Sample No. 1 had a single mode of size distribution with a median size of 196+/−41 nanometers standard deviation. Testing of Sample No. 2, determined that the clusters of water containing CBD and minerals had 3 modes of size distributions: 77 percent had a median size of 190+/−50 nanometers standard deviation; 13 percent had a median size of 9+/−1 nanometer standard deviation; and 10 percent had a median size of about 5000+/−600 nanometers standard deviation, according to a Malvern Zetasizer instrument analysis. Testing of Sample No. 3 determined that the clusters of water containing CBD and minerals had 4 modes of size distributions: 69 percent had a median size of 198+/−71 nanometers standard deviation; 17 percent had a median size of 2.4+/−0.3 nanometers standard deviation; and 8 percent had a median size of 34+/−8 nanometers standard deviation; and 6 percent had a median size between 5000-6000 nanometers.

The Malvern data for this experimental batch suggested that the process may be suitable for making a nanosized CBD drink product from UPW by using the apparatus depicted in FIG. 23. This conclusion was based on the observation that the Malvern Zetasizer instrument determined Samples Nos. 1, 2, and 3 contained a mode size distribution where at least 69 percent of the nanosized clusters of water containing CBD and nanosized clusters of water containing minerals had a median size of approximately 200 nanometers. Only 6-10 percent of the clusters of water containing CBD and nanosized clusters of water containing minerals were found to have a mode size distribution which was larger than 200 nanometers.

In some embodiments another carbonate salt may be substituted for the sodium carbonate to obtain the alkalinizing aqueous medium for creating the aqueous suspension of CBD in UPW. Another carbonate salt may be substituted for the sodium carbonate to obtain the alkalinizing aqueous medium for creating the aqueous suspension of CBD in a water other than UPW, such as for example a reverse osmosis (RO) water, distilled water, carbon filtered water, or a water that has been filtered using a submicron filter. This alkalinizing anion may be selected from the group consisting of a carbonate, a phosphate, a sulfate, a methanesulfonate, a conjugate base of a polyprotic acid, a dicarboxylate, a tricarboxylate, a di-sulfate, a di-phosphate, a phosphonate, a sulfonate, an oxalate, a malonate, a citrate, an isocitrate, a maleate, a succinate, a fumarate, an itaconate, a glucuronate, an aspartate, a glutamate, a borate, a boronate ester, a hydroxide, and any combination thereof. Cations accompanying the alkalinizing anion used to increase the pH in processes of the present invention may be selected from the group consisting of lithium, sodium, potassium, cesium, aluminum, iron, copper, magnesium, calcium, strontium, titanium, vanadium, manganese, zinc, silver, ammonium, and any other biologically non-toxic metal cation. In some embodiments of the present invention the chemicals may be used to improve the suspension of the CBD function by increasing the pH (alkalinizing) of the Concentrate and also comprise anionic molecules which function as a pH buffer.

To reduce or eliminate a fraction of the water clusters containing CBD particles exceeding a size of 500 nanometers, some embodiments of the present invention include a process step of homogenization employing a Ross Homogenizer (Haupauge, NY) or employing a Bee International Homogenizer (South Easton, MA) as a means for homogenizing the aqueous CBD Concentrate prior to the blending of the Concentrate into the bulk UPW.

Drink embodiments of the present invention may comprise one or more cannabinoids selected from the group consisting of CBG, CBGM, CBGV, CBC, CBD, CBDM, CBDV, CBD-$C_1$, THC, THC-$C_4$, THCV, THC-$C_1$, Delta-7-cis-iso-tetrahydrocannabivarin, Delta-8-THC, CBLA, CBL-V, CBE, CBN, CBNM, CBN-$C_4$, CBV, CBN-$C_2$, CBN-$C_1$, CBND, CBVD, CBT, 10-ethoxy-9-hydroxy-delta-6a-tetrahydrocannabinol, 8,9-Dihydroxy-delta-6a-tetrahydrocannabinol, CBTV, CBTVE, DCBF, CBF, CBCN, OTHC, cis-THC, OH-iso-HHCV, CBR, triOH-THC, and any combination thereof. For some embodiments of the present invention the amount of the cannabinoids in a 500 milliliter drink may be selected to be between 0.01 milligrams to about 500 milligrams.

One or more terpenoids may be selected from the group of terpenoids listed in Table 2 of the present specification for use in a formulation embodiment of the present invention. For example, a few drops of selected terpenoids may added to a drink embodiment of the invention to add a flavor and/or scent. For some invention embodiments, the volume amount of terpenoids added to a 500 milliliter drink embodiment of the invention could be between 2 microliters to about 250 microliters, but in some embodiments could be perhaps one milliliter or more. The additions of small volumes of terpenoids is useful as a means for adding a characteristic scent that would be smelled immediately as the bottle is opened as some fraction of the terpenoid(s) will tend to float as an oil film on the top surface of the aqueous drink.

For some embodiments of the present invention, the cannabinoids which are present in a particular hemp oil Cannabis plant extract, can be used after a further partial extraction into an alkaline aqueous medium or a more complete extraction by a repeated extraction process with multiple aliquot extracts of the alkaline aqueous medium as means to partition the cannabinoids between the alkaline aqueous phase and the hemp oil phase as may be needed in a particular drink product embodiment of the present invention.

Basic Example 4—CBD Concentrate Using Ethanol or Glycerine Instead of UPW to Make a CBD Concentrate To make a version of NuAqua CBD drink, it is conceived that 48 grams of CBD may be completely dissolved in a gallon of (a) glycerin, (b) a gallon of ethanol, (c) a gallon of 50% ultrapure water-ethanol or (d) in a gallon of 50% glycerine-ultrapure water. For dispensing the (a), (b), (c), or (d) CBD Concentrate solutions a fixed rate, a metered pump is used. Then (a), (b), (c), or (d) may be precisely injected into a process stream over 20 minutes wherein the process stream is 300 gallons of a dilute sodium carbonate ultrapure water (UPW) solution. Either the process apparatus depicted in FIG. 22 or FIG. 23 would be used. The CBD would no longer be soluble in the process stream and would an amorphous precipitation in the sodium carbonate water which would contain about 60 grams of sodium carbonate in 300 gallons of UPW. The advantage of this approach is its few steps with no need for a Ross machine step nor a vacuum step.

Preferred embodiments of the present invention comprise computer controlled manufacturing processes for making nanowater hypotonic mineral drinks for a human or an animal needing rapid hydration for routine exercise or for rapidly reversing their dehydration.

Preferred embodiments of the present invention comprise computer controlled manufacturing processes for making nanowater PNC-27 aqueous pharmaceutical formulations for treating a human or an animal at risk of or suffering a cancer and needing a single, repeated, or continuous dosing of that pharmaceutical by a route of administration.

Preferred embodiments of the present invention comprise computer controlled manufacturing processes for making improved bioavailability nanowater formulations of approved pharmaceutical for treating a medical condition of a human or an animal needing a single, repeated, or continuous dosing of that pharmaceutical by a route of administration.

Preferred embodiments of the present invention comprise computer controlled manufacturing processes for making nanowater-based, improved-bioavailability compositions for growing vineyard grapes, crops, trees, fruits, grains, fruit, and grasses on land and also hydroponically, as well as for improving farm chicken and beef production, as well as for improving fish farming of depleted stocks of ocean fish, and as well improving crustacean and mollusk farming.

Some composition embodiments of the invention comprise nanosized clusters of water containing a nanosized non-$H_2O$ substances, wherein the nanosized clusters of water containing a nanosized non-$H_2O$ substances have a median size that is measureable using a Malvern Zetasizer instrumental analysis, and wherein the measured median size is selected from the group consisting of between about 2 nanometers to about 10 nanometers, between about 10 nanometers to about 30 nanometers, between about 30 nanometers to about 60 nanometers, between about 60 nanometers to about 120 nanometers, between about 120 nanometers to about 250 nanometers, between about 250 nanometers to about 500 nanometers, and any combination thereof.

Figure 10:
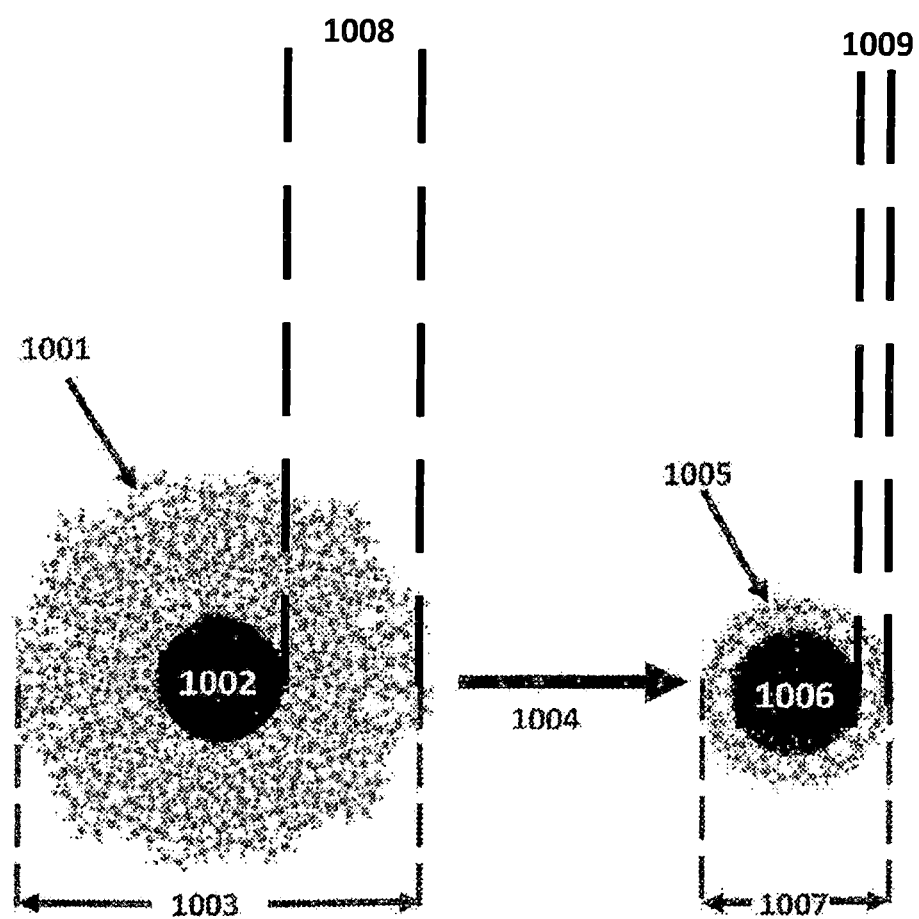
FIG. 10 left side, presents highly schematic views of therapeutic particle 1001 which contains a non-H₂O substance 1002 particle enlarged to a size 1003 with water clusters 1008 of hydrogen bonded H₂O molecules.

For example, depicted in FIG. 10 in a highly schematic view are two water clusters of many $H_2O$ molecules which are surrounding a non-$H_2O$ substance core which is a CBD particle. It is an object of the present invention processes to nanosize a blended ultrapure water blend of CBD particles from the size depicted in the left hand side of FIG. 10 to a reduced size water cluster depicted in the right side of FIG. 10.

Process embodiments of the present invention can reduce product water cluster size. In some embodiments, the present invention is a process for reducing water cluster sizes in an aqueous composition containing a non-$H_2O$ substance in order to improve bioavailability of the aqueous composition, the process comprising the steps of:

choosing an amount of the non-$H_2O$ substance to add to a volume of ultrapure water;

adding the amount of the non-$H_2O$ substance to the volume of ultrapure water in a mixing tank to form a blended aqueous formulation containing the non-$H_2O$ substance in the ultrapure water;

pumping the blended aqueous formulation at a selected flow rate from the mixing tank to a nozzle with one jet opening or a plurality of jet openings inside a hollow cylinder; using the one jet opening or the plurality of jet openings in the nozzle to jet the blended aqueous formulation at a higher flow rate into the hollow cylinder;

using the higher flow rate of the blended aqueous formulation from the one jet opening or the plurality of jet openings inside the hollow cylinder to reduce sizes of the water clusters in the blended aqueous formulation of the non-$H_2O$ substance in the ultrapure water;

removing the aqueous composition with the reduced size water clusters containing the non-$H_2O$ substance at the selected flow rate from inside the hollow cylinder; and using the reduced size water clusters containing the non-$H_2O$ substance in the aqueous medium to improve the bioavailability of the aqueous composition.

In some embodiments, the present invention is a process wherein more specifically the reduced size water clusters containing the non-$H_2O$ substance in the aqueous medium may have a median water cluster size selected from the group consisting of between about 2 to 10 nanometers, about 10 to 50 nanometers, about 50 to 100 nanometers, about 100 to 200 nanometers, about 200 to 300 nanometers, about 300 to 400 nanometers, and a combination thereof.

Continuous Manufacturing Processes for Making Nanosized CBD in Nanowater.

Some embodiments of the present invention are continuous manufacturing processes for making nanowater based aqueous cannabinoid compositions.

CBD is a cannabinoid derived from the Cannabis plant are often referred to as the phytocannabinoids. Cannabis is the genus name and there are pure and hybrid varieties. Three Cannabis species are known *Cannabis sativa, Cannabis indica* and *Cannabis ruderalis*. Cannabis varieties have been developed which have accentuated plant characteristics and/ or altered levels of cannabinoids. Cannabis varieties are branded by growers to distinguish the plant's taste, color, smell, and origin. Several varieties of Cannabis also known as hemp have a very low cannabinoid content but are used for fiber and seeds. There are at least five chemo-taxonomic types of Cannabis: (1) a Cannabis with high levels of THC, (2) a Cannabis which is more fibrous and has higher levels of CBD, (3) a Cannabis with intermediate levels of THC and CBD, (4) a Cannabis with a high level of cannabigerol (CBG), and a Cannabis with a very low cannabinoid levels (Canabis strains, Wikipedia, 2019).

Hybrid Varieties of Cannabis Provide Different Amounts of CBD.

Hybrid varieties of cannabis are known with varying ratios of the species *Cannabis indica, Cannabis sativa*, and *Cannabis ruderalis*. The White Widow hybrid has a 60% indica and 40% sativa ancestry and retains some traits from both parental types. There are also commercial crossbred hybrids which contain a mix of both ruderalis, indica or sativa genes, and they are usually auto-flowering. They are bred for the medicinal cannabis market. Also there is an early auto-flowering hybrid known as Lowryder which retains the flowering behavior of ruderalis plants while producing large amounts of THC and CBD. When cannabis is cultivated for its psychoactive or medicinal properties, male Cannabis plants are often separated from the female Cannabis plants to avoid fertilization of the female plants so as to facilitate flowering or simply to control breeding. Male plant pollen can be stored until needed for breeding. To stabilize a cannabis variety a technique known as cubing is used. The technique breeds a selected-trait hybrid plant with a parent plant. The same selected-traits are sought in the inbred offspring, and then this process is repeated usually for three or more generations to stabilize the variety's genetics. (Canabis strains, Wikipedia, 2019).

Cannabis breeders distinctly name their strains to differentiate them from their competitors' strains and popular strains may have a name similar to their parent strain. Some known cannabis strains are: (1) Acapulco Gold which is a golden-leafed *Cannabis sativa* strain originally from Acapulco, southwest Mexico; (2) Bedrocan which is a Dutch medical marijuana strain of *Cannabis sativa* with 22% THC and 1% CBD that is dispensed through pharmacies to patients with a prescription; (3) Blue Dream which is a hybrid cannabis strain for medical and recreational uses; (4) Charlotte's Web which is a high CBD Cannabis strain with less than 0.3% THC that is sold as an extract by the Stanley brothers, CO, USA; (5) Purple Kush which is a short *Cannabis indica* strain grown indoors; (6) Skunk which is a strong smelling hybrid of *Cannabis sativa* and *Cannabis indica*. grown indoors; and (7) Sour Diesel is a *Cannabis sativa* dominant hybrid strain. (Canabis strains, Wikipedia, 2019).

Cannabis is the genus name of plants containing CBD and THC as well as a large number of other cannabinoids and terpenes. *Cannabis indica* and *Cannabis sativa* are known species and marijuana is a generic name for both species. About 483 chemical compounds have been identified which are unique to Cannabis. This includes more than 66 cannabinoids and about 140 terpenes. For the present invention the term cannabinoid shall include a group of C21 terpenophenolic compounds found in the Cannabis plants. Plant cannabinoids are also called phytocannabinoids.

The Cannabis plant synthesizes at least eight cannabinoid acids which are below named. Cannabis cannabinoid precursors during biosynthesis form CBGA which in turn is converted into THCA, CBDA, and CBCA. When these three cannabinoids are subjected to heat they are decarboxylated to respectively form THC, CBD, and CBC. Cannabis cannabinoid precursors during biosynthesis also form CBGVA which in turn is converted into THCVA, CBDVA, and CBCVA and as above mentioned, when these three cannabinoids are subjected to heat they become decarboxylated to respectively form THCV, CBDV, and CBCV.

CBGA (Cannabigerolic acid)
THCA ($\Delta^9$-tetrahydrocannabinolic acid)
CBDA (Cannabidiolic add)
CBCA (Cannabichromenenic acid)
CBGVA (Cannabigerovarinic acid)
THCVA (Tetrahydrocanabivarinic acid)
CBDVA (Cannabidivarinic acid)
CBCVA (Cannabichromevarinic acid)

The 66 cannabinoids found in Cannabis have been divided into 10 subclasses by Brenneisen (2007) Table 1 presented below.

TABLE 1

| | Cannabinoids | |
|---|---|---|
| Compound | Structure | Main pharmacological characteristics |
| Cannabigerol class | | |
| Cannabigerolic acid (CBGA) | 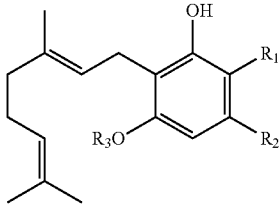 $R_1 = COOH, R_2 = C_5H_{11}, R_3 = H$ | Antibiotic |
| Cannabigerolic acid monomethylether (CBGAM) | $R_1 = COOH, R_2 = C_5H_{11}, R_3 = CH_3$ | |
| Cannabigerol (CBG) | $R_1 = H, R_2 = C_5H_{11}, R_3 = H$ | Antibiotic Antifungal Anti-inflammatory Analgesic |
| Cannabigerol monomethylether (CBGM) | $R_1 = H, R_2 = C_5H_{11}, R_3 = CH_3$ | |
| Cannabigerovarinic acid (CBGVA) | $R_1 = COOH, R_2 = C_3H_7, R_3 = H$ | |
| Cannabigerovarin (CBGV) | $R_1 = H, R_2 = C_3H_7, R_3 = H$ | |
| Cannabichromene class | | |
| Cannabichromerinoc acid (CBCA) | 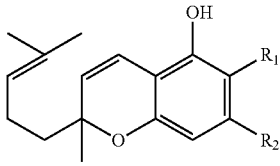 $R_1 = COOH, R_2 = C_5H_{11}$ | |
| Cannabichromene (CBC) | $R_1 = H, R_2 = C_5H_{11}$ | Anti-inflammatory Antibiotic Antifungal Analgesic |
| Cannabichromevarinic acid (CBCVA) | $R_1 = COOH, R_2 = C_3H_7$ | |
| Cannabichromevarin (CBCV) | $R_1 = H, R_2 = C_3H_7$ | |

TABLE 1-continued

Cannabinoids

| Compound | Structure | Main pharmacological characteristics |
|---|---|---|
| *Cannabidiol class* | | |
| Cannabidiolic acid (CBDA) | 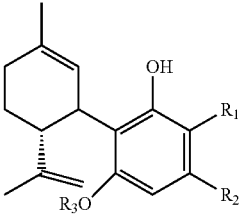 $R_1 = COOH, R_2 = C_5H_{11}, R_3 = H$ | Antibiotic |
| Cannabidiol (CBD) | $R_1 = H, R_2 = C_5H_{11}, R_3 = H$ | Anxiolytic Antipsychotic Analgesic Anti-inflammatory Antioxydant Antispasmodic |
| Cannabidiol monomethylether (CBDM) | $R_1 = H, R_2 = C_5H_{11}, R_3 = CH_3$ | |
| Cannabidiol-C$_4$ (CBD-C$_4$) | $R_1 = H, R_2 = C_4H_9, R_3 = H$ | |
| Cannabidivarinic acid (CBDVA) | $R_1 = COOH, R_2 = C_3H_7, R_3 = H$ | |
| Cannabidivarin (CBDV) | $R_1 = H, R_2 = C_3H_7, R_3 = H$ | |
| Cannabidiorcol (CBD-C$_1$) | $R_1 = H, R_2 = CH_3, R_3 = H$ | |
| *Delta-9-tetrahydrocannabinol class* | | |
| Delta-9-tetrahydrocannabinolic acid A (THCA-A) | 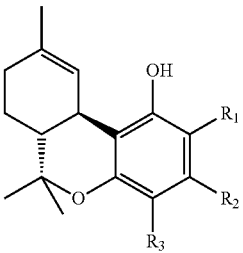 $R_1 = COOH, R_2 = C_5H_{11}, R_3 = H$ | |
| Delta-9-tetrahydrocannabinolic acid B (THCA-B) | $R_1 = H, R_2 = C_5H_{11}, R_3 = COOH$ | |
| Delta-9-tetrahydrocannabinol (THC) | $R_1 = H, R_2 = C_5H_{11}, R_3 = H$ | Euphoriant Analgesic Anti-inflammatory Antioxidant Antiemetic |
| Delta-9-tetrahydrocannabinolic acid-C$_4$ (THCA-C$_4$) | $R_1 = COOH, R_2 = C_4H_9, R_3 = H$ or $R_1 = H, R_2 = C_4H_9, R_3 = COOH$ | |
| Delta-9-tetrahydrocannabinol-C$_4$ (THC-C$_4$) | $R_1 = H, R_2 = C_4H_9, R_3 = H$ | |
| Delta-9-tetrahydrocannabivarinic acid (THCVA) | $R_1 = COOH, R_2 = C_3H_7, R_3 = H$ | |
| Delta-9-tetrahydrocannabivarin (THCV) | $R_1 = H, R_2 = C_3H_7, R_3 = H$ | Analgesic Euphoriant |

TABLE 1-continued

Cannabinoids

| Compound | Structure | Main pharmacological characteristics |
|---|---|---|
| Delta-9-tetrahydrocannabiorcolic acid (THCA-$C_1$) | $R_1$ = COOH, $R_2$ = $CH_3$, $R_3$ = H or $R_1$ = H, $R_2$ = $CH_3$, $R_3$ = COOH | |
| Delta-9-tetrahydrocannabiorcol (THC-$C_1$) | $R_1$ = H, $R_2$ = $CH_3$, $R_3$ = H | |
| Delta-7-cis-iso-tetrahydrocannabivarin | $R_1$ = $C_3H_7$ | |

Delta-8-tetrahydrocannabinol class

| Compound | Structure | Main pharmacological characteristics |
|---|---|---|
| Delta-8-tetrahydrocannabinolic acid ($\Delta^8$-THCA) | $R_1$ = COOH, $R_2$ = $C_5H_{11}$ | |
| Delta-8-tetrahydrocannabinol ($\Delta^8$-THC) | $R_1$ = H, $R_2$ = $C_5H_{11}$ | Similar to THC (less potent) |

Cannabicyclol class

| Compound | Structure | Main pharmacological characteristics |
|---|---|---|
| Cannabicyclolic acid (CBLA) | $R_1$ = COOH, $R_2$ = $C_5H_{11}$ | |
| Cannabicyclol (CBL) | $R_1$ = H, $R_2$ = $C_5H_{11}$ | |
| Cannabicyclovarin (CBLV) | $R_1$ = H, $R_2$ = $C_3H_7$ | |

Cannabielsoin class

| Compound | Structure | Main pharmacological characteristics |
|---|---|---|
| Cannabielsoic acid A (CBEA-A) | $R_1$ = COOH, $R_2$ = $C_5H_{11}$, $R_3$ = H | |

TABLE 1-continued

Cannabinoids

| Compound | Structure | Main pharmacological characteristics |
|---|---|---|
| Cannabielsoic acid B (CBEA-B) | $R_1 = H, R_2 = C_5H_{11}, R_3 = COOH$ | |
| Cannabielsoin (CBE) | $R_1 = H, R_2 = C_5H_{11}, R_3 = H$ | |

Cannabinol and cannabinodiol class

| Compound | Structure | Main pharmacological characteristics |
|---|---|---|
| Cannabinolic acid (CBNA) | $R_1 = H, R_2 = COOH, R_3 = C_5H_{11}$ | |
| Cannabinol (CBN) | $R_1 = H, R_2 = H, R_3 = C_5H_{11}$ | Sedative Antibiotic Anticonvulsant Anti-inflammatory |
| Cannabinol methylether (CBNM) | $R_1 = CH_3, R_2 = H, R_3 = C_5H_{11}$ | |
| Cannabinol-$C_4$ (CBN-$C_4$) | $R_1 = H, R_2 = H, R_3 = C_4H_9$ | |
| Cannabivarin (CBV) | $R_1 = H, R_2 = H, R_3 = C_3H_7$ | |
| Cannabinol-$C_2$ (CBN-$C_2$) | $R_1 = H, R_2 = H, R_3 = C_2H_5$ | |
| Cannabiorcol (CBN-$C_1$) | $R_1 = H, R_2 = H, R_3 = CH_3$ | |
| Cannabinodiol (CBND) | $R = C_5H_{11}$ | |
| Cannabinodivarin (CBVD) | $R = C_3H_7$ | |

Cannabitriol class

| Compound | Structure | Main pharmacological characteristics |
|---|---|---|
| Cannabitriol (CBT) | $R_1 = H, R_2 = OH, R_3 = C_5H_{11}$ | |
| 10-Ethoxy-9-hydroxy-delta-6a-tetrahydrocannabinol | $R_1 = H, R_2 = OC_2H_5, R_3 = C_5H_{11}$ | |
| 8,9-Dihydroxy-delta-6a-tetrahydrocannabinol | $R_1 = OH, R_2 = H, R_3 = C_5H_{11}$ | |
| Cannabitriolvarin (CBTV) | $R_1 = H, R_2 = OH, R_3 = C_3H_7$ | |
| Ethoxy-cannabitriolvarin (CBTVE) | $R_1 = H, R_2 = OC_2H_5, R_3 = C_3H_7$ | |

TABLE 1-continued
Cannabinoids
| Compound | Structure | Main pharmacological characteristics |
|---|---|---|
| Miscellaneous cannabinoids class | | |
| Dehydrocannabifuran (DCBF) | 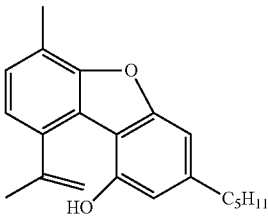 | |
| Cannabifuran (CBF) | 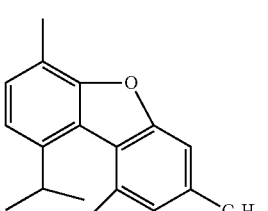 | |
| Cannabichromanon (CBCN) | 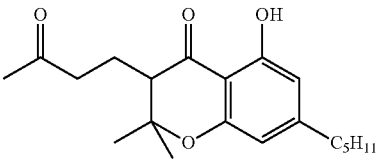 | |
| Cannabicitran (CBT) | 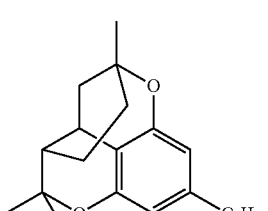 | |
| 10-Oxo-delta-6a-tetrahydrocannabinol (OTHC) | 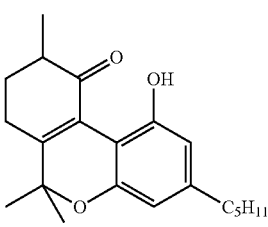 | |
| Delta-9-cis-tetrahydrocannabinol (cis-THC) | 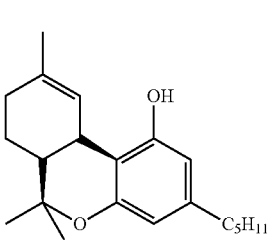 | |

TABLE 1-continued

Cannabinoids

| Compound | Structure | Main pharmacological characteristics |
|---|---|---|
| 3,4,5,6-Tetrahydro-7-hydroxy-alpha-alpha-2-trimethyl-9-n-propyl-2,6-methano-2H-1-benzoxocin-5-methanol (OH-iso-HHCV) | 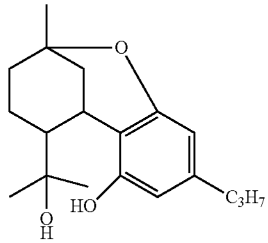 | |
| Cannabiripsol (CBR) | 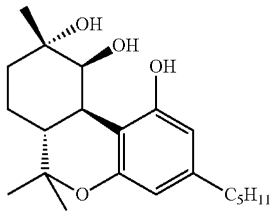 | |
| Trihydroxy-delta-9-tetrahydrocannabinol (triOH-THC) | 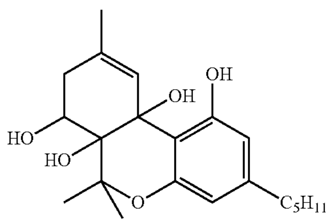 | |

Terpenoids of the Essential Oil from Cannabis by Brenneisen (2007) are in Table 2 presented below:

TABLE 2

Terpenoids of the Essential Oil From Cannabis

| Compound | Class[a] | Structure | Percentage Ref. 32 | Ref. 29 |
|---|---|---|---|---|
| Myrcene | M | | 32.9-67.1 | 29.4-65.8 |
| Limonene | M | | 16.3-17.7 | 0.9-1.5 |

TABLE 2-continued

Terpenoids of the Essential Oil From Cannabis

| Compound | Class[a] | Structure | Percentage Ref. 32 | Ref. 29 |
|---|---|---|---|---|
| Linalool | M | | 2.8-5.1 | 0.002 |
| trans-Ocimene | M | | | 2.3-5.7 |
| beta-Pinene | M | | 2.2-2.5 | 1.3-1.6 |
| alpha-Pinene | M | | 1.1-1.6 | 6.0-8.4 |
| beta-Caryophyllene | S | | 1.3-5.5 | 19.5-31.4 |
| delta-3-Carene | M | | | 0.8-1.0 |
| trans-gamma-Bisabolene | S | | 0.7-3.9 | |

TABLE 2-continued

Terpenoids of the Essential Oil From Cannabis

| Compound | Class[a] | Structure | Percentage Ref. 32 | Ref. 29 |
|---|---|---|---|---|
| trans-alpha-Farnesene | S | | 0.6-2.7 | |
| beta-Fenchol | M | | 0.4-1.0 | |
| beta-Phellandrene | M | | | 0.4 |
| alpha-Humulene (alpha-Caryophyllene) | S | | 0.3-2.1 | 3.3-3.4 |
| Guajol | S | | 0.3-1.8 | |
| alpha-Guaiene | S | | 0.3-1.2 | |
| alpha-Eudesmol | S | | 0.2-1.4 | |

TABLE 2-continued

Terpenoids of the Essential Oil From Cannabis

| Compound | Class[a] | Structure | Percentage Ref. 32 | Ref. 29 |
|---|---|---|---|---|
| Terpinolene | M | | 0.2-1.1 | 3.4-5.6 |
| alpha-Selinene | S | | 0.2-0.7 | |
| alpha-Terpineol | M | | 0.2-0.5 | |
| Fenchone | M | | 0.2-0.4 | |
| Camphene | M | | 0.2-0.4 | |
| cis-Sabinene hydrate | M | | 0.2-0.5 | |
| cis-Ocimene | M | | traces-0.2 | 0.2-0.3 |
| beta-Eudesmol | S | | 0.1-1.1 | |

TABLE 2-continued
Terpenoids of the Essential Oil From Cannabis
| Compound | Class[a] | Structure | Percentage Ref. 32 | Ref. 29 |
|---|---|---|---|---|
| beta-Selinene | S | 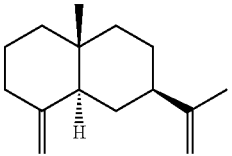 | 0.1-0.6 | 0.2-0.4 |
| alpha-trans-Bergamotene | S | 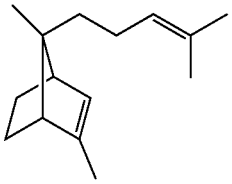 | 0.1-0.5 | 0.4-0.6 |
| gamma-Eudesmol | S | 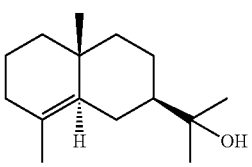 | 0.1-0.5 | |
| Borneol | M | 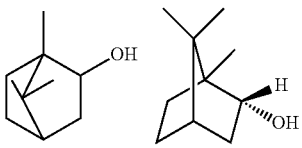 | 0.1-0.3 | 0.008 |
| cis-beta-Farnesene | S | 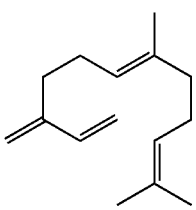 | 0.1-0.3 | 0.6-0.9 |
| gamma-Curcumene | S | 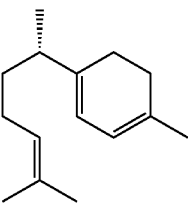 | 0.1-0.3 | |
| cis-gamma-Bisabolene | S | 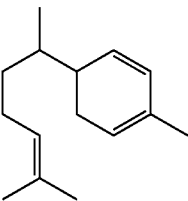 | 0.1-0.3 | |

TABLE 2-continued

Terpenoids of the Essential Oil From Cannabis

| Compound | Class[a] | Structure | Percentage Ref. 32 | Ref. 29 |
|---|---|---|---|---|
| alpha-Thujene | M | 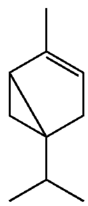 | | 0.1-0.2 |
| epi-alpha-Bisabolol | S | 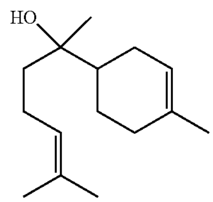 [SMILES: CC(C)=CCCC(C)(O)C1CC=C(C)CC1] | | 0.1-1.2 |
| Ipsdienol | M | 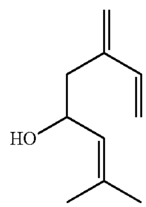 | | traces-0.1 |
| alpha-Ylangene | S | 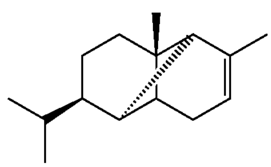 | | traces-0.1 |
| beta-Elemene | S | 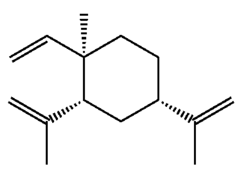 | | traces-0.2 |
| alpha-cis-Bergamotene | S | 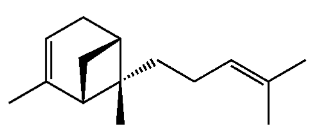 | | traces-0.6 |
| gamma-Muurolene | S | 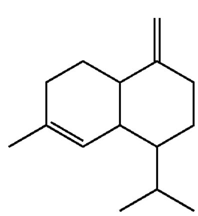 | | traces-0.1 |
| alpha-Cadinene | S | 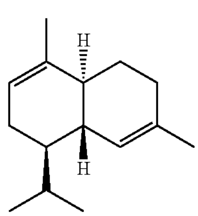 | | traces-0.1 |

TABLE 2-continued

Terpenoids of the Essential Oil From Cannabis

| Compound | Class[a] | Structure | Percentage Ref. 32 | Ref. 29 |
|---|---|---|---|---|
| alpha-Longipinene | S | | traces-0.1 | |
| Caryophyllene oxide | S | | traces-0.8 | |

[a]M, monoterpene; S, sesquiterpene.

More generally, the field of the invention relates compositions with improved bioavailability, the compositions comprising an aqueous medium with reduced-size water cluster populations of $H_2O$ molecules and a selected non-aqueous substance. The field of the invention also relates to methods for making the improved bioavailability compositions comprising the aqueous medium with the reduced-size water cluster populations of $H_2O$ molecules and a selected non-aqueous substance. The field of the invention also relates to methods for using the improved bioavailability composition comprising aqueous medium with the reduced-size water cluster populations of $H_2O$ molecules and a selected non-aqueous substance.

Invention Attributes

Embodiments of the present invention have a number of useful and novel properties. The process creates nano-sized clusters of water molecules which envelope non-$H_2O$ substances which have been added in the process of the invention. For example, some process embodiments of the invention can be used to make nano-sized clusters of water molecules enveloping nano-sized particles of CBD. Based on Malvern Zetasizer measurements, the nano-sized clusters of water molecules enveloping nano-sized particles of CBD have a measured size of between about 10 nanometers to about 200 nanometers. Surprisingly, the nanosize of these products are stable for years. Also surprising is the increased bioavailability of these nanosized products of the invention which appear to be a more efficient cellular delivery system for particles or nutritional agents. Interestingly, nanosized products of the invention are stable and functional in both ionic and non-ionic environments. The size range of the nano-sized products depends upon the kind of non-$H_2O$ substance. The size of the nano-sized products commonly has been measured to be between about 5 nm to about 200 nm range.

Example Utility Embodiments of the Present Invention

Some example embodiments of the present invention are a hydration drink for mammals including humans and animals. Drinks for meals, for water bottles, for water coolers, for beverages sold in bottles, beer, wine—all can have a higher bioavailability when manufactured using an embodiment process of the invention. Higher bioavailability beverages are needed by athletes, outdoors persons, office workers, people camping and hiking.

Some embodiments of the present invention are expected to be an effective means for increasing growth and body weight in mammals including humans and farm animals, such as chickens, pigs, and cattle. It is anticipated that some embodiments of the present invention can greatly improve fish and seafood farms using large ponds of nanowater containing nano-sized minerals and food particles. Other embodiments of the present invention are expected to be useful as a means for stimulating root and leaf development in plants, increasing growth rates, increasing heat tolerance, and drought tolerance. Invention embodiments are also expected to be useful for improving the quality and yields of organic foods grown from plants and fruit production from trees. It is hypothesized that this may be due to the increased rates of water uptake, mineral uptake, and photosynthesis by plants and trees that will allow them to use less water, smaller amounts of fertilizer, and need less hours of sunlight to grow.

Some embodiments of the present invention, may be more effective as a source of water for making an isotonic saline for intravenous use in a mammal. Some pharmaceutical formulation embodiments of the present invention formulated using nanowater and a pharmaceutical drug may be expected to have improved pharmacokinetics including increased bioavailability. The expected number of useful applications of some embodiments of the invention is expected to become a result of greater usefulness of nanowater containing nano-sized non-$H_2O$ ingredients in hospital settings including operations involving heart transplants, liver transplants, lung transplants, and kidney transplants. In addition, some embodiments of the present invention are expected to replace current forms of water (deionized water, doubly-distilled water, and sterile water products) used in cell culture, tissue, and organ studies. In addition, when an organ donor provides urgently needed organs, the organ retrieval, hours of transport and storage may be improved when the source of water used to prepare the saline used to incubate the organ is made from a nanowater embodiment of the present invention.

It is contemplated that specific embodiments of the present invention may use nano-sized particles in ultra-purified water as a means for increasing oral drug bioavailability, and used as a means for increasing drug potency, and lowering the dosing of the mammalian patient with a drug. The use of lesser amounts of a drug is expected to be beneficial by causing a lower drug loading of the patient and less drug side effects, less development of metabolic, psychological tolerance and less liver metabolic stress. For example, nano-sized particles of a selected drug in ultra-purified water could be used as a means for increasing drug potency of antibiotics, or analgesics.

It is expected that some specific embodiments of the present invention which comprise nano-sized particles of a selected drug in ultra-purified water may be useful drug formulation which is more efficient for increasing exercise ability of in a mammal, for increasing mental alertness, for increasing recovery from dehydration, for treating hypothermia in a mammal, or for treating heat stroke in a mammal.

In some cases the nano-sized particles of a selected drug in ultra-purified water may create a more efficient drug delivery device for improving the mental thinking or for treating psychological depression in a mammal.

In some embodiments of the present invention, an administration of nano-sized particles of a selected anti-inflammatory drug in ultra-purified water in combination with an immune system dis-inhibitor in ultra-purified water could be a therapeutic means for more effectively treating shock and inflammation caused from a severe trauma to a mammal.

Figure 11:
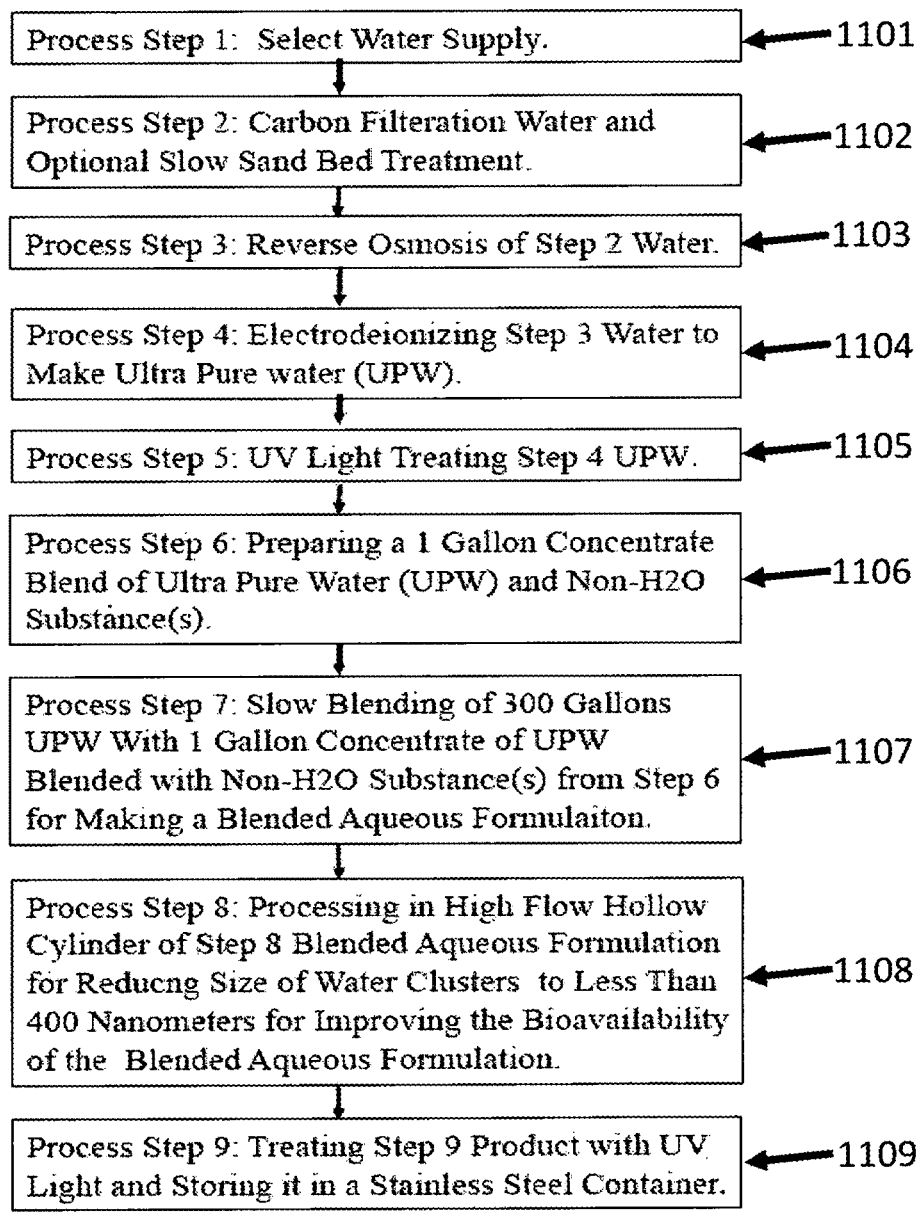
FIG. 11 depicts a flow chart for an experimental prototype process of the present invention with 9 process steps for making an invention embodiment which is an aqueous medium with nanosized water clusters coating a non-H₂O particle. The nanosizing process of the non-H₂O particle improves the bioavailability of the non-H₂O particle. After considerable experimentation, the inventors uncovered a number of limitations in the nine-step process depicted in the FIG. 11 flow chart. There are at least five limitations with the FIG. 11 production process. First, all steps 1101 to 1109 need to be controlled manually for successful operation of the apparatus. Second, blending step 1107 is particularly time-consuming and potentially results in an incomplete blending process. Third, the nanosizing equipment used in step 1108 is only a single unit hollow cylinder with one nozzle and is likely to do incomplete nanosizing of the water clusters of the non-H₂O particles. Fourth, the system was designed to only operate up to a 300 gallon size production batch. Fifth, the initial process steps 1101-1105 are not designed to continuously make ultrapure water so production cannot be continuous.

Example of the Steps of a Process for a Nano-water Containing a Nano-sized Non-H$_2$O Ingredient Embodiment of the Present Invention in Accordance with the List of Steps Depicted in FIG. 11.

Process Step 1 is Selecting a Suitable Water Supply (See FIG. 11)

Process Step 1 is selecting a suitable water supply to purify to make ultrapure water (UPW) in a four-step process. By the present invention, an example process for making most embodiments of the present invention, involves a first process step which is selecting a suitable water supply and preferably this is a fresh water supply. If one must begin the process by selecting a sea water or high salt containing water as a water supply then a distilling of or an evaporating of a salt-containing water is a means for making a fresh water condensate that can be used as a fresh water supply. A preferred fresh water supply is safe to drink and includes water from a municipal treated water supply, a fresh water lake, a fresh water river, or an uncontaminated ground water supply. Safe to drink means the fresh water has been tested to determine if the water supply is orally non-toxic to a mammal, meaning the safe to drink water contains nil levels or amounts of pathogenic microorganisms and toxic chemicals.

For example, a safe to drink fresh water supply preferably has immeasurable (meaning "nil") levels/amounts of the following pathogens and toxins: (a) pathogenic bacteria (for example fecal coliform), viruses (for example hepatitis viruses, hemorrhagic viruses, retroviruses such as AIDS virus), fungi, mycoplasm, protozoa, prokaryotes, Protista, parasites, microorganisms causing infectious diseases, and their spores, eggs, DNA, RNA, or related reproductive constituents, prions, (b) toxic biochemical including toxic proteins, lipids, carbohydrates, toxic nucleic acids, known carcinogens, and chemotherapy drugs; (c) toxic inorganic chemicals (soluble and insoluble in water, and including toxic heavy metals) and their particles; (d) toxic organic chemicals (soluble and insoluble in water, and pesticides) and their particles; (e) non-water organic liquids (miscible and immiscible); (f) radioactive minerals, and (g) toxic gases including ammonia, arsenic pentafluoride, arsine, bis(trifluoromethyl)peroxide, boron tribromide, boron trichloride, boron trifluoride, bromine, bromine chloride, boromethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde, germane, hexylethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perfluoroisobuytlene, phosgene, phosphine, phosphorus pentafluoride, selenium hexafluoride, silicon hexafluoride, silicon tetrachloride, stilbene, disulfur decafluoride, sulfur tetrafluoride, tellurium hexafluoride, tetraethyl pyrophosphate, tetraethyl dithiopyrophosphate, trifluoroacetyl chloride, tungsten hexafluroide, and radon. A nil levels or nil amounts means that the level or amount is so low that it is technically immeasurable or undetectable.

Process Step 2A is a Carbon Filtering of the Suitable Water Supply (See FIG. 11)

FIG. 11 provides a flow chart of an example of a 9-step process for making a product of the present invention and is not intended as a limiting example for embodiments of the invention directed to making products of the invention. Step 2 is a carbon filtering of the suitable water supply to be sure to remove any chlorine chemicals content (see FIG. 11, 1101). For example, several hundred gallons of Process Step 1 water may be used to perform Step 2 so that chlorine chemicals are removed prior to the Step 3 reverse osmosis process. This is done because chlorine chemicals can damage reverse osmosis membranes. In addition, carbon filtering is a method of filtering that uses a bed of activated carbon to usefully remove contaminants and impurities, using chemical adsorption. Each particle, or granule, of carbon provides a large surface area, or pore structure, allowing contaminants the maximum possible exposure to the active sites within the filter media. One gram of activated carbon has a surface area in excess of 3,000 meters$^2$ (32,000 sq. ft.). Activated carbon works via a process called adsorption, whereby pollutant molecules in the fluid to be treated are trapped inside the pore structure of the carbon substrate. Active charcoal carbon filters are most effective at removing chlorine, particles such as sediment, volatile organic compounds (VOCs), taste and odor from water. They are not effective at removing minerals, salts, and dissolved inorganic substances. Typical particle sizes that can be removed by carbon filters range from 0.5 to 50 micrometers (from Carbon Filtering—Wikipedia, Oct. 1, 2018). Carbon filtering of the suitable water supply with a carbon filtration process is useful for removing chlorine when the suitable water supply from a municipal drinking water supply using chlorination (Wikipedia, Carbon Filtration).

Process Step 2B is an Optional Slow Sand Filter Treatment (See FIG. 11, 1102)

Optionally, a Process Step 2B is added for a filtering of the suitable water supply with a slow sand filter. If the water supply is low quality water then a process of the filtering of the suitable water supply from Process Step 1 with a slow sand filter process Step 2B may be necessary prior to or following the step of filtering of the suitable water supply with the carbon filtration process. For example, the slow sand filter can be used in water purification for treating raw water to produce a potable product. The slow sand filter may be 3-6 feet deep, and rectangular or cylindrical in cross section. The length and breadth of the tanks will be in part determined by the flow rate desired by the filters, which typically have a loading rate of 50-100 gallons per hour per square yard (or 0.2-0.4 cubic yards per square yard per hour). A slow sand filter works through the formation of a gelatinous layer (or biofilm) called the hypogeal layer or Schmutzdecke in the top few millimeters of the fine sand layer. The Schmutzdecke is formed in the first 10-20 days of operation and consists of bacteria, fungi, protozoa, rotifera and a range of aquatic insect larvae. As an epigeal biofilm ages, more algae tend to develop and larger aquatic organisms may be present including some bryozoa, snails and annelid worms. The surface biofilm is the layer that provides the effective purification in potable water treatment, the underlying sand providing the support medium for this biological treatment layer. As water passes through the hypogeal layer, particles of foreign matter are trapped in the mucilaginous matrix and soluble organic material is adsorbed. The contaminants in the water coming into the slow sand filter are metabolized by the bacteria, fungi and protozoa. The water produced from an efficient slow sand filter can have a 90-99% bacterial cell count reduction. Slow sand filters gradually lose their performance as the biofilm thickens and thereby reduces the rate of flow through the filter. Eventually, it is necessary to refurbish the filter. Two methods are commonly used to do this. In the first, the top few millimeters of fine sand is scraped off to expose a new layer of clean sand. Water is then decanted back into the filter and re-circulated for a few hours to allow a new biofilm to develop. The filter is then filled to full volume and brought back into service. The second method, sometimes called wet harrowing, involves lowering the water level to just above the hypogeal layer, stirring the sand; thus precipitating any solids held in that layer and allowing the remaining water to wash through the sand. The filter column is then filled to full capacity and brought back into service. Wet harrowing can allow the filter to be brought back into service more quickly. Unlike other water filtration technologies that produce water on demand, slow sand filters produce water at a slow, constant flow rate and are usually used in conjunction with a storage tank for peak usage. Slow sand filters are recognized by the World Health Organization, Oxfam, and the United States Environmental Protection Agency as being superior technology for the treatment of surface water sources. According to the World Health Organization, "Under suitable circumstances, slow sand filtration may be not only the cheapest and simplest but also the most efficient method of water treatment." (Wikipedia, Slow Sand Filter). Process Step 3 is a Reverse Osmosis Water Purification (See FIG. 11, 1103)

Process Step 3 is performing a reverse osmosis water purification technology that uses, for example, a semipermeable membrane to remove ions, molecules and larger particles from drinking water (see FIG. 11, 1103) (Reverse Osmosis—Wikipedia). During the step 3 reverse osmosis process, an applied pressure is used to overcome osmotic pressure, a colligative property that is driven by chemical potential differences of the solvent, a thermodynamic parameter. Reverse osmosis can remove many types of dissolved and suspended species from water, including bacteria, and is used in both industrial processes and the production of potable water. The result is that the solute is retained on the pressurized side of the membrane and the pure solvent is allowed to pass to the other side. To be "selective", this membrane should not allow large molecules or ions through the pores (holes), but should allow smaller components of the solution (such as solvent molecules) to pass freely.

In the normal osmosis process, the solvent naturally moves from an area of low solute concentration (high water potential), through a membrane, to an area of high solute concentration (low water potential). The driving force for the movement of the solvent is the reduction in the free energy of the system when the difference in solvent concentration on either side of a membrane is reduced, generating osmotic pressure due to the solvent moving into the more concentrated solution. Applying an external pressure to reverse the natural flow of pure solvent, thus, is reverse osmosis. The process is similar to other membrane technology applications. However, key differences are found between reverse osmosis and filtration. The predominant removal mechanism in membrane filtration is straining, or size exclusion, so the process can theoretically achieve perfect efficiency regardless of parameters such as the solution's pressure and concentration. Reverse osmosis also involves diffusion, making the process dependent on pressure, flow rate, and other conditions. Reverse osmosis is most commonly known for its use in drinking water purification from seawater, removing the salt and other effluent materials from the water molecules. Rain water collected from storm drains is purified with reverse osmosis water processors and used for landscape irrigation and industrial cooling as a solution to the problem of water shortages. It is also used to clean effluent and brackish groundwater. The effluent in larger volumes (more than 500 m3/day) should be treated in an effluent treatment plant first, and then the clear effluent is subjected to reverse osmosis system. Treatment cost is reduced significantly and membrane life of the reverse osmosis system is increased. The process of reverse osmosis can be used for the production of deionized water. Reverse osmosis process for water purification does not require thermal energy. Flow-through reverse osmosis systems can be regulated by high-pressure pumps. The recovery of purified water depends upon various factors, including membrane sizes, membrane pore size, temperature, operating pressure, and membrane surface area. John Cadotte, of FilmTec Corporation, discovered that membranes with particularly high flux and low salt passage could be made, for example, by an interfacial polymerization of m-phenylene diamine and trimesoyl chloride. For these reverse osmosis membranes, an activated carbon filter to trap organic chemicals and chlorine, which will attack and degrade thin film composite membrane reverse osmosis membranes.

Formally, reverse osmosis is the process of forcing a solvent from a region of high solute concentration through a semipermeable membrane to a region of low solute concentration by applying a pressure in excess of the osmotic pressure. The largest and most important application of reverse osmosis is the separation of pure water from seawater and brackish waters; seawater or brackish water is pressurized against one surface of the membrane, causing transport of salt-depleted water across the membrane and emergence of potable drinking water from the low-pressure side. The membranes used for reverse osmosis have a dense layer in the polymer matrix—either the skin of an asymmetric membrane or an interfacially polymerized layer within a thin-film-composite membrane—where the separation occurs. In most cases, the membrane is designed to allow only water to pass through this dense layer while preventing the passage of solutes (such as salt ions). This process requires that a high pressure be exerted on the high concentration side of the membrane, usually 2-17 bar (30-250 psi) for fresh and brackish water, and 40-82 bar (600-1200 psi) for seawater, which has around 27 bar (390 psi) natural osmotic pressure that must be overcome. This process is best known for its use in desalination (removing the salt and other minerals from sea water to produce fresh water), but since the early 1970s, it has also been used to purify fresh water for medical, industrial, and domestic applications.

However, in some systems, an alternative method for performing Process Step 3 of the present invention is that the carbon pre-filter is omitted, and a cellulose triacetate membrane is used. CTA (cellulose triacetate) is a paper by-product membrane bonded to a synthetic layer and is made to allow contact with chlorine in the water. Up to 50% of the seawater input can be recovered as fresh water, though lower recoveries may reduce membrane fouling and energy consumption. High pressure pump—The high pressure pump supplies the pressure needed to push water through the membrane, even as the membrane rejects the passage of salt through it. Typical pressures for brackish water range from 1.6 to 2.6 MPa (225 to 376 psi). In the case of seawater, they range from 5.5 to 8 MPa (800 to 1,180 psi).

Membrane assembly: The layers of a membrane—The membrane assembly consists of a pressure vessel with a membrane that allows feed water to be pressed against it. The membrane must be strong enough to withstand whatever pressure is applied against it. Reverse osmosis membranes are made in a variety of physical configurations, with the two most common configurations being spiral-wound and hollow-fiber. Only a part of the saline feed water pumped into the membrane assembly passes through the membrane with the salt removed. The remaining "concentrate" flow passes along the saline side of the membrane to flush away the concentrated salt solution. The percentage of desalinated water produced versus the saline water feed flow is known as the "recovery ratio". This varies with the salinity of the feed water and the system design parameters: typically 20% for small seawater systems, 40%-50% for larger seawater systems, and 80%-85% for brackish water. The concentrate flow is at typically only 3 bar/50 psi less than the feed pressure, and thus still carries much of the high pressure pump input energy. The desalinated water purity is a function of the feed water salinity, membrane selection and recovery ratio. To achieve higher purity a second pass can be added which generally requires re-pumping. Purity expressed as total dissolved solids typically varies from 100 to 400 parts per million (ppm or mg/liter on a seawater feed. Reverse osmosis is an effective barrier to pathogens, but post-treatment provides secondary protection against compromised membranes and downstream problems. Disinfection by means of ultra violet (UV) lamps (sometimes called germicidal or bactericidal) may be employed to sterilize pathogens which bypassed the reverse osmosis process. Chlorination or chloramination (chlorine and ammonia) protects against pathogens which may have lodged in the distribution system downstream, such as from new construction, backwash, compromised pipes, etc. Due to its fine membrane construction, reverse osmosis not only removes harmful contaminants present in the water, but it also may remove many of the desirable minerals from the water. Since the 1970s, pre-filtration of high-fouling waters with another larger-pore membrane, with less hydraulic energy requirement, has been evaluated and sometimes used. However, this means that the water passes through two membranes and is often re-pressurized, which requires more energy to be put into the system, and thus increases the cost. Other recent developmental work has focused on integrating reverse osmosis with electro-dialysis to improve recovery of valuable deionized products, or to minimize the volume of concentrate requiring discharge or disposal. The latest developments in reverse osmosis membrane technology include nanoscale and graphene membranes.

Process Step 4 is an EDI Treatment (Electro-deionization Treatment) (See FIG. 11)

Process Step 4 is an electro-deionization (EDI) water treatment that utilizes electricity, ion exchange membranes and resin to deionize water and separate dissolved ions (impurities) from water—Wikipedia). It differs from other water purification technologies in that it is done without the use of chemical treatments and is usually a polishing treatment to the reverse osmosis (RO) treatment. There are also EDI units that are often referred to as continuous electro-deionization (CEDI) since the electric current regenerates the resin mass continuously. CEDI technique can achieve very high purity, with conductivity below 0.1 µS/cm. Recently, Argonne National Laboratory developed a process called Resin-Wafer Electro-deionization (RW-EDI), which uses a unique porous resin wafer mold made from immobilized loose ion-exchange resin beads. The resin wafer material enhances mass transfer between solid (resin bead) and liquid (feed solution) phases to achieve a high purity, especially when treating impaired or brackish water. When fed with low TDS (total dissolved solids) feed (e.g., feed purified by RO (reverse osmosis), the product can reach very high purity levels (e.g., 18 meg-ohms cm). The ion exchange resins act to retain the ions, allowing these to be transported across the ion exchange membranes. The main applications of EDI (electro-deionization) technology, such as that supplied by Ionpure, E-cell and SnowPure, are in electronics, pharmaceuticals and power generation.

The means by which an EDI process can work is as follows. The process uses two electrodes in an electrochemical cell. Each electrode may function as either the anode or the cathode depending on the voltage applied to the cell. One option is to use a bipolar electrode that can function as the anode of one cell and the cathode of another cell. When using a bipolar electrode each cell will have an electrode and a water soluble electrolyte with ions that can undergo either an oxidation or a reduction. The electrolyte in the electrochemical cell is a source of free ions so that the cell can conduct electricity between its two electrodes.

EDI occurs as the reverse osmosis water made from Process Step 3 is then passed between an anode (positive electrode) and a cathode (negative electrode). Ion-selective membranes allow the positive ions to separate from the water toward the negative electrode and the negative ions toward the positive electrode. This clear the water of remaining mobile anions and cations so that a high purity deionized water results An alternative method to practicing Process Step 4 of the present invention is to use Resin-Water Electro-deionization—RW-EDI is a process that targets the desalination of impaired water or water with salt levels of 1,000-10,000 ppm. RW-EDI process uses a porous ion exchange resin wafer with 195 cm² (cross-section surface area). Water is run through the wafer, while an electric current is applied to setup. Between resin wafer compartments there are concentrate compartments from which brine flows. An anode is situated on one side of the concentrate compartment and the cathode is situated on the other side of the concentrate compartment. When an electric current is used to charge ions that need to be removed by the EDI, positively charged ions that are formed will flow toward the cathode and then can be rinsed away in one direction by a flowing concentrate stream. Negatively charged ions that are formed will flow toward the anode and then can be rinsed away in the same direction by another flowing concentrate stream. As a result, there is a production of purified water between the cathode and the anode electrodes which can flow in the opposite direction from the waste charged ions produced by the EDI. The resin-wafer technology usefully increases the energy efficiency of the desalination process by 5-10 fold. (EDI-Wikipedia). The term in the art of water purification is that EDI process is a "final polishing treatment". EDI is very important because it is a process which increases the resistivity of the water to nearly its theoretical maximum of 18 meg-ohms Cm. In one embodiment of the present invention the method for making the ultra-pure water (UPW) is completed once the Process Step 4 of EDI is completed, and in that case the UPW can be stored in a stainless steel holding tank until it is needed. The process for making ultrapure water (UPW), for some embodiments of the present invention, may require about 8 hours to run thru process steps 1 to 4 to make 300 gallons of 18 meg-ohm Cm resistivity UPW. If it is decided to proceed to Process Steps 5-9 for making an embodiment of the invention, then preferably the UPW is prepared and stored for only a few hours before the UPW is carefully mixed with the non-$H_2O$ substance in the next step which is Process Step 3. UltraPure Water (UPW) has about an 18.2 MΩ·cm resistivity. Small concentrations of ion impurities in UPW will greatly reduce UPW resistivity (increased electrical conductivity) which is why measurements of water resistivity a direct and rapid method to analyze quality of a volume of UPW before its use in the present processes of the invention.

Process Step 5 is a UV Light Exposure for Sterilizing the UPW (See FIG. 11, 1105)

Process step 5 is used as a means for sterilizing UPW. For example, the UPW may be treated with UV radiation at 260 nm for about 20 minutes. One option is to perform this UV radiation exposure of the UPW while the UPW is recirculating in a tank with a closed recirculation loop (see FIG. 12 for details). In one embodiment a volume of 300 Gallons of UPW is recirculated in a tank with a closed recirculation loop for at least 20 minutes. For example, the invention embodiments of the process for making the invention which are being tested in a Tampa, Florida clean room 1208 (see FIG. 12) indicate that the UV treatment of the UPW can heat the UPW to between 80° F. to 98° F. (Fahrenheit) from its initial of 70° F. to 85° F. (the temperature of the water supply entering the clean room 1208). Studies will test making invention embodiments at other temperature ranges for their utility in making the invention embodiments. The temperatures of the water processing in the present patent application are merely example temperatures. The process of making the invention is conceived to be possible with at any liquid water temperature but may need various parameters of the process of making the invention may need to be modified or optimized further.

Process Step 6 is an Initial Mixing of Non-$H_2O$ Substance(s) with 1 Gallon of UPW (See FIG. 11, 1106 and FIG. 12 Process Apparatus Schematic)

The mixing of non-$H_2O$ substance(s) with UPW preferably takes place in two separate containers. This allows one to carefully prepare the mixture of the Non-$H_2O$ substance(s) with UPW and to minimize how much air and dust may get into the process batch at this stage. First a particular formulation of non-$H_2O$ substances is selected to make almost 300 gallons of the composition of the invention. The Detailed Description of the Invention later on provides examples of formulations of the present invention.

In a "clean room" with Hepa air filtration, one mixing method is to place 30 ounces of UPW 1201 in a 32 ounce commercial blender 1202 such as a Blendex. One third of the non-$H_2O$ ingredients 1203 are then added to the ultra-purified water 1201 in the blender 1202. The UPW should be at least 15 meg-ohm cm resistivity. More preferably the resistivity UPW is between 16-18 meg-ohm cm. The mixture 1205 of UPW 1201 and non-$H_2O$ ingredients 1203 is then mixed by the blender 1202 for a period of time selected from the group consisting of 0.5, 1, 1.5, 2, 2.5, 3, 3.5, 4, 4.5, 5, 10, 15, 20, and 25 minutes. A blending time more than three minutes is used only if there the non-$H_2O$ substance that is being used has a poor water solubility. Optionally, three such blender 1202 mixings will be ultimately done one after the other and combined. This creates about one gallon of a mixed concentrate 1205 of the non-$H_2O$ substance in UPW. Some air may have been taken up into the gallon of the mixed concentrate.

Process Step 7 is a Blending of the 1 Gallon Concentrate 1205 into 300 Gallons of UPW (See FIG. 11, 1107 and FIG. 12 Process Apparatus Schematic)

Process of Blending the Concentrate 1205 with 300 Gallons of UPW 1207

Once mixed concentrate 1205 has been prepared by process step 6, then process step 7 is started. For process step 7, a closed mixing tank 1206 to which has been added 300 gallons of UPW 1207 in the clean room 1208 is pumped in a closed recirculation loop 1209 from the tank bottom drain 1214 to the top entry port of mixing tank 1206 using recirculation pump 1210. The closed mixing tank 1206 has a micron-size air filter 1211 to shield the tank contents from any dust particle introduction. While the mixing tank 1206 is recirculating the 300 gallons of UPW 1207, the gallon of the mixed concentrate 1205 is slowly pumped over about 20 minutes using a concentrate pump 1212 and a pipe 1200 to slowly add the mixed concentrate 1205 into mixing tank 1206 containing the 300 gallons of UPW 1207. As a result, after a minimum of 20 minutes the process ensures that the mixing tank 1206 contains a blended aqueous formulation 1213 of about 300 gallons in volume. When the term "non-$H_2O$ substance 1203" is used it means the same thing as the "non-$H_2O$ ingredients 1203".

Invention process temperatures at the inventor's production facility caused the blended aqueous formulation 1213 at the end of Process Step 5 to have a temperature between 77° F. and 98° F. For example in one experiment, the blended aqueous formulation 1213 comprising a blend of the UPW 1201, the UPW 1207 and the non-$H_2O$ substance 1203 at the end of Process Step 5 was measured to have a temperature of 96.4° F., a pH of 6.06, and an oxidation-reduction potential (ORP) of 89.5 mV. The pH and ORP values measured at the end of process step 5 can have different values depending upon the chemistry of the ingredients once mixed in the UPW. The term "additives to the UPW" shall mean the same as "the non-$H_2O$ substance added to the UPW". For some embodiments of the present invention, in the Process steps 1 to 5, the temperature of the UPW, its pH, and the ORP will be adjusted and controlled before proceeding to Process step 6. One method of controlling the UPW temperature, pH, and ORP for the present invention is to use a controlled temperature clean room and tanks with cooling equipment. Also, a pH buffer and an ORP buffer system can be included in the UPW containing the non-$H_2O$ substance to control the pH and ORP.

Process Step 8 is a Reducing the Size of Water Clusters in the UPW Containing Non-$H_2O$ Substance(s). (See FIG. 11, 1108 and FIG. 12 Process Apparatus Schematic).

Process Step 8 and its apparatus are well detailed in FIG. 12. Process Step 8 is performed so as to reduce the size of water clusters in blended aqueous formulation 1213. Blended aqueous formulation 1213 is pumped by a variable speed controlled pump 1216 using a transfer pipe 1217 from the closed mixing tank 1206 to a hollow cylinder 1218. The cylinder top 1219 of the hollow cylinder 1218 has a 1 inch inner diameter (ID) center top hole 1221 as an access means for the transfer pipe 1217 to deliver the blended aqueous formulation 1213 comprising UPW 1201, UPW 1207, and non-H$_2$O substance(s) 1203 into the hollow cylinder 1218. The fluid pressure in the transfer pipe 1217 may be varied by changing the speed of the transfer pipe pump 1216. The fluid pressure in the transfer pipe 1217 is selected from the group consisting of 10-20 psi, 20-30 psi, 30-40 psi, 40-50 psi, 50-60 psi and 60-70 psi. The inventors discovered that the transfer pipe 1217 fluid pressure surprisingly and significantly affects the size of water clusters in the UPW containing non-H$_2$O substance(s). If the transfer pipe 1217 fluid pressure is too low during the process Step 8 process, then there is an insufficient decrease in the size distribution of the water clusters in the UPW containing non-H$_2$O substance(s). When the transfer pipe 1217 fluid pressure is too high during the process Step 8 process then there is an unwanted increase in the size of the water clusters in the UPW containing non-H$_2$O substance(s). Thus for some embodiments, the invention apparatus for the process Step 8 functions with optimum transfer pipe 1217 fluid pressure between about 25-50 pounds per square inch (psi), more preferably about 30-40 psi. For other embodiments for the invention apparatus, the psi values for the fluid pressure in transfer pipe 1217 will be different because the fluid pressure in transfer pipe 1217 depend upon the various sizes of the diameters, shapes and lengths of the invention apparatus pipes, jets, and chambers which are critical to process Step 8 fluid path flow. Specific variables include transfer pipe 1217 length and ID, nozzle 1222 and nozzle jet(s) 1223 lengths, dimensions and orientations, and hollow cylinder 1218 dimensions and exit flow dimensions, as well as the temperature and the aqueous viscosity of the blended aqueous formulation 1213. Optionally, during the pumping of the blended aqueous formulation 1213 the pressure in the transfer pipe 1217 may be stepped up and down between various selected pressures between various selected flow rates either manually by a process operator or automatically by a computer program algorithm providing a flow fluctuation wave form instructions to a microprocessor regulating the invention process apparatus. For some embodiments of the invention, the transfer pipe pump 1216 is used to create a transfer pipe 1217 fluid pressure between about 20-60 pounds/square inch (psi), more preferably between about 27-53 psi.

Relationship between Flow Rate in Transfer Pipe 1217 and Pressure in Said Pipe.

In addition, the fluid flow rate in the transfer pipe 1217 is directly proportional to the transfer pipe 1217 pressure. By varying the transfer pipe pump 1216 speed, the flow rate in the 1" ID transfer pipe 1217 may be selected from the group consisting of 10-25, 10, 11, 12, 14, 15, 16, 18, 20, 22, 24, and 25 gallons per minute (gal/min). Preferably the flow rate in a 1" ID transfer pipe 1217 is between 12-18 gal/min and more preferably the transfer pipe 1217 flow rate is 14-16 gallons per minute. Optionally, during the pumping by the transfer pipe pump 1216, the transfer pipe 1217 flow rate may be stepped up or down between various selected flow rates either manually by a process operator or automatically by a computer program algorithm providing a flow fluctuation wave form instructions to a microprocessor regulating the invention process apparatus.

Flow Rate Dependence of Some Processes of the Invention.

In Table 1 for Process Step 8 there is a study of the flow rate (10-16 gallons per minute) in terms of the flow rate dependence of some measureable fluid properties in the transfer pipe, in the hollow cylinder, and after expulsion from the hollow cylinder. See FIG. 12 for the process 8 apparatus. A sample (the "before" sample) is taken from transfer pipe 1217 before the hollow cylinder 1218 where the water cluster size is reduced during process Step 8 process. After the hollow cylinder 1218 where the water cluster size is reduced during process Step 8 a sample is taken from drain pipe 1235 (the "after" sample). When blended aqueous formulation 1213 is first pumped via transfer pipe 1217 into the hollow cylinder 1218, a centrally-located vertical vapor space in the hollow cylinder 1218 forms soon after flow is initiated. It is unclear what the source is of the vapor space. The vertical vapor space is noticed to be wider in diameter at lower flow rates through the hollow cylinder 1218 and this may be perhaps due to lower flow rates being associated with lower fluid driving pressures in transfer pipe 1217. Table 1 also lists that there is a 1 to 2° F. cooling of the blended aqueous formulation 1213, and a 1.5 pH drop in the blended aqueous formulation 1213 after versus compared to before the blended aqueous formulation 1213 has passed through the hollow cylinder 1218. At the lowest flow rate of 10 gallons per minute the pH drop is less, only 0.6 pH units. The pH drop in the blended aqueous formulation 1213 does not appear to be due to air contamination or acidifying carbon dioxide, because the largest pH drop would have occurred at the lowest flow rate, but this was not observed. The process 8 step is not exothermic but There is a pH drop for some unknown reason.

TABLE 1

Process Step 8 Example - Study of Flow Rate Dependence of Fluid Properties in the Transfer Pipe, in Hollow Cylinder, and after expulsion from Hollow Cylinder.

| | 16 gal/min | 14 gal/min | 12 gal/min | 10 gal/min |
|---|---|---|---|---|
| Transfer pipe flow rate (gallons/minute, gal/min) | | | | |
| Hollow cylinder inner dimensions in inches (width ", length ") | 4" × 18" | 4" × 18" | 4" × 18" | 4" × 18" |
| Temperature before (° F.) | 96.4° F. | 96.4° F. | 96.4° F. | 96.4° F. |
| Temperature after (° F.) | 94.5° F. | 94.5° F. | 95.3° F. | 95.4° F. |
| pH "before" | 6.06 | 6.06 | 6.06 | 6.06 |
| pH "after" | 4.49 | 4.49 | 4.49 | 5.43 |
| ORP (millivolts, mV) before | +89.5 mV | +89.5 mV | +89.5 mV | +89.5 mV |
| ORP (millivolts, mV) after (Oxidation Reduction Potential) | +148.6 mV | +148.6 mV | +146.3 mV | +140.9 mV |

An important objective of process Step 8 is to modify water clusters in the blended aqueous formulation 1213 to create an aqueous medium product with water clusters containing the non-H$_2$O substance(s) that are below 200 nanometers in size, preferably below 100 nanometers in size, and most preferably below 50 nanometers in size. When process variables have been optimized, then the reduced size of the water clusters containing the non-H₂O substance(s) in the aqueous medium product has been found to possess surprisingly improved bioavailability compared to ordinary water containing the non-H₂O substance(s). In other words, an important objective of the invention is that the process embodiments of the invention make improved bioavailability products. The product embodiments for various use formulations are generally described in some locations of the patent application by the term "product 1220". See FIG. 12, and FIG. 13.

Measurement of Water Cluster Size Containing a Non-H₂O Substance by the Malvern Zetasizer Instrument It is an important objective of the inventors that process embodiments, product embodiments, composition embodiments, formulation embodiments, and treatment method embodiments of the present invention are characterized by testing as best as technology presently permits. Some invention embodiments of the invention have been found to have surprising properties and cause surprising results, both of which have been validated by experiments described in the present specification. The reduction in water cluster size in nanometers in the products of the invention processes to about two (2) nanometers from more than 200 to 1000 nanometers in size can be measured using a Malvern Zetasizer as a "particle size". During production of product embodiments of the invention, measuring the size of the water clusters surrounding the non-H₂O substance will be quality validation test. The term "nano-sized non H₂O ingredients encapsulated in nano-sized water clusters shall mean a nano-sized water clustered structure. The terms encapsulating with water molecules, enveloping with water molecules, and water clustering have a similar meaning for the present invention. Unique to the present invention methods, processes, products, and treatment methods is the initial use of UPW (ultrapure water) in the invention processes used for making invention products. The terms nano-sized, nano-sizing, nanowater, and UPW nanosized with a non H₂O ingredient refer to and all relate to nano-sized structure resulting from interactions of ultrapure water with a non-H₂O substance.

Figure 7:
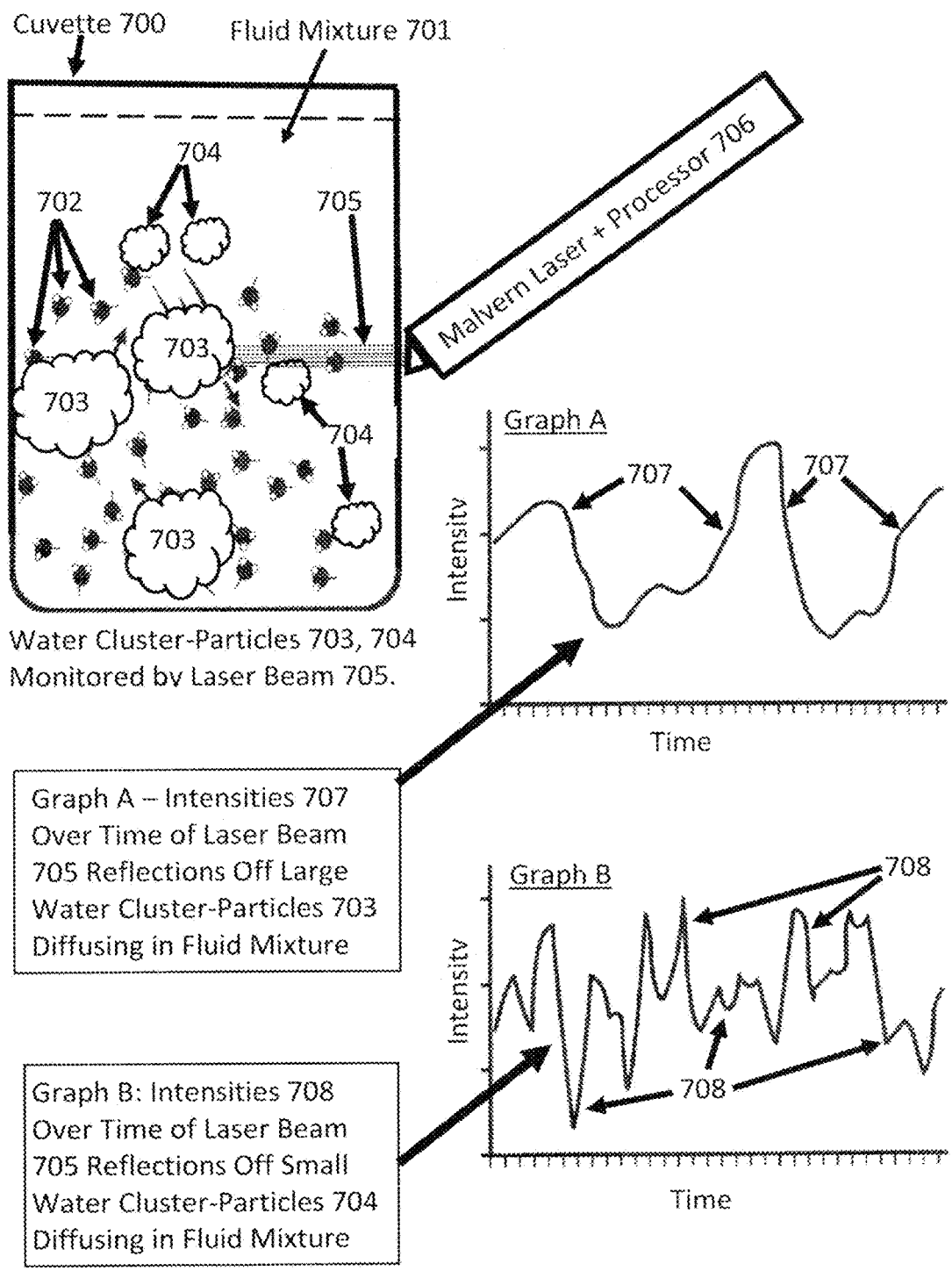
FIG. 7 depicts a method for measuring nano-sized particles by dynamic light scattering (DLS). Depicted is a hypothetical DLS test wherein a Malvern Laser+Processor send a scanning laser beam(s) 705 into the side wall of a laser light transparent cuvette 700 which contains a fluid mixture 701 in which there are water molecules 702, large water-clustered non-$H_2O$ particles 703, and small water-clustered non-$H_2O$ particles 704. By Brownian motion there is random diffusion of the water molecules 702, large water-clustered non-$H_2O$ particles 703, and small water-clustered non-H₂O particles 704 small water-clustered non-H₂O particles 704. When the laser beam 705 irradiates water-clustered non-H₂O particles 703 or 704, the laser beam 705 scatters reflections back to the Malvern laser light detectors. The scattered light then goes through a second polarizer where the scattered light is collected by a photo-multiplier and the resulting scattered light image is projected onto a screen. There is a scattered light speckle pattern which represents the molecules in the test sample solution being detected in such a way that the molecules diffract the light in all directions. The diffracted light from the laser light detected molecules can either interfere constructively (light regions) or destructively (dark regions). This process is repeated at short time intervals and the resulting set of speckle patterns are analyzed by an auto-correlator that compares the intensity of light at each spot over time. The polarizers can be set up in two geometrical configurations. One is a vertical/vertical (VV) geometry, where the second polarizer allows light through that is in the same direction as the primary polarizer. In vertical/horizontal (VH) geometry the second polarizer allows light not in same direction as the incident light.
Figure 8:
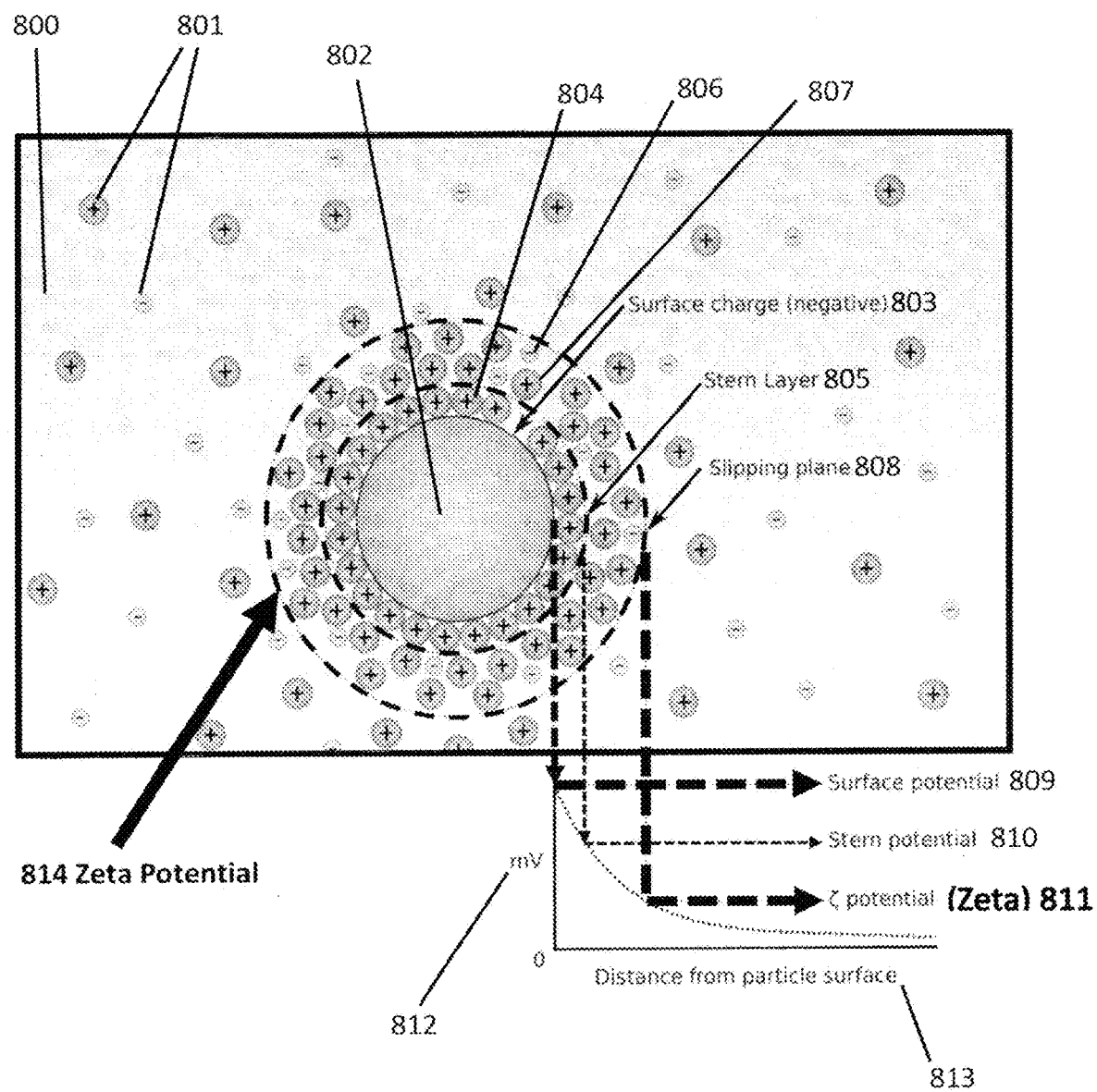
FIG. 8 depicts a prior art diagram of a theoretical model for a radial electrostatic charge distance 813 (mv) neutralization 812 of the static charge on the surface of a colloidal charged particle 802 at an interface 807 with an ionic aqueous medium 800 with cations 801 and anions 801. In this aqueous radial electrostatic charge neutralization model there are three regions 809, 810, and 811 with an electric potential. This model predicts 2 layers of aqueous ions. There is a measurable Zeta potential 811 but potentials 809 and 810 are theoretical.
Figure 9:
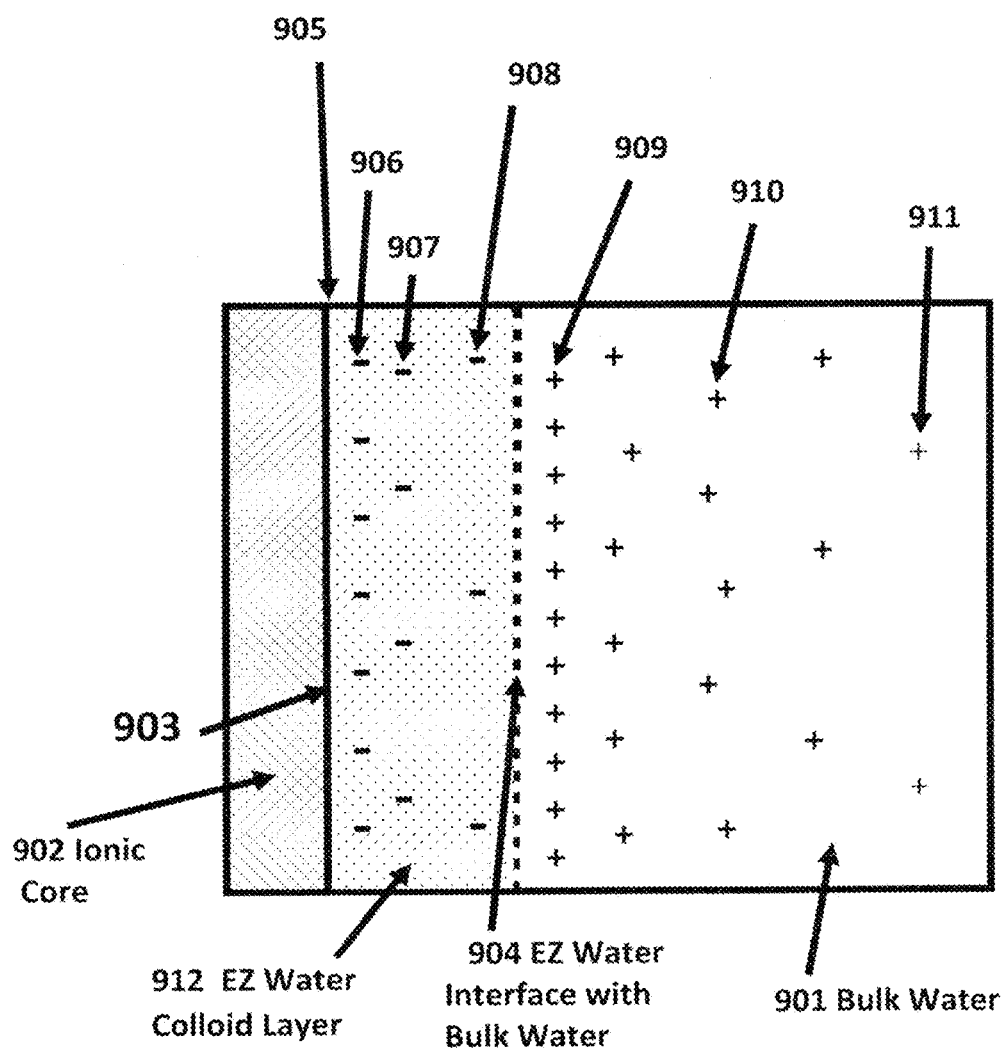
FIG. 9 depicts an alternative prior art theoretical model of the effect of a charged colloid in bulk ionic medium which contrasts with the theoretical model of FIG. 9.

For achieving reliable nanoparticle sizing, the inventors are using a Malvern Zetasizer Instrument with a HE-Ne laser ($\lambda$=633 nanometers) for performing a DLS (Dynamic Light Scattering) technology. Inventors are measuring nanowater encapsulated non-H₂O substances measurements in highly-purified and micron filtered aqueous media used in present invention process embodiment steps, final product embodiments which are compositions of non-H₂O substances in UPW, and in treatment embodiments of the present invention. Within testing constraints DLS is reliable. DLS is a method of using light scattering which is a consequence of the interaction of light with the electric field of a small particle or molecule. An incident photon induces an oscillating dipole in the electron cloud. As the dipole changes, energy is radiated in all directions. This radiated energy is called "scattered light" (Ryan Shaw, Atascientifc Au, 2019). The use of Dynamic Light Scattering is depicted in FIG. 7, which depicts that a particulate (or reflective object in a fluid such as a water cluster size) can be measured in nanometers using a Malvern Instruments Company Zetasizer. Particles in a fluid are constantly moving due to Brownian motion which is defined as the erratic random movement of microscopic particles in a fluid, as a result of continuous bombardment from molecules of the surrounding medium. The extent of the Brownian motion of a particle in a fluid is related to the size of the particles. Larger water clusters move slowly compared to smaller water clusters which move faster due to Brownian motion particle collisions. A direct light scattering (DLS) instrument can analyze the Brownian motion of the particles in fluid under controlled conditions. An aqueous medium sample of the water clusters in a product 1220 (see FIG. 12 for an example of the process apparatus invention embodiment) of the invention or an intermediate product containing particles or water clusters can be tested using the Malvern Zetasizer Instrument. The Zetasizer tracks the random movement of the water clusters using laser light scattering and then correlates the laser speckle pattern in the sample. From the changes in the intensity of the laser speckle pattern, the Malvern Zetasizer software calculates the nanometer sizes of the non-H₂O particles in water.

Using a Malvern Zetasizer DLS instrument, samples of ultrapure water were tested to determine ultrapure water (UPW) cluster sizes. It was not possible to study UPW with this instrument unless a very small amount of a non-H₂O substance was present in the UPW. It is expected that a non-H₂O substance in water will always be surrounded by a capsule of water molecules. The overall size of composites of non-H₂O particles in UPW is believed to be the nanosize measured by the Malvern Zetasizer DLS Instrument. Essentially the Zetasizer uses DLS (dynamic light scattering) to obtain data on a nanosized product of the present invention in an aqueous medium, and then uses a set of computer programs to identify various population size details concerning the nanosized product (nanoparticle) of the present invention in an aqueous medium. The Zetasizer instrument graphs the data to depict the nanoparticle size distributions. It becomes clear how many modes of nanoparticle sizes there are; the mean or median size at each mode, the width of each mode's distribution of sizes, and the skew/kurtosis profile of each mode's size distribution. See FIG. 7 for further details. The median water cluster sizes in an aqueous formulation of the present invention (invention processes intermediate products) were measured by a histogram data analysis of particle size data obtained using the Malvern Instruments Company Zetasizer DLS instrument on liquid samples of various embodiments of the present invention. Clusters of water containing non-H₂O substances are measured in nanometers and reported in FIGS. 15, 16, 17, 18, 27, and 28 in a Malvern Instruments Zetasizer particle size distribution report by Intensity. The Y-axis of the histogram indicates a linear scale for percent abundance of DLS detected particles. The X-axis of the histogram indicates a logarithmic scale ranging between 0.1 to 1000 nanometers for the aqueous non-H₂O particle sizes. Each report provides a specific computer calculated data aqueous non-H₂O particle size histogram. The inventors utilize this histogram data and its calculated aqueous non-H₂O particle median size data for studying invention embodiment products comprising formulation compositions which are aqueous medium comprising the water clusters with a non-H₂O substance(s). The DLS detected nanoparticles measured and analyzed by the Malvern Instruments Zetasizer DLS Instrument are assumed to be measurements of the invention embodiment water clusters containing non-H₂O substances.

Variations in Hollow Cylinder Apparatus and its Use in Process Step 8

For some apparatus embodiments for the process of making the products of the present invention, the angle of the long axis of the hollow cylinder 1218 is at an angle relative to the ground that may be changed. A vertical angle for the hollow cylinder 1218 is depicted in FIG. 12. Furthermore, the angle of the long axis of the hollow cylinder 1218 is defined 180° from the ground when the cylinder top 1219 is pointing away from gravity by 180°. In this case the tank drain 1227 points down (see FIG. 12 and FIG. 13). In another embodiment the cylinder top 1219 points downward and so the axis of the hollow cylinder is defined as pointing at 0°. When the axis of the hollow tank is horizontal then the axis of the hollow tank 2118 is 90° relative the force of gravity. In some embodiments the angle of the axis of the hollow tank is adjustable by a gimbal means supporting the hollow tank 1218. When the adjustable gimbal means is supporting the hollow tank, then the angle of the long axis of the hollow cylinder 1218 may be selected as an angle from the group consisting of 0°, 15°, 30°, 45°, 60°, 75°, 90°, 105°, 120°, 135°, 150°, 165°, and 180° degrees.

The interior surface 1225 of the hollow cylinder 1218 may be comprised of a plastic, a metal, or a glass material or another material capable of having a smooth surface or may have a smooth ridged surface in some embodiments. The interior surface 1225 should preferably be comprised of a material with a surface which will not undergo a chemical reaction with the blended aqueous formulation 1213. However, in some invention apparatus embodiments, a chemical reaction of the interior surface 1225 of the hollow cylinder 1218 and the blended aqueous formulation 1213 is an object of an embodiment of the invention. Such embodiments and processes will be later described. In one preferred embodiment the hollow cylinder 1218 has a wall 1226 of stainless steel. In some preferred embodiments a portion of the wall 1226 has a window section of the wall of a transparent material or the entire wall 1226 is all transparent material such as a transparent plastic such as transparent polyvinyl chloride (PVC) or polyethylene (PE) plastic. When the wall 1226 is transparent then the flow and continuity appearance of the blended aqueous formulation 1213 during Process Step 8 can be monitored.

In some apparatus embodiments of the invention, the hollow cylinder 1218 has a length 1228 which is between two to twenty-five (2 to 25) times longer than the inner width 1229 of the hollow cylinder 1218. Preferably the hollow cylinder 1218 has a length 1228 which is between 3 to 10 times longer than the inner width 1229 of the hollow cylinder 1218. More preferably the hollow cylinder 1218 has a length 1228 which is between 4-8 times longer than the inner width 1229 of the hollow cylinder 1218. Most preferably the hollow cylinder 1218 has a length 1228 which is between 4 to 5 times longer than the inner width 1229 of the hollow cylinder 1218. In one preferred embodiment for a 300 gallon mixing tank 1206, the transfer pipe 1217 has a 1" ID, the hollow cylinder 1218 has an inner length 1228 between 18 to 24 inches and an inner width 1229 between 3 to 5 inches. In a first prototype process example which is depicted in FIG. 12, the inventors used a transfer pipe 1217 with a 1" ID and a hollow cylinder 1218 with an inner length 1228 of about 18 inches and an inner width 1229 of about 4 inches. In a second prototype process the inventors used a transfer pipe 1217 with a 1" ID, and a hollow cylinder 1218 with an inner length 1228 of about 24 inches and an inner width 1229 of about 4 inches. Substitutes to hollow cylinder 1218 are contemplated which have other shape geometries and size ratios. It is planned to scale up the dimensions of the hollow cylinder 1218 for the Process 8 process as there becomes a need for a higher rate Process Step 8 and/or a more efficient Process Step 8.

Figure 13:
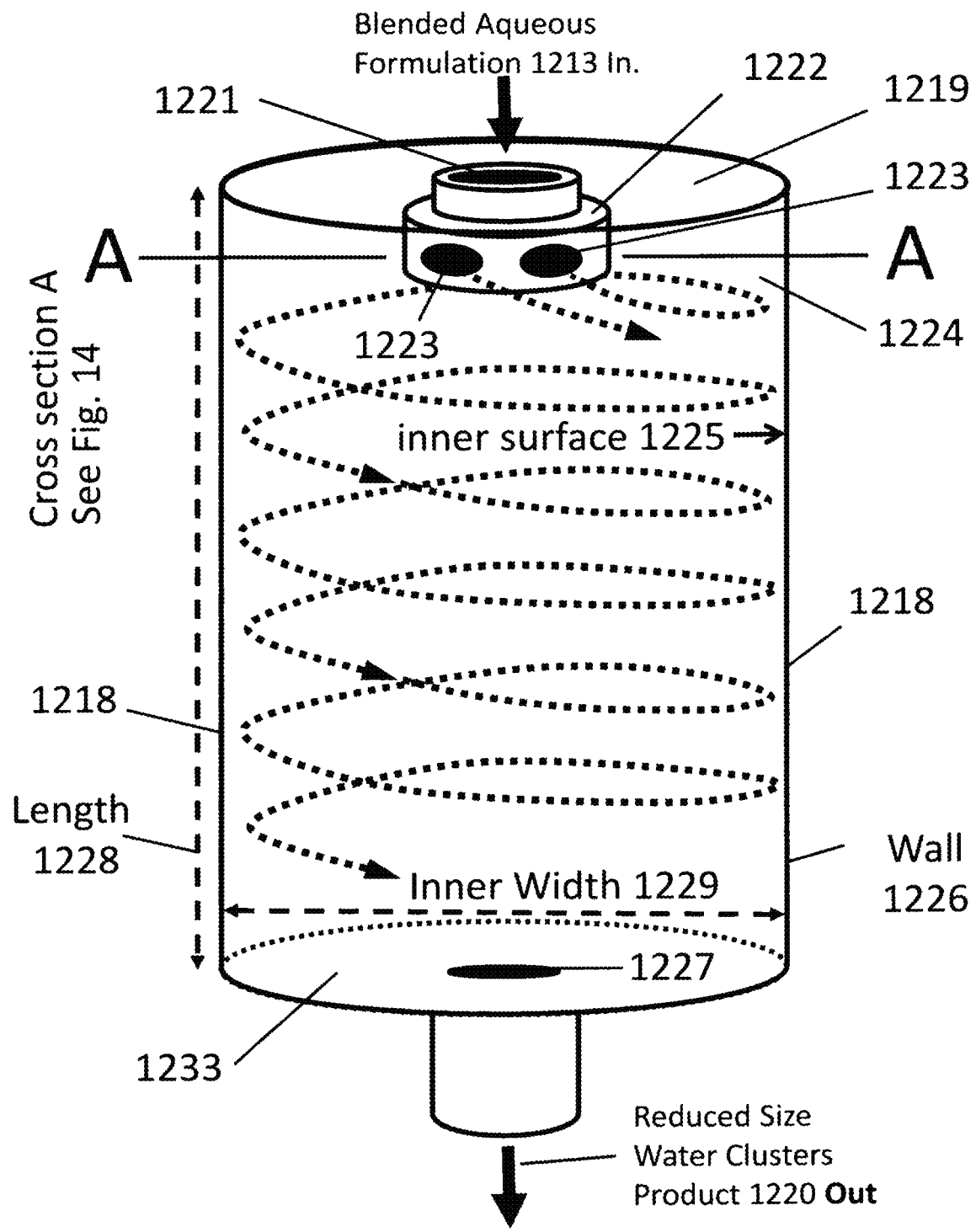
FIG. 13 depicts a schematic of the interior of a hollow cylinder 1218. The blended aqueous formulation 1213 from transfer pipe 1217 enters into the top 1219 of hollow cylinder 1218 where the hollow cylinder has a hole 1221. The rapid flowing of the blended aqueous formulation 1213 exits the nozzle 1222 jet openings 1223 and contacts inner surface 1225. The blended aqueous formulation 1213 flows in a circular pattern as suggested by the circular dashed line the from top 1219 to bottom 1233 and then can exit from the interior of the hollow cylinder 1218 where the hollow cylinder has a hole 1227. Surprisingly, for this particular hollow cylinder 1218 to optimally nanosize the rate of fluid flow in hollow cylinder 1218 is preferably 14-16 gallons per minute.
Figure 14:
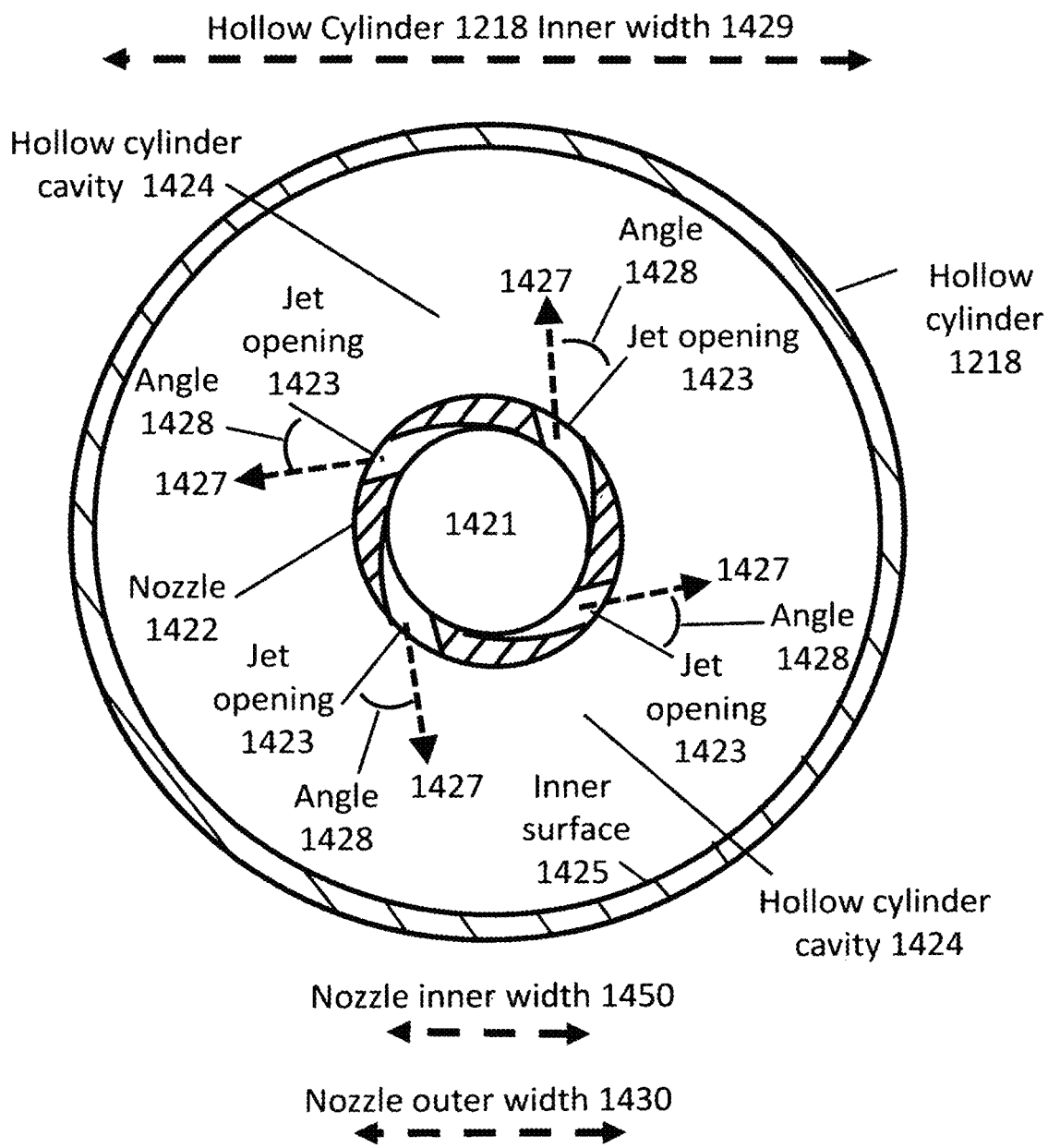
FIG. 14 is schematic depiction of a "Cross Section A" of the hollow cylinder 1218 taken at location "A-A" marked in FIG. 12, and in FIG. 13. The hollow cylinder 1218 is depicted as a round cylinder in FIGS. 12, 13, 21, 22, and 23 like a disk, and thus in cross-section appears like a round disk. The blended aqueous formulation 1213 flows from nozzle 1422 thru each bore hole 1427, and then exits each bore hole 1427 thru a jet opening 1423 in the direction indicated by dashed arrow 1427. Thus the initial bulk flow of the blended aqueous formulation 1213 is exiting from the nozzle 1422 at an angle 1428. The arc angle 1428 has a value which can be calculated by treating a perpendicular line as being 0 degrees with the perpendicular line drawn from a tangent to the outer curvature of the nozzle 1422 so that the tangent is contacting the outer curvature of nozzle 1422 at the midpoint of the jet opening 1423 on the outer curvature of nozzle 1422. It is intended that each arrow 1427 points outward from the jet openings 1423 in a direction which is the best approximation for a straight line that would be parallel to the center axis of each bore hole 1427. The term "approximation" is used above because each bore hole 1427 may not have a straight central axis but may be curved to some extent. In some embodiments of the present invention the bore hole 1427 through shaft wall of nozzle 1422 is a flow path with acute angle edges and obtuse angle edges. Some embodiments of the present invention use a flow path for the blended aqueous formulation 1213 through each bore hole 1427 which has an acute angle edge and an obtuse angle edge. The acute angle edge and the obtuse angle edge should sum to 180 degrees. The acute angle edge may be selected by selecting the angle 1428 during manufacturing of nozzle 1422, because the selected acute angle edges for use the bore hole 1427 will be approximately the same angle as is selected as angle 1428.

Cross Sectional View of the Hollow Cylinder 1218 Depicts Example Jet Openings of a Nozzle. In one example embodiment of the present invention, FIG. 14 depicts a schematic of a Cross Section A of the hollow cylinder 1218. The same example embodiment is depicted in FIG. 13 in a long axis view to illustrate that the inside of the hollow cylinder 1218 has a nozzle 1222 that is situated near the top 1219 inside of the hollow cylinder 1218. As depicted in FIG. 12, the transfer pipe 1217 is intended to transport a blended aqueous formulation 1213 (i.e, the water clusters in the UPW containing non-$H_2O$ substance(s)) from the mixing tank 1206, the water clusters in the fluid medium flow to the end of the transfer pipe 1217 and enter a nozzle(s) 1222. Blended aqueous formulation 1213 in the nozzle 1222 then exits from the nozzle by either by one or more jet opening(s) 1223. In one embodiment of the invention, the jet opening(s) 1223 are positioned inside the top hollow space 1224 of the hollow cylinder 1218. It is preferred that the nozzle 1222 has 1-10 jet openings 1223, more preferably 3 to 6 jet openings 1223, and most preferably 4 jet openings 1223. In some embodiments the inner diameter (ID) of each jet opening(s) 1223 is several-fold smaller than the transfer pipe 1217 ID, with the effect that the inner diameter of the jet opening(s) 1223 can expel the water clusters in the UPW containing non-$H_2O$ substance(s) at a fluid pressure about 2-25 times higher than the fluid pressure in the transfer pipe 1217 fluid.

The number of jet opening(s) 1223 of the nozzle 1222 can be selected from the group consisting of 1, 2, 3, 4, 5, 6, 7, 8, 9, 10, 11, 12, 13, 14, 15, 16, 17, 18, 19, 20 and any combination thereof.

Ratio of Nozzle Outer Width to Cylinder Inner Width Example for Hollow Cylinder 2018. In the example embodiment hollow cylinder 1218 that is depicted in the FIG. 14 Cross Section A, the nozzle outer width 1230 and the cylinder inner width 1229 are in a ratio of 1:3. In the example embodiment hollow cylinder 1218 that is depicted in the FIG. 13 long axis view the nozzle outer width 1230 and the cylinder inner width 1229 are in a ratio of 1:5. The test data presented in FIG. 15, FIG. 16, FIG. 17, and FIG. 18 are based on a prototype process (see FIG. 12.) in which the hollow cylinder 1218 has a nozzle outer width 1230 and a cylinder inner width 1229 in a ratio of 1:4.

For the present invention, some embodiments are contemplated to have in regard to the ratio of the nozzle 1222 outer width 1230 to the cylinder inner width 1229 for the hollow cylinder 1218, with the ratio selected from the group consisting a ratio of about 1:1.15 to about 1.1.25, a ratio of 1:1.25 to about 1:1.33, a ratio of about 1:1.33 to about 1:1.50, a ratio of about 1:1.50 to about 1:1.75, a ratio of about 1:1.75 to about 1:2.0, a ratio of about 1:2.0 to about 1:2.35, a ratio of about 1:2.35 to about 1:2.70, a ratio of about 1:2.70 to about 1:3.0, a ratio of about 1:3.0 to about 1:3.40, a ratio of about 1:3.40 to about 1:3.70, a ratio of about 1:3.70 to about 1:4.0, a ratio of about 1:4.0 to about 1:4.30, a ratio of about 1:4.60 to about 1:4.80, a ratio of about 1:4.80 to about 1:5.10, a ratio of about 1:5.10 to about 1:5.50, a ratio of about 1:5.50 to about 1:5.90, a ratio of about 1.5.90 to about 1:6.50, a ratio of about 1:6.50 to about 1:7.50, and about a ratio of 1:7.50 to about 1:10.0.

FIG. 14 is schematic depiction of a "Cross Section A" of the hollow cylinder 1218 taken at location "A-A" marked in FIG. 12, and in FIG. 13. The hollow cylinder 1218 is depicted as a round cylinder in FIGS. 12, 13, 21, 22, and 23 like a disk, and thus in cross-section appears like a round disk. The blended aqueous formulation 1213 flows from nozzle 1422 thru each bore hole 1427, and then exits each bore hole 1427 thru a jet opening 1423 in the direction indicated by dashed arrow 1427. Thus the initial bulk flow of the blended aqueous formulation 1213 is exiting from the nozzle 1422 at an angle 1428. The angle 1428 has a value which can be calculated by treating a perpendicular line as being 0 degrees with the perpendicular line drawn from a tangent to the outer curvature of the nozzle 1422 so that the tangent is contacting the outer curvature of nozzle 1422 at the midpoint of the jet opening 1423 on the outer curvature of nozzle 1422. It is intended that each arrow 1427 points outward from the jet openings 1423 in a direction which is the best approximation for a straight line that would be parallel to the center axis of each bore hole 1427. The term "approximation" is used above because each bore hole 1427 may not have a straight central axis but may be curved to some extent. In some embodiments of the present invention the bore hole 1427 through shaft wall of nozzle 1422 is a flow path with acute angle edges and obtuse angle edges. Some embodiments of the present invention use a flow path for the blended aqueous formulation 1213 through each bore hole 1427 which has an acute angle edge and an obtuse angle edge. The acute angle edge and the obtuse angle edge should sum to 180 degrees. The acute angle edge may be selected by selecting the angle 1428 during manufacturing of nozzle 1422, because the selected acute angle edges for use the bore hole 1427 will be approximately the same angle as is selected as angle 1428. In FIG. 14, the nozzle 1422 with bore holes 1427, and jet openings 1423 can be manufactured as needed by for example a 3-D printing system and machine or by a molding process. The nozzle material may be comprised of a plastic such as ABS, nylon, another hard plastic, a ceramic, a metal or some other hard material that is non-toxic and substantially not altered when exposed to an aqueous formulation.

It is an important object of the present invention to perform a process step comprising nanosizing clusters of water surrounding a non-$H_2O$ substance in the blended aqueous formulation so as to improve the bioavailability of the clusters of water surrounding a non-$H_2O$ substance in the blended aqueous formulation. It is contemplated that this important object of the present invention can be accomplished when the hollow cylinder 1218 is designed with various cross-sectional shapes. Thus the apparatus depicted in FIG. 14 is but one example of contemplated cross sectional shapes for a hollow cylinder embodiment of the present invention. It is contemplated a cross sectional shape for the hollow cylinder may be selected from the group consisting of an oval, an ellipse, a triangle, a square, a rectangle, a pentagon, a hexagon, a heptagon, an octagon, a polygon with any number of sides between 8 sides to 25 sides, and any combination thereof. The polygon with any number of sides between 8 sides to 25 sides has sides selected from the group consisting of flat sides, curved sides and a combination thereof.

To make compositions comprising high-bioavailability nanosized clusters of water surrounding a non-$H_2O$ substance, there are multiple factors which contribute to accomplishing this goal. The process for making the compositions requires blending an amount of ultrapure water with an amount of a non-$H_2O$ substance. The process requires an apparatus for practicing the invention process. Some example features of an apparatus needed for practicing the invention process are depicted in FIGS. 13 and 14. The hollow cylinder nozzle 1422, bore holes 1427, and jet openings 1423 are apparatus factors important and range of flow rates and pressures for the process stream inside the hollow cylinder 1218 are important process factors. In practicing the present invention, it is contemplated that the chemical and physical properties of the non-$H_2O$ substance (a) may require that special adjustments be made to practicing the invention process step embodiments of the present invention, (b) may alter the chemical and physical quality of composition embodiments of the present invention, and (c) may require that specialized apparatus embodiments of the invention be used. For example, the chemical stability of a non-$H_2O$ substance is an important factor needs to be taken into account known so that the apparatus and the processes of the invention will not destabilize or change the non-$H_2O$ substance during the making of an invention product that is intended to contain the non-$H_2O$ substance in a selected amount. Another example is that the degree of solubility and extent of dissolution of the non-$H_2O$ substance in the final blended aqueous formulation that is to enter the hollow cylinder 1218 have the potential to set a limit on the degree to which the invention processes may nanosize the clusters of water surrounding the nanosized non-$H_2O$ substance unless special measures are taken. For example, an amount of an insoluble non-$H_2O$ substances will be more difficult to nanosize than a water-soluble non-$H_2O$ substance. An as small as possible physical size for an-insoluble non-$H_2O$ substance may be required to make a useful product from a process embodiment of the present invention.

During Invention Process Step 8 a pressurized blended aqueous formulation 1213 flows into a nozzle fluid entry hole from distal end of the transfer pipe 1217 using the fluid pressure force generated by operation of a pipe transfer pump 1216. In accordance with one embodiment of the present invention, which is depicted schematically in FIG. 14, the blended aqueous formulation 1213 the flows into nozzle 1422 and out nozzle jet openings 1423. As can be seen in terms of the invention embodiments depicted in FIG. 13 and FIG. 14, the jet openings 1423 are arranged together around the outer width 1430 of the nozzle in a circular plane which is orthogonal to the long axis of the hollow cylinder 1218. In some invention embodiments the jet openings 1423 have a shape which when viewed perpendicular to the outer circumference of the nozzle 1422 appears to be an elliptical shape or an oval shape in FIG. 13.

FIG. 14 depicts a "Cross-section A" from FIG. 12 of the hollow cylinder 1218 embodiment at the height of the nozzle 1422. FIG. 14 depicts the nozzle in 2D (2D means in two (2) dimensions) as round in circumference but the nozzle 1422 could have a perimeter in a shape which is not round but instead has a perimeter with a 2D shape which is rectangular, square, hexagonal, or any kind of perimeter shape in cross section A view including a shape which is elliptical, or in 3D (3D means in three (3) dimensions) could look like a spherical cap. In FIG. 14, the depicted nozzle 1422 in cross section has four (4) jet openings 1423. Each jet opening 1223 is identified by its own "radially-oriented" headless arrow 1423. Each headless arrow 1423 is radially oriented in that each headless arrow 1423 is pointing perpendicular to the outer surface of each jet opening 1423 of the nozzle 1422 in FIG. 14.

Note also that the shape of the long axis bore hole 1427 of the jet opening 1423 of nozzle 1422 is depicted in FIG. 14 as curving 45 degrees in a counterclockwise direction from the 90 degree angle of the headless arrow 1423 to the nozzle exterior surface arrow 1427. So this counterclockwise backward 45 degree angle has been termed a "redirection angle". Thus the transfer pipe 1217 (See FIG. 12) pumps blended aqueous formulation 1213 to nozzle input opening 1221. See FIG. 14 where nozzle input opening is numbered 1421. From nozzle 1422 input opening 1421, the blended aqueous formulation can flow through the nozzle's curved bore holes 1427 which redirect the flow by an angle 1428

The transfer pipe pressure mainly controls the flow rate of the blended aqueous formulation 1213. The flow rate of the blended aqueous formulation 1213 may be slightly increased due to the force of gravity acting on the hydrostatic column height of the blended aqueous formulation 1213 once it is present in the hollow cylinder 1218. This can only happen because the hollow cylinder 1218 as depicted in FIG. 13, has a hole 1221 at its top 1219 and has a bottom drain hole 1227 at its bottom end 1233. Some flow of the blended aqueous formulation 1213 inside the hollow cylinder will be contacting curved inner surfaces 1225 of the hollow cylinder 1218. Some of this flow contacting the inner surface 1225 may move around the curved inner surfaces 1225. Inventors have illustrated this possible circular flow around the inside of the hollow cylinder by the circular dashed line in FIG. 13. The blended aqueous formulation 1213 that is in the hollow cylinder 1218 will exit from the center hole drain 1230 of the hollow cylinder bottom 1233.

In one embodiment for example, the center drain hole has a 1" ID exit hole. The calculated hollow cylinder volume 1218 is 226 cubic inches for a hollow cylinder with an inner width of 4 inches and a height of 18 inches. A gallon is 231 cubic inches. Therefore for example, when the transfer pipe flow rate is 14-16 gallons per minute, then the fluid in the hollow cylinder is exchanging 14-16 times per minute or getting replaced about once every 4 seconds. When only 10-20 gallons of a 300 gallon batch of the blended aqueous formulation 1213 remains in the mixing tank 1206 during the process step 6 process, then some air from the mixing tank 1206 can get sucked down into the transfer pipe 1217, moves into the transfer pipe pump 1216 and causes a fall in the transfer pipe 1217 fluid pressure and flow rate. When the mixing tank 1206 air reaches the hollow cylinder 1218, then process Step 8 will be stopped.

Processes for making the intermediates and final products by the processes of the present invention have special and conditions and certain limitations that must be emphasized to distinguish the operations and uses and products by the processes of the present invention from the prior art inventions and processes. Water clusters sizes hydrating a non-$H_2O$ substance can be reduced in size by the processes of the present invention to less than 400 nanometers median size, preferably to less than 300 nanometers median size according to Malvern Zetasizer DLS testing. Water clusters sizes in the range of 2 nanometers to 300 nanometers can be achieved by the present invention provided that the size of the non-$H_2O$ substance is recognized as having a significant controlling role in what will be the minimum size water cluster of a particular non-$H_2O$ substance enveloped in water clustering. The present invention cannot reduce a water cluster to a size which is smaller than the simplest hydrated water cluster size of a particular non-$H_2O$ substance particle.

In contrast to published prior art invention processes and apparatuses known to the inventors, the novel present invention apparatus and provides surprising results. The present invention processes comprises making an aqueous composition comprising an aqueous medium with reduced size water clusters containing a non-$H_2O$ substance. The process of the present invention has been found to have an optimal range of rates of flowing of the blended aqueous formulation of the ultrapure water with the non-$H_2O$ substance(s) into a nozzle 1222 in the hollow cylinder 1213. The jetting of the blended aqueous formulation from one or a plurality of jet opening(s) 1223 has been discovered to be a process which is necessarily operated with a surprisingly restricted range of flowing rates of the blended aqueous formulation preceding its flowing into the hollow cylinder 1218. Accordingly, channels of the jet opening 1223 in some embodiments of the present invention having a plurality of acute and obtuse edges are optimal. This has been discovered through experimentation of process parameters including the flow rate of the blended aqueous formulation inside of the hollow cylinder through the jet opening(s) 1223 of the nozzle 1222. It may be that the invention apparatus occurring in Step 8 process of using the hollow cylinder is creating pressure fluctuations of the blended aqueous formulation flowing inside the hollow cylinder passing through the jet opening(s) 1223 is creating pressure fluctuations of the blended aqueous formulation inside of the hollow cylinder. These pressure fluctuations have not been measured but the pressure fluctuations of the blended aqueous formulation through the jet openings 1223 are conceived to be a means for reducing water cluster sizes in the blended aqueous formulation 1213.

It has been quantified for the invention embodiment depicted in FIG. 12 that there is a limited range of process flows rates that can optimally work for the process 8 occurring in the prototype invention apparatus depicted in FIGS. 12, 13, and 14. The nanosizing of the water clusters of the blended aqueous formulation before and after the blended aqueous formulation is flowing through the hollow cylinder 1218 has been quantified using Malvern Zetasizer data histogram charting of distributions and number of modes of the water clusters size distributions.

Surprisingly, low flow rates of the blended aqueous formulation 1213 were measured by the Zetasizer cause process 8 problems. In some of the embodiments of the invention having flowing rates below about 10-12 gallons per minute produced a multiple number of median modes in the quantified distribution of sizes of the water clusters which is inferred to mean that the using low flow rates in the processes of the present invention are causing an incomplete nanosizing of the blended aqueous formulation 1213 below about 300 nanometers lead to an incomplete conversion of the populations of large water clusters. For the apparatus schematically depicted in FIG. 12, it was found that using experiments there is preferably a flow rate of 14-16 (fourteen to sixteen) gallons per minute for nanosizing the initial median sizes of median water cluster sizes. This optimal flowing rate is surprisingly in a narrow range and a flow rate as high as 20 gallons per minute also increases the number of median modes in the distributions of water cluster sizes.

Pressurizing of the blended aqueous formulation may be occurring outside the hollow cylinder 1218. Inventors experimentally tested the blended aqueous formulation before and after the hollow cylinder 1218 and quantified with Zetasizer water measured laser reflection movements in test samples for analysis and production of charts depicting water cluster size distributions which are for example presented as histograms of the size distributions water clusters in FIGS. 15, and 16.

Processes of the Present Invention Involve Using a UPW Concentrate of Ingredients In some embodiments of the invention the process comprises using a continuous stream of the blended aqueous formulation flowing within a hollow cylinder comprising an inflow transfer pipe with a plurality of nozzle jets and an outflow drain pipe. Non-$H_2O$ ingredients in some embodiments of the invention are mixed with an amount of UPW, preferably about 1-10 gallons of the UPW which in these embodiments comprises a range of about 0.1% to about 5% relative to the total volume of the blended aqueous formulation in the mixing tank 1206. The blended aqueous formulation 1213 leaving hollow cylinder 1218 is not recirculated in a cylinder, and no exothermic reaction occurred in the hollow cylinder. The blended aqueous formulation pH may acidify very slightly in hollow cylinder. Embodiments of the invention, after forming various products, have not been storing the product under pressure, or adding any gases.

Processes of the Invention may Include Sterilizing UV Radiation

Preferably, the process will use UV radiation for sterilizing the product but is an optional process step. One means for UV sterilizing is to employ a pipe with a quartz lamp emitting UV and located concentrically in the pipe so as to have the blended aqueous formulation sterilized prior to hollow cylinder 1218 and/or depicted in FIG. 11 process steps 1-9 as step 9.

Summary of Processes of the Present Invention Surprisingly Affecting the Product The process embodiments of the present invention are useful for causing a size reduction of the blended aqueous formulation 1213 water clusters. The process embodiments of the present invention are also useful for improving bioavailability of product embodiments of the invention which are produced by the process. The water cluster nano-sizing in the product embodiments of the invention have been shown using the Zetasizer to have remarkably long-lasting storage stability of the nano-sized water clusters, for example up to 2.5 years. Embodiments of the invention are surprisingly useful for adding substances later to product embodiments of the present invention without disrupting the median size of the nano-sized water cluster nor increasing numbers of modes of the size distributions of the nano-sized water clusters in the invention product.

Preferred Ratio of Transfer Pipe to Hollow Cylinder Diameters

There is a preferred ratio for some embodiments of the present invention of transfer pipe 1217 to hollow cylinder 1218 inner diameter. Also some embodiments of the invention have a preferred width to length ratio for the hollow cylinder 1218 depicted in FIGS. 12, 21, 22 and 23.

Generally it is useful to immediately use the UPW (ultra-pure water) that has just been created by processes of the invention so as to make properly nano-sized water cluster products. In such cases the UPW can be manufactured on site by a number of processes which have been described in the specification of this patent application.

Compositions of Materials Used in Apparatuses of the Present Invention

In some embodiment apparatuses of the invention for conducting various process embodiments of the invention, the piping and tanks have a composition of matter selected from the group consisting of a polyethylene plastic, an ABS plastic, a polycarbonate plastic, a nylon plastic, a mixture of plastics, a plastic which is externally reinforced with fiberglass materials, a stainless steel alloy, a borosilicate glass, an aluminosilicate glass, a Pyrex glass, a polypropylene plastic, a vinyl plastic, and a combination thereof. When the processing may be light sensitive because there is a light sensitive non-$H_2O$ substance within the blended aqueous formulation in which case the piping and the tanks may be non-transparent or processing may occur in a dark room or a room illuminated with a low wattage or a long wave length light illumination which may be selected from the group consisting of a LED light source, an incandescent light source or a light source with a selected wave length(s) light filter, or a combination thereof. For consumer products, the process is conducted with food grade ingredients.

Process Step 7 is a Storage of the Reduced Size of Water Clusters in the UPW Containing Non-$H_2O$ Substance(s).

One example embodiment for Process step 7 involves storing the product 1219 temporarily in a suitable air-tight stainless steel tank 1220. The product 1219 is the aqueous medium comprising the reduced size of water clusters with non-$H_2O$ substance(s). The shelf life of the product 1219 for various use formulations (see below) of the invention is being investigated using long term stability testing.

Possible Process Parameters Measured for a Computer Controlled Process:

Preferred process parameters in the process steps of the present invention and for some apparatus embodiments in some sections of the process apparatus of the present invention are selected from the group consisting of a process input water pressure range (in pounds per square inch, or psi), a process input water chloride content range (in ppm), a range of the degree of process input water purification so as to remove a charcoal-absorbable contaminant which depends on selecting a type of a charcoal and situating the selected type of the charcoal material in a selected charcoal absorption process container, a process water pressure range in various sections of the process piping apparatus, a water pressure range in process system tanks, a flow rate range in process apparatus piping, a volume capacity range of process apparatus tanks, a volume capacity range of blending apparatus tanks, a volume capacity range of apparatus holding tanks, a range of conductivity (mhos) values for the fluids in various sections of the process apparatus during a product production step, a range of resistivity (megaohms) values of the fluids in various sections of the process apparatus during a product production step, a temperature range of the fluids in various sections of the process apparatus during a product production step, a dissolved gas partial pressure range in process fluids, and a combination thereof.

Sensors for Monitoring Processes in Some Embodiments of the Invention

Some apparatus embodiments of the present are depicted in FIGS. 21, 22 and 23 have process parameter monitoring using a computer with process parameter sensors situated at various process steps in the apparatus embodiments of the present invention. A sensor may be useful for example which is used for an in-situ continuous monitoring testing of a fluid in the process apparatus, for testing a starting ingredient, for testing a UPW source, and/or for testing a final product or intermediate product. The sensor may be selected from the group consisting of a pressure sensor, a flow rate sensor, a choride ppm sensor, a Na+ ion sensor, a reduction potential sensor, an oxidation sensor, a pH sensor, a free radical sensor of hydrogen peroxide, a free radical sensor of hydroperoxides, a free radical sensor of hydroxide radical, a hydrogen peroxide sensor, a polychlorobiphenyls (PCBs) sensor, an osmolality sensor (milliosmoles), conductivity sensor, a resistivity sensor, a temperature sensor, a viscosity sensor, a partial pressure of gases sensor, a Malvern zetasizer nano-size of water clusters sensor, a particulate sensor, a light sensor, a beta particle radiation sensor, an alpha particle sensor, a gamma ray sensor, an ultraviolet spectroscopy sensor, an infared spectroscopy sensor, a mass spectroscopy, a visible light wavelength sensor, and any combination thereof. Sensor outputs maybe used for an automation of a process step embodiment of the present invention.

A. General and Some Specific Embodiments of the Present Invention

Some Steps for Improving Product by Process Bioavailability

In some embodiments, the present invention is a process for reducing water cluster sizes in an aqueous composition containing a non-H₂O substance in order to improve bioavailability of the aqueous composition, the process comprising the steps of: choosing an amount of the non-H₂O substance to add to a volume of ultrapure water; adding the amount of the non-H₂O substance to the volume of ultrapure water in a mixing tank to form a blended aqueous formulation containing the non-H₂O substance in the ultrapure water; pumping the blended aqueous formulation at a selected flow rate from the mixing tank to a nozzle with one jet opening or a plurality of jet openings inside a hollow cylinder; using the one jet opening or the plurality of jet openings in the nozzle to jet the blended aqueous formulation at a higher flow rate into the hollow cylinder; using the higher flow rate of the blended aqueous formulation from the one jet opening or the plurality of jet openings inside the hollow cylinder to reduce sizes of the water clusters in the blended aqueous formulation of the non-H₂O substance in the ultrapure water; removing the aqueous composition with the reduced size water clusters containing the non-H₂O substance at the selected flow rate from inside the hollow cylinder; and using the reduced size water clusters containing the non-H₂O substance in the aqueous medium to improve the bioavailability of the aqueous composition.

Process and Product Reduce Water Clusters to Preferred Nanometer Sizes

In some embodiments, the present invention is a process wherein more specifically the reduced size water clusters containing the non-$H_2O$ substance in the aqueous medium may have a median water cluster size selected from the group consisting of between about 2 to 10 nanometers, about 10 to 50 nanometers, about 50 to 100 nanometers, about 100 to 200 nanometers, about 200 to 300 nanometers, about 300 to 400 nanometers, and a combination thereof.

Quantities of Non-$H_2O$ Substances Which May be Present Per Gallon in Product

In some embodiments, the present invention is a process, wherein more specifically the non-$H_2O$ substance comprises a ionizable salt, and wherein the amount of the ionizable salt added per gallon of the ultrapure water may be selected from the group consisting of between about 10 micrograms to 50 micrograms, about 50 micrograms to 100 micrograms, about 100 micrograms to 200 micrograms, about 200 micrograms to 400 micrograms, about 400 micrograms to 800 micrograms, about 800 micrograms to 1.6 milligrams, about 1.6 milligrams to 3.2 milligrams, about 3.2 milligrams to 6.4 milligrams, about 6.4 milligrams to 30 milligrams, and a combination thereof.

Some of the Ionic Non-Water Substances Which May be Added to Make a Product

In some embodiments, the present invention is a process, wherein more specifically the ionizable salt may be comprised of ions selected from the group consisting of aluminum ion, ammonium ion, antimony ion, arsenic ion, barium ion, beryllium ion, bismuth ion, boron ion, bromide ion, cadmium ion, calcium ion, cerium ion, cesium cation, chloride ion, chromium ion, cobalt ion, copper ion, dysprosium ion, erbium ion, europium ion, fluoride ion, gadolinium ion, gallium ion, germanium ion, gold ion, hafnium ion, holmium ion, indium ion, iodine ion, iridium ion, iron ion, lanthanum ion, lead ion, lithium ion, lutetium ion, magnesium ion, manganese ion, mercury ion, molybdenum ion, neodymium ion, nickel ion, niobium ion, osmium ion, palladium ion, phosphorus ion, platinum ion, potassium ion, praseodymium ion, rhenium ion, rhodium ion, rubidium ion, ruthenium ion, samarium ion, scandium ion, selenium ion, silicon ion, silver ion, sodium ion, strontium ion, sulfate ion, tantalum ion, tellurium ion, terbium ion, thallium ion, thorium ion, thulium ion, tin ion, titanium ion, tungsten ion, vanadium ion, ytterbium ion, yttrium ion, zinc ion, zirconium ion, and a combination of thereof Transfer Pipe Flow Volume Per Minute is Multiple of Hollow Cylinder Volume In some embodiments, the present invention is a process, wherein more specifically the selected flow rate from the mixing tank to the nozzle may result in a flow volume per minute which is a multiple of the hollow cylinder volume, the multiple selected from the group consisting of about 1 to 2, about 2 to 3, about 3 to 4, about 4 to 5, about 5 to 6, about 6 to 7, about 7 to 8, about 8 to 9, about 9 to 10, about 10 to 11, about 11 to 12, about 12 to 13, about 13 to 14, about 14 to 15, about 15 to 16, about 16 to 17, about 17 to 18, about 18 to 19, about 19 to 20, about 20 to 21, about 21 to 22, about 22 to 23, about 23 to 24, about 24 to 25, about 25 to 26, about 26 to 27, about 27 to 28, about 28 to 29, about 29 to 30.

Some Hollow Cylinder Inner Width Dimensions

In some embodiments, the present invention is a process, wherein more specifically the hollow cylinder has an inner width in inches which may be selected from the group consisting of between about 1 to 2 inches, about 2 to 3 inches, about 3 to 4 inches, about 4 to 5 inches, about 5 to 6 inches, about 6 to 7 inches, about 7 to 8 inches, about 8 to 9 inches, about 9 to 10 inches, about 10 to 11 inches, about 11 to 12 inches, about 12 to 13 inches, about 13 to 14 inches, about 14 to 15 inches, about 15 to 16 inches, about 16 to 17 inches, about 17 to 18 inches, about 18 to 19 inches, about 19 to 20 inches, and a combination thereof.

Some Hollow Cylinder Length Dimensions

In some embodiments, the present invention is a process, wherein more specifically the hollow cylinder has an inner length in inches may be selected from the group consisting of between about 2 to 4 inches, about 4 to 6 inches, about 6 to 8 inches, about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, about 26 to 28 inches, about 28 to 30 inches, about 32 to 34 inches, about 34 to 36 inches, about 36 to 38 inches, about 38 to 40 inches, about 40 to 42 inches, about 42 to 44 inches, about 44 to 46 inches, about 46 to 48 inches, about 48 to 50, about 50 to 52, about 52 to 54, about 54 to 56, about 56 to 58, about 58 to 60, about 60 to 62, about 62 to 64, about 64 to 66, about 66 to 68, about 68 to 70, about 70 to 72, about 72 to 74, about 74 to 76, about 76 to 78, about 78 to 80 and a combination thereof.

Some Ratios of Outer Nozzle Diameter to Hollow Cylinder Inner Diameter

In some embodiments, the present invention is a process, wherein more specifically the ratio of the nozzle outer diameter in inches to the hollow cylinder inner diameter in inches is a ratio which may be selected from the group consisting of about a ratio of 1:1.15 to about 1:1.25, a ratio of 1:1.25 to about 1:1.33, a ratio of about 1:1.33 to about 1:1.50, a ratio of about 1:1.50 to about 1:1.75, a ratio of about 1:1.75 to about 1:2.0, a ratio of about 1:2.0 to about 1:2.35, a ratio of about 1:2.35 to about 1:2.70, a ratio of about 1:2.70 to about 1:3.0, a ratio of about 1:3.0 to about 1:3.40, a ratio of about 1:3.40 to about 1:3.70, a ratio of about 1:3.70 to about 1:4.0, a ratio of about 1:4.0 to about 1:4.30, a ratio of about 1:4.30 to about 1:4.60, a ratio of about 1:4.60 to about 1:4.80, a ratio of about 1:4.80 to about 1:5.10, a ratio of about 1:5.10 to about 1:5.50, a ratio of about 1:5.50 to about 1:5.90, a ratio of about 1.5.90 to about 1:6.50, a ratio of about 1:6.50 to about 1:7.50, and about a ratio of 1:7.50 to about 1:12.0, and a combination thereof.

Possible Numbers of Jet Openings in Nozzle of Hollow Cylinder

In some embodiments, the present invention is a process, wherein more specifically the nozzle may have the one jet opening or the plurality of the jet openings selected from the group consisting of 1, 2, 3, 4, 5, 6, 7, 8, 9, 10, 11, 12, 13, 14, 15, 16, 17, 18, 19, and 20.

Preferred are four (4) jet openings on a nozzle of the invention.

Ratio of Total Area of Nozzle Jet Openings to Area of Nozzle Inner Diameter

In some embodiments, the present invention is a process, wherein more specifically the ratio of sum total area of jet openings on nozzle outer side to area of nozzle inner diameter may be selected from the group consisting of the ratio of about 0.01 to 0.05, a ratio of about 0.05 to 0.10, a ratio of about 0.10 to 0.15, a ratio of about 0.15 to 0.20, a ratio of about 0.20 to 0.25, a ratio of about 0.25 to 0.30, a ratio of about 0.30 to 0.35, a ratio of about 0.35 to 0.40, a ratio of about 0.40 to 0.45, a ratio of about 0.45 to 0.50, a ratio of about 0.50 to 0.55, a ratio of about 0.55 to 0.60, a ratio of about 0.60 to 0.65, a ratio of about 0.65 to 0.70, a ratio of about 0.70 to 0.75, a ratio of about 0.75 to 0.80, a ratio of about 0.80 to 0.85, a ratio of about 0.85 to 0.90, a ratio of about 0.90-1.0, a ratio of about 1.0 to 1.2, a ratio of about 1.2 to 1.5, a ratio of about 1.5 to 1.7, and a combination thereof.

Possible Degrees in Angle 1428 (See Depiction of Angle 1428 in FIG. 14.)

In some embodiments, the present invention is a process, wherein more specifically the nozzle 1422 may have one curved bore hole 1427 with jet opening 1423 with one angle 1428, or each nozzle 1422 may have a plurality of the curved bore holes 1427 with jet openings 1423 providing an angle 1428 in degrees, wherein the angle 1428 may be selected from the group consisting of 0, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, and 90 degrees. In some embodiments, the present invention is a process, wherein more specifically the nozzle 1422 has the curved bore hole 1427 jet opening 1423 providing the angle 1428 in a clockwise direction or in a counter-clockwise direction.

Ratio of Volume of Concentrate to Volume of Additional UPW Used

In some embodiments, the present invention is a process for reducing water cluster sizes in an aqueous composition containing a non-$H_2O$ substance in order to improve bioavailability of the aqueous composition, the process comprising the steps of: choosing an amount of non-$H_2O$ substance to be added to a large volume of ultrapure water; blending all of the non-$H_2O$ substance in a small volume of the ultrapure water to make a small volume concentrate of the non-$H_2O$ substance in the ultrapure water; wherein the small volume concentrate of the non-$H_2O$ substance blended with the ultrapure water is a percent of the large volume of the ultrapure water that has been chosen, the percent may be selected from the group consisting of a 0.01 to 0.05 percent, a 0.05 to 0.1 percentage, a 0.1 to 0.2 percentage, a 0.2 to 0.3 percent, a 0.3 to 0.4 percent, a 0.4 to 0.5 percent, a 0.5 to 0.6 percent, a 0.6 to 0.7 percent, a 0.7 to 0.8 percent, a 0.8 to 0.9 percent, a 0.9 to 1.0 percent, a 1.0 to 2.0 percent, a 2.0 to 3.0 percent, a 3.0 to 4.0 percent, a 4.0 to 5.0 percent, a 5.0 to 10.0 percent, a 10.0 to 20.0 percent, and a combination thereof; filtering optionally, the small volume concentrate of the non-$H_2O$ substance in the ultrapure water using a clean filter to remove micron-sized particulates from the small volume concentrate, wherein the minimum particle sizes removed by the clean filter may be selected from the group consisting of about 1 to 2 microns, 2.5 microns, 3 microns, 4 to 7 microns, 6 microns, 8-10 microns, 11 microns, and 12-25 microns, and a combination thereof; recirculating the large volume of the ultrapure water in a mixing tank and slowly adding the small volume concentrate of the non-$H_2O$ substance in the ultrapure water to the mixing tank to form a blended aqueous formulation containing the non-$H_2O$ substance in an aqueous medium; wherein the large volume amount of the ultrapure water may be selected from the group consisting of about 10 to 20 gallons, about 20 to 50 gallons, about 50 to 100 gallons, about 100-300 gallons, about 300 to 600 gallons, about 600 gallons to about 1000 gallons, about 1000 gallons to about 2500 gallons, and a combination thereof, and wherein the adding of the small volume concentrate volume of the non-$H_2O$ substance in the ultrapure water to the mixing tank to form a blended aqueous formulation containing the non-$H_2O$ substance in the aqueous medium may be accomplished over a time period selected from the group consisting of about 1 to 5 minutes, about 5 to 10 minutes, about 10 to 15 minutes, about 15 to 20 minutes, about 20 to 25 minutes, about 25 to 30 minutes, about 30 to 35 minutes, about 35 to 40 minutes, and a combination thereof; pumping the blended aqueous formulation at a selected flow rate from the mixing tank to a nozzle with a jet opening inside a hollow cylinder; using the jet opening in the nozzle to jet the blended aqueous formulation at a higher flow rate into the hollow cylinder; using the higher flow rate of the blended aqueous formulation from the jet opening inside the hollow cylinder to reduce sizes of the water clusters in the blended aqueous formulation of the non-$H_2O$ substance in the ultrapure water; removing the aqueous composition with the reduced size water clusters containing the non-$H_2O$ substance at the selected flow rate from inside the hollow cylinder; and using the reduced size water clusters containing the non-$H_2O$ substance in the aqueous medium to improve the bioavailability of the aqueous composition.

One Embodiment Process for Producing Some Embodiment Products

In some embodiments, the present invention is a process, wherein more specifically the ultrapure water is prepared by a process comprising the steps of: filtering a volume of water from a supply of water with a carbon filter to produce an amount of water with a low chlorine content; removing ions by a reverse osmosis process from the carbon filtered water with the low chlorine content so as to produce a supply of a deionized water; electro-deionizing the supply of the deionized water from the reverse osmosis process to make an ultrapure water supply; testing the resistivity of the ultrapure water to determine if the resistivity of the ultrapure water is between about 17-18.2 meg-ohm cm; repeating a process step for preparing the ultrapure water and retesting the resistivity of the ultrapure water until the ultrapure water has a measured resistivity of between about 17 meg-ohm cm to 18.2 meg-ohm cm; irradiating the supply of the ultrapure water having a measured resistivity of between about 17 meg-ohm cm to 18.2 meg-ohm cm with ultraviolet light to make a sterilized ultrapure water supply; and storing the sterilized ultrapure water in a stainless steel container until sterilized ultrapure water is needed to be added in the process to make an aqueous composition comprising an aqueous medium with reduced size water clusters containing a non-$H_2O$ substance to improve bioavailability of the aqueous composition.

Example Weights of Some Ions that may be used as Non-H2O Ingredients

In some embodiments, the present invention is a process, wherein more specifically the non-$H_2O$ substance comprises a ionizable salt, wherein the amount of the ionizable salt added per gallon of the ultrapure water may be selected from the group consisting of between about 20 micrograms to 100 micrograms, about 100 micrograms to 500 micrograms, about 500 micrograms to 2.5 milligrams, about 2.5 milligrams to 5 milligrams, about 5 milligrams to 10 milligrams, wherein the ionizable salt is comprised of ions selected from the group consisting of boron ion, bromide ion, calcium ion, cerium ion, cesium cation, chloride ion, chromium ion, cobalt ion, copper ion, fluoride ion, gold ion, indium ion, iodine ion, iridium ion, iron ion, lanthanum ion, lithium ion, lutetium ion, magnesium ion, manganese ion, molybdenum ion, neodymium ion, niobium ion, osmium ion, palladium ion, phosphorus ion, platinum ion, potassium ion, rhenium ion, rhodium ion, rubidium ion, ruthenium ion, scandium ion, selenium ion, silicon ion, silver ion, sodium ion, strontium ion, sulfate ion, tantalum ion, tin ion, titanium ion, tungsten ion, vanadium ion, zinc ion, zirconium ion, and a combination of thereof.

Dimensions of Inner Hollow Cylinder for Some Embodiments

In some embodiments, the present invention is a process, wherein more specifically the hollow cylinder has an inner width in inches which may be selected from the group consisting of between about 3 to 4 inches, about 4 to 5 inches, about 5 to 6 inches, about 6 to 7 inches, about 7 to 8 inches, and a combination thereof, and wherein the hollow cylinder has an inner length in inches selected from the group consisting of between about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, and a combination thereof.

Some Ratios of Flow Rate/Minute of Transfer Pipe to Hollow Cylinder Volume

In some embodiments, the present invention is a process, wherein more specifically the selected flow rate from the mixing tank to the nozzle results in a flow volume per minute which is a multiple of the hollow cylinder volume, the multiple selected from the group consisting of about 12 to 13, about 13 to 14, about 14 to 15, about 15 to 16, about 16 to 17, about 17 to 18, about 18 to 19, and a combination thereof. In some embodiments, the present invention is a process, wherein more specifically the reduced size water clusters containing the non-$H_2O$ substance in the aqueous medium have a median water cluster size from about 3 nanometers to about 300 nanometers.

Some Example Ranges of Ionic Non-Water Ingredient Weight/Fifty Gallons UPW

In some embodiments, the present invention is a process, wherein more specifically the non-$H_2O$ substances are added to a volume of 50 gallons of ultrapure water, and
wherein the non-$H_2O$ substances comprise:
between about 10 to 1200 milligrams of potassium chloride;
between about 0.0017 to 500 milligrams of vitamin B6;
between about 0.001 to 100 milligrams of ferric chloride;
between about 0.0011 to 800 milligrams of magnesium sulfate;
between about 0.6 to 5000 milligrams of sodium chloride;
between about 0.5 to 75 grams of Ionic Trace Minerals;
between about 1.1 to 1000 milligrams of kelp;
between about 10-500 milligrams of taurine;
between about 5.4 to 100 milligrams of alfalfa; and
between about 0.0022 to 60 milligrams of sodium borate.

Definitions of Some Terms Commonly Used in Pharmacokinetics Analyses

Pharmacokinetics is a field of Pharmacology which describes how the body affects a specific xenobiotic/chemical after administration through the mechanisms of absorption and distribution, as well as the metabolic changes of the substance in the body (e.g. by metabolic enzymes such as cytochrome P450 or glucuronosyltransferase enzymes), and the effects and routes of excretion of the metabolites of the drug. Pharmacokinetic properties of chemicals are affected by the route of administration and the dose of administered drug. These may affect the absorption rate. Models have been developed to simplify conceptualization of the many processes that take place in the interaction between an organism and a chemical substance. One of these, the multi-compartmental model, is the most commonly used approximations to reality; however, the complexity involved in adding parameters with that modelling approach means that mono-compartmental models and above all two compartmental models are the most-frequently used.

One way to describe multiple compartment models is to use the term commonly referred to as the ADME scheme and is also referred to as LADME if liberation is included as a separate step from absorption. The letters in the acronyms ADME and LADME refer to:

Liberation refers to the process of release of a drug from the pharmaceutical formulation.[4][5] See also IVIVC.

Absorption refers to the process of a substance entering the blood circulation.

Distribution refers to the dispersion or dissemination of substances throughout the fluids and tissues of the body.

Metabolism, biotransformation are process for causing modifications of a foreign substance and involve a recognition by the organism that a foreign substance is present and then, an irreversible transformation of parent compounds into metabolites which may be water soluble.

Elimination refers to the removal of the substances from the body. Metabolism and excretion processes may be collectively termed as processes of elimination. (Pharmacokinetics, Wikipedia, 2019).

Some invention embodiments may contain a pharmaceutical drug, a biological based drug, an antibody-based drug, or a vaccine based drug as the non-$H_2O$ substance. A nanosized ultrapure water cluster of a nanosized non-$H_2O$ substance may use a non-$H_2O$ substance selected from the group consisting of adalimumab, esomeprazole, rosuvastatin, etanercept, fluticasone, salmeterol, infliximab, Lantus™, insulin glargine, pegfilgrastim, glatiramer, rituximab, tiotropium bromide, sitagliptin, emtricitabine, tenofovir, efavirenz, duloxetine, bevacizumab, pregabalin, celecoxib, epoetin alfa, tenofovir, emtricitabine, valsartan, detemir, imatinib, trastuzumab, lisdexamfetamine, ranibizumab, ezetimibe, ipratropium bromide, salbutamol, budesonide, formoterol, memantine, insulin aspart, rivaroxaban, insulin aspart, insulin lispro, buprenorphine, sildenafil, quetiapine, telaprevir, testosterone, enoxaparin, methylphenidate, salbutamol, pemetrexed, liraglutide, palivizumab, interferon beta 1a, insulin, lidocaine, caffeine, aspirin, benzocaine, sevelamer, interferon beta 1a, tadalafil, fingolimod, mometasone, ustekinumab, ciclosporin ophthalmic, budesonide, acetaminophen, ibuprophen, fluticasone propionate, omega-3 fatty acid ethyl esters, darunavir, raltegravir, sitagliptin, metformin, epoetin alfa, doxycycline, abatacept, amphetamine mixed salts, solifenacin, dexlansoprazole, insulin lispro, filgrastim, lidocaine, eszopiclone fenofibrate, abiraterone, atazanavir, cinacalcet, metoprolol, rabeprazole, levothyroxine, olmesartan, pneumococcal conjugate vaccine, omalizumab, atorvastatin, olmesartan, hydrochlorothiazide elvitegravir, cobicistat, emtricitabine, tenofovir, zostavax, dabigatran, ezetimibe, simvastatin, oseltamivir, denosumab, raloxifene, capecitabine, darbepoetin alfa, valproate, everolimus, interferon beta 1b, rilpivirine, Revlimid™, thalidomide, Optivo™, Keytruda™, Herceptin™, Avastin™, Rituxan™, rituximab, Imbruvica™, ibrutinab, Neuralasta™, pegfilgrastin, Ibrance™, palbaciclib, Xtandi™, enzalutamide, and disoproxil fumarate.

Routes of Administration of a Drug or Fluid to an Individual

A route of administration of a foreign substance such as a drug into an individual with respect to the pharmacology and toxicology is the path by which a drug or other substance has been administered into the body of the individual. One way to describe the routes of administration is to classify the route by the location at which the substance is administered to the individual. Routes of administration can also be evaluated based on where the site of drug action is going to occur. For example, a drug action may have a location which is topical meaning on a skin location, enteral meaning within the gastrointestinal tract, or parenteral meaning within the body by a route of administration other than directly into the gastrointestinal tract (GI tract). The routes of administration may use a solid, fluid, gas, drug, or a drug formulation.

The route of administration is selected from the group consisting of oral, parenteral, gastric, duodenal, into large intestine, intravenous, intramuscular, arterial, by inhalation, pulmonary, intranasal, intraocular, auricular, subcutaneous, epidural, transdermal, rectal, uretral, intra-vesicular, intravaginal, intra-ureteral, into fat tissue, cerebrospinal, intrathecal, into GI tract, a section of the small intestine, sublingual, buccal, intracerebral, by a direct injection, subcutaneous, transdermal, intra-arterial, intra-articular, intradermal, intralesional, intramuscular, intraocular, intraosseous infusion, intraperitoneal, intrathecal, intrauterine, intravenous, intra-vesicular, intravitreal, subcutaneous, transdermal patches, perivascular, transmucosal, topical and a combination thereof.

Administration into the gastrointestinal tract can be subdivided into routes which are oral or rectal administrations. It is generally understood that a drug in the GI tract will be absorbed into the body mostly by passing into by crossing the small intestine section of the GI tract. Absorption of drugs into the blood stream after an oral drug administration occurs slightly across the stomach wall, under the tongue, between the cheek and gums/gingiva. Generally drugs will be formulated as a tablet, capsule, or drop when the drug is to be administered orally. A gastric feeding tube or a gastrostomy may be used as a method for administering a drug into the stomach. A duodenal feeding tube may be used for administering a drug into the small intestine. A rectal route of administration is an effective route of administration for a drug. When a medication is delivered to the distal one-third of the rectum, then there is the advantage that there is less liver metabolism of the drug as the drug is transported from the GI tract into the blood circulation of the individual. A suppository is a rectal formulation of a drug which is useful for very young children or a person who cannot take an oral dose of the drug. During hospice care of an individual needing administration of a drug, a rectal catheter may be used to deliver a drug. Parenteral administration generally occurs using a hypodermic syringe needle, or an indwelling catheter to administer the drug into a body compartment other than the GI tract. Parenteral administration into the central nervous system can occur by an injection or infusion into the epidural space. In some instances an intracerebral route of administration is used. This is a direct injection route into the brain. The intracerebral route be used to avoid the blockade of drug passage from the blood stream across the blood brain barrier. An injection under the skin is called a subcutaneous route of administration and is often used for local anesthesia. There are transdermal routes of administration which employ a patch on top of the skin containing a formulation of a drug which releases the drug to the skin. Sublingual administration involves placing the drug under the tongue. Buccal medication means placing the drug under the tongue or between the gums and the cheek. Sublingual and buccal medications generally are formulated as tablets, films, or sprays. Examples of drugs administered by a sublingual route of administration include some cardiovascular drugs, steroids, barbiturates, opioid analgesics, some enzymes, some vitamins and minerals. Nasal administration can be used for rapidly administration of a drug into an individual. Intra-arterial drug administration is sometimes been used to administer a drug with an arterial site of action such as vasodilator drugs for localized treatment of vasospasm and thrombolytic drugs. Intra-articular drug administration can be used to deliver a drug into a joint space. Intradermal administration of a substance means into the dermal skin layer and is used for testing of allergens, and the mantoux test for tuberculosis. An intralesional administration of an ointment of antibiotics into a skin wound is a common method for preventing a wound infection or treating a wound already infected. The term intramuscular administration refers giving a medication into a muscle and is often used for administering for example, a vaccine, an antibiotic, or an anti-inflammatory agent. Intraocular administration of a drug is a drug administration of the drug to the interior chamber of the eye. Drug administration by an intraosseous infusion means into the bone marrow and is also an indirect intravenous access because the bone marrow drains directly into the venous system. This route is occasionally used for drugs and fluids in emergency medicine and pediatrics when intravenous access is difficult. An intraperitoneal administration of a drug or fluid is an infusion or injection route. Intrathecal administration meaning into the spinal canal for giving spinal anesthesia and administering a chemotherapy drug. Intrauterine means an administration route to the inside of the uterus. Intravaginal administration means to inside the vagina. Intravenous meaning into a vein is a route of administration of drugs used commonly in a hospital setting during a medical operation and for bed patients so that a drug can be immediately or continually administered to a patient. An intravesicular infusion refers to a drug administration into the chamber of the urinary bladder. An intravitreal administration refers to drug administration into the vitreous humor of the eye. A subcutaneous administration of a drug is under the skin. A transdermal drug administration occurs by a diffusion of the drug through the intact skin for systemic treatment rather than a topical of the skin. The drug is formulated and used in a transdermal patches which is set down on the top of the skin like a band aid. Drugs administered by a transdermal patch include fentanyl in pain therapy, nicotine patches for treatment of addiction and nitroglycerine for treatment of angina pectoris. A perivascular administration refers to a location around a blood vessel and is often used by a surgeon during open vascular surgery. Drug administration by a transmucosal route is based on a diffusion of the drug from a mucous surface such as in the mouth, lungs, rectum, vagina, under the tongue, gingiva, nose, or another mucous membrane surface. The route or course the active substance takes from application location to the location where it has its target effect is usually rather a matter of pharmacokinetics of the drug which concern the processes of drug uptake, drug distribution, and elimination of the drug. However, transdermal and transmucosal routes are merely routes of administration. The location of the target effect of active substances is often used. A topical drug administration may be used to describe a local application location and local drug target.

Pharmacokinetic Measurements Are Related to Drug Blood Levels Over Time

There are a number of standard pharmacokintetic measurement and terms including drug dose, Cmax, Tmax, Cmin, Volume of Distribution, Blood Plasma Concentration, The drug dose refers to the amount of the drug that is administered to an individual. A drug dose formulation refers to a pharmaceutical formulation of a drug which typically contains a fixed amount of a drug per unit of the drug formulation. The drug formulation is designed to facilitate a reproducible therapeutic administration of the drug dose to an individual using a known route of administration. Cmax refers to the peak or maximum achieved plasma or blood concentration of a drug after administration of the drug to the individual. Tmax refers to the time to reach Cmax after administration of the drug to the individual. Cmin refers to the lowest concentration that a drug reaches before the next drug dose is administered to the individual. The pharmacokinetic measurement known as the Cmin is sometimes called the Trough level. The pharmacokinetic measurement known as the Volume of Distribution of a drug refers to the apparent volume of drug distribution in biological space(s) where a drug becomes distributed. The Volume of Distribution has units of liters. The pharmacokinetic measurement known as the Blood Plasma Concentration of a drug refers to the amount of the drug in a given volume of the blood plasma. The pharmacokinetic measurement known as the Elimination half-life refers to the time required for the concentration of the drug in some location, often in the blood plasma compartment, to reach half of its original value wherever the original value is selected. The pharmacokinetic measurement known as the Elimination rate constant is the rate at which a drug is removed from the body or a body compartment. Pharmacokinetic concept known as the Body Compartment refers to a tissue space which generally can be sampled or tested or measured by some means. A drug concentration may be measured in a body compartment. The pharmacokinetic measurement known as the Infusion rate refers to the rate of infusion of a drug into a compartment space of an individual required to balance elimination of the drug from a compartment space of an individual.

The pharmacokinetic measurement known as the Area under the Curve (AUC) is determined using drug blood plasma samples taken over time. The integral is calculated for the area under the curve of the blood plasma drug concentration for a given total time period. The drug administration may be a single dose, multiple drug doses, or a continuous drug administration. The AUC is used to calculate drug bioavailability. The AUC is measured in blood plasma samples taken from an individual at selected time periods following the single dose, the multiple drug doses, or the continuous drug administration to the individual. The calculated AUC is divided by the total amount of the drug dose administered and that fraction times 100% is the bioavailability of the drug in that individual al amount of the drug that created the total amount of the drug. The AUC of any compartment can be calculated where a drug may accumulate over time after its administration by a route of administration.

The pharmacokinetic measurement known as the Clearance (CL) is the volume of plasma cleared of the drug per unit time. Fluctuation is a pharmacokinetic measurement known in some cases specifically as a trough fluctuation within one dosing interval at steady state. In pharmacokinetics, steady state refers to the situation where the overall intake of a drug is fairly in dynamic equilibrium with its elimination. In practice, it is generally considered that steady state drug levels can be reached in a period of time which is between about 4 to 5 times the elimination half-life (T½) for a drug after a single drug dose or after a steady stage drug level causes by a period of constant time intervals (constant frequency) of drug dose administrations (Pharmacokinetics, Wikipedia, 2019).

An important property of embodiments of the present invention is their improved bioavailability to an individual. An important object of embodiments of the present invention is their improved bioavailability to an individual. One definition of the pharmacokinetic measurement known as the Bioavailability is the systemically available fraction of a drug after it has been given by a selected route of administration. Oral bioavailability is a pharmacokinetic measurement that can be obtained following an oral administration of a drug to an individual and refers to what percentage of a drug dose formulation is orally absorbed by an individual. Oral bioavailability can be determined by measuring the drug concentration in a series of blood plasma samples taken from the individual over a time of minutes to hours. The integral of the area under the curve (AUC) of the drug's blood plasma concentration over the time of minutes to hours following oral administration is one method that may allow for a calculation of the oral bioavailability of the drug dose formulation in the individual, (Pharmacokinetics, Wikipedia, 2019). Body compartment spaces in an animal include spaces that can be selected from the group consisting of a brain, a brain region, spinal cord, a cerebrospinal fluid, a skeletal muscle, a cardiac muscle, a body fat, a venous blood plasma, an arterial blood plasma, a placental blood, a cancer tumor, a bone, a cartilage, an intracellular space, an interstitial space, a lymph fluid, a lymph nodes, a pulmonary alveolar fluid, a pulmonary airway, a urine, a stomach fluid, a small intestine fluid, colon, a bile sample, a saliva, a vitreous humor of the eye, a uterine fluid, a testicular sample, a stool sample, a tear from an eye, a nasal discharge, a subcutaneous skin sample, a hair sample, a hair follicle sample, a subdermal sample, and a combination thereof.

Body compartment spaces in an plant include spaces which can be selected from the group consisting of a flower, a stem, a root, a leaf, a xylem, a phloem, chloroplast, a vesicle, a plant oil body, a seed, an endosperm, and a combination thereof. A number of factors may be evaluated in some product embodiments of the present invention for selecting a route of administration for the product. These factors include the following. Considered are physical and chemical properties of the drug such as its physical state as a solid, liquid or gas, and what other substances are present with the drug during its administration. Considered as well are a drug's chemical properties including drug solubility, stability, pH, and molecular weight. Considered is the target location for the drug to reach following drug administration. The target location may be localized, or widely distributed in the body of the individual. Considered is the rate and extent of absorption of the drug from different routes of administration. Considered is the degradative effect of digestive enzymes, the stomach acidity, the duodenal alkalinity, or need for actions of the digestive enzymes, the stomach acidity, the duodenal alkalinity. Considered is first pass metabolism of drugs phenomena which is that drug first pass thru the liver before reaching the blood stream after the drug's small intestinal absorption. Considered is the age, race, sex, and health of the individual.

Frequently in acute situations, in emergency medicine and intensive care medicine, a drug needs to be administered by an intravenous route such as an IV. This is the most reliable route, as in acutely ill patients the absorption of substances from the tissues and from the digestive tract can often be unpredictable due to altered blood flow or bowel motility.

In acute situations, in emergency medicine and intensive care medicine, drugs are most often given intravenously. This is the most reliable route, as in acutely ill patients the absorption of substances from the tissues and from the digestive tract can often be unpredictable due to altered blood flow or bowel motility. Also, identical drugs can produce different results depending on the route of administration. For example, some drugs are not significantly absorbed into the bloodstream from the gastrointestinal tract, and their action after enteral administration is therefore different from that after parenteral administration. For example the drug naloxone (Narcan) has different effects depending upon its route of administration. Naloxone is a well-known opiate drug antagonist used to antagonist an opiate drug effect in the central nervous system (CNS). In this case, the naloxone is administered by an intravenously route so as to very rapidly reverse an opiate overdose in the individual who may be unconscious. The same drug, when swallowed, acts exclusively on the bowels so as to reverse large intestinal immobility (constipation) which is a side effect in an individual taking an opiate pain therapy. In the prior art, an oral naloxone does not affect the pain-reducing effect of a systemic opiate pain therapy.

Some embodiments of the present invention are drug product formulations designed to have an increased bioavailability relative to prior art formulations of the drug. This is evidenced as one or more changes in pharmacokinetics for said drug. A drug formulation embodiment of the present invention may be specifically formulated so as to have a desired change in a pharmacokinetic parameter in a particular body space or location. Some embodiments of the invention are designed for modifying the speed of or extent of a drug action, the location of a drug action or the extent of a drug side effect. The pharmacokinetic parameter for modifying is selected from the group consisting of a reduced Tmax, an increased Tmax, an increased Cmax, a decreased Cmax can increased AUC, a changed T½, a changed kind of drug metabolites, a changed extent of drug metabolism, an increase in number of target locations of the drugs, new uses for the drug, or a combination of these changes in pharmacokinetics of the drug.

The oral route is generally the most convenient and costs the least. However, some drugs can cause gastrointestinal tract irritation. For drugs that come in delayed release or time-release formulations, breaking the tablets or capsules can lead to more rapid delivery of the drug than intended. The oral route is limited to formulations containing small molecules only while biopharmaceuticals (usually proteins) would be digested in the stomach and thereby become ineffective. Biopharmaceuticals have to be given by injection or infusion. However, recent research found an organic ionic liquid suitable for oral insulin delivery (a biopharmaceutical) into the blood stream Inhaled medications can be absorbed quickly and act both locally and systemically. Proper technique with inhaler devices is necessary to achieve the correct dose. Some medications can have an unpleasant taste or irritate the mouth.

Parenteral—The term injection encompasses intravenous (IV), intramuscular (IM), subcutaneous (SC) and intradermal (ID) administration. A peripheral IV may be located on a hand. A medical professional typically performs an intradermal (ID) injection. Parenteral administration generally acts more rapidly than topical or enteral administration, with onset of action often occurring in 15-30 seconds for IV, 10-20 minutes for IM and 15-30 minutes for SC. They also have essentially 100% bioavailability and can be used for drugs that are poorly absorbed or ineffective when they are given orally. Some medications, such as certain antipsychotics, can be administered as long-acting intramuscular injections. Ongoing IV infusions can be used to deliver continuous medication or fluids.

Disadvantages of injections include potential pain or discomfort for the patient and the requirement of trained staff using aseptic techniques for administration. However, in some cases, patients are taught to self-inject, such as SC injection of insulin in patients with insulin-dependent diabetes mellitus. As the drug is delivered to the site of action extremely rapidly with IV injection, there is a risk of overdose if the dose has been calculated incorrectly, and there is an increased risk of side effects if the drug is administered too rapidly.

Inhalation by smoking a substance is likely the most rapid way to deliver drugs to the brain, as the substance travels directly to the brain without being diluted in the systemic circulation. The severity of dependence on psychoactive drugs tends to increase with more rapid drug delivery.

In some embodiments, the present invention is a process, wherein more specifically the non-$H_2O$ substances are added to a volume of 50 gallons of ultrapure water, and wherein the non-$H_2O$ substances comprise:
  between about 0.02 ozs. to 25 ozs. of Capsaicin,
  between about 0.05 milligrams to 16 milligrams of Resveratrol,
  between about 10 milligrams to 850 milligrams of Quercetin,
  between about 500 milligrams to 12,000 milligrams of Vitamin D3, and
  between about 4 milligrams to 4,000 milligrams of Panax Ginseng.

In some embodiments, the present invention is a process, wherein more specifically the non-$H_2O$ substances are added to a volume of 50 gallons of ultrapure water, and, wherein the non-$H_2O$ substances comprise:
  between about 0.001 grams to 1000 grams of Synapta;
  between about 0.001 grams to 3000 grams of magnesium chloride;
  between about 0.0001 liters to 3 liters of Concentrace Trace Mineral Drops; and
  between about 0.01 grams to 100 grams sodium benzoate.

In some embodiments, the present invention is a process, wherein more specifically the non-$H_2O$ substances are added to a volume of 50 gallons of ultrapure water, and, wherein the non-$H_2O$ substances comprise:
  between about 0.001 grams to 1000 grams of Synapta;
  between about 0.001 grams to 3000 grams of magnesium chloride;
  between about 0.0001 liters to 3 liters of Concentrace Trace Mineral Drops; and
  between about 0.01 grams to 100 grams sodium benzoate.

In some embodiments, the present invention is a process, wherein more specifically the non-$H_2O$ substances are added to a volume of 50 gallons of ultrapure water, and, wherein the non-$H_2O$ substances comprise:
- between about 0.001 grams to 1000 grams of Synapta;
- between about 0.001 grams to 3000 grams of magnesium chloride;
- between about 0.0001 liters to 3 liters of Concentrace Trace Mineral Drops; and between about 0.01 grams to 100 grams sodium benzoate.

In some embodiments, the present invention is a process, wherein more specifically the reduced size water clusters containing the non-$H_2O$ substance in the aqueous medium is used to improve the bioavailability of the aqueous composition for a treatment of a chronic dehydration disorder in a mammal which has been producing physiological problems selected from the group consisting of dyspeptic pain, stress, depression, high blood cholesterol, high blood pressure, excess body weight, chronic fatigue, arthritis, asthma, allergy, insulin independent diabetes, and rheumatoid arthritis.

In some embodiments, the present invention is a process, wherein more specifically the reduced size water clusters containing the non-$H_2O$ substance in the aqueous medium is used to improve the bioavailability of a solution administered to a mammal in need of an acute rehydration.

In some embodiments, the present invention is a process, wherein more specifically the reduced size water clusters containing the non-$H_2O$ substance in the aqueous medium is used to improve the bioavailability of an aqueous composition of a pharmaceutical which is administered by an oral route, a parenteral route, a pulmonary route, an ocular route, an inter-nasal route, an intravenous route, and a sublingual route of administration.

In some embodiments, the present invention is a process, wherein more specifically the reduced size water clusters containing the non-$H_2O$ substance in the aqueous medium is used to improve the bioavailability of the aqueous composition of a beverage.

In some embodiments, the present invention is a process, wherein more specifically the reduced size water clusters containing the non-$H_2O$ substance in the aqueous medium is used to improve the bioavailability of a therapeutic water source capable of providing a hydration treatment to a mammal for a hydration benefit selected from the group consisting of a healthy body weight, an increased metabolism, an increased energy levels, a reduced join back pain, an easier flushing a body waste, a prevention of headaches including migraine headaches, alleviating headaches, a better skin hydration and skin health, a slowing of aging, and a stimulation of nutrient intake from food.

B. Experimental Data Examples and Related Process Information Examples

Example 1—Experimental Data on Products of the Invention

The inventors observed a significant reduction in sizes of water clusters in blended aqueous formulations comprising ultrapure water and a non-$H_2O$ substance(s).

A water cluster of the present invention is defined to mean a clustering of water molecules about a non-$H_2O$ substance. A non-$H_2O$ substance can be a therapeutic particle. Note the present invention title indicates that the Invention has processes making an aqueous therapeutic particle have stable exterior water clustering with nanosized thickness.

The clustering of water molecules about a non-$H_2O$ substance which can be a therapeutic particle is what can be detected by DLS measurements conducted by a Malvern Zetasizer. Also note that for the present invention, that a water cluster of the present invention is essentially an embodiment of the invention and includes cluster of water molecules derived from Ultrapure water (UPW) that can cluster about, or that can envelope, or that can encapsulate, or can surround a non-$H_2O$ substance such as for example a very small particle of CBD (cannabinoid). See FIG. 10 for a highly schematic or conceptual model depiction of a water cluster surrounding a very small CBD particle. The depiction in FIG. 10 is of an embodiment of the present invention (A) before nano-sizing of the water cluster and (B) after nano-sizing the water cluster. A very small CBD particle is merely one example of a non-$H_2O$ substance. The Process Step 8 of the present invention process which can be accomplished in a hollow cylinder 1218 or 1222 apparatus embodiment of the present invention is useful with non-$H_2O$ substances which may be considered hard or soft substances and/or which may be water insoluble or water soluble or dissociate in water. A water cluster embodiment of the present invention is also defined as being detectable by DLS technology and measured by a Malvern Zetasizer which creates a histogram of "particle sizes" with a median size. The measured size of water clusters which encapsulate a non-$H_2O$ substance are treated by the Malvern Zetasizer Instrument as if a diffusing particle by a DLS process. Therefore when the words "particle size" appear in this Specification and any claims that may result, then the words "particle size" shall mean the Malvern Zetasizer DLS process which measures the median size(s) of water clusters of UPW containing a non-$H_2O$ substance.

Figure 16:
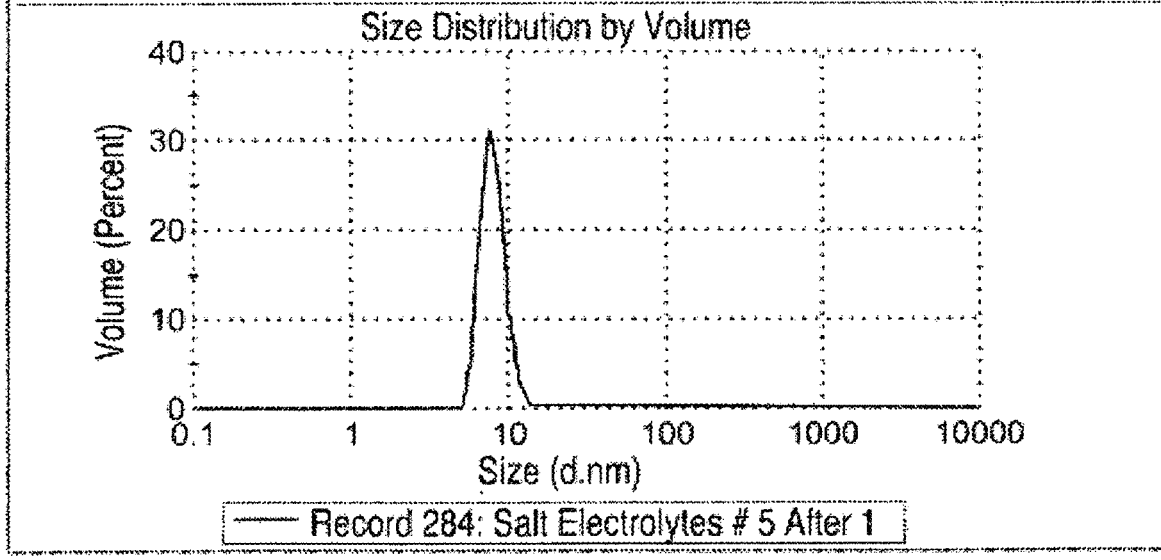
FIG. 16 presents Malvern Zetasizer instruments DLS data "Size distribution Reported by Volume" which are measurements of water clustered trace mineral ions sizes in a first sample taken from the flowing blended aqueous formulation 1213 in the transfer pipe 1217 (see FIG. 12 for transfer pipe 1217 location) after the flowing blended aqueous formulation 1213 enters into hollow cylinder 1218. The hollow cylinder 1218 process causes a reduction in the DLS based size measurement on the flowing blended aqueous formulation 1213. This concerns Process Step 8, and see FIGS. 11, 12, 13 and 14 for details of the manually-controlled apparatus for the nanosizing process. The non-$H_2O$ substance includes salt ions. There is a single mode distribution with a reported median size of 8 nanometers (nm) in the sample data record presented as FIG. 16 and it has a standard deviation of about 1.4 nanometers. See histogram at bottom of FIG. 16 for size distribution of the measured water clusters in the tested sample. This embodiment of the present invention based on testing of this first test sample, reduced the size of water clustered salt ion therapeutic particles in a flowing blended aqueous formulation 1213 from a median value of 358 nanometers to a median size of 8 nanometers.

FIG. 16 presents Zetasizer measurements of water cluster sizes in a first sample taken from the flowing blended aqueous formulation 1213 in the transfer pipe 1217 (see FIG. 12 for transfer pipe 1217 location) after the flowing blended aqueous formulation 1213 enters into hollow cylinder 1218. The hollow cylinder 1218 process (process Step 8, see FIGS. 11, 12, 13 and 14 for details) reduced median water cluster size in the flowing blended aqueous formulation 1213 to a Zetasizer measured median size of 8 nanometers (nm) in the sample data record presented as FIG. 16. See histogram at bottom of FIG. 16 for size distribution of the measured water clusters in the tested sample. FIG. 16 data represents proof of a reduction to practice of the invention. Embodiments of the present invention based on testing of this first sample reduced water cluster size in flowing blended aqueous formulation 1213.

Figure 15:
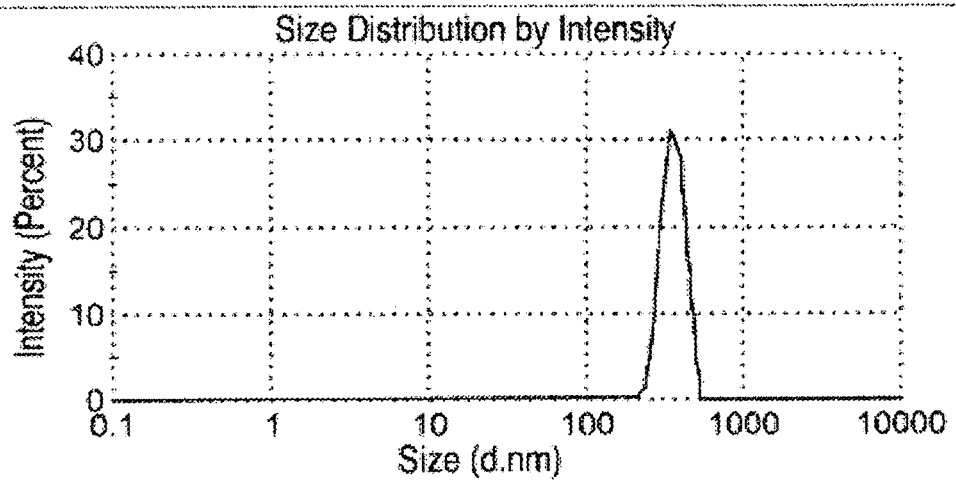
FIG. 15 presents Malvern Zetasizer instruments DLS data "Size distribution Reported by Volume" which are measurements of water clustered trace mineral ions sizes in a first sample obtained by the first inventor using the apparatus depicted schematically in FIG. 12. This first sample was obtained from the flowing blended aqueous formulation 1213 in the transfer pipe 1217. See FIG. 12 for transfer pipe 1217 location. The first sample was taken before the flowing blended aqueous formulation 1213 had entered into the hollow cylinder 1218 for processing to form nanosized clusters of water surrounding a nanosized non-$H_2O$ substance, In this experiment, the non-$H_2O$ substance comprises a mixture of mostly sodium, potassium, magnesium, chloride and sulfate ions which are water soluble ions. The Malvern Zetasizer instrument uses DLS methods to measure a laser detectable "particles" which are the individual nanosized clusters of water surrounding a nanosized non-$H_2O$ substance re is a single mode distribution with a reported median water cluster size of 358 nanometers (nm) in the sample data record presented as FIG. 15 and it has a standard deviation of about 58 nanometers. See histogram at bottom of FIG. 15 for size distribution of the measured water clusters in the tested sample.

FIG. 17 presents Zetasizer data "Size distribution Reported by Volume" which is measurements of water cluster sizes in an "early" sample taken at the start of operating the process when the flow rate in the hollow cylinder was low and before the flowing blended aqueous formulation 1213 enters into hollow cylinder 1218. The data unlike FIGS. 15 and 17 depicts three modes of size distributions with median sizes of 310 nm, 542 nm, and 20 nm. The standard deviation is 293 nm for the mode with a median value of 542 nm, and is 108 nm for the data with the median value of 310. See histogram at bottom of FIG. 17 for size distribution of the measured water clusters in the tested sample. FIG. 17 illustrates problem data that arises when the invention apparatus and its process are not operational or the process is poorly controlled.

For the present invention, low rates of flow as well as irregular flow rates through the hollow cylinder 1218 cause problems with the water cluster size distributions, including the production of several median size water cluster (particle sizes), thus particle sizes with multi-modal size distributions are detected. This can mean that many water clusters in the invention product will not have the desired particle size reduction and so a portion of a product might not have an optimal improvement in bioavailability to an individual consuming the product orally. Note that about 84% of the water clusters in before samples depicted in FIG. 17 have median size water clusters of 309 nanometer. Zetasizer measurements of samples after hollow cylinder 1218 indicate that 55% of the water clusters still have a median size of about 309 nm. At the same time there has been a 28% creation of 606 nm water clusters and only a 5% creation of 10 nanometer water clusters. At same time there is a disappearance of 11% large water clusters of 5400 nm. A precise understanding of what is happening is not clear other than a low flow rate and/or flow rate fluctuations through the hollow cylinder 1218 interferes with the processes causing nano-sizing. A preferred flow rate is 14 gallons per minute for the process apparatus depicted in FIG. 12. It was also discovered that too high flow rates through the hollow cylinder 1218 also are less efficient at reducing the water cluster sizes.

TABLE 2

Tabulated below are supporting data related to samples taken to measure Size Distributions of Water Clusters in Blended aqueous formulation 1213 by Process Step 6.

| Transfer pipe flow rate (16 gallons/minute) * | Sample 1,4 | Sample 2,5 | Sample 3,6 |
|---|---|---|---|
| Hollow cylinder Inner dimensions (width, length, inches") | 4' × 18' | 4' × 18' | 4' × 18' |
| Temperature before (° F.) | 93.2° F. | 93.2° F. | 93.0° F. |
| Temperature after (° F.) | 92.6° F. | 92.6° F. | 92.6° F. |
| Aqueous Medium pH before Step 6 | 7.81 | 5.88 | 5.79 |
| Aqueous Medium pH after Step 6 | 5.64 | 5.71 | 5.82 |
| ORP (millivolts, mV) before | +55.3 mV | +69.1 mV | +76.1 mV |
| ORP (millivolts, mV) after (Oxidation Reduction Potential) | +80.2 mV | +76.3 mV | +81.8 mV |

* Measured viscosity of the Aqueous Medium was 0.8872 centipoise before and after process step 6 process on Samples 1, 2, and 3.
** Samples 1, 2, and 3 contained Hangover Formulation TMC electrolytes and a salt as the non-$H_2O$ substance.

Example 2: Products with Reduced Size Water Clusters have Improved Bioavailability Inventors have been using the Malvern Zetasizer to measure the median size of the water clusters in experimental product embodiments of the present invention, and have been evaluating the improvements in bioavailability of experimental product embodiments of the present invention arising from the novel invention process of the present invention. The inventors observed that a composition with aqueous medium comprising UltraPure Water (UPW) and a non-$H_2O$ substance(s) has improved bioavailability when the median size of the water clusters in the aqueous medium is reduced to below 300 nanometers, preferably below a median size of 150 nanometers size, more preferably to below a median size of 75 nanometers, most preferably to below a median size of 40 nanometers size based on using a Malvern Zetasizer to determine median size of the water cluster size of the products of the invention. The inventor observed that an aqueous medium containing a non-$H_2O$ substance water clusters with a median size exceeding 400 nanometers has a poor bioavailability.

The inventors conclude that aqueous medium compositions which comprise a blended mixture of UPW with a non-$H_2O$ substance(s) and which have been manufactures by a process of the present invention are found to have (a) reduced size water clusters based on Malvern Zetasizer testing by the inventor, and (b) an improved bioavailability based on bioavailability testing by the inventor.

The Malvern Zetasizer DLS instrument was used by inventors to perform DLS (Dynamic Light Scattering) experiments to measure the median values of therapeutic aqueous particle sizes with nanosized water clusters present in the invention process product fluid. The aqueous particles being measured are water clusters containing non-$H_2O$ ingredients in a purified water intended to become a hydration drink. These experimental batches of the hydration drink were not commercialized. FIGS. 15, 16, 17, and 18. depict histograms of aqueous particle size data obtained from the Malvern Zetasizer DLS instrument. From these histograms the median aqueous particle sizes in the purified water are readily apparent in most cases. For the experimental hydration drink product batches, their particle size histograms are used: (1) to determine the number of aqueous particle size distribution modes; (2) to determine the median sizes of the aqueous particle size distributions; and (3) to evaluate the breadth of the aqueous particle size distributions to assess the variability of the aqueous particle sizes.

As mentioned previously, the FIGS. 21, 22, and 23 provide schematic depictions of invention apparatus designs that are marked improvements over the FIG. 12 process apparatus. FIG. 23 depicts two hollow cylinders 1218 and 2322 in a serial configuration or arrangement. In some embodiments of the present invention the number of hollow cylinders used in an invention apparatus and an invention process is selected from the group consisting of 1, 2, 3, 4, 5, 6, 7, 8, 9, 10, 11, 12, 13, 14, 15, 16; 17, 18, 19, 20, and any combination thereof. The hollow cylinders may be arranged in parallel or in series configurations or arrangements as wished or needed to optimize the nanosizing process used for reducing the sizes of water clusters containing a non-$H_2O$ substance(s). The FIG. 23 apparatus has been tested with a new experimental drink product which comprises nano-sized CBD particles in nano-sized UPW water. The Malvern Zetasizer histograms for nanometer particle size measurements of experimental production batches of this CBD drink product are depicted in FIGS. 27 and 28.

Example 3: Storage Stability of Invention Products Having Reduced Size of Water Clusters in the UPW Containing Non-$H_2O$ Substance(s)

In one example, the Process step 7 product by the process depicted in FIG. 11 and FIG. 12 is stored temporarily in a suitable air-tight stainless steel tank 1220. The product 1219 is an aqueous medium which comprises the nanosized water clusters with nanosized non-$H_2O$ substance(s). The shelf life of the product 1219 for various use formulations of the invention is being investigated using long term stability testing. Product 1219 development and DLS measurements of product 1219 water cluster size distributions have been an ongoing research experiment for eight years by one inventor. This inventor here reports that surprisingly and quite unexpectedly, that the nanosized water cluster size distributions in one batch of a product 1219 formulation has remained substantially unchanged and thus appears to be stable for at least 8 years after its production by the FIG. 12 invention process. Secondly, the inventor confirmed that the nanosized water cluster size distributions in a second batch of a product 1219 formulation which is 2 years old also has stable nanosized water cluster sizes that encapsulate a nano-sized non-$H_2O$ substance.

Example 4: Football Nanowater Sports Drink Prevents Severe Dehydration

A confidential proof of concept study of a drink embodiment of the present invention was conducted using college football teams' players. Testing of the drink embodiment was conducted under three different weather conditions during football games: (a) very hot temperatures, (b) moderately hot temperatures, and (c) comfortable temperatures. The proof of concept study was conducted in the southern United States where the weather can be humid and very hot. The home team participants believed they were simply drinking PowerAde™ and told to drink it whenever they wanted (ad libitum). It was noticed that many home team participants were frequently drinking a test sports drink formulation of the present invention during their football games. The goal of the inventors sports drink study was to find evidence to support the inventors hypothesis that the test sports drink formulation (which was a drink embodiment of the present invention) provided an essential high bioavailability benefit which football players need and it was superior to the benefit they received by simply drinking PowerAde™. It was hypothesized by the inventors that their test sports drink formulation should demonstrate a higher bioavailability than PowerAde™ could, and therefore it should be a better hydration drink for football players. The Troy University Football Team (Troy, Alabama) played about 50 players in each of their football games. Apparently about 60% of the Troy University Football Team players (N=approx. 30 players) drank the experimental sports drink formulation of the present invention whenever they wanted. Other Troy University Football Team payers (N=Approx. 20 players) drank a different sports drink formulation embodiment of the present invention as they wished. This drink contained PowerAde™ sports drink powder, so as to make the drink useful as a sports hydration drink.

For the first seven weeks of their football game season Troy football players played football games in warm-very hot weather with temperatures ranging between 76° F. to 97° F. In warm to very hot weather, their opponent football teams had to deal with the problem that twenty-two (22) of their football players had a medical emergency that immediately needed an IV (intravenous fluid) treatment on the football field or later to treat a football player who had become severely dehydrated. The proof of concept evidence for the drink invention having a high bioavailability came when it was discovered that not even one Troy Football Team player had a medical emergency needing an IV (intravenous fluid) treatment on the football field or afterwards.

For the last five weeks of their football game season Troy football players played football games in cooler temperatures between 52° F. to 58° F. Even in a cool weather, the Opponent Football teams had seven (7) of their football players with a medical emergency needing an IV treatment on the football field or after the game to treat their significant dehydration. Surprisingly, Troy Football players had not even one football player having a medical emergency needing an IV treatment to help them to rehydrate from their muscles cramping or from another sign of dehydration in cool weather.

In the last week of their football season, Troy had a Championship Football Bowl game. The Opponent Football Team had three (3) football players who played in the Bowl Game and had a medical emergency needing IV treatments on the football field or afterwards due to their significant dehydration. Surprisingly, Troy Football Team had not even one football player who as a result of playing in the Bowl Game had a medical emergency needing an IV treatment on the football field during the time of the game or afterwards.

The straightforward design of this sports drink study and surprising test results mentioned above, established that the Troy Football players were continually better hydrated in contrast to the football teams they played. The simple conclusion is that a football sports team can significantly benefit by drinking a high bioavailability sports drink formulation of the present invention. The experiment also established that conventional sports hydration drinks can fail to adequately hydrate a football team players, particularly in hot weather. The opposing teams needed 32 intravenous re-hydrations of football players during the football season and at the same time not even one intravenous rehydration was needed by a Troy University football player. The odds of this being a random result appear extremely unlikely. The inventors believe this sports drink study shows the present invention sports drink is a surprisingly improved water bioavailability product compared to prior art hydration drinks used by college football teams, both in hot and cool weather.

Example 5: More Details on Enabling the Use of Malvern Zetasizer to Make Nanometer Size Measurements of the Water Clusters Containing a Non-$H_2O$ Substance(s) by Using Dynamic Light Scattering Technology There are methods to measure particle size, for example by Dynamic Light Scattering (DLS) which is a technique in physics that can be used to determine the size distribution profile of small particles in suspension or polymers in solution, as well as the size distribution profile of the size of water clusters in the UPW containing non-$H_2O$ substance(s).

In the scope of DLS, temporal fluctuations are usually analyzed by means of the intensity or photon auto-correlation function (also known as photon correlation spectroscopy or quasi-elastic light scattering). In the time domain analysis, the autocorrelation function (ACF) usually decays starting from zero delay time, and faster dynamics due to smaller particles lead to faster decorrelation of scattered intensity trace. It has been shown that the intensity ACF is the Fourier transformation of the power spectrum, and therefore the DLS measurements can be equally well performed in the spectral domain. DLS can also be used to probe the behavior of complex fluids such as concentrated polymer solutions. (Dynamic light scattering, Wikipedia, 2018).

A monochromatic light source, usually a laser, is shot through a polarizer and into a sample. The scattered light then goes through a second polarizer where it is collected by a photomultiplier and the resulting image is projected onto a screen. This is known as a speckle pattern.

All of the molecules in the solution are being hit with the light and all of the molecules diffract the light in all directions. The diffracted light from all of the molecules can either interfere constructively (light regions) or destructively (dark regions). This process is repeated at short time intervals and the resulting set of speckle patterns are analyzed by an auto correlator that compares the intensity of light at each spot over time. The polarizers can be set up in two geometrical configurations. One is a vertical/vertical (VV) geometry, where the second polarizer allows light through that is in the same direction as the primary polarizer. In vertical/horizontal (VH) geometry the second polarizer allows light not in same direction as the incident light.

When light hits small particles, the light scatters in all directions (Rayleigh scattering) as long as the particles are small compared to the wavelength (below 250 nm). Even if the light source is a laser, and thus is monochromatic and coherent, the scattering intensity fluctuates over time. This fluctuation is due to small molecules in solutions undergoing Brownian motion, and so the distance between the scatterers in the solution is constantly changing with time. This scattered light then undergoes either constructive or destructive interference by the surrounding particles, and within this intensity fluctuation, information is contained about the time scale of movement of the scatterers. Sample preparation either by filtration or centrifugation is critical to remove dust and artifacts from the solution. At short time delays, the correlation is high because the particles do not have a chance to move to a great extent from the initial state that they were in. The two signals are thus essentially unchanged when compared after only a very short time interval. As the time delays become longer, the correlation decays exponentially, meaning that, after a long time period has elapsed, there is no correlation between the scattered intensity of the initial and final states. This exponential decay is related to the motion of the particles, specifically to the diffusion coefficient. To fit the decay (i.e., the autocorrelation function), numerical methods are used, based on calculations of assumed distributions. If the sample is monodisperse then the decay is simply a single exponential. The Siegert equation relates the second-order autocorrelation function with the first-order autocorrelation function.

A correction factor that depends on the geometry and alignment of the laser beam in the light scattering setup. It is roughly equal to the inverse of the number of speckle (see Speckle pattern) from which light is collected. A smaller focus of the laser beam yields a coarser speckle pattern, a lower number of speckle on the detector, and thus a larger second order autocorrelation.

The most important use of the autocorrelation function is its use for size determination. The dynamic information of the particles is derived from an autocorrelation of the intensity trace recorded during the experiment. The second order autocorrelation curve is generated from the intensity trace.

Dynamic light scattering provides insight into the dynamic properties of soft materials by measuring single scattering events, meaning that each detected photon has been scattered by the sample exactly once. However, the application for many systems of scientific and industrial relevance has been limited due to often-encountered multiple scattering, wherein photons are scattered multiple times by the sample before being detected. Accurate interpretation becomes exceedingly difficult for systems with non-negligible contributions from multiple scattering. Especially for larger particles and those with high refractive index contrast, this limits the technique to very low particle concentrations, and a large variety of systems are, therefore, excluded from investigations with dynamic light scattering. It is possible to suppress multiple scattering in dynamic light scattering experiments via a cross-correlation approach. The general idea is to isolate singly scattered light and suppress undesired contributions from multiple scattering in a dynamic light scattering experiment. Different implementations of cross-correlation light scattering have been developed and applied. Currently, the most widely used scheme is the so-called 3D-dynamic light scattering method. The same method can also be used to correct static light scattering data for multiple scattering contributions. Alternatively, in the limit of strong multiple scattering, a variant of dynamic light scattering called diffusing-wave spectroscopy can be applied.

Depending on the anisotropy and polydispersity of the system, a resulting plot of ($\Gamma/q2$) vs. q2 may or may not show an angular dependence. Small spherical particles will show no angular dependence, hence no anisotropy. A plot of ($\Gamma/q2$) vs. q2 will result in a horizontal line. Particles with a shape other than a sphere will show anisotropy and thus an angular dependence when plotting of ($\Gamma/q2$) vs. q2. The intercept will be in any case the Dt. Thus there is an optimum angle of detection $\theta$ for each particle size. A high quality analysis should always be performed at several scattering angles (multi-angle DLS). This becomes even more important in a poly-disperse sample with an unknown particle size distribution. At certain angles the scattering intensity of some particles will completely overwhelm the weak scattering signal of other particles, thus making them invisible to the data analysis at this angle. DLS instruments which only work at a fixed angle can only deliver good results for some particles. Thus the indicated precision of a DLS instrument with only one detection angle is only ever true for certain particles. (Dynamic light scattering, Wikipedia, 2018).

Dt is often used to calculate the hydrodynamic radius of a sphere through the Stokes-Einstein equation. It is important to note that the size determined by dynamic light scattering is the size of a sphere that moves in the same manner as the scatterer. So, for example, if the scatterer is a random coil polymer, the determined size is not the same as the radius of gyration determined by static light scattering. It is also useful to point out that the obtained size will include any other molecules or solvent molecules that move with the particle. So, for example, colloidal gold with a layer of surfactant will appear larger by dynamic light scattering (which includes the surfactant layer) than by transmission electron microscopy (which does not "see" the layer due to poor contrast).

In most cases, samples are poly-disperse. Thus, the autocorrelation function is a sum of the exponential decays corresponding to each of the species in the population It is tempting to obtain data for g1(q;τ) and attempt to invert the above to extract G($\Gamma$). Since G($\Gamma$) is proportional to the relative scattering from each species, it contains information on the distribution of sizes. However, this is known as an ill-posed problem. The methods described below (and others) have been developed to extract as much useful information as possible from an autocorrelation function.

One of the most common methods is the cumulant method, from which in addition to the sum of the exponentials above, more information can be derived about the variance of the system as follows:

where $\Gamma$ is the average decay rate and $\mu2/\Gamma2$ is the second order polydispersity index (or an indication of the variance). A third-order polydispersity index may also be derived but this is necessary only if the particles of the system are highly poly-disperse. The z-averaged translational diffusion coefficient Dz may be derived at a single angle or at a range of angles depending on the wave vector q.

One must note that the cumulant method is valid for small r and sufficiently narrow G($\Gamma$). One should seldom use parameters beyond µ3, because overfitting data with many parameters in a power-series expansion will render all the parameters including F less precise. The cumulant method is far less affected by experimental noise than the methods below. CONTIN algorithm An alternative method for analyzing the autocorrelation function can be achieved through an inverse Laplace transform known as CONTIN developed by Steven Provencher. CONTIN analysis is ideal for hetero-disperse, poly-disperse, and multimodal systems that cannot be resolved with the cumulant method. The resolution for separating two different particle populations is approximately a factor of five or higher and the difference in relative intensities between two different populations should be less than 1:10-5.

Maximum entropy method is an analysis method that has great developmental potential. The method is also used for the quantification of sedimentation velocity data from analytical ultracentrifugation. The maximum entropy method involves a number of iterative steps to minimize the deviation of the fitted data from the experimental data and subsequently reduce the $\chi^2$ of the fitted data.

Scattering of non-spherical particles—If the particle in question is not spherical, rotational motion must be considered as well because the scattering of the light will be different depending on orientation. According to Pecora, a rotational Brownian motion will affect the scattering when a particle fulfills two conditions; they must be both optically and geometrically anisotropic. Rod shaped molecules fulfill these requirements, so a rotational diffusion coefficient must be considered in addition to a translational diffusion coefficient. In its most succinct form the equation appears as Where A/B is the ratio of the two relaxation modes (translational and rotational), Mp contains information about the axis perpendicular to the central axis of the particle, and Ml contains information about the axis parallel to the central axis.

In 2007, Peter R. Lang and his team decided to use dynamic light scattering to determine the particle length and aspect ratio of short gold nanorods. They chose this method due to the fact that it does not destroy the sample and it has a relatively easy setup. Both relaxation states were observed in VV geometry and the diffusion coefficients of both motions were used to calculate the aspect ratios of the gold nanoparticles.

Applications—DLS is used to characterize size of various particles including proteins, polymers, micelles, vesicles, carbohydrates, nanoparticles, biological cells, and gels. If the system is not disperse in size, the mean effective diameter of the particles can be determined. This measurement depends on the size of the particle core, the size of surface structures, particle concentration, and the type of ions in the medium.

Since DLS essentially measures fluctuations in scattered light intensity due to diffusing particles, the diffusion coefficient of the particles can be determined. DLS software of commercial instruments typically displays the particle population at different diameters. If the system is monodisperse, there should only be one population, whereas a poly-disperse system would show multiple particle populations. If there is more than one size population present in a sample then either the CONTIN analysis should be applied for photon correlation spectroscopy instruments, or the power spectrum method should be applied for Doppler shift instruments.

Stability studies can be done conveniently using DLS. Periodical DLS measurements of a sample can show whether the particles aggregate over time by seeing whether the hydrodynamic radius of the particle increases. If particles aggregate, there will be a larger population of particles with a larger radius. In some DLS machines, stability depending on temperature can be analyzed by controlling the temperature in situ.

Malvern Instruments sells the Zetasizer Nano ZSP which is a high performance system and particularly suitable for the characterization of proteins and nanoparticles where the highest sensitivity for size and zeta potential measurement is required. It includes a Protein Measurement option for protein mobility measurements. The system incorporates a two angle particle and molecular size analyzer for the enhanced detection of aggregates and measurement of small or dilute samples, and samples at very low or high concentration using dynamic light scattering with 'NIBS' optics. The ZSP also incorporates a zeta potential analyzer that uses electrophoretic light scattering for particles, molecules and surfaces, and a molecular weight analyzer using static light scattering. Using Non-Invasive Backscatter optics (NIBS) it has significantly better performance than systems using 90 degree scattering optics. In addition, a micro-rheology option is available for measuring sample viscosity and viscoelastic properties. The flow mode option enables the system to be connected to an SEC or an FFF system to use as a detector for the size of proteins or nanoparticles. A choice of cuvettes are available, from disposable single-use to specific cells for viscous or high concentration samples or measuring the zeta potential of surfaces.

Parameters measured: Particle and molecule size, translational diffusion, electrophoretic mobility, zeta potential of particles at high and low concentrations, viscosity and viscoelasticity of protein and polymer solutions, concentration, MW, $A_2$, $k_D$. An optional accessory enables measurement of the zeta potential of solid surfaces. Exceptional sensitivity for the zeta potential measurement of proteins and nanoparticles using patented M3-PALS. Size measurement from 0.3 nm (diameter) to 10 microns using patented NIBS (Non-Invasive Back Scatter) technology. Zeta potential of surfaces using accessory cell. Molecular weight measurement down to 980 Da. Micro-rheology option to measure viscosity and viscoelasticity. Outstanding protein size measurement sensitivity, 0.1 mg/mL (Lysozyme). Sample concentrations from 0.1 ppm to 40% w/v. Built-in protein calculators, including protein charge, $A_2$, $k_D$, and molecular conformation. A 'Quality Factor' and 'Expert Advice System' gives the confidence of having an expert at your shoulder. 21CFR part 11 software option to enable compliance with ER/ES. Research software option to give access to further features and analysis algorithms for the light scattering specialist. Automation of measurements using an auto-titrator option. Chromatography detector capability to enable use as a size detector with GPC/SEC or FFF. Optical filter option to improve measurements with fluorescent samples. Note that polystyrene latex standards are used to demonstrate the accuracy, reliability and reproducibility of the Nano-Sampler accessory for the Zetasizer Nano series of instruments. 60 nm Polystyrene LTX3060A and 200 nm beads LTX3200A standard deviations of about 0.5% in batch, auto-sampled, as well as aliquot to. Automate particle size measurements for the Zetasizer Nano using the Nano-Sample—a versatile, compact sample management accessory that precisely and reproducible loads your samples into the Zetasizer Nano. Automated measurements reduce operator bias and improve laboratory efficiency. Automate sample loading, reproducibility studies and increase sample throughput. Unattended multivariate analysis simplifies exploration of the effect of key formulation parameters. Makes the Zetasizer Nano even easier to use and enables 24/7 operation Simple change over from automated to manual measurement.

Example 6: Nano-Sized Particle Shape (Nanoparticle Shape) Surface Area to Volume of Nano-Sized Particles Measurements of nanoparticle dimensions allow calculations of average nanoparticle surface area (SA) and average nanoparticle volume (Vol). A SA/Vol ratio can be calculated assuming the nanoparticle has a smooth and simple geometric surface and volume.

Below Tables 1-4, compare calculated values of SA, Vol, and SA/Vol for four different nanoparticle volume shapes: cube, sphere, long round rod, and flat cylinder. In these examples, the long round rod has been made six times longer than its diameter. The flat cylinder has a diameter which is six times greater than its height.

In Tables 1, 2, 3, and 4, the SA, the Vol, and the SA/Vol are shown for 1, 10, 100, and 1000 nm size nanoparticles.

TABLE 1

| Nanoparticle Cube SD = side wall | Smallest Dimension ("SD") (nm) | Surface Area ('SA') ($nm^2$) $SA = 6d^2$ | Volume ('Vol') ($nm^3$) $Vol = d^3$ | SA/Vol ($nm^{-1}$) | SA/Vol change compared to a 1 micron nanoparticle |
|---|---|---|---|---|---|
| | 1 | 6 | 1 | 6.0 | 1,000 |
| | 10 | 600 | 1,000 | 0.60 | 100 |
| | 100 | 60,000 | 1,000,000 | 0.060 | 10 |
| | 1,000 | 6,000,000 | 1,000,000,000 | 0.0060 | 1 |

TABLE 2

| Nanoparticle sphere SD = diameter | Smallest Dimension ("SD") (nm) | Surface Area ('SA') ($nm^2$) $SA = 4\pi(d/2)2 = \pi d^2$ | Volume ('Vol') ($nm^3$) Volume = $(4/3)\pi(d/2)^3 = (1/6)\pi d^3$ | SA/Vol ($nm^{-1}$) | SA/Vol change compared to a 1 micron nanoparticle |
|---|---|---|---|---|---|
| | 1 | 3.14 | 0.524 | 6.0 | 1,000 |
| | 10 | 314 | 524 | 0.60 | 100 |
| | 100 | 31,400 | 524,000 | 0.060 | 10 |
| | 1000 | 3,140,000 | 524,000,000 | 0.0060 | 1 |

Note 1: Table 1 and Table 2 calculations indicate a sphere with a diameter the same as the side wall length of a cube, has about one-half the surface area and about one half the volume of the cube.

Note 2: Table 1 and Table 2 calculations show that the SA/Vol ratio of the cube and sphere both increase 1,000-fold and at the same rate as the nanoparticle diameter becomes 1,000-fold less.

TABLE 3

| Nanoparticle Rod. SD = D and Length = 6D. | Smallest Dimension ("SD") (nm) | Surface Area ('SA') ($nm^2$) $SA = 2\pi(d/2)2 + (6d)2\pi d/2 = 6.5 \pi d^2$ | Volume ('Vol') ($nm^3$) $Vol = 6d\pi(d/2)^2 = 1.5 \pi d^3$ | SA/Vol ($nm^{-1}$) | SA/Vol change compared to a 1 micron nanoparticle |
|---|---|---|---|---|---|
| | 1 | 20.4 | 4.71 | 4.3 | 1,000 |
| | 10 | 2,040 | 4,710 | 0.43 | 100 |
| | 100 | 204,000 | 4,710,000 | 0.043 | 10 |
| | 1,000 | 20,400,000 | 4,710,000,000 | 0.0043 | 1 |

TABLE 4

| Nanoparticle Disk of Thickness = D/6 | Smallest Dimension is diameter ("D") (nm) | Surface Area ('SA') ($nm^2$) $SA = 2\pi(d/2)2 + (d/6)2\pi d/2 = (2/3)\pi d^2$ | Volume ('Vol') ($nm^3$) $Vol = (d/6)\pi(d/2)^2 = (2/3)\pi d^3$ | SA/Vol ($nm^{-1}$) | SA/Vol change compared to a 1 micron nanoparticle |
|---|---|---|---|---|---|
| | 1 | 2.09 | 2.09 | 1 | 1,000 |
| | 10 | 209 | 2090 | 0.1 | 100 |
| | 100 | 20,900 | 2,090,000 | 0.01 | 10 |
| | 1000 | 2,900,000 | 2,090,000,000 | 0.001 | 1 |

The rates and amounts of molecular events occurring at the surface of the nanoparticle are scaled as a function of the SA per nanoparticle and these events may alter an environment outside the nanoparticle as a function of the total SA of the nanoparticles dispersed in this environment. The surface of the nanoparticle with respect to its external environment creates an interface where various chemical, thermodynamic, and entropic forces interplay. Due to differences between the surface and its events in relation to external environment differences and events, the zone above the nanoparticle in which there the chemical, thermodynamic, and entropic forces need to be considered can be viewed as having a thickness. Thus the interface should not be visualized as necessarily a thin surface but as a potentially complex atmosphere surrounding a nanoparticle, particularly when the nanoparticle is contained within a biological external environment.

Figure 1:
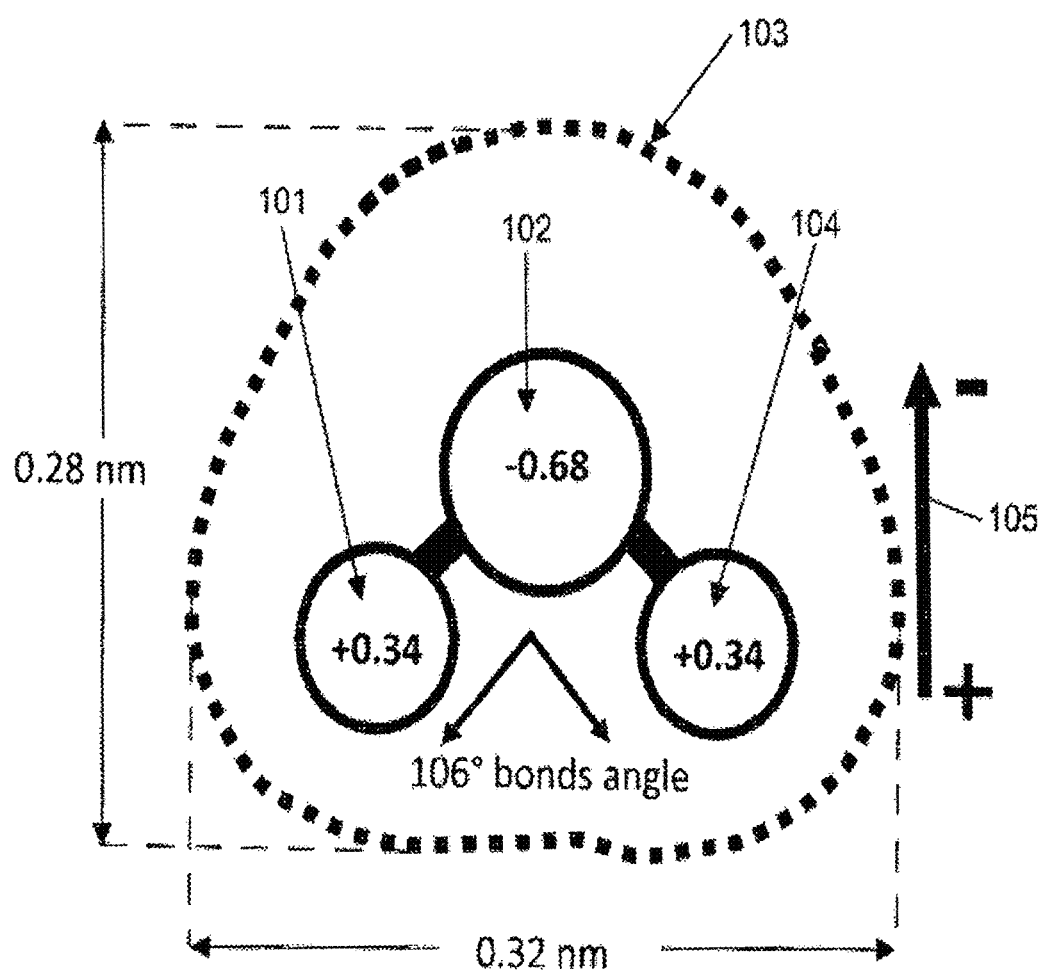
FIG. 1 depicts a prior art diagram of a gas phase water molecule in which water is portrayed as a simple molecule containing 2 hydrogen atoms and 1 oxygen atom with a bond angle of 106 degrees and as a polar molecule.
Figure 2:
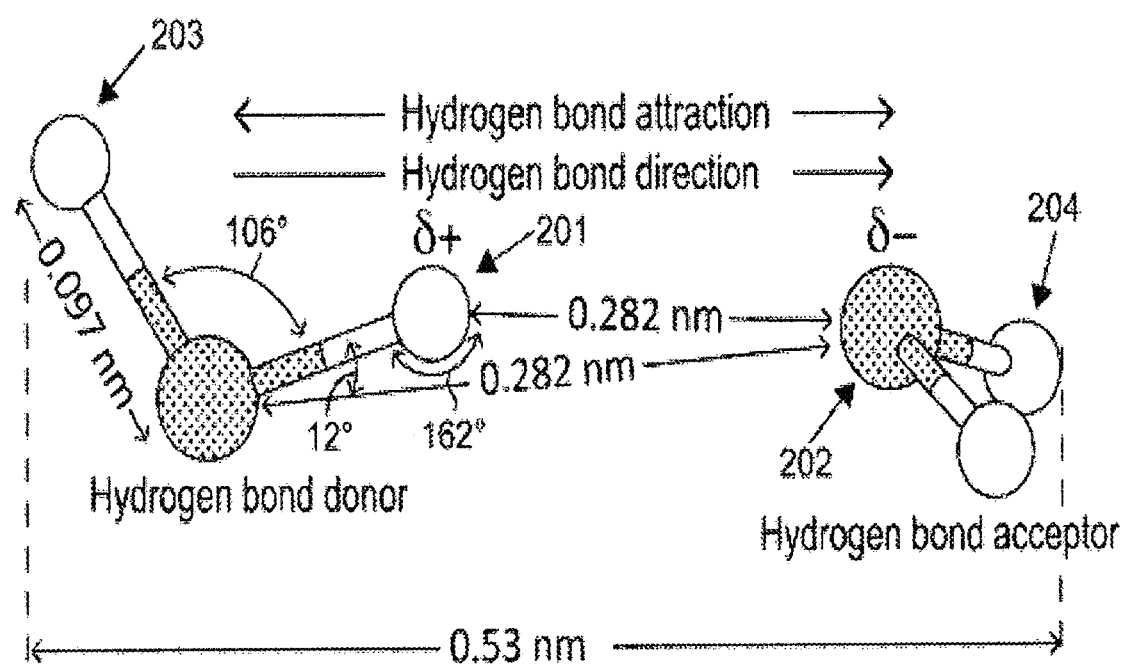
FIG. 2 depicts a prior art diagram of 2 water molecules engaged in hydrogen bonding one water molecule oxygen atom 202 and the second water molecule hydrogen atom 201 form an H-bond. Such a simple 2 molecule interaction may be uncommon in liquid water where formations of a larger number of water molecules in interactions together involving 2, 3, and 4 hydrogen bonding events with neighboring water molecules are more commonly observed.
Figure 3:
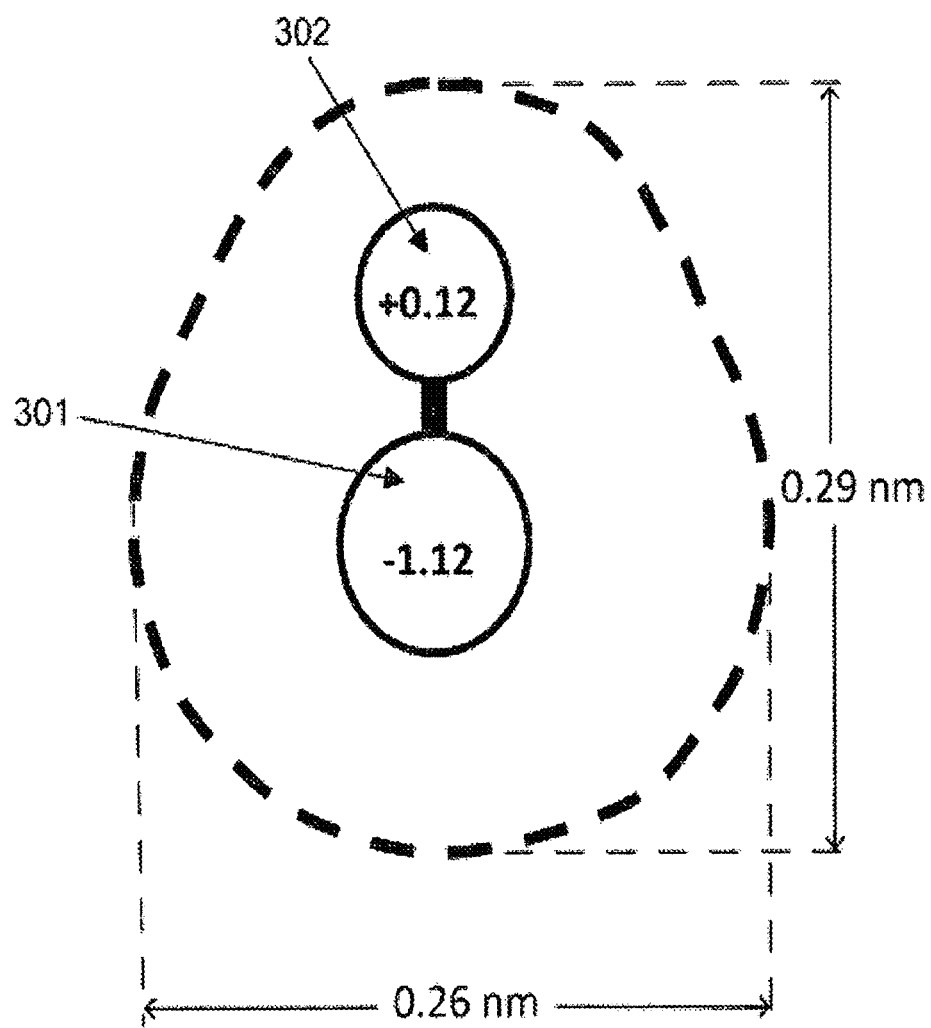
FIG. 3 depicts a prior art diagram in an overly simplified structure for the hydroxonium ion (—OH) in water which has also been called the hydroxide anion.
Figure 4:
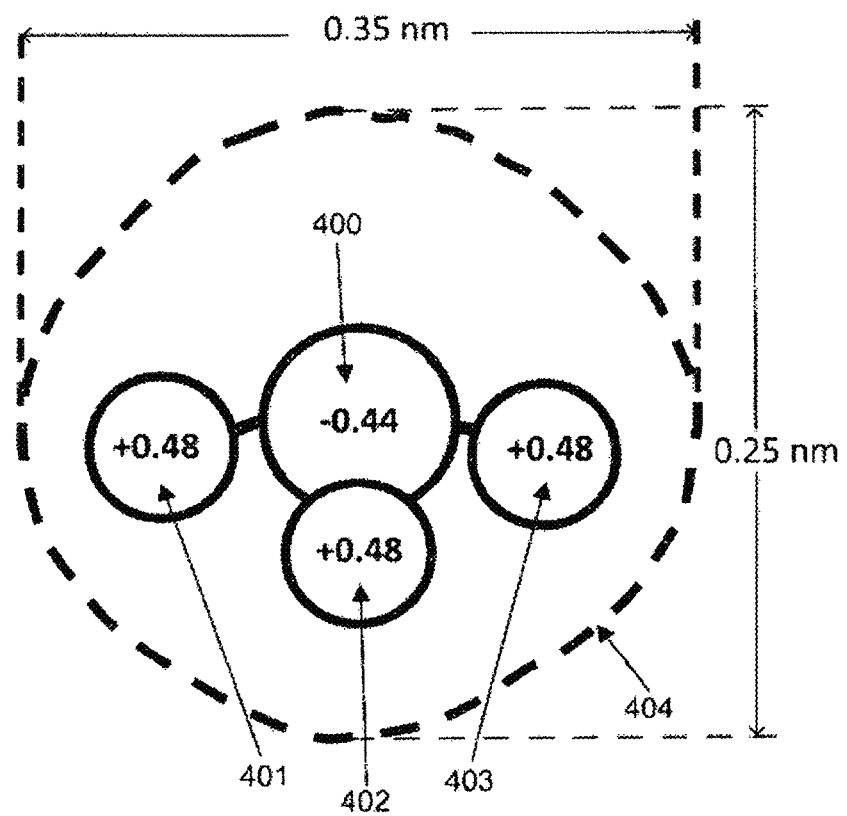
FIG. 4 depicts a prior art diagram of hydronium ion molecule in an overly simplified form as having 3 hydrogen atoms and 1 oxygen atom.
Figure 5:
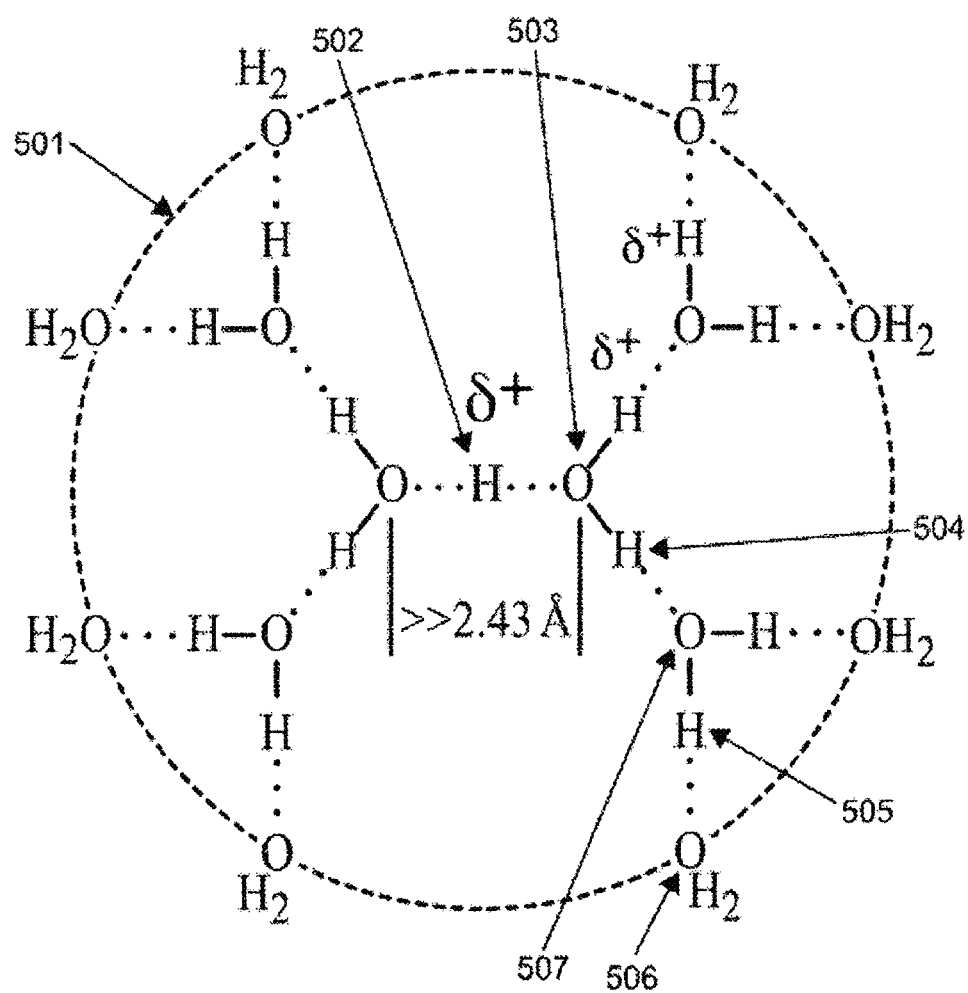
FIG. 5 depicts a prior art model of how a hydrogen ion (proton) might become situated between 2 oxygen atoms of 2 different water molecules as a means for a neutralization or a delocalization of some of the positive charge of the proton. This model was proposed by Stoyanov in 2010 and represents a 6 water molecule planar network of hydrogen bonding within the dashed circle 501. This 6 molecule water structure has been assigned the molecular formula $H_{13}O_6^+$.
Figure 6:
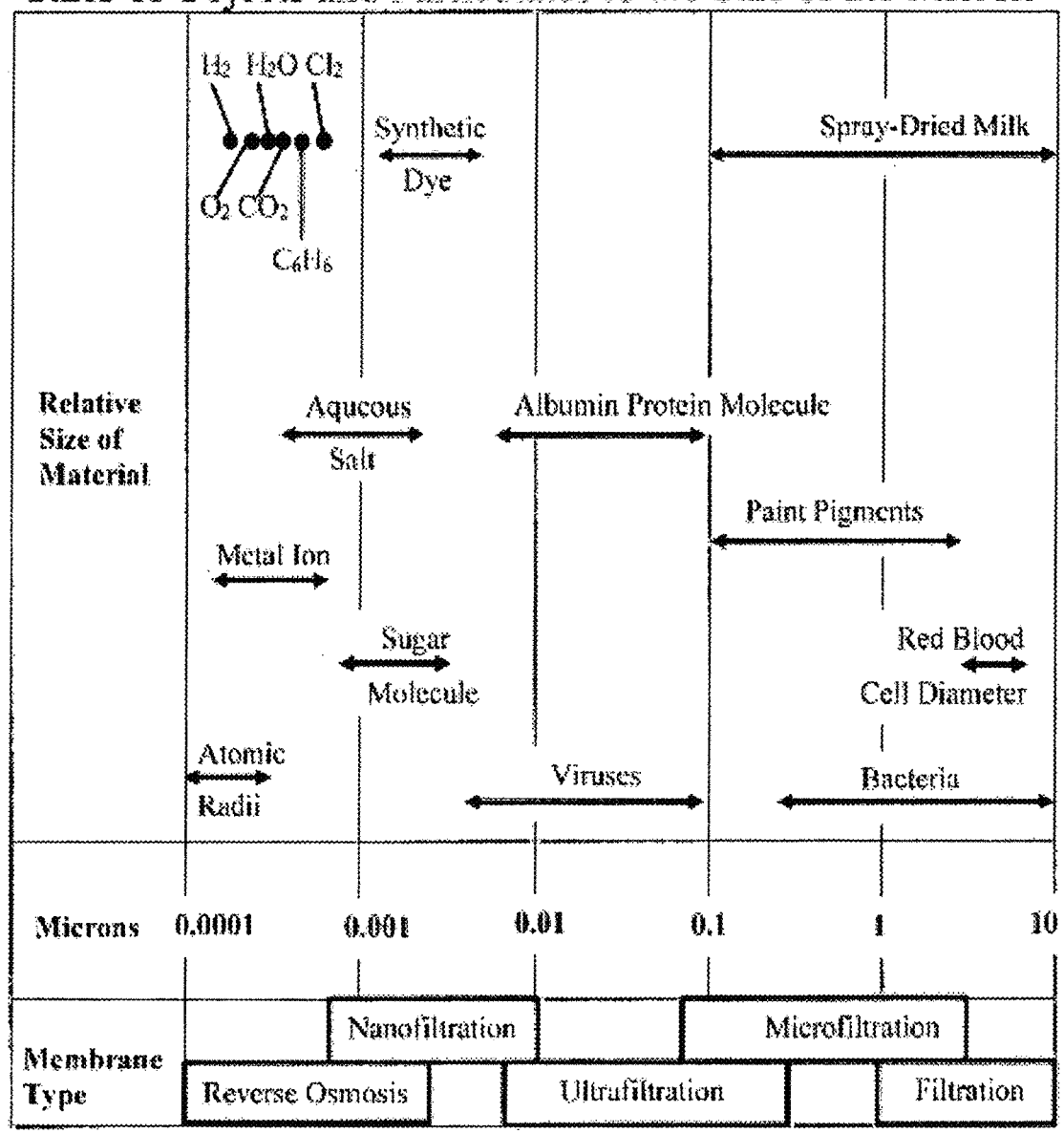
FIG. 6 depicts a prior art diagram listing the ranges of sizes of substances (microorganisms, proteins, sugars, aqueous salts, metal ions and water molecules). The diagram does not suggest hydrogen bond related water clusters, aggregates of water molecules, organized arrays of water molecules or the like whatsoever, particularly note in aqueous salt size ranges. Only large particle sizes (100 nm or larger sizes) are shown for solids in the FIG. 6 diagram.

Example 7—Example of Validation Method to Support Quantification of Particles and Water Clusters Size by Using Calibrated Zetasizer Dynamic Light Scattering The presence of individual nanoparticles can be confirmed and their size distribution characterized by dynamic light scattering (DLS). DLS reported a bimodal distribution for hydrodynamic diameter ranging between 70-90 and 160-200 nm with mean values of 80 and 178 nm, respectively (Keretsztessy et al. 2009). FIG. 2 from page 4 of Keretsztessy, which is incorporated by reference, illustrates the size distribution of chitosan-FITC/poly-γ-glutamic acid-folate nanoparticles as determined by DLS. by plotting scattering intensity as a function of hydrodynamic diameter (nm), with accompanying data on volume and number-weighted distributions. Calibration standards may be considered for a quantitative proof of invention concept testing.

Example 8—Fundamental Need for Products of the Present Invention

Due to chronic dehydration the fundamental terrain of the human body experiences over time, and especially during aging of a large number of indices, signs, and measures of physiological dehydration which include: (1) dyspeptic pain, (2) stress, (3) depression, (4) high blood cholesterol, (5) high blood pressure, (6) excess body weight, (7) chronic fatigue, (8) arthritis, (9) asthma, (10) allergy, (11) insulin independent diabetes, and (12) rheumatoid arthritis.

Evidence for chronic dehydration is the rehydration response of a dehydrated person. The benefits of hydration include: (1) a healthy body weight; (2) increased metabolism, (3) increased energy levels, (4) reduced join back pain, (5) easier flushing out of body waste, (6) preventing headaches; (7) alleviating headaches, (8) better skin hydration and skin health, (9) slower aging, (10) stimulation of the primary mode of transport of all nutrients because nutrient transport needs bioavailable water due to its primary role as solute in dissolving nutrients. One factor is smaller water clusters can be a better solute in breaking down cellular debris and allow for its transfer more effectively.

Example 9: Contemplated Uses of the Present Invention Include the Following (1) Human Health Uses, (2) Modulating cellular performance, (3) Intra-cellular & extra-cellular hydration, (4) Delivery system for nutritional agents or medicine, (5) Agriculture Uses, (6) superior delivery of fertilizers/nutritional agents, (7) Superior hydration method for all forms of plant species, (8) Livestock Farming Uses, (9) Improving health and lifespan of livestock (chickens, horses), and (10) Immune enhancement of livestock Example 10: Use of Present Invention in Improving Tissue Bio-Preservation A growing body of evidence indicates that organ and tissue preservation is now achievable. Recent promising discoveries include organ cryopreservation and subzero cooling, perfusion, interventions before organ and tissue recovery, and adaptations that allow dozens of species in nature to enter suspended animation at subfreezing temperatures. Together, these approaches form a blueprint for a leap forward in preservation capabilities, centered on a combination of two promising strategies: (1) Providing organ 'life support' by recapitulating aspects of the organ's healthy physiological environment. (2) Effectively controlling biological time by slowing or halting metabolism to decrease the rate of deterioration. Progress on both fronts is needed because each preservation approach involves tradeoffs often requiring the application of combined strategies in the same organ or tissue. For instance, slowing organ deterioration for extended preservation periods can be achieved by lowering organ temperature and metabolic rates, but this also entails the loss of normal organ function and opportunities for beneficial interventions, such as organ assessment, repair, and functional augmentation. Thus, some embodiments of the present invention may concern protecting cadaver tissues. The aim of bio-preservation is first an environment to keep a particular organ or tissue healthy on its way to transplantation (or use in research), and a process during which the organ or tissue traverses multiple preservation conditions and temperature ranges that are used synergistically. To make an integrated approach to preservation successful, we must combine and advance a family of research areas that includes cryopreservation, programmed metabolic suppression, subzero preservation and super cooling, and perfusion and ex vivo maintenance at a variety of temperatures, ranging from hypothermia (refrigeration) to normothermia (body temperature), and donor management before organ and tissue recovery. In one embodiment the present invention concerns a bio-preservation media for a hypothermic 2-8° C. biopsy sample preservation. Optionally may be included components that scavenge free radicals, provide pH buffering, oncotic/osmotic support, energy substrates, and ionic concentrations that balance the intracellular state at low temperatures. These components can reduce post-preservation necrosis and apoptosis and extend post-preservation viability.

Example 11: Use of the Present Invention as a Hydration Drink

Embodiments of the present invention can be used in the commercial beverage industry as the primary ingredient of any given trademarked bottling formula, in order to maintain critical consistency of taste, clarity, and color. Below table is an example embodiment of the present invention that can be used as healthy drinks and can be a good substitute to a person drinking purified water, particularly for a person who is an athlete engaged in muscular work needing continual good hydration or a person engaged in a lot of intellectual work.

| | |
|---|---|
| Ultrapure Water (UPW) | 8 fluid ounces |
| Sugar | 4.1 mg |
| Vitamin C (citrate) * | 0.027 mg |
| Magnesium* | 0.068 mg |
| Chloride * | 0.23 mg |
| Sodium * | 0.0045 mg |
| Potassium * | 0.045 mg |
| Sulfate * | 0.011 mg |
| Boron + | 0.36 mcg |
| Total weight of ions * | 0.38 mg |

+ Boron is an unstable +3 cation.
In water $B(OH)_4^-$ forms.

The present Invention drink embodiments frequently include an amount of minerals from a Trace Mineral Concentrates™ (TMC™) as a convenient concentrated source of a non-$H_2O$ substance for use in Process steps 6 and 7. The ions that are present at more than a 0.5 mcg/ml concentration in the Trace Minerals Concentrate™ (TMC) are listed in the table below.

| Chemical Ion Species | Concentration Called For by Specification |
|---|---|
| Aluminum | <10 micrograms/ml |
| Boron | 0.420-0.650 milligrams/ml |
| Calcium | <165 micrograms/ml |
| Chloride | 264-350 milligrams/ml |
| Copper | not established |
| Fluoride | <100 micrograms/ml |
| Iodine | <25 micrograms/ml |
| Iron | <31 micrograms/ml |
| Magnesium | 101.5-110 milligrams/ml |
| Phosphorus | <10 micrograms/ml |
| Potassium | 1.25-2.5 milligrams/ml |
| Rubidium | <2 micrograms/ml |
| Silicon | <5 micrograms/ml |
| Sodium | <4 milligrams/ml |
| Sulfate | 16.5-35 milligrams/ml |
| Titanium | <4 micrograms/ml |
| Zinc | <3.5 micrograms/ml |
| Zirconium | <3.5 micrograms/ml |

Boron, chloride, magnesium, potassium, sodium and sulfate are the predominate ions in the TMC Concentrate used to make one embodiment of the hydration drink.

A preferred genus of the ions is selected from the group consisting of TMC ions present at more than a 0.5 mcg/ml concentration in the Trace Minerals Concentrate™ (TMC™) lists including the following lists.

A Non-$H_2O$ substance may be a cation and an anion combination which maintains charge electro-neutrality. For example the combination of ions can make an electrolyte solution. such combinations of an anion(s) and a cation(s) may selected from the group consisting of an aluminum cation, an antimony cation, an arsenic cation, a barium cation, a beryllium cation, a bismuth cation, a boron ion, a bromide anion, a cadmium cation, a calcium cation, a cerium cation, a cesium cation, a chloride anion, a chromium cation, a cobalt cation, a copper cation, a dysprosium cation, an erbium cation, a europium cation, a fluoride anion, a gadolinium cation, a gallium cation, a germanium cation, a gold cation, a hafnium cation, a holmium cation, an indium cation, a iodine anion, an iridium cation, a iron cation, a lanthanum cation, a lead cation, a lithium cation, a lutetium cation, a magnesium cation, a manganese cation, a mercury cation, a molybdenum cation, a neodymium cation, a nickel cation, a niobium cation, an osmium cation, a palladium cation, a phosphorus anion, a platinum cation, a potassium cation, a praseodymium cation, a rhenium cation, a rhodium cation, a rubidium cation, a ruthenium cation, a samarium cation, a scandium cation, a selenium cation, a silicon cation, a silver cation, a sodium cation, a strontium cation, a sulfate anion, a tantalum cation, a tellurium cation, a terbium cation, a thallium cation, a thorium cation, a thulium cation, a tin cation, a titanium cation, a tungsten cation, a vanadium cation, a ytterbium cation, a yttrium cation, a zinc cation, and a zirconium cation.

A small mixture of trace minerals may be useful. A non-$H_2O$ substance may be a cation and an anion combination which maintains charge electro-neutrality. For example the combination of ions can make an electrolyte solution. Such combinations of an anion(s) and a cation(s) may selected from the group consisting of an aluminum cation, an antimony cation, a barium cation, a bismuth cation, a boron ion, a bromide anion, a calcium cation, a cerium cation, a cesium cation, a chloride anion, a chromium cation, a cobalt cation, a copper cation, a dysprosium cation, an erbium cation, a europium cation, a fluoride anion, a gadolinium cation, a gallium cation, a germanium cation, a gold cation, a hafnium cation, a holmium cation, an indium cation, a iodine anion, an iridium cation, a iron cation, a lithium cation, a lutetium cation, a magnesium cation, a manganese cation, a molybdenum cation, a neodymium cation, a niobium cation, an osmium cation, a palladium cation, a phosphorus anion, a platinum cation, a potassium cation, a praseodymium cation, a rhenium cation, a rhodium cation, a rubidium cation, a ruthenium cation, a samarium cation, a scandium cation, a selenium cation, a silicon cation, a silver cation, a sodium cation, a strontium cation, a sulfate anion, a tantalum cation, a tellurium cation, a terbium cation, a thulium cation, a tin cation, a titanium cation, a tungsten cation, a vanadium cation, a ytterbium cation, a yttrium cation, a zinc cation, and a zirconium cation.

An even shorter list of minerals may be useful. A non-$H_2O$ substance may be a cation and an anion combination which maintains charge electro-neutrality. For example the combination of ions can make an electrolyte solution. Such combinations of an anion(s) and a cation(s) may selected from the group consisting of an antimony cation, a barium cation, a bismuth cation, a boron ion, a bromide anion, a calcium cation, a cerium cation, a chloride anion, a chromium cation, a cobalt cation, a copper cation, a europium cation, a fluoride anion, a gold cation, a iodine anion, an iron cation, a lithium cation, a magnesium cation, a manganese cation, a molybdenum cation, a an osmium cation, a palladium cation, a phosphorus anion, a platinum cation, a potassium cation, a rubidium cation, a ruthenium cation, a scandium cation, a selenium cation, a silicon cation, a silver cation, a sodium cation, a strontium cation, a sulfate anion, a tantalum cation, a tin cation, a titanium cation, a tungsten cation, a vanadium cation, and a zinc cation.

Example 12

Listed below are some general and specific formulation embodiments of the present invention. Note—the fluid measure oz. means ounces A general formulation for treating a brain health need of a person or an animal comprises: ultrapure water (UPW); Synapta (SynaptaGenX™ dietary supplement); a magnesium salt; and ConcenTrace Trace Mineral Drops™. A specific formulation for treating a brain health need of a person or an animal comprises: 300 gallons of ultrapure water, 0.01-500 grams of Synapta™, 0.02 to 1500 grams of magnesium chloride; and 0.1 to 4 liters of Trace Mineral Drops™.

A general formulation for treating an anxiety disorder of a person or an animal comprises: ultrapure water; 40K Volts Electrolyte Concentrate™ (Trace Minerals, Utah); CBD; sodium bicarbonate; and Concentrace Trace Mineral Drops™. A specific formulation for treating an anxiety disorder of a person or an animal comprises: 300 gallons ultrapure water, 0.004 to 400 grams of CBD, 0.002 to 11 liters of Trace Mineral Drops™, 0.002 to 7 liters of 40K Volts Electrolyte Concentrate™ 40K, and 0.5 to 400 grams sodium bicarbonate.

A general CBD formulation for treating inflammation or for treating anxiety in a person or an animal comprises: ultrapure water, CBD (Cannabidiol), 40K Volts Electrolyte Concentrate™, Concentrace Trace Mineral Drops™, and Sodium Bicarbonate. A specific CBD formulation for treating inflammation or anxiety in a person or an animal comprises a mixture of (a) 100 gallons of UPW containing crystalline CBD 2.5 to 40 grams, and 40K Volts Electrolyte Concentrate™ 1 to 9 oz., and Trace Mineral Drops™ 1 to 5 oz.; and (b) 250 to 300 gallons of UPW containing CBD 12 to 33 g, 40K Volts Electrolyte Concentrate™ 10 to 40 oz, and Trace Mineral Drops™ 6 to 40 oz.

A general hydration formulation for treating dehydration in a person or an animal comprises: UPW, 40K Volts Electrolyte Concentrate™, and Concentrace Trace Mineral Drops™. A specific general hydration formulation for treating dehydration in a person or an animal comprises: a mixture of (a) UPW 50 gallons, 40K Volts Electrolytes™ 0.5 to 5 oz, Trace Mineral Drops™ 0.04 to 2 oz; and (b) UPW 250-290 gallons, 40K Volts Electrolytes™ 0.5 to 10 oz, and Trace Mineral Drops™ 0.5 to 6 oz.

A general alkaline electrolyte formulation for treating an electrolytes deficiency in a person or an animal comprises: UPW, Concentrace Trace Mineral Drops™, Himalayan Pink Salt, 40K Volts Electrolyte Concentrate™, and Sodium Bicarbonate. A specific alkaline electrolyte formulation for treating an electrolytes deficiency in a person or an animal comprises: a mixture of (a): UPW (UltraPure Water) 50 to 60 gallons, Trace Mineral Drops™ 0.1 to 1 oz, Himalayan Pink Salt 20 to 1000 mg, Sodium Bicarbonate 0.5 to –15 oz, and 40K Volts Electrolyte Concentrate™ 0.5 to 9 oz; and (b) UPW 250 to 290 gallons, Trace Mineral Drops™ 0.2 to 6 oz, Himalayan Pink Salt 0.5 to 8 gm, and 40K Volts Electrolyte Concentrate™ 1 to 15 oz.

A general dyspepsia formulation for treating dyspepsia in a person or an animal comprises: UPW, Bio Nutrition Gout Out™, and Tart Cherry. A specific dyspepsia formulation for treating dyspepsia in a person or an animal comprises: UPW 50 gallons, Bio Nutrition Gout Out™ 1-10 caps, and Tart Cherry 1 to 6 caps.

A general headache formulation for treating a person or an animal with a headache comprises: UPW, Resveratrol™, Liver Care™, D-Ribose, 40K Volts Electrolyte Concentrate™, and Concentrace Trace Mineral Drops™. A specific headache formulation for treating a person or an animal with a headache comprises: a mixture of (a) UPW 50 gallons, Resveratrol™ 0.5 pill of a 10 mg pill (Reseveratrol Nutrition, Gainsville, FL), Liver Care™ 0.05 to 80 mg, D-Ribose 0.05 to 0.9 mg, 40K Electrolyte Concentrate™ 0.5 to 5 oz, and Trace Mineral Drops™ 5 to 150 drops; and (b) UPW 275 gallons, Resveratrol™—2 pills, Liver Care™ 0.5 to 3 gm, D-ribose 1 to 3 tablets, 40K Electrolyte Concentrate™ 1–5 oz, and/275 gallons Trace Mineral Drops™ 150-400 drops.

An agriculture humic formulation for combining minerals to make them into organic compounds that can be ingested by plants more easily and for enabling the soil to hold more water and for increasing the water infiltration of the soil, comprises: Ultra Pure Water, and Fulvic Humic Liquid. A specific agriculture humic formulation comprises: UPW 275 gallons, and Fulvic Humic liquid 1 to 50 ozs (the Fulvic Humic from mineral mined natural Humic).

A general cold remedy formulation for treating a person or an animal with a cold comprises: UPW, CBD, Capsaicin, Concentrace Trace Mineral Drops™, and Resveratrol™. A specific cold remedy formulation for treating a person or an animal with a cold comprises: a mixture of (a) UPW 50 gallons, CBD 0.05 to 3 grms, Capsaicin (Cayenne pepper) 0.5 to 5 ozs, Trace Mineral Drops™ 0.1 to 0.8 oz, and Resveratrol™ 0.05 to 3 mg; and (b) UPW 275 gallons, CBD 0.5 to 15 grms, Capsaicin 0.5 to 20 oz, Trace Mineral Drops™ 0.5 to 5 oz, and Resveratrol™ 0.5 to 12 mg.

A general elder care formulation for treating an elder person or an elder animal comprises: UPW, Multi 5 Collagen™, Silicon/Choline™, Nicotinamide Riboside, Trans-Resveratrol™, B Vitamin Complex, and Vitamin C. A specific elder care formulation for treating an elder person or an elder animal comprises a mixture of (a) UPW 50 gallons, Multi 5 Collagen™ 0.2 to 5 gm (Axe Products), Silicon/Choline™ 1 to 15 drops, Nicotinamide Riboside (Niagin) 0.1 to 1.5 tabs, Trans-Resveratrol™ 0.05 to 1.3 cap, B Vitamin Complex 0.2-4 cap, Vitamin C 0.5 to 15 gm; and (b) UPW 275 gallons, Multi 5 Collagen™ 3 to 12 gms, Silicon/Choline™ 5 to 40 drops, Nicotinamide 0.5 to 7 tabs, Trans-Resveratrol™ 0.1 to 5 caps, B Vitamin Complex 0.5 to 5 caps, and Vitamin C 2 to 16 gm.

A general diabetic binge formulation for treating a person or an animal suffering from a diabetic binge comprises: UPW, Berberine HCL™ (Health Direction.com), Zychrome™ (Optimized Chromium by Quality Supplements and Vitamins), Gymnema Sylvestre™ (Organix Glucose Gymnema Elite by Nutrusta), R-ALA (R-Alpha Lipoic Acid), Cinnamon, Panax Ginseng™ (Fermented Korean Panax Ginseng), Magnesium Chloride, and Fenugreek™ (Barlowe's). A specific diabetic binge formulation for treating a person or an animal suffering from a diabetic binge comprises a mixture of (a) UPW 50 gallons, Berberine HCL™ 100 to 800 mg, Zychrome™ 5 to 175 mcg, Gymnema Sylvestre™ 10 to 190 mg, R-Alpha Lipoic Acid 1 to 50 mg, Cinnamon 0.05 to 5 gm, Panax Ginseng™ 5 to 125 mg, Magnesium as a magnesium salt such as magnesium chloride 5 to 250 mg, and Fenugreek™ 2 to 500 mg; and (b) UPW 275 gallons, Berberine HCL™ 900 to 3200 mg, Zychrome™ 75 to 750 mcg, Gymnema Sylvestre™ 250 to 750 mg, R-Alpha Lipoic Acid 75 to 200 mg, Cinnamon 1 to 8 gm, Panax Ginseng™ 200 to 800 mg, Magnesium as a magnesium salt such as magnesium chloride 90-700 mg, and Fenugreek™ 100 to 2200 mg.

Reflex Neurology Formulation

Formulation Ingredients are: Ultra Pure Water, R-ALA (Alpha Lipoic Acid), B-Complex, Acetyl-L-Carnitine, GLA (Gamma Linolenic Acid), Chromium, Curcumin, Vitamin C, Vitamin E, Vitamin K2 & D3, Magnesium, Corydalis, Cayenne, L-Arginine, and Feverfew™ (*Tanacetum Parthenium*)

Formulation Ingredients Ratio: 50 gallons concentrate (A) is blended with 275 gallons part (B). Concentrate (A) is made to contain: Ultra Pure Water—50 gallons, R-ALA—(⅒-½ capsule/50 gallons), Acetyl-L-Carnitine—(50-280 mg/50 gallons), GLA—(50-400 mg/50 gallons), Chromium—(25-125 mcg/50 gallons), Curcumin ((20-160 mg/50 gallons), AntiFungal, antibacterial, antiviral, and antioxidant properties from Tumeric Extract.), Vitamin C—(200-2000 mg/50 gallons), Vitamin K-2 & D-3—(25-100 mcg/50 gallons), Magnesium—(20-120 mg/50 gallons), Corydalis—(125-375 mg/50 gallons), Cayenne—(10-150 mg/50 gallons), and L-Arginine—(60-1000 mg/50 gallons).

275 gallons part (B) is made to contain: Ultra Pure Water—275 gallons, R-ALA—(0.5-3 capsule/275 gallons), B-Complex—(1-5 capsules/275 gallons), Acetyl-L-Carnitine—(100-350 mg/275 gallons), GLA—(15-2000 mg/275 gallons), Chromium—(300-500 mg/275 gallons), Curcumin—(50-500 mg/275 gallons), Vitamin C—(40-450 mg/275 gallons), Vitamin E—(100-300 mg/275 gallons), Vitamin K2 & D3—(0.2-0.6 mcg (1 capsule)/275 gallons), Magnesium—(20-140 mg/275 gallons), Corydalis—(50-150 mg/275 gallons), Cayenne—(50-250 mg/275 gallons), L-Arginine—(250-5000 mg/275 gallons), and Feverfew™—(35-450 mg (1 capsule)/275 gallons).

ED Formulation Formulation Ingredients: Ultra Pure Water, L-arginine, Horny Goat Weed, Long Jack™ (Note: 200 mg/50 gallons Libido, and stamina booster from natural herbs), Tribulus Terrestrius (Note: Fruit-producing Me3ditterean plant that assists n prostrate health.), and Tadalafil Formulation Ingredients Ratio: 50 gallons concentrate (A) is blended with 275 gallons part (B). Concentrate (A) is made to contain: Ultra Pure Water—50 gallons, L-Arginine—5.5-25 g/50 gallons, Horny Goat Weed—1.5-7 g/50 gallons, Long Jack™—2-300 mg/50 gallons, Tribulus Terrestrius—10-140 mg/50 gallons, and Tadalafil—5-40 mg/50 gallons. 275 gallons part (B) is made to contain: Ultra Pure Water—275 gallons, L-Arginine—4-7 g/275 gallons, Horny Goat Weed—2-5 g/275 gallons, Mondia Whitei—350-700 mg/275 gallons, Long Jack™—60-1200 mg/275 gallons, Panax Ginseng™—300-800 mg/275 gallons, Yohimbine—0.2-12 mg/140-210 gallons, Tribulus Terrestrius—900-1100 mg/275 gallons, and Tadalafil—15-50 mg/275 gallons.

CNS Wellness Formulation

Formulation Ingredients: Ultra Pure Water, Caffeine, Theanine, B 6 Complex, Ginkgo Biloba, Curcumin, Huperzine A™, Cognizine Citicoline™, 40K Volts Electrolyte Concentrate™, Concentrace Trace Mineral Drops™, Medium Chain Triglyceride Oil Powder, Nicotinamide, Riboside, Rhodiola, Ketone Esters, and Resveratrol™.

Formulations Ingredients ratio: A concentrate 100 gallons concentrate (A) is blended with a 50 gallons concentrate (B) and a 200 gallons part (C).

Concentrate (A) is made to contain: Ultra Pure Water—100 gallons, Caffeine—0:25-6 mg/100 gallons, and Theanine—0.125-400 mg/100 gallons (Note: Stress reduces and relaxer, reduces elevated blood pressure and improves heart rate). B 6 Complex—0.250-500 mg/50 gallons.

Concentrate (B) is made to contain: Ultra Pure Water—50 gallons, B 6 Complex—0.250-500 mg/50 gallons, Ginkgo Biloba—0.10-30 mg/50 gallons, Curcumin—0.625 mg/50 gallons, Huperzine A™—150-175 mg/50 gallons (Note: Whole herb assisting in memory and focus.), Cognizine Citicoline™—0.07-0.9 mg/50 gallons, 40K Volts Electrolyte Concentrate™—1-5 ozs/50 gallons, Trace Mineral Drops™—0.2-0.8 ozs/50 gallons, MCT Oil Powder™—2-4 g/50 gallons (C8 MCT and Acacia fibers known to be brain food), Nicotinamide Riboside—100-200 mg/50 gallons, Rhodiola—0.3-0.6 ml (two full drop)/50 gallons. Note: Extract from roots that assists in memory and reduces stress), Ketone Esters—4.7 g/50 gallons. (Note: Ketone salts that includes calcium and potassium for energy boosting), and Resveratrol™—0.12-36 mg/50 gallons. (Note: Resveratrol is by Reseveratrol Nutrition, Gainsville, FL, a dietary supplement made from grapes).

Concentrate (C) is made to contain: Ultra Pure Water—200 gallons, Theanine—0.6 mg/200 gallons, B 6 Complex—200 gallons, Ginkgo Biloba—0.4-0.8 mg/200 gallons, Curcumin—1500 mg/200 gallons, Huperzine A—0.94 mg/200 gallons, Cognizine Citicoline™-0.438 mg/200 gallons, 40K Volts Electrolyte Concentrate™—16 ozs/200 gallons, Trace Mineral Drops™—3 ozs/200 gallons, MCT Oil Powder—14.0 gallons, Nicotinamide Riboside 250-1250 mg/200 gallons, Rhodiola—3.6-4.8 ml (7-11 full drops)/200 gallons, Ketone Esters—2-0.2 g/200 gallons, and Resveratrol™—80-290 mg/200 gallons.

Examples of Pharmacy Store Products that may be improved when formulated as part of an embodiment of the present invention include the following products. It is contemplated that the list of non-$H_2O$ substances comprises many examples of drugs and of healthcare products that might be processed as the non-$H_2O$ substance in some kind of composition embodiments of the present invention. The list of non-$H_2O$ substances which could be improved by their processing as a non-$H_2O$ substance in some composition and process embodiments is selected from the group consisting of a 50% isopropyl rubbing alcohol, a lip balm broad spectrum spf 30, an accelerated dark spot corrector for skin care, an acne and blemish product for skin care, an acne and line correcting serum for skin care, a therapeutic sulfur mask for skin care, an adult glycerin laxative, an adult long lasting-cough relief, an allergy and congestion relief, an mineral moisturizer for skin care, an age defying moisturizer spf 18 for skin care, an alaffia face for facial skin care, an alahist cf antiallergy medication, an alcohol prep pad with benzocaine, alcohol prep pads, a heartburn relief chews, alkmene anti spot pad, an allergy eye drops, an allergy get relief, an aloe propolis soothing gel, a vaporizing chest rub, an anal glide, an analgesic, an anti-aging treatment mask for skin care, an antihistamine, an antimicrobial, an ap-24 whitening toothpaste, an antibacterial foam handwash, an antibacterial handwash, a medicated acne body for skin care a wash scrub acne medication for skin care, an acne soap bar, ibuprofen, a topical analgesic, a first aid triple antibiotic, a triple antibiotic protection, a moisturizing and pain relief for skin care, an active naturals eczema therapy hand for skin care, an eczema therapy itch relief balm for skin care, a sunscreen, a neoendorphin mask pack, a childrens cough and cold, a childrens pain and fever medication, a dry spf 8 for skin care, a foundation broad spectrum spf 20 for skin care, an acne clearing treatment serum for skin care, aspirin, a skin moisturizer light spf 20 for skin care, a skin moisturizer medium spf 20 for skin care, a topical anesthetic, lansoprazole, a migraine formula, a skin protectant, a lip balm spf 15, a sun spf30 for skin care, a sun spf20 for skin care, an advanced whitening toothpaste formula, an intensive stain removal product, an anti-bacterial hand gel, an antibacterial hand sanitizer, a antimicrobial foam soap, an antiseptic, a face spf 25 for skin care, a mist spf 50 for skin care, a kids sunscreen 35 for skin care, an enamel care product, a blackhead clearing scrub for skin care, an antimicrobial soap with triclosan, an antiseptic skin cleanser, a bodyshaper warming product for skin care, an instant hand sanitizer with aloe and vitamin e, an instant hand sanitizer with moisturizers, a vitamin e product, a skin repair serum for skin care, a hydrogel eye patch, a sore throat honey lemon, an antibacterial soap bar, a pro eczema soothing moisturizer, an antacid softchew, a hand sanitizer, a childrens cough and cold syrup, a childrens cough and cold long-acting medicine, eye drops, an a eye drops eye redness reliever medication, a clarifying pressed powder for skin care, a clarifying toner for skin care, a broad spectrum spf 15 sunscreen for skin care, a broad spectrum spf 15 sunscreen for skin care, an acne spot treatment for skin care, a daily facial scrub, a daily pore cleansing pads, a clemastine fumarate, a clematis base cushion, a clotrimazole 1% athletes foot, a clotrimazole antifungal, a cold and flu relief nighttime multi-symptom medication, a children's daytime cough and chest congestion relief medication, a children's nighttime cold and cough relief syrup, a topical anesthetic, a cold and flu day night medication, a cold and flu maximum strength, spf 70 sunscreen for skin care, cosedal cough drops, a cosmeceutical mask pack for skin care, a primer with anti-acne treatment for skin care, a foundation spf 30 sunscreen for skin care, a whitening therapy sensitivity care, an anti-cavity, hydrogen peroxide, a saline laxative, a fragrance free anti-itch medication, a gentle laxative, a spf 30 sunscreen for skin care, a maximum strength antifungal liquid with aloe and vitamin e, a maximum strength dandruff shampoo, a dandruff conditioner for a dry scalp, an antibacterial foaming wash, a daytime severe cold and flu relief maximum strength medication, a severe cold multi-symptom medication, a broad spectrum spf 30 sunscreen for skin care, a broad spectrum spf 50 sunscreen for skin care, a 48 h antiperspirant, a dish detergent, a whitening formula anti cavity fluoride toothpaste, a broad spectrum spf 15 sunscreen for skin care, a cough syrup, an antibacterial foaming hand wash with antioxidants, an antibacterial foaming hand wash, a makeup pore-refining effect with sunscreen broad spectrum spf 35 for skin care, a makeup everlasting wear pore-refining effect with sunscreen broad spectrum spf 35 for skin care, a hydra healing color corrector for skin care, a hydra healing tension pact for skin care, a hydrogen peroxide 3%, antiperspirant, a sunscreen broad spectrum spf 40 for skin care, a whitening g2 serum for skin care, ear drops, a childrens cetirizine hydrochloride, a childrens diphenhydramine hydrochloride, a dw egf derma oneshot ampoule for skin care, an eight hour cream lip protectant spf 15 for skin care, an eight hour cream nourishing lip balm spf 20, a collagen mask pack for skin care, a whitening maskpack, a hand sanitizer, a moisturizing dandruff medicated formula, a pain relieving cream lidocaine, a pain relieving ultra-strength, hydrated face makeup foundation spf 15 for skin care, a sun shield plus spf 35 pa for skin care, spf50, antimicrobial foam handwash, a fantacell ampoule fantacell ampoule, a witch hazel formulation, an antiseptic hand cleansing, a moisture bomb hand cream for skin care, a natural sun bb spf 50 pa for skin care, a therapy upset stomach relief, a triple antibiotic and pain relief maximum strength, a sunscreen broad spectrum spf 15 for skin care, a deodorant and antiperspirant roll on, a skin protectant, hand wipes, a long wearing fluid foundation with sunscreen broad spectrum spf 20 for skin care, cleansing pads, a mucus relief cold and sinus, gout reliever, a hand sanitizer spray, an infants pain and fever medication, an extra strength pain relieving medication, an anti hair loss, an anti-hair loss day tonic, an adult tussin dm, an aloe vera petroleum, a mucus relief dm, a mucus relief severe cold, a stomach relief medication, cough drops, a medicated plaster extra strength, hyaluronic acid micro, a hyaluronic filler serum for skin care, a hydrocortisone cream for skin care g, an industrial strength sunscreen for skin care, a deep pore cleansing foam, an itch relief medication for skin care, bio-restorative day balm broad-spectrum sunscreen spf 30 for skin care, spf50 broad spectrum sunscreen for skin care, ibuprofen, a deodorant and antiperspirant, an anti-age self-tanning face lotion spf 15, anti-wrinkle broad spectrum spf 15 sunscreen, tinted moisturizer—broad spectrum spf 20 sunscreen—bronze radianc—lbel effet parfait maximum comfort and long-lasting foundation spf 10 for skin care, collagen peptide serum for skin care, hydrocortisone with aloe, ticonazole, an anti-cavity toothpaste, a facial moisturizer—sun protectant spf 50 normal to oily skin for skin care, an anti-cavity fluoride rinse, an ultra-antifungal, menthol throat drops, a maxichlor peh dm, antiseptic, cleansing towelette, a pore opening sheet for skin care, pain relief patches, menthol 5% medication, a menthol and methyl salicylate medication, a miconazole nitrate cream usp for skin care, a 2%, mineral sunscreen lip balm spf 15, mineral sunscreen moisturizer broad spectrum spf 20 for skin care, a povidone-iodine swabstick non-sterile, a povidone-iodine swabstick sterile, a mucus relief dm maximum strength medication, a mucus relief dm immediate medication, a liquid multi-vitamin formulation, a mucus relief dm expectorant and cough suppressant, a maximum strength nasal decongestant, a nasal decongestant inhaler, a nausea relief, a nighttime cold and flu relief medication, a nighttime cold and flu relief alcohol free medication, a topical anesthetic, a triple antibiotic plus, omega 3 ointment, a severe toothache maximum strength fast-acting formula, an aspirin 325 mg, a spf 46 broad spectrum sunscreen, an antimicrobial hand cleaning wipes, a nasal decolonization spray, a muscle care pain relieving gel, a non-drowsy daytime cold and flu formulation, a red eye relief eyedrop, an anti-bacterial hand sanitizer, a psoriasis medication for skin care, a moisturizing dandruff medicated formula, an eye wash and a skin flush, a severe sinus pain and congestion daytime medicine, shinmo saengbaleum hair shampoo, a non-aspirin—extra strength antacid, a sinus pressure and pain pe maximum strength, a broad spectrum spf15 sunscreen for skin care, a general protection spf 50 sunscreen for skin care, a spf 50 uva/uvb sunscreen, a low dose aspirin, a mucus relief cough children's, a milk of magnesia, an insect repellent sunscreen, a sunscreen zinc, throat relief lozenges, a broad spectrum spf for skin care, a childrens allergy relief nasal 24 hour, a nicotine gum, a broad spectrum spf 25 water resistant sunscreen, a laxative, a hair regrowth treatment for men, an acne control for skin care, uva/uvb spf 15 sunscreen, a vapour rub, a scalp relief, an anti-itch, an anti-sagging and ultra-hydrating day broad spectrum spf15 sunscreen for skin care, a sunscreen broad spectrum spf 15 for skin care, a sunscreen broad spectrum spf 30 for skin care, a feng shi pain relieving plaster, and any combination thereof.

Listed below are some drugs, vitamins, amino acids, and other organic chemicals which can be administered as a therapeutic particle in an invention embodiment of the present invention to treat depression, anxiety and ptsd (post-traumatic stress disorder).

Tryptamine is 3-(2-aminoethyl)indole/2-(1H-indol-3-yl)ethanamine. In an example invention dosage form (spray, inhalation, drink, capsule, table) for oral or inhalation use, the dose may range from about 1-30 mg.

Bufotenin is 5-hydroxy-N,N-dimethyltryptamine. Dosing for Intranasal or sublingual: Low dose: 20-30 mg. Average dose: 30-60 mg. High dose: 60-100 mg.

$N_\omega$-Methylserotonin is 5-hydroxy-N-methyltryptamine.

Serotonin is 5-hydroxytryptamine. In an example invention dosage form (spray, inhalation, drink, capsule, table) for oral or inhalation use, the dose start with a dose of 50-100 mg two times per day and increase to the appropriate dose over a two-week period.

DMT is N,N-dimethyltryptamine. Inhalation in dose form is 15-60 mg.

Melatonin is 5-methoxy-N-acetyltryptamine. One milligram oral tablets can be cut in half to achieve a 0.5 mg dose if smaller doses are not available for purchase. Lower doses may work for some people, while others may need a higher dose, up to 3 to 5 mg.

N-Acetylserotonin is 5-hydroxy-N-acetyltryptamine.

5-Bromo-DMT is 5-bromo-N,N-dimethyltryptamine. In an example invention dosage form (spray, inhalation, drink, capsule, table) for oral or inhalation use, the dose may range from about 25-35 mg.

5-MeO-DMT is 5-methoxy-N,N-dimethyltryptamine. In an example invention dosage form (spray, inhalation, drink, capsule, table) for oral or inhalation use, the dose may range from about 25-35 mg.

5-MeO-NMT is 5-methoxy-N-methyltryptamine. In an example invention dosage form (spray, inhalation, drink, capsule, table) for oral or inhalation use, the dose may range from about 25-35 mg.

NMT is N-methyltryptamine.

Norbaeocystin is 4-phosphoryloxy-tryptamine.

Baeocystin is 4-phosphoryloxy-N-methyl-tryptamine.

Psilocybin is 4-phosphoryloxy-N,N-dimethyltryptamine. A common oral dose is 1-2.5 grams per adult.

Psilocin is 4-hydroxy-N,N-dimethyltryptamine. A common oral dose is 1-2.5 grams per adult.

Tryptophan is α-carboxyltryptamine. A common dose is 8 to 12 grams by mouth per day. The supplement should be taken in divided doses of three or four times a day.

DET is N,N-diethyltryptamine. In an example invention dosage form (spray, inhalation, drink, capsule, table) for oral or inhalation use, the dose may range from about 10-25 mg.

DPT is N,N-dipropyltryptamine. In an example invention dosage form (spray, inhalation, drink, capsule, table) for oral or inhalation use, the dose may range from about 10-25 mg.

DiPT is N,N-diisopropyltryptamine. In an example invention dosage form (spray, inhalation, drink, capsule, table) for oral or inhalation use, the dose may range from about 10-25 mg.

DALT is N,N-diallyltryptamine. In an example invention dosage form (spray, inhalation, drink, capsule, table) for oral or inhalation use, the dose may range from about 10-25 mg.

5-MeO-DALT is 5-methoxy-N,N-diallyltryptamine. In an example invention dosage form (spray, inhalation, drink, capsule, table) for oral or inhalation use, the dose may range from about 12-25 mg 5-MeO-MALT is 5-methoxy-N-Methyl-N-allyltryptamine. In an example invention dosage form (spray, inhalation, drink, capsule, table) for oral or inhalation use, the dose may range from about 12-25 mg.

5-MeO-DIPT is 5-methoxy-N,N-diisopropyltryptamine. In an example invention dosage form (spray, inhalation, drink, capsule, table) for oral or inhalation use, the dose may range from about 12-25 mg.

5-MeO-MiPT is 5-methoxy-N,N-methylisopropyltryptamine. In an example invention dosage form (spray, inhalation, drink, capsule, table) for oral or inhalation use, the dose may range from about 12-25 mg.

5-MT-NBOMe is 5-methoxy-N-(ortho-methoxybenzyl)tryptamine. In an example invention dosage form (spray, inhalation, drink, capsule, table) for oral or inhalation use, the dose may range from about 12-25 mg.

5-BT is 5-Benzyloxytryptamine. In an example invention dosage form (spray, inhalation, drink, capsule, table) for oral or inhalation use, the dose may range from about 12-25 mg.

5-CT is 5-Carboxamidotryptamine. In an example invention dosage form (spray, inhalation, drink, capsule, table) for oral or inhalation use, the dose may range from about 12-25 mg.

5-Ethoxy-DMT is 5-ethoxy-N,N-dimethyltryptamine. In an example invention dosage form (spray, inhalation, drink, capsule, table) for oral or inhalation use, the dose may range from about 12-25 mg.

5-Ethyl-DMT is 5-ethyl-N,N-dimethyltryptamine. In an example invention dosage form (spray, inhalation, drink, capsule, table) for oral or inhalation use, the dose may range from about 12-25 mg.

5-Fluoro-DMT is 5-fluoro-N,N-dimethyltryptamine. In an example invention dosage form (spray, inhalation, drink, capsule, table) for oral or inhalation use, the dose may range from about 12-25 mg.

5-Methyl-DMT is 5,N,N-trimethyltryptamine. In an example invention dosage form (spray, inhalation, drink, capsule, table) for oral or inhalation use, the dose may range from about 12-25 mg.

5-(Nonyloxy)tryptamine is 5-nonyloxytryptamine. In an example invention dosage form (spray, inhalation, drink, capsule, table) for oral or inhalation use, the dose may range from about 12-25 mg.

4-HO-DET is 4-hydroxy-N,N-diethyltryptamine. In an example invention dosage form (spray, inhalation, drink, capsule, table) for oral or inhalation use, the dose may range from about 10-25 mg.

4-AcO-DMT is 4-acetoxy-N,N-dimethyltryptamine. In an example invention dosage form (spray, inhalation, drink, capsule, table) for oral or inhalation use, the dose may range from about 12-25 mg.

4-HO-MET is 4-hydroxy-N-methyl-N-ethyltryptamine. In an example invention dosage form (spray, inhalation, drink, capsule, table) for oral or inhalation use, the dose may range from about 12-25 mg.

4-HO-EPT is 4-hydroxy-N-ethyl-N-propyltryptamine. In an example invention dosage form (spray, inhalation, drink, capsule, table) for oral or inhalation use, the dose may range from about 12-25 mg.

4-HO-MPT is 4-hydroxy-N-methyl-N-propyltryptamine. In an example invention dosage form (spray, inhalation, drink, capsule, table) for oral or inhalation use, the dose may range from about 12-25 mg.

4-HO-MiPT is 4-hydroxy-N-isopropyl-N-methyltryptamine. In an example invention dosage form (spray, inhalation, drink, capsule, table) for oral or inhalation use, the dose may range from about 12-25 mg.

4-HO-McPT is 4-hydroxy-N-cyclopropyl-N-methyltryptamine. In an example invention dosage form (spray, inhalation, drink, capsule, table) for oral or inhalation use, the dose may range from about 12-25 mg.

4-HO-McPeT is 4-hydroxy-N-cyclopentyl-N-methyltryptamine. In an example invention dosage form (spray, inhalation, drink, capsule, table) for oral or inhalation use, the dose may range from about 12-25 mg.

4-HO-DPT is 4-hydroxy-N,N-dipropyltryptamine. In an example invention dosage form (spray, inhalation, drink, capsule, table) for oral or inhalation use, the dose may range from about 12-25 mg.

4-HO-DIPT is 4-hydroxy-N,N-diisopropyltryptamine. In an example invention dosage form (spray, inhalation, drink, capsule, table) for oral or inhalation use, the dose may range from about 12-25 mg.

4-HO-DSBT is 4-hydroxy-N,N-disecbutyltryptamine. In an example invention dosage form (spray, inhalation, drink, capsule, table) for oral or inhalation use, the dose may range from about 12-25 mg.

Zolmitriptan is 5-(4-(S)-1,3-oxazolidin-2-one)-N,N-dimethyltryptamine. In an example invention dosage form (spray, inhalation, drink, capsule, table) for oral or inhalation use, the dose may range from about 12-25 mg.

LSD is Lysergic acid diethylamide. In an example invention dosage form (spray, inhalation, drink, capsule, table) for oral or inhalation use, the dose may range from about 100 Micro Grams.

Mescaline is 3,4,5-trimethoxyphenethylamine. In an example invention dosage form (spray, inhalation, drink, capsule, table) for oral or inhalation use, the dose may range from about 200-400 mg.

Ayahuasca can be used for example in an invention dosage form (spray, inhalation, drink, capsule, table) for oral or inhalation use, the dose may range from about 0.75 mg/kg-1.0 mg/kg.

MDMA is 3,4-methylenedioxymethamphetamine. In an example invention dosage form (spray, inhalation, drink, capsule, table) for oral use, the dose may range from about 1.5 mg/kg.

MDA is 3,4-methylenedioxyamphetamine.

MDEA is 3,4-methylenedioxyethylamphetamine. Scientists are testing how pharmaceutical-grade MDMA can be used in combination with psychotherapy to help patients who have a severe form of PTSD that has not responded to other treatments. Unlike street drugs, which may be adulterated and unsafe, researchers use a pure, precisely dosed form of the drug.

Opium is used for treatment of pain orally or inhaled.

Ketamine for example may be used in an invention dosage form (spray, inhalation, drink, capsule, table) for oral or inhalation use, the dose may range from about 0.5 mg/kg-1.0 mg/kg. Ketamine is a medication mainly used for starting and maintaining anesthesia It induces a trance-like state while providing pain relief, sedation, and memory loss Other uses include sedation in intensive care and treatment of pain and depression. Heart function, breathing, and airway reflexes generally remain functional. Effects typically begin within five minutes when given by injection, and last up to approximately 25 minutes.

Ketamine is given IV, IM, Intra nasal. Most recent research has shown Ketamine is having profound impact on treatment resistant depression and anxiety.

Amino Acids: In an example invention dosage form (spray, drink, capsule, tablet) for oral or inhalation use, the dose may range from 240 mg/kg a day and up to 25 grams a day Amino acids are the structural units (monomers) that make up proteins. They join together to form short polymer chains called peptides or longer chains called either polypeptides or proteins. These polymers are linear and unbranched, with each amino acid within the chain attached to two neighboring amino acids. The process of making proteins encoded by DNA/RNA genetic material is called translation and involves the step-by-step addition of amino acids to a growing protein chain by a ribozyme that is called a ribosome. The order in which the amino acids are added is read through the genetic code from an mRNA template, which is an RNA copy of one of the organism's genes.

Controlled amino acid therapy (CAAT) is a protocol developed for patients with cancer that includes strict dietary guidelines and nutritional supplements that focus on controlling amino acid and carbohydrate intake. 1,2 The protocol was developed by the A.P. John Institute for Cancer Research and is touted to be based on extensive clinical research, but studies in humans or animal models of the entire CAAT protocol have not been published, nor have results of case studies or observational studies from the institute been published. The exact protocol is not reported and the website for the institute is no longer functioning. Findings from one study suggest that a substantial decrease in overall protein intake inhibits cell proliferation in castration-resistant prostate cancer cells and amino acid starvation culture conditions (ie, amino acids not present in culture medium) combined with gefitinib resulted in cytotoxicity of EGFR-expressing cancer cell lines.

The amino acids are: Alanine, Arginine, Asparagine, Aspartic acid, Cysteine, Glutamine, Glutamic acid, Glycine, Histidine, Isoleucine, Leucine, Lysine, Methionine, Phenylalanine, Proline, Serine, Threonine, Tryptophan, Tyrosine, Tyrosine, and Valine.

Antioxidant: In an example invention dosage form (spray, inhalation, drink, capsule, tablet) for oral or inhalation use, the dose may range from about 500 and 5,000 mg daily. Because the results of such research seemed very promising, large, long-term studies—many of which were funded by the National Institutes of Health (NIH)—were conducted to test whether antioxidant supplements, when taken for periods of at least a few years, could help prevent diseases such as cardiovascular diseases and cancer in people. In these studies, volunteers were randomly assigned to take either an antioxidant or a placebo (an identical-looking product that did not contain the antioxidant). The research was conducted in a double-blind manner (neither the study participants nor the investigators knew which product was being taken). Studies of this type—called clinical trials—are designed to provide clear answers to specific questions about how a substance affects people's health.

Example antioxidants include: Ascorbic acid, Glutathione, Lipoic acid, Uric acid, Carotenes, α-Tocopherol, and Ubiquinol.

Example 15

Formulation embodiments of the present invention for treating a cancer patient comprise a nano-sized clusters of water containing an amount of a cancer cell membrane pore-forming peptide (CCMPFP). An effective method for treating a person or an animal that is suffering a cancer comprises: administering an effective amount of nano-sized clusters of water containing an amount of a cancer cell membrane pore-forming peptide to the person or to the animal suffering an cancer, and using the administered nano-sized clusters of water containing an amount of a. cancer cell membrane pore-forming peptide in the person or in the animal for killing the cancer cells in the person or in the animal.

The methods of using cancer cell membrane pore-forming peptides for killing cancer cells while not killing normal cells concerns using cancer cell membrane pore-forming peptides including PNC-27, PNC-28, PNC-26, SLH-1, SLH-2 and related cancer cell membrane pore-forming peptides, including other anti-cancer peptides described in present specification.

The PNC-27 peptide Amino Acid Sequence SEQ ID NO. 45 is the following:

```
    1            5             10             15
H-Pro-Pro-Leu-Ser-Gln-Glu-Thr-Phe-Ser-Asp-Leu-Trp-Lys-Leu-Leu-
             20             25             30
Lys-Lys-Trp-Lys-Met-Arg-Arg-Asn-Gln-Phe-Trp-Val-Lys-Val-Gln-Arg-Gly-
OH.
```

The PNC-28 peptide Amino Acid Sequence SEQ ID No. 46 (using sequence numbering for PNC-27) is the following:

```
    1            5             10             15
             H-Glu-Thr-Phe-Ser-Asp-Leu-Trp-Lys-Leu-Leu-
             20             25             30
Lys-Lys-Trp-Lys-Met-Arg-Arg-Asn-Gln-Phe-Trp-Val-Lys-Val-Gln-Arg-Gly-
OH.
```

All publications, patents and patent applications referred to herein are incorporated by reference in their entirety to the same extent as if each individual publication, patent or patent application was specifically and individually indicated to be incorporated by reference in its entirety. All information, specification, and claims of the published patent applications and issued patents that are Canadian Patent No. 2,477,878, U.S. Pat. Nos. 7,551,515, 9,765,117 7,883,888, 7,745,405, 9,115,213, 8,822,419, 9,539,327, US2017/0209521, US2014/03711156, Australian Patent No. 2004220114, and US2020/0121715 A1 are incorporated herein by reference each in their entirety.

Some embodiments of the present invention are a product which is useful for treating a cancer in a person or in an animal or for preventing a cancer in a person or in an animal. Cancer treating product embodiments of the present invention include products containing UPW and a peptide. The product may comprise an amount of nano-sized UPW with an amount of nanosized SLH-1 peptide as a non-$H_2O$ substance or with amount of another nanosized cancer cell membrane pore-forming peptide as the non-$H_2O$ substance. The median size in nanometers for the UPW and the non-$H_2O$ peptide substance can be measured using a Malvern Zetasizer.

In preferred embodiments of the present invention the formulation comprises a formulation made according to a process depicted in FIG. 12, 21, 22, or 23. In preferred embodiments of the present invention the formulation comprises nanosized water clusters of ultrapure water and a nanosized non-$H_2O$ substance, wherein the non-$H_2O$ substance is a cell membrane pore-forming peptide selected from the group consisting of PNC-27, PNC-28 a cell membrane pore-forming peptide, a cancer cell membrane pore-forming peptide, and a combination thereof, wherein the cell membrane pore-forming peptide consists of a first amino acid peptide sequence and a second amino acid sequence. In some method embodiments of the present invention, note that the pharmaceutical formulation of the membrane pore-forming peptide and excipient may be for example, a mixture wherein the amount of the membrane pore forming peptide per 100 mg of the excipient in the pharmaceutical formulation is selected from the group consisting of about 0.01 microgram to about 1 microgram, about 1 microgram to about 100 micrograms, about 100 micrograms to about 10 milligrams, about 10 milligrams to about 50 milligrams, about 50 milligrams to about 5 grams, about 5 grams to about 20 grams and any combination thereof. An excipient is a non-active ingredient in the pharmaceutical formulation. For the present invention the excipient can be an ultrapure water (UPW).

Described here is an example general formula for making a CCMPFP Concentrate for titrating into 275 gallons of ultrapure water (UPW) using a process apparatus such as the process apparatuses depicted in FIG. 12, 21, 22, or 23. Select 2-10 grams of a cancer cell membrane pore-forming peptide (CCMPFP) such as PNC-27 and dissolve it in a one half gallon container of ultrapure water. Mix 2 fluid ounces of ConcenTrace™ trace minerals liquid into a second half gallon container. Blend the half gallon concentrate solution of the CCNPFP into 275 gallons of UPW in a blending tank and then blend in the half gallon concentrate of the ConcenTrace™ trace minerals. Then process all of the blended substances through one hallow cylinder 1218 or through a series of two hollow cylinders and send the product to a blending tank where 10 fluid ounces of sodium benzoate can be blended in as a preservative to the 275 gallon batch. Package the product as desired in bottles or in a 275 gallon tote.

In practicing some method embodiments of the present invention, the non-$H_2O$ substance is selected from the group consisting of a cancer cell membrane pore-forming peptide, a substance which is not a drug, a mixture of ions, a carbohydrate, a protein, a nutraceutical, a pharmaceutical, an herbal extract, a liquid other than $H_2O$, and any combination thereof. For the present invention, the frequency of administration of a dose of a product embodiment of the present invention may be selected from the group consisting of a single dose, a single dose per day for two days, a single dose per day for three days, a single dose per week, for two days a single dose per day for two days n intravenous infusion for as long as 4 hours, a single dose per two weeks, a single dose per month, an intravenous dose continuously for as long as 8 hours, an intravenous dose continuously for 10 minutes, an intravenous dose continuously for as long as 1 hour, an intravenous dose continuously for as long as 3 hours, an intravenous dose continuously for as long as 8 hours, an intravenous dose continuously for as long as 1 day, a single dose each hour, a single dose every three hours, a single dose every six hours, a single dose every 12 hours, a single dose every three days, a single dose every fourth day, a single dose per month, a single dose every two months, a single dose every four months, a single dose once a year, and a combination thereof. In practicing some method embodiments of the present invention, note that for example, the dose of the membrane pore-forming peptide per kilogram of body weight of the mammal may be selected from the group consisting of about 0.1 mg to about 20 mg, about 0.001 mg to about 0.1 mg, about 0.1 mg to about 1 mg, about 1 mg to about 10 mg, about 10 mg to about 50 mg, about 20 mg to about 100 mg, and a combination thereof per kilogram of body weight.

In some embodiments of the present invention, the first amino acid sequence of the cell membrane pore-forming peptide comprises between 6 to 15 contiguous amino acids of amino acid sequence
PPLSQETFSDLWKLL, [SEQ ID NO. 1]

wherein optionally an L of the amino acid sequence PPLSQETFSDLWKLL [SEQ ID NO.1] may be substituted by an Ile or a Val, wherein optionally an S of the amino acid sequence PPLSQETFSDLWKLL [SEQ ID NO.1] may be substituted by a Thr, wherein optionally a Q of the amino acid sequence PPLSQETFSDLWKLL [SEQ ID NO.1] may be substituted by an Asn, wherein optionally an E of the amino acid sequence PPLSQETFSDLWKLL [SEQ ID NO.1] may be substituted by an Asp, wherein optionally a T of the amino acid sequence PPLSQETFSDLWKLL [SEQ ID NO.1] may be substituted by a Ser, wherein optionally an F of the amino acid sequence PPLSQETFSDLWKLL [SEQ ID NO.1] may be substituted by a Met, a Leu, or a Tyr, wherein optionally a D of the amino acid sequence PPLSQETFSDLWKLL [SEQ ID NO.1] may be substituted by a Glu, wherein optionally a W of the amino acid sequence PPLSQETFSDLWKLL [SEQ ID NO.1] may be substituted by a Tyr, and wherein optionally a K of the amino acid sequence PPLSQETFSDLWKLL [SEQ ID NO.1] may be substituted by an Arg, a Gln, or a Glu.

In some embodiments of the present invention, the second amino acid sequence of the cell membrane pore-forming peptide is selected from the group consisting of amino acid sequence
KKWKMRRNQFWVKVQRG, [SEQ ID NO. 2]

amino acid sequence
YGRKKRRQRRRPPQ, [SEQ ID NO. 3]

amino acid sequence
GRKKRRQRRRPPQ, [SEQ ID NO. 4]

amino acid sequence
PKKKRKV, [SEQ ID NO. 5]

amino acid sequence
KRPAAIKKAGQAKKKK, [SEQ ID NO. 6]

amino acid sequence
TRQARRNRRRRWRERQR, [SEQ ID NO. 7]

amino acid sequence
RRRRNRTRRNRRRV, [SEQ ID NO. 8]

amino acid sequence
KMTRAQRRAAARRNRWTAR, [SEQ ID NO. 9]

amino acid sequence
TRRQRTRRARRNR, [SEQ ID NO. 10]

amino acid sequence
KLTRAQRRAAARKNKRNTR, [SEQ ID NO. 11]

amino acid sequence
NAKTRRHERRRKLAIER, [SEQ ID NO. 12]

amino acid sequence
MDAQTRRRERRAEKQAQWKAAN, [SEQ ID NO. 13]

amino acid sequence
TAKTRYKARRAELIAERR, [SEQ ID NO. 14]

amino acid sequence
TRRNKRNRIQEQLNRK, [SEQ ID NO. 15]

amino acid sequence
SQMTRQARRLYV, [SEQ ID NO. 16]

amino acid sequence
KRRIRRERNKMAAAKSRNRRRELTDT, [SEQ ID NO. 17]

amino acid sequence
RIKAERKRMRNRIAASKSRKRKLERIAR, [SEQ ID NO. 18]

amino acid sequence
KRARNTEAARRSRARKLQRMKQ, [SEQ ID NO. 19]

amino acid sequence
KLALKLALKALKAALKLA, [SEQ ID NO. 20]

amino acid sequence
LLIILRRRIRKQAKAHSK' [SEQ ID NO. 21]

amino acid sequence
RRRR, [SEQ ID NO. 22]

amino acid sequence
RRRRR, [SEQ ID NO. 23]

amino acid sequence
RRRRRR, [SEQ ID NO. 24]

amino acid sequence
RRRRRRR, [SEQ ID NO. 25]

amino acid sequence
RRRRRRRR, [SEQ ID NO. 26]

amino acid sequence
RRRRRRRRR, [SEQ ID NO. 27]

```
amino acid sequence
                             [SEQ ID NO. 28]
RRRRRRRRR, amino acid sequence
                             [SEQ ID NO. 29]
RRRRRRRRRR, amino acid sequence
                             [SEQ ID NO. 30]
RRRRRRRRRRR, amino acid sequence
                             [SEQ ID NO. 31]
RRRRRRRRRRRR, amino acid sequence
                             [SEQ ID NO. 32]
RRRRRRRRRRRRR, amino acid sequence
                             [SEQ ID NO. 33]
RRRRRRRRRRRRRR, amino acid sequence
                             [SEQ ID NO. 34]
RRRRRRRRRRRRRRR, .

amino acid sequence
                             [SEQ ID NO. 35]
RRRRRRRRRRRRRRRR, amino acid sequence
                             [SEQ ID NO. 36]
RKKRRQRRR, amino acid sequence
                             [SEQ ID NO. 37]
TRSSRAGLQFPVGRVHRLLRK, amino acid sequence
                             [SEQ ID NO. 38]
GWTLNSAGYLLGKINKALAALAKKIL, amino acid sequence
                             [SEQ ID NO. 39]
RQIKIWFQNRRMKWKK, amino acid sequence
                             [SEQ ID NO. 40]
KETWWETWWTEWSQPKKKRKV, amino acid sequence
                             [SEQ ID NO. 41]
RGGRLSYSRRRFSTSTGR, amino acid sequence
                             [SEQ ID NO. 42]
TSPLNIHNGQKL, amino acid sequence
                             [SEQ ID NO. 43]
AGYLLGKINLKALAALAKKIL,
and amino acid sequence
                             [SEQ ID NO. 44]
KFFKFFKFFK,
``` and
wherein optionally an alpha helical stabilizing amino acid may be added at the amino terminal of the HDM2 binding component, with the alpha helical stabilizing amino acid selected from the group consisting of Leu, Glu, Met, Phe, and a combination thereof.

In some embodiments of the present invention the second amino acid sequence of the cell membrane pore forming peptide may contain at least one d-amino acid and/or may have leupeptin or another peptidase-inhibiting peptide attached to the carboxyl terminal end of the cell membrane pore forming peptide so as to reduce the action of peptidases in the mammal to damage the cell membrane pore forming peptide of the invention.

Leader sequences (also known as MRP, membrane resident peptide) function to import the peptides of the invention into a cell and may be derived from a variety of sources. An Example of an MRP is the MRP used in PNC-27, PNC-28, and PNC-26 which is KKWKMRRNQFWVKVQRG [SEQ ID NO.2] which is the transmembrane-penetrating peptide sequence from antennapedia, also known as penetratin. Preferably, the positively charged leader sequence of the penetratin leader sequence of antennapedia protein is used. This leader sequence has the following amino acid sequence: KKWKMRRNQFWVKVQRG [SEQ ID NO.2]. Preferably, the leader sequence is attached to the carboxyl terminal end of the p53 peptide to enable the synthetic peptide to kill transformed and malignant cells.

Preferably, the leader sequence comprises predominantly positively charged amino acid residues since a positively charged leader sequence stabilizes the alpha helix of a subject peptide. Examples of leader sequences which may be linked to the peptides of the present invention are described in Futaki, S. et al (2001) Arginine-Rich Peptides, J. Biol. Chem. 276:5836-5840.

Leader sequences may be selected from the group consisting of penetratin which is KKWKMRRNQFWVKVQRG, [SEQ ID NO.2], and R-TAT which is G(R)$_9$PPQ [SEQ ID NO.51].

For use in a product of the present invention, a cell membrane pore forming peptide may comprise amino acid sequence PPLSQETFSDLWKLL (SEQ ID NO.1) further comprising membrane penetrating amino acid sequence, wherein said membrane penetrating sequence forms the carboxy terminal sequence of said peptide, and wherein said membrane penetrating sequence comprises the amino acid sequence: KKWKMRRNQFWVKVQRG [SEQ ID NO.2].

Amino Acid Names and their three and one-letter abbreviations are listed in below table.

| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acid insertional derivatives of the peptides of the present invention include amino and/or carboxyl terminal fusions as well as intra-sequence insertions of single or multiple amino acids. Insertional amino acid sequence variants are those in which one or more amino acid residues are introduced into a predetermined site in a subject peptide although random insertion is also possible with suitable screening of the resulting product. Deletional variants may be made by removing one or more amino acids from the sequence of a subject peptide. Substitutional amino acid variants are those in which at least one residue in the sequence has been removed and a different residue inserted in its place. For the present invention, amino acid substitutions can be made in accordance with the following table. Substitutional Amino Acid Variants for Cancer Cell Membrane Pore-Forming Peptides

| Original Amino Acid | Amino Acid Substitute |
|---|---|
| Alanine (A) | Serine |
| Arginine (R) | Lysine |
| Asparagine (N) | Glutamine, Histidine |
| Aspartic Acid (D) | Glutamic Acid |
| Cysteine (C) | Serine |
| Glutamic Acid (E) | Aspartic Acid |
| Glycine (G) | Proline |
| Histidine (H) | Asparagine, Glutamine |
| Isoleucine (I) | Leucine, Valine |
| Leucine (L) | Isoleucine, Valine |
| Lysine (K) | Arginine, Glutamine, Glutamic Acid |
| Methionine (M) | Leucine, Isoleucine |
| Phenylalanine (F) | Methionine, Leucine, Tyrosine |
| Serine (S) | Threonine |
| Threonine (T) | Serine |
| Tryptophan (W) | Tyrosine |
| Tyrosine (Y) | Tryptophan, Phenylalanine |
| Valine (V) | Isoleucine, Leucine |

For use in a product of the present invention, a cell membrane pore forming peptide may comprise a peptide with the amino acid sequence: H-Pro-Pro-Leu-Ser-Gln-Glu-Thr-Phe-Ser-Lys-Lys-Trp-Lys-Met-Arg-Arg-Asn-Gln-Phe-Trp-Val-Lys-Val-Gln-Arg-Gly-OH [SEQ ID NO 47]. For use in a product of the present invention, a cell membrane pore forming peptide having a length of 17 amino acids to 35 amino acids, may comprise PPLSQETEFS [SEQ ID NO 48] or ETFSDLWKLL. [SEQ ID NO 49]. Peptides including PNC-27 or other cancer cell membrane pore-forming peptides, may be modified to include a D-amino acid on the amino terminal end in order to slow peptidase activity of the molecule or the peptidase inhibitor leupeptin may be attached to the carboxyl terminal end of the cancer cell membrane pore-forming peptide to slow peptidase activity and lengthen the half-life of the molecules.

The synthetic cancer cell membrane pore-forming peptides may be synthesized by a number of known techniques. For example, the peptides may be prepared using the solid-phase technique initially described by Merrifield (1963) in J. Am. Chem. Soc. 85:2149-2154. Other peptide synthesis techniques may be found in M. Bodanszky et al. Peptide Synthesis, John Wiley and Sons, 2d Ed., (1976) and other references readily available to those skilled in the art. A summary of polypeptide synthesis techniques may be found in J. Sturm/and J. S. Young, Solid Phase Peptide Synthesis, Pierce Chemical Company, Rockford, Ill., (1984). Peptides may also be synthesized by solution methods as described in The Proteins, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, Protective Groups in Organic Chemistry, Plenum Press, New York, N.Y. (1973). The peptides of the present invention may also be prepared by chemical or enzymatic cleavage from larger portions of the p53 protein or from the full length p53 protein. Likewise, leader sequences for use in the synthetic peptides of the present invention may be prepared by chemical or enzymatic cleavage from larger portions or the full length proteins from which such leader sequences are derived. the disclosure of which is incorporated by reference herein as if fully set forth.

Definitions: The word peptide means a molecule having an amino acid sequence of at least 5 amino acids in length. The word cancer refers to a group of diseases involving abnormal cell growth including but not limited to solid tissue tumor and non-solid tissue tumor cancers. The word person means a human. The word animal includes mammals, fish, birds, reptiles, and amphibian. The word plant includes vascular plants, monocots, dicots, plants living in fresh water, plants living in seawater, trees, species of *cannabis*, grasses, and agricultural plants grown for food.

Some embodiments of the present invention are a method for treating cancer in a person or an animal by administering to the person or animal a product of the present invention which comprises a dose of nanosized ultrapure water encapsulating a nanosized non-$H_2O$ substance which is a cell membrane pore forming peptide, wherein the cancer being treated is a cancer selected from the group consisting of: astrocytoma, bladder cancer, brain cancer, breast cancer, cervical cancer, colorectal cancer, endometrial cancer, gastric cancer, lung cancer, melanoma, leukemia, lymphoma, ovarian cancer, pancreatic cancer, prostate cancer, renal carcinoma, sarcoma, thyroid cancer, glioblastoma, multiple myeloma, myelodysplastic syndrome, mesothelioma, acute myeloid leukemia, childhood leukemia, chronic myeloid leukemia, myelodysplastic syndrome, Hodgkin's lymphoma, and Polycythemia Vera.

Some embodiments of the present invention are for treating a human cancer or an animal cancer, wherein the cancer of the human or animal is selected from the group consisting of a pancreatic cancer, a lung cancer, a breast cancer, a liver cancer, an intrahepatic bile duct cancer, an acute myeloid leukemia cancer, a bronchus cancer, an esophagus cancer, a gallbladder cancer, a stomach cancer, a brain cancer, a nervous system cancer, a myeloma cancer, an ovary cancer, a uterine cancer, a cervix cancer, a chronic myeloid cancer, and oral cavity cancer, a pharynx cancer, a colon cancer, a rectum cancer, a small intestine cancer, a bone cancer, a joint cancer, a soft tissue cancer, a heart cancer, an acute lymphocytic leukemia cancer, a non-Hodgkin lymphoma cancer, a kidney cancer, a renal pelvis cancer, a chronic lymphocytic leukemia cancer, a urinary bladder cancer, an eye cancer, and eye orbit cancer, a uterine corpus cancer, a Hodgkin lymphoma cancer, a melanoma canter, a skin cancer, a lymph node cancer, a penile cancer, an adrenal cancer, a thymus cancer, a thyroid cancer, a prostrate cancer, a metastatic cancer, a cancer stem cell cancer, a cancer progenitor cell cancer, and a combination thereof.

In practicing some method embodiments of the present invention, note that an animal or a human is administered a pharmaceutical formulation comprising a nanosized ultrapure water and a cancer cell membrane pore forming peptide as a cancer treatment method which for example, may be selected from the group consisting of (a) killing treatment-resistant cancer stem cells in the mammal at any time in their life, (b) killing treatment-resistant cancer progenitor cancer cells in the mammal at any time in their life, (c) killing treatment-resistant cancer stem cells in the mammal which cancer surgery could not remove, (d) killing treatment-resistant cancer progenitor cancer cells in the mammal which cancer surgery could not remove, (e) killing the treatment resistant cancer cells in the mammal which have metastasized from the primary tumor, (f) killing the treatment-resistant cancer cells in the mammal as a prophylactic treatment, (g) killing the treatment-resistant cancer cells in tumors which are inoperable, (h) killing the treatment-resistant cancer cells in the blood circulation without causing an immune system suppression, (i) killing the treatment-resistant cancer cells in the mammal without killing normal cells in the mammal, (j) killing the treatment-resistant cancer stem cells in a human without killing the normal cells in the human, (k) killing the treatment-resistant cancer cells in the human as an adjunct to a chemotherapy to kill chemotherapy sensitive cancer cells, (l) killing the treatment-resistant cancer cells in the human as the adjunct to a radiation therapy to kill radiation therapy sensitive cancer cells, (m) killing the treatment-resistant cancer cells in the human as the adjunct to an immunotherapy to kill the immunotherapy sensitive cancer cells, (n) killing the treatment resistant cancer cells in cancer patients after a targeted cancer pathway chemotherapy, (o) killing the treatment resistant cancer cells in cancer patients who are at a known risk for a cancer recurrence after cancer surgery or conventional cancer treatments, and a combination thereof.

In practicing some method embodiments of the present invention the route of administration of the cell membrane pore-forming peptide may be for example, selected from the group consisting of oral, parenteral, intravenous, intramuscular, into the tumor by injection, into the arterial circulation of a tumor, into hepatic artery, into hepatic vein, into CNS spinal fluid, intraocular, nasal, rectal, into the bladder, cervical, into brain, into artery, intra-peritoneal, into a lymphatic circulation, into a lymph node, by inhalation, by a ventilator, and a combination thereof. The terms membrane pore forming peptide, membrane pore-forming peptide, cell membrane pore-forming peptide, and cell membrane pore forming peptide mean the same. The terms cell membrane and cell plasma membrane have the same meaning.

A precise therapeutically effective amount of a cancer cell membrane pore forming peptide for treating cancer in a person (human) or an animal cannot be stated due to variations in stage of neoplastic disease, tumor size and aggressiveness, the presence or extent of metastasis, etc. In addition, an individual's weight, gender, and overall health must be considered and will effect dosage. It can be generally stated, however, that the synthetic peptides of the present invention be administered in an amount of at least about 10 mg per dose, more preferably in an amount up to about 1000 mg per dose. Since the peptide compositions of the present invention will eventually be cleared from the bloodstream, re-administration of the pharmaceutical compositions is indicated and preferred.

In preferred embodiments of the present invention the formulation comprises a formulation made according to a process depicted in FIG. 12, 21, 22, or 23. In preferred embodiments of the present invention the formulation comprises nanosized water clusters of ultrapure water and a nanosized on-$H_2O$ substance, wherein the non $H_2O$ substance is selected from the group of PNC-27, and a cell membrane forming peptide, and a combination thereof, wherein the cell membrane forming peptide consists of a first amino acid peptide sequence and a second amino acid sequence. In practicing some method embodiments of the present invention, note that the pharmaceutical formulation of the membrane pore-forming peptide may be for example, a simple or complex mixture of the membrane pore-forming peptide in an excipient or combination of excipients selected from the group consisting of with an isotonic saline, a pH buffered aqueous solutions, ethanol, glycerol, propylene glycol, a polyol, a polyethylene glycol, a surfactants, a fatty acid, a microemulsion, a liposome, a microsphere, a peptide nanoparticle, a microemulsion, a gelatin, a vegetable oil, a saccharide, a polysaccharide, an excipient for an oral table formulation, an excipient for an oral capsule formulation, a hard gelatin capsule, a soft shell gelatin capsule, an elixir, a fruit juice, a sugar cube, a candy, a suspension, a syrup, an excipient for an oral formulation, an excipient for a suppository, an excipient for an intravenous solution, an excipient for a syringe injection formulation, an excipient for a catheter injectable formulation, an excipient for a transdermal patch, an excipient for a parenteral injection, an excipient for an eye drop formulation, and excipient for an injection into the CNS, and a combination thereof.

(A) Purified water and therapeutic particle embodiments of the present invention can be used in the pharmaceutical industry. Water of this grade is widely used as a raw material, ingredient, and solvent in the processing, formulation, and manufacture of pharmaceutical products, active pharmaceutical ingredients (APIs) and intermediates, compendia articles, and analytical reagents. The microbiological content of the water is of importance and the water must be regularly monitored and tested to show that it remains within microbiological control. Embodiments of the present invention are useful source of water for a pharmaceutical use, manufacturing of pharmaceutical products, medical devices, biologics, cell- and tissue-based products, and many other medical products. The two major categories are bulk water (i.e., produced on-site where used from an internal water system) and packaged water (i.e., produced elsewhere, packaged, sterilized to preserve microbial quality throughout the packaged shelf life, and purchased). Regardless of whether its bulk water or packaged water, the type of water is then determined by the testing performed, as defined by United States Pharmacopeia (USP)<1231> Namely—USP<1231> Water for Pharmaceutical Purposes. (Rockville, MD, Mar. 8, 2017. There are a number of pharmaceutical water types. Purified water is most commonly used as a diluent in the production of non-sterile products for injection, infusion or implantation, cleaning equipment, and cleaning non-sterile product-contact components. Purified water systems must be validated to consistently produce and distribute water of acceptable chemical and microbiological quality. However, they may be susceptible to biofilms, undesirable levels of viable microorganisms, or endotoxins, which means frequent sanitization and monitoring to ensure appropriate quality at the points of use. Water for injection (WFI) is most often used as an excipient in the production of sterile products and other preparations when endotoxin content must be controlled. Examples are pharmaceutical applications such as cleaning of certain equipment and sterile product-contact components. WFI must meet all the same chemical requirements of purified water with added bacterial endotoxin specifications, because endotoxins are produced by microorganisms that are prone to inhabit water. As with a water system producing purified water, WFI systems also must be validated to reliably and consistently produce and distribute water of acceptable chemical and microbiological quality. Pure steam is intended for use in steam-sterilizing porous loads and equipment and in other processes, such as cleaning, where condensate would directly contact official articles, containers for these articles, process surfaces that would in turn contact these articles, or materials which are used in analyzing such articles. Pure steam is prepared from suitably pretreated source water, analogous to the pretreatment used for purified water or WFI, vaporized with a suitable mist elimination, and distributed under pressure. Water for hemodialysis is specifically for hemodialysis applications and primarily for the dilution of hemodialysis concentrate solutions. Water for hemodialysis is typically produced and used on site as bulk water. This water contains no added antimicrobials and is not intended for injection.

Sterile purified water is packaged and rendered sterile. It is used for preparation of sterile products or in analytical applications requiring purified water when access to a validated system is not practical and only a small quantity is needed. It is also used when bulk packaged purified water is not suitably microbiologically controlled. Sterile water for injection is packaged and rendered sterile. This water is for the processing of sterile products intended to be used intravenously. Additionally, it is used for other applications where bulk WFI or purified water is indicated but access to a validated water system is either not practical or only a relatively small quantity is needed. Sterile WFI is typically packaged in single-dose containers that are typically less than 1 L in size. Sterile water for irrigation is packaged and rendered sterile. This water is commonly used when sterile water is required, but when the application does not have particulate matter specifications. Sterile water for irrigation is often packaged in containers that are typically greater than 1 L in size. Sterile water for inhalation is packaged and rendered sterile. This water is usually intended for use with inhalators and in preparation of inhalation solutions. It carries a less stringent specification for bacterial endotoxins than sterile WFI and, therefore, is not suitable for parenteral applications.

Bacteriostatic water for injection is a sterile water for injection to which one or more suitable antimicrobial preservatives have been added. This water is typically intended for use as a diluent in the preparation of sterile products, mostly for multi-dose products that require repeated content withdrawals, such as liquid pharmaceuticals. It may be packaged in single-dose or multiple-dose containers, usually less than 30 mL. With nine different types of water, each with specific testing requirements and applications, it is crucial to understand how they can impact products. In summary, embodiments of the present invention can be used for a pharmaceutical grade water use may be selected from the group consisting of a purified water, water for injection (WFI), pure steam, a water for hemodialysis, an intravenous water, an enema water, an eye wash, an eye drop, a nose drop, an ear drop, a sterile water for injection, a sterile water for inhalation including a ventilator delivering an aerosol to the nasal cavity or pulmonary airway, a sterile water for irrigation of a body cavity, a bacteriostatic water for injection, and a combination thereof.

Embodiments of the present invention can be used in a laboratory use. Technical standards on water quality have been established by a number of professional organizations, including the American Chemical Society (ACS), ASTM International, the U.S. National Committee for Clinical Laboratory Standards (NCCLS) which is now CLSI, and the U.S. Pharmacopeia (USP). The ASTM, NCCLS, and ISO 3696 or the International Organization for Standardization classify purified water into Grade 1-3 or Types I-IV depending on the level of purity. These organizations have similar, although not identical, parameters for highly purified water. Note that the European Pharmacopeia uses Highly Purified Water (HPW) as a definition for water meeting the quality of Water For Injection, without however having undergone distillation. In the laboratory context, highly purified water is used to denominate various qualities of water having been "highly" purified. Regardless of which organization's water quality norm is used, even Type I water may require further purification depending on the specific, laboratory application. For example, water that is being used for molecular-biology experiments needs to be DNase or RNase-free, which requires special additional treatment or functional testing. Water for microbiology experiments needs to be completely sterile, which is usually accomplished by autoclaving. Water used to analyze trace metals may require the elimination of trace metals to a standard beyond that of the Type I water norm. IN some cases, an embodiment of the present invention could be used in lab work and biological experiments. Electrical conductivity—The electrical conductivity of ultra-pure water is $5.5 \times 10^{-6}$ S/m (18 MΩ·cm in the reciprocal terms of electrical resistivity) and is due only to H+ and OH— ions produced in the water dissociation equilibrium. This low conductivity is only achieved, however, in the presence of dissolved monatomic gases. Completely de-gassed ultrapure water has a conductivity of $1.2 \times 10-4$ S/m, whereas on equilibration to the atmosphere it is $7.5 \times 10-5$ S/m due to dissolved $CO_2$ in it. The highest grades of ultrapure water should not be stored in glass or plastic containers because these container materials leach (release) contaminants at very low concentrations. Storage vessels made of silica are used for less-demanding applications and vessels of ultrapure tin are used for the highest-purity applications. It is worth noting that, although electrical conductivity only indicates the presence of ions, the majority of common contaminants found naturally in water ionize to some degree. This ionization is a good measure of the efficacy of a filtration system, and more expensive systems incorporate conductivity-based alarms to indicate when filters should be refreshed or replaced. For comparison,[12] sea water has a conductivity of perhaps 5 S/m (53 mS/cm is quoted), while normal un-purified tap water may have conductivity of 5 mS/m (50 μS/cm) (to within an order of magnitude), which is still about 2 or 3 orders of magnitude higher than the output from a well-functioning demineralizing or distillation mechanism, so low levels of contamination or declining performance are easily detected. [citation needed]

Embodiments of the present invention may be used as an "ingredient" in many cosmetics and pharmaceuticals, where it is sometimes referred to as "aqua" on product ingredient labels; see International Nomenclature of Cosmetic Ingredients. When used as a rinse after washing cars, windows, and similar applications, some embodiments of the present invention dry without leaving spots caused by dissolved solutes; embodiments of the present invention may be used in humidors to prevent cigars from collecting bacteria, mold, and contaminants, as well as to prevent residue from forming on the humidifier material. Embodiments of the present invention may be used by window cleaners using water-fed pole systems also use purified water because it enables the windows to dry by themselves leaving no stains or smears.

Some embodiments of the present invention are useful water sources for drinking or for use as a water supply for an animal, including an insect, invertebrates, shell fish, lobsters, crabs, oysters, fish, amphia, reptiles, birds, mammals including a human. Some embodiments of the present invention are useful water sources for growing plants, germinating seeds, and in various cell culture aqueous media and gels/agars. Some embodiments of the present invention are useful The drinking of purified water as a replacement of drinking water has been both advocated and discouraged for health reasons. Purified water lacks minerals and ions such as calcium that play key roles in biological functions, such as in nervous system homeostasis, and are normally found in potable water. The lack of naturally occurring minerals in distilled water has raised some concerns. The Journal of General Internal Medicine published a study on the mineral contents of different waters available in the US. The study found that "drinking water sources available to North Americans may contain high levels of calcium, magnesium, and sodium and may provide clinically important portions of the recommended dietary intake of these minerals". It encouraged people to "check the mineral content of their drinking water, whether tap or bottled, and choose water most appropriate for their needs". Since distilled water is devoid of minerals, supplemental mineral intake through diet is needed to maintain proper health. The consumption of "hard" water (water with minerals) is associated with beneficial cardiovascular effects. As noted in the American Journal of Epidemiology, the consumption of hard drinking water is negatively correlated with atherosclerotic heart disease.

Ultra Pure Water (UPW)

According to Wikipedia (2018), Ultrapure water (also UPW or high-purity water) is water that has been purified to uncommonly stringent specifications. Ultrapure water is a commonly used term in the semiconductor industry to emphasize the fact that the water is treated to the highest levels of purity for all contaminant types, including: organic and inorganic compounds; dissolved and particulate matter; volatile and non-volatile, reactive and inert; hydrophilic and hydrophobic; and dissolved gases. UPW and commonly used term deionized (DI) water are not the same. In addition to the fact that UPW has organic particles and dissolved gases removed, a typical UPW system has three stages: a pretreatment stage to produce purified water, a primary stage to further purify the water, and a polishing stage, the most expensive part of the treatment process. A number of organizations and groups develop and publish standards associated with the production of UPW. Pharmaceutical plants follow water quality standards as developed by pharmacopeial, of which three examples are the United States Pharmacopeia, European Pharmacopeia, and Japanese Pharmacopeia. The most widely used requirements for UPW quality are documented by ASTM D5127 "Standard Guide for Ultra-Pure Water Used in the Electronics and Semiconductor Industries" and SEMI F63 "Guide for ultrapure water used in semiconductor processing". Bacteria, particles, organic and inorganic sources of contamination vary depending on a number of factors including the feed water to make UPW as well as the selection of the piping materials to convey it. Bacteria are typically reported in colony-forming units (CFU) per volume of UPW. Particles use number per volume of UPW. Total organic carbon (TOC), metallic contaminants, and anionic contaminants are measured in dimensionless terms of parts per notation, such as ppm, ppb, ppt and ppq. Bacteria have been referred to as one of the most obstinate in this list to control. Techniques that help in minimizing bacterial colony growth within UPW streams include occasional chemical or steam sanitization (which is common in the pharmaceutical industry), ultrafiltration (found in some pharmaceutical, but mostly semiconductor industries), ozonation and optimization of piping system designs that promote the use of Reynolds Number criteria for minimum flow along with minimization of dead legs. In modern advanced UPW systems positive (higher than zero) bacteria counts are typically observed in the newly constructed facilities. This issue is effectively addressed by sanitization using ozone or hydrogen peroxide. With proper design of the polishing and distribution system no positive bacteria counts are typically detected throughout the life cycle of the UPW system. Particles can be controlled by use of filtration and ultrafiltration. Sources can include bacterial fragments, the sloughing of the component walls within the conduit's wetted stream and also the cleanliness of the jointing processes used to build the piping system.

Total organic carbon (TOC) in ultrapure water can contribute to bacterial proliferation by providing nutrients, can substitute as a carbide for another chemical species in a sensitive thermal process, react in unwanted ways with biochemical reactions in bioprocessing and, in severe cases, leave unwanted residues on production parts. TOC can come from the feed water used to produce UPW, from the components used to convey the UPW (additives in the manufacturing piping products or extrusion aides and mold release agents), from subsequent manufacturing and cleaning operations of piping systems or from dirty pipes, fittings and valves.

Metallic and anionic contamination in UPW systems can shut down enzymatic processes in bioprocessing, Depending on the level of purity needed, detection of these contaminants can range from simple conductivity (electrolytic) readings to sophisticated instrumentation such as ion chromatography (IC), atomic absorption spectroscopy (AA) and inductively coupled plasma mass spectrometry (ICP-MS).

Applications—The polishing stage is a set of treatment steps and is usually a recirculation and distribution system, continuously treating and recirculating the purified water in order to maintain stable high purity quality of supplied water. Traditionally the resistivity of water serves as an indication of the level of purity of UPW. Deionized (DI) water may have a purity of at least one million ohms-centimeter or one Mohm·cm. Typical UPW quality is at the theoretical maximum of water resistivity (18.18 Mohm·cm at 25° C.). Therefore the term has acquired measurable standards that further define both advancing needs and advancing technology in ultrapure water production. If in-line conductivity exceeds values additional testing is required before a conclusion can be made. Refer to the respective pharmacopoeia for details.

Ultrapure water is treated through multiple steps to meet the quality standards for different users. The "ultrapure water" term became more popular in the later 1970s and early 1980s as a way of describing the particular quality of water used in power, pharmaceutical, or semiconductor facilities. While each industry uses what it calls "ultrapure water", the quality standards vary, meaning that the UPW used by a pharmaceutical plant is different than that used in a semiconductor fab or a power station. The standards tie into the UPW use. For instance, semiconductor plants use UPW as a cleaning agent, so it is important that the water not contain dissolved contaminants that can precipitate or particles that may lodge on circuits and cause microchip failures. The power industry uses UPW as a source to make steam to drive steam turbines; pharmaceutical facilities will use UPW as a cleaning agent, as well as an ingredient in products, so they seek water free of endotoxins, microbials, and viruses.

Ion exchange (IX) and electrodeionization (EDI) are the primary deionization technologies associated with UPW production, in most cases following reverse osmosis (RO). Depending on the required water quality, UPW treatment plants often also feature degasification, microfiltration, ultrafiltration, ultraviolet irradiation, and measurement instruments (e.g., total organic carbon [TOC], resistivity/conductivity, particles, pH, and specialty measurements for specific ions). In pure water systems, electrolytic conductivity or resistivity measurement is the most common indicator of ionic contamination. The same basic measurement is read out in either conductivity units of microsiemens per centimeter ($\mu$S/cm), typical of the pharmaceutical and power industries or in resistivity units of megohm-centimeters (Mohm·cm) used in the microelectronics industries. These units are reciprocals of each other. Absolutely pure water has a conductivity of 0.05501 μS/cm and a resistivity of 18.18 Mohm·cm at 25° C., the most common reference temperature to which these measurements are compensated. An example of the sensitivity to contamination of these measurements is that 0.1 ppb of sodium chloride raises the conductivity of pure water to 0.05523 μS/cm and lowers the resistivity to 18.11 Mohm·cm.

Ultrapure water is easily contaminated by traces of carbon dioxide from the atmosphere passing through tiny leaks or diffusing through thin wall polymer tubing when sample lines are used for measurement. Carbon dioxide forms conductive carbonic acid in water. For this reason, conductivity probes are most often permanently inserted directly into the main ultrapure water system piping to provide real-time continuous monitoring of contamination. These probes contain both conductivity and temperature sensors to enable accurate compensation for the very large temperature influence on the conductivity of pure waters. Conductivity probes have an operating life of many years in pure water systems. They require no maintenance except for periodic verification of measurement accuracy, typically annually. Sodium is usually the first ion to break through a depleted cation exchanger. Sodium measurement can quickly detect this condition and is widely used as the indicator for cation exchange regeneration. The conductivity of cation exchange effluent is always quite high due to the presence of anions and hydrogen ion and therefore conductivity measurement is not useful for this purpose. Sodium is also measured in power plant water and steam samples because it is a common corrosive contaminant and can be detected at very low concentrations in the presence of higher amounts of ammonia and/or amine treatment which have a relatively high background conductivity. On-line sodium measurement in ultrapure water most commonly uses a glass membrane sodium ion-selective electrode and a reference electrode in an analyzer measuring a small continuously flowing side-stream sample. The voltage measured between the electrodes is proportional to the logarithm of the sodium ion activity or concentration, according to the Nernst equation. Because of the logarithmic response, low concentrations in sub-parts per billion ranges can be measured routinely. To prevent interference from hydrogen ion, the sample pH is raised by the continuous addition of a pure amine before measurement.

Calibration at Low Concentrations is Often Done

Non-volatile residue—Another type of contamination in UPW is dissolved inorganic material, primarily silica. Silica is one of the most abundant mineral on the planet and is found in all water supplies. TOC—Total organic carbon is most commonly measured by oxidizing the organics in the water to $CO_2$, measuring the increase in the $CO_2$ concentration after the oxidation. Oxidation of organics to $CO_2$ is most commonly achieved in liquid solutions by the creation of the highly oxidizing chemical species, the hydroxyl radical (OH•). For the typical TOC levels in UPW systems most methods utilize hydroxyl radicals in the liquid phase. There are multiple methods to create sufficient concentrations of hydroxyl radicals needed to completely oxidize the organics in water to $CO_2$, each method being appropriate for different water purity levels. For typical raw waters feeding into the front end of an UPW purification system the raw water can contain TOC levels between 0.7 mg/L to 15 mg/L and require a robust oxidation method that can insure there is enough oxygen available to completely convert all the carbon atoms in the organic molecules into $CO_2$. Robust oxidation methods that supply sufficient oxygen include the following methods; Ultraviolet light (UV) & persulfate, heated persulfate, combustion, and super critical oxidation. Typical equations showing persulfate generation of hydroxyl radicals follows.

$$S_2O_8^{-2} + h\nu \ (254 \ nm) \rightarrow 2 \ SO_2^{-1}\bullet \ and \ SO_2^{-1}\bullet + H_2O \rightarrow HSO_4^{-1} + OH\bullet$$

When the organic concentration is less than 1 mg/L as TOC and the water is saturated with oxygen UV light is sufficient to oxidize the organics to $CO_2$, this is a simpler oxidation method. The wavelength of the UV light for the lower TOC waters must be less than 200 nm and is typically 184 nm generated by a low pressure Hg vapor lamp. The 184 nm UV light is energetic enough to break the water molecule into OH and H radicals. The hydrogen radicals quickly react to create $H_2$. The equations follow: $H_2O + h\nu \ (185 \ nm) \ OH\bullet + H\bullet$ and $H\bullet + H\bullet \rightarrow H_2$ UPW Purification process (Wikipedia, 2018) involves the following processes. Typically city feed water (containing all the unwanted contaminants previously mentioned) is taken through a series of purification steps that, depending on the quality of UPW wanted, includes gross filtration for large particulates, carbon filtration, water softening, reverse osmosis, exposure to ultraviolet (UV) light for TOC and/or bacterial static control, polishing using either ion exchange resins or electro-deionization (EDI) and finally filtration or ultrafiltration.

Some systems use direct return, reverse return or serpentine loops that return the water to a storage area, providing continuous re-circulation, while others are single-use systems that run from point of UPW production to point of use. The constant re-circulation action in the former continuously polishes the water with every pass. The latter can be prone to contamination build up if it is left stagnant with no use. For modern UPW systems it is important to consider specific site and process requirements such as environmental constraints (e.g., wastewater discharge limits) and reclaim opportunities (e.g., is there a mandated minimum amount of reclaim required). UPW systems consist of three subsystems: pretreatment, primary, and polishing. Most systems are similar in design but may vary in the pretreatment section depending on the nature of the source water.

Pretreatment: Pretreatment produces purified water. Typical pretreatments employed are two pass Reverse Osmosis, Demineralization plus Reverse Osmosis or HERO (High Efficiency Reverse Osmosis). In addition, the degree of filtration upstream of these processes will be dictated by the level of suspended solids, turbidity and organics present in the source water. The common types of filtration are multimedia, automatic back washable filters and ultrafiltration for suspended solids removal and turbidity reduction and Activated Carbon for the reduction of organics. The Activated Carbon may also be used for removal of chlorine upstream of the Reverse Osmosis of Demineralization steps. If Activated Carbon is not employed then sodium bisulfite is used to de-chlorinate the feed water. Primary: Primary treatment consists of ultraviolet light (UV) for organic reduction, EDI and or mixed bed ion exchange for demineralization. The mixed beds may be non-regenerable (following EDI), in-situ or externally regenerated. The last step in this section may be dissolved oxygen removal utilizing the membrane degasification process or vacuum degasification.

Polishing: Polishing consists of UV, Heat exchange to control constant temperature in the UPW supply, non-regenerable ion exchange, membrane degasification (to polish to final UPW requirements) and ultrafiltration to achieve the required particle level. Some semiconductor Fabs require hot UPW for some of their processes. In this instance polished UPW is heated in the range of 70 to 80 C before being delivered to manufacturing. Most of these systems include heat recovery wherein the excess hot UPW returned from manufacturing goes to a heat recovery unit before being returned to the UPW feed tank to conserve on the use of heating water or the need to cool the hot UPW return flow.[39]

Stainless steel remains a piping material of choice for the pharmaceutical industry. Due to its metallic contribution, most steel was removed from microelectronics UPW systems in the 1980s and replaced with high performance polymers of polyvinylidene fluoride (PVDF), [1] perfluoroalkoxy (PFA), ethylene chlorotrifluoroethylene (ECTFE) and polytetrafluoroethylene (PTFE) in the US and Europe. In Asia, polyvinyl chloride (PVC), chlorinated polyvinyl chloride (CPVC) and polypropylene (PP) are popular, along with the high performance polymers.

The polishing stage is a set of treatment steps and is usually a recirculation and distribution system, continuously treating and recirculating the purified water in order to maintain stable high purity quality of supplied water. Traditionally the resistivity of water serves as an indication of the level of purity of UPW. Deionized (DI) water may have a purity of at least one million ohms-centimeter or one Mohm·cm. Typical UPW quality is at the theoretical maximum of water resistivity (18.18 Mohm·cm at 25° C.).

Example Apparatus for Processing Embodiment of the Invention

In one embodiment some of the apparatus and/or processing steps comprises using the apparatus or processes in the following steps using the following devices and or processing apparatus in the following order of steps; (step 1) using a carbon filter device for removing gases and organic matter, (step 2) using a reverse osmosis (RO) device for removing ionized particles, ionized molecules and ions from minerals, (in addition the process may be using a devise for performing a sterilization of equipment using the ozone bubbles following downstream of the RO device. (step 3) an electro-deionization (EDI) device for raising the fluid stream resistivity to approximately 12 to about 17 megohms by removing trace residual ions present after the RO device, (step 4) mixed dead resin chromatography column (MDRCC), (step 5) ultraviolet radiation (UV) sterilization device, (step 6) plurality of 0.1 to 10 micron parallel filters device (wherein the fluid stream from the parallel filters device comprises an ultrapure water (UPW), (step 7) a static blending pipe for blending inline a combination of the UPW fluid stream from the parallel filters device, and a concentrate (CONCENTRATE) comprising a selected volume of UPW and containing a one or a plurality of non-$H_2O$ which may comprise an amount of one or more cannabinoids some other non-$H_2O$ substances which may comprise an amount of trace minerals comprising optionally an amount of Contrace™ TMS, an amount of 40,000 volts trace minerals, a pH adjusting medium, and a selected volume (gallons) of UPW selected from the group consisting of 0.1, 0.5, 1.0, 2.0, 3.0, 4.0, 5.0, 6.0, 7.0, 8.0, 9.0, 10, 20, 30, 40, 50, 60, 70, 80, 90, 100, and any combination thereof. Optionally the concentrate maybe prepared adjacent to the apparatus which is used to prepare the UPW or in a special room which has FDA or food grade sterile conditions. The blended fluid stream exiting the static blending pipe is flowing at flow rate (gallons per minute) selected from the group consisting of 10, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, and any combination thereof. The flowing of the blended fluid stream maybe produced using a device which may be selected from the group consisting of pumping device, a gravity feeding device, vacuum creating device, a pressure creating device and any combination thereof. For example, the flowing of the blended fluid stream is used for delivering the blended fluid stream to a hollow cylinder 1218 alone, or with hollow cylinder 1218 in series with a hollow cylinder 2122, or the hollow cylinder 1218 in parallel with hollow cylinder 2122. In other embodiments of the invention, a series arrangement or a parallel arrangement is used for the number of hollow cylinders which number of the hollow cylinders may be selected from the group consisting of 1, 2, 3, 4, 5, 6, 7, 8, 9, 10, and any combination thereof. The flow of the blended fluid stream flowing through the hollow cylinder(s) in some embodiments of the invention comprised a method for nanosizing water molecules in clusters containing a non-$H_2O$ wherein the sizes in nanometers are quantified as modes with median size values reported as a distribution function histograms using a Malvern Zetasizer instrument analyses. The hollow cylinder(s) processing of the water molecules in clusters containing a non-$H_2O$ creates sizes of water molecules in clusters containing a non-$H_2O$ wherein the sizes maybe selected from the group consisting of 2, 4, 6, 8, 10, 15, 20, 30, 40, 50, 60, 70, 80, 90, 100, 150, 200, 250, 300, 350, 400, 450, 500, 550, 600, 650, 700, 750, 800, 850, 900, 950, 1000, and any combination thereof.

The nanosizing water molecules in clusters containing a non-$H_2O$ is producing a product wherein the product is filtered optionally through a filtering device which has an ability for restricting particles, the micron filter exclusion size in microns selecting from the group consisting of 0.1, 0.2, 0.3, 0.4, 0.5, 1.0, 1.5, 2.0, 4.0, 5.0, 6.0, 10.0, 15.0, 20.0 and any combination thereof. Whether the product comprising nanosized water molecules in clusters containing a non-$H_2O$ have been subjected to a filtering process or not the next step in the processing of the product comprises and ozonating step in a tank. The ozonating step is a process comprising is a bubbling ozone gas through product in the tank as a means for sterilizing the product as well as for sterilizing for any apparatus in the apparatus downstream from the ozonating tank. The product which has been ozonated which comprises a volume of the nanosized water molecules in clusters containing a non-$H_2O$ maybe stored in a suitable sized holding tank or may be immediately used for bottling in drinking containers.

1. A process for making a composition of an aqueous therapeutic particle having stable exterior water clustering with nanosized thickness, the process comprising the steps of:

combining a first amount of an ultrapure water in a first container with a first solute comprising a first non-$H_2O$ substance so as to make a first fluid with a first solute concentration of the aqueous therapeutic particle;

pumping the first fluid from the first container at a first flow rate thru a first pipe which is connected a junction with a second pipe;

pumping a second volume of the ultrapure water with a second solute as a second fluid at a second flow rate thru the second pipe so the second fluid combines with the first fluid at the junction of the second pipe with the first pipe and creates a third fluid which has a third fluid solute concentration of the aqueous therapeutic particle;

wherein second fluid flow rate is set higher than the first fluid flow rate so as to cause the third fluid solute concentration to be lower than the first solute concentration; and pumping the third fluid at a third fluid flow rate through a nanosizer comprising a hollow cylinders having a jet nozzle for nanosizing exterior water clustering of the aqueous therapeutic particle to make a composition of an aqueous therapeutic particle having stable exterior water clustering with nanosized thickness for having stable exterior water clustering with nanosized thickness.

2. The process of claim 1, wherein thickness of the exterior water clustering of the aqueous therapeutic particle including the therapeutic particle is between about 2 to about 400 nanometers.

3. The method of claim 1, wherein the third fluid flow rate is between about 5 to about 30 gallons per minute.

4. The method of claim 1, wherein the third fluid flow rate is between about 12 to about 20 gallons per minute.

5. The method of claim 1, wherein the third fluid flow rate is between about 14 to about 16 gallons per minute.

6. The method of claim 1, wherein the width of the hollow cylinder is about 4 inches, and hollow cylinder inner length is about 18 inches.

7. The method of claim 1, wherein the third fluid is under a pressure of between about 10 to about 70 pounds per square inch.

8. The method of claim 1, wherein the third fluid is under a pressure of between about 25 to about 40 pounds per square.

9. The method of claim 1, wherein the resistivity of the first solution of ultrapure water is between about 17 to about 18.2 meg-ohm cm.

10. The method of claim 1, wherein the first solution of ultrapure water is prepared using carbon filtration, followed by using reverse osmosis, followed by using electro-deionization, and then ultraviolet light exposure.

11. The method of claim 1, wherein the jet nozzle directs the ultrapure water by an average of between about 0 to about 90 degrees relative to a long axis of the hollow cylinder.

12. The method of claim 1, wherein the one or more solutes comprise an ion of an ionizable salt.

13 The method of claim 1, wherein the ion is selected from the group consisting of selected from aluminum ion, ammonium ion, antimony ion, arsenic ion, barium ion, beryllium ion, bismuth ion, boron ion, bromide ion, cadmium ion, calcium ion, cerium ion, cesium cation, chloride ion, chromium ion, cobalt ion, copper ion, dysprosium ion, erbium ion, europium ion, fluoride ion, gadolinium ion, gallium ion, germanium ion, gold ion, hafnium ion, holmium ion, indium ion, iodine ion, iridium ion, iron ion, lanthanum ion, lead ion, lithium ion, lutetium ion, magnesium ion, manganese ion, mercury ion, molybdenum ion, neodymium ion, nickel ion, niobium ion, osmium ion, palladium ion, phosphorus ion, platinum ion, potassium ion, praseodymium ion, rhenium ion, rhodium ion, rubidium ion, ruthenium ion, samarium ion, scandium ion, selenium ion, silicon ion, silver ion, sodium ion, strontium ion, sulfate ion, tantalum ion, tellurium ion, terbium ion, thallium ion, thorium ion, thulium ion, tin ion, titanium ion, tungsten ion, vanadium ion, ytterbium ion, yttrium ion, zinc ion, and zirconium ion.

14. The method of claim 1, wherein a CBD drink product is formed suing a suspension of CBD in a carbonate solution.

Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import. Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for making a composition comprising nanosized water clusters encapsulating therapeutic particles of a non-$H_2O$ substance in a purified water, the process comprising the steps of:
 mixing an ingredient comprising the therapeutic particles of the non-$H_2O$ substance with the purified water to make a mixture comprising water clusters encapsulating the therapeutic particles of the non-$H_2O$ substance in the purified water;
 flowing a process stream comprising the mixture through a transfer pipe and a nozzle having a single jet opening into and through a hollow cylinder cavity in a hollow cylinder to make the composition comprising the nanosized water clusters encapsulating the therapeutic particles of the non-$H_2O$ substance in the purified water in the process stream,
 wherein the nozzle having the single jet opening is situated at a proximal end inside the hollow cylinder cavity and comprises:
  (i) a nozzle proximal side with one nozzle input opening connected to the transfer pipe;
  (ii) the single jet opening with one jet bore hole through the nozzle connected to the one nozzle input opening; and
  (iii) a nozzle distal side where the one jet bore hole is directed to expel the process stream from outer surface of the nozzle at an angle into the hollow cylinder cavity towards an inner surface of the hollow cylinder, and
 wherein the process stream contacts the inner surface of the hollow cylinder wall and has a spiral flow pattern through the hollow cylinder cavity directed towards distal end of the hollow cylinder; and
 removing the composition comprising the nanosized water clusters encapsulating the therapeutic particles of the non-$H_2O$ substance in the purified water from the hollow cylinder cavity, wherein the composition comprising the nanosized water clusters encapsulating the therapeutic particles of the non-$H_2O$ substance in the purified water has an increased bioavailability compared to the bioavailability of the mixture comprising the water clusters encapsulating the therapeutic particles of the non-$H_2O$ substance in the purified water.

2. The process according to claim 1, wherein the purified water is purified by a water purification treatment comprising a 0.1 micron to 20 microns filter exclusion size filtration treatment, a distillation treatment, a carbon filtration treatment, a reverse osmosis treatment, an electro-deionization treatment, a molecular sieve chromatography treatment, an ultraviolet light irradiation treatment, a sand filtration treatment, or any combination thereof.

3. The process according to claim 1, wherein the process stream flowing through the transfer pipe is at a flow rate in gallons per minute selected from the group consisting of 0.5 to about 5, about 5 to 5.5, about 5.5 to 6, about 6 to 6.5, about 6.5 to 7, about 7 to 7.5, about 7.5 to 8, about 8 to 8.5, about 8.5 to 9, about 9 to 9.5, about 9.5 to 10, about 10 to 10.5, about 10.5 to 11, about 11 to 11.5, about 11.5 to 12, about 12 to 12.5, about 12.5 to 13, about 13 to 13.5, about 13.5 to 14, about 14 to 14.5, about 14.5 to 15, about 15 to 15.5, about 15.5 to 16, about 16 to 17, about 17 to 17.5, about 17.5 to 18, about 18 to 18.5, about 18.5 to 19, about 19 to 19.5, about 19.5 to 20, about 20 to 20.5, about 20.5 to 21, about 21 to 21.5, about 21.5 to 22, about 22 to 22.5, about 22.5 to 23, about 23 to 23.5, about 23.5 to 24, about 24 to 24.5, about 24.5 to 25, about 25 to 30, about 30 to 35, and about 35 to 40, about 40 to 45, about 45 to 50, about 50 to 60, about 60 to 70, about 70 to 80, about 80 to 90, about 90 to 100, about 100 to 150, about 150 to 300, and any combination thereof.

4. The process according to claim 1, wherein the process stream flowing through the transfer pipe is at a pressure in pounds per square inch selected from the group consisting of 10-20 psi, 20-30 psi, 30-40 psi, 40-50 psi, 50-60 psi, and 60-70 psi.

5. The process according to claim 1, wherein the hollow cylinder cavity has an inner width in inches selected from the group consisting of about 1 to 2 inches, about 2 to 3 inches, about 3 to 4 inches, about 4 to 5 inches, about 5 to 6 inches, about 6 to 7 inches, about 7 to 8 inches, about 8 to 9 inches, about 9 to 10 inches, about 10 to 11 inches, about 11 to 12 inches, about 12 to 13 inches, about 13 to 14 inches, about 14 to 15 inches, about 15 to 16 inches, about 16 to 17 inches, about 17 to 18 inches, about 18 to 19 inches, about 19 to 20 inches, and any combination thereof, and wherein the hollow cylinder cavity has an inner length in inches selected from the group consisting of about 2 to 4 inches, about 4 to 6 inches, about 6 to 8 inches, about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, about 26 to 28 inches, about 28 to 30 inches, about 32 to 34 inches, about 34 to 36 inches, about 36 to 38 inches, about 38 to 40 inches, about 40 to 42 inches, about 42 to 44 inches, about 44 to 46 inches, about 46 to 48 inches, about 48 to 50, about 50 to 52, about 52 to 54, about 54 to 56, about 56 to 58, about 58 to 60, about 60 to 62, about 62 to 64, about 64 to 66, about 66 to 68, about 68 to 70, about 70 to 72, about 72 to 74, about 74 to 76, about 76 to 78, about 78 to 80, and any combination thereof.

6. The process according to claim 1, wherein the process stream flowing through the transfer pipe is at a flow rate in gallons per minute which is a multiple of the hollow cylinder cavity volume in gallons, the multiple selected from the group consisting of about 1 to 2, about 2 to 3, about 3 to 4, about 4 to 5, about 5 to 6, about 6 to 7, about 7 to 8, about 8 to 9, about 9 to 10, about 10 to 11, about 11 to 12, about 12 to 13, about 13 to 14, about 14 to 15, about 15 to 16, about 16 to 17, about 17 to 18, about 18 to 19, about 19 to 20, about 20 to 21, about 21 to 22, about 22 to 23, about 23 to 24, about 24 to 25, about 25 to 26, about 26 to 27, about 27 to 28, about 28 to 29, and about 29 to 30.

7. The process according to claim 1, wherein the nano-sized water clusters encapsulating the therapeutic particles of the non-$H_2O$ substance in the purified water have sizes based on a DLS instrument measurement between about 1 nanometer to about 400 nanometers.

8. The process according to claim 1, wherein the nano-sized water clusters encapsulating the therapeutic particles of the non-$H_2O$ substance in the purified water have sizes based on a DLS instrument measurement selected from the group consisting of between about 2 nanometers to about 10 nanometers, between about 10 nanometers to about 30 nanometers, between about 30 nanometers to about 60 nanometers, between about 60 nanometers to about 120 nanometers, between about 120 nanometers to about 250 nanometers, between about 250 nanometers to about 500 nanometers, and any combination thereof.

9. The process according to claim 1, further comprising a pump for controlling a flow rate of the process stream.

10. The process according to claim 1, wherein the angle into the hollow cylinder cavity is selected from the group consisting of 0, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, and 90 degrees.

11. The process according to claim 1, wherein the angle into the hollow cylinder cavity is about 45 degrees.

12. The process according to claim 1, wherein the non-$H_2O$ substance comprises an organic liquid.

13. The process according to claim 1, wherein the non-$H_2O$ substance comprises a fulvic humic liquid.

14. The process according to claim 1, wherein the non-$H_2O$ substance comprises a potassium ion, a calcium ion, a magnesium ion, a copper ion, an iron ion, a manganese ion, a molybdenum ion, a zinc ion, a cobalt ion, a vanadium ion, a phosphate ion, a hydrogen phosphate ion, a dihydrogen phosphate ion, a nitrate ion, a nitrite ion, an ammonium ion, an amide ion, a sulfate ion, a sulfite ion, a borate ion, or a silicate ion.

* * * * *

SEQUENCE LISTING

<160> NUMBER OF SEQ ID NOS: 51

<210> SEQ ID NO 1
<211> LENGTH: 15
<212> TYPE: PRT
<213> ORGANISM: ARTIFICIAL SEQUENCE
<220> FEATURE:
<223> OTHER INFORMATION: PEPTIDE BINDS TO HDM-2 PROTEIN.

<400> SEQUENCE: 1

Pro Pro Leu Ser Gln Glu Thr Phe Ser Asp Leu Trp Lys Leu Leu
1               5                   10                  15

<210> SEQ ID NO 2

```
<211> LENGTH: 17
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 2

Lys Lys Trp Lys Met Arg Arg Asn Gln Phe Trp Val Lys Val Gln
1               5                   10                  15

Arg Gly

<210> SEQ ID NO 3
<211> LENGTH: 14
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 3

Tyr Gly Arg Lys Lys Arg Arg Gln Arg Arg Pro Pro Gln
1               5                   10

<210> SEQ ID NO 4
<211> LENGTH: 13
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 4

Gly Arg Lys Lys Arg Arg Gln Arg Arg Pro Pro Gln
1               5                   10

<210> SEQ ID NO 5
<211> LENGTH: 7
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 5

Pro Lys Lys Lys Arg Lys Val
1               5

<210> SEQ ID NO 6
<211> LENGTH: 16
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 6

Lys Arg Pro Ala Ala Ile Lys Lys Ala Gly Gln Ala Lys Lys Lys
1               5                   10                  15

Lys

<210> SEQ ID NO 7
<211> LENGTH: 17
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 7

Thr Arg Gln Ala Arg Arg Asn Arg Arg Arg Trp Arg Glu Arg
1               5                   10                  15
```

Gln Arg

<210> SEQ ID NO 8
<211> LENGTH: 14
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 8

Arg Arg Arg Arg Asn Arg Thr Arg Arg Asn Arg Arg Arg Val
1               5                   10

<210> SEQ ID NO 9
<211> LENGTH: 19
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 9

Lys Met Thr Arg Ala Gln Arg Arg Ala Ala Ala Arg Arg Asn Arg
1               5                   10                  15

Trp Thr Ala Arg

<210> SEQ ID NO 10
<211> LENGTH: 13
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 10

Thr Arg Arg Gln Arg Thr Arg Arg Ala Arg Arg Asn Arg
1               5                   10

<210> SEQ ID NO 11
<211> LENGTH: 19
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 11

Lys Leu Thr Arg Ala Gln Arg Arg Ala Ala Ala Arg Lys Asn Lys
1               5                   10                  15

Arg Asn Thr Arg

<210> SEQ ID NO 12
<211> LENGTH: 17
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 12

Asn Ala Lys Thr Arg Arg His Glu Arg Arg Lys Leu Ala Ile
1               5                   10                  15

Glu Arg

<210> SEQ ID NO 13
<211> LENGTH: 22
<212> TYPE: PRT
<213> ORGANISM: ARTIFICIAL SEQUENCE

```
<220> FEATURE:
<223> OTHER INFORMATION: PEPTIDE IS AN MRP (MEMBRANE RESIDENT PEPTIDE).

<400> SEQUENCE: 13

Met Asp Ala Gln Thr Arg Arg Glu Arg Ala Glu Lys Gln
1               5                   10                  15

Ala Gln Trp Lys Ala Ala Asn
            20

<210> SEQ ID NO 14
<211> LENGTH: 18
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 14

Thr Ala Lys Thr Arg Tyr Lys Ala Arg Arg Ala Glu Leu Ile Ala
1               5                   10                  15

Glu Arg Arg

<210> SEQ ID NO 15
<211> LENGTH: 16
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 15

Thr Arg Arg Asn Lys Arg Asn Arg Ile Gln Glu Gln Leu Asn Arg
1               5                   10                  15

Lys

<210> SEQ ID NO 16
<211> LENGTH: 12
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 16

Ser Gln Met Thr Arg Gln Ala Arg Arg Leu Tyr Val
1               5                   10

<210> SEQ ID NO 17
<211> LENGTH: 26
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 17

Lys Arg Arg Ile Arg Arg Glu Arg Asn Lys Met Ala Ala Ala Lys
1               5                   10                  15

Ser Arg Asn Arg Arg Arg Glu Leu Thr Asp Thr
            20                  25

<210> SEQ ID NO 18
<211> LENGTH: 28
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 18
```

```
Arg Ile Lys Ala Glu Arg Lys Arg Met Arg Asn Arg Ile Ala Ala
1               5                   10                  15

Ser Lys Ser Arg Lys Arg Lys Leu Glu Arg Ile Ala Arg
            20                  25
```

<210> SEQ ID NO 19
<211> LENGTH: 22
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 19

```
Lys Arg Ala Arg Asn Thr Glu Ala Ala Arg Arg Ser Arg Ala Arg
1               5                   10                  15

Lys Leu Gln Arg Met Lys Gln
            20
```

<210> SEQ ID NO 20
<211> LENGTH: 18
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 20

```
Lys Leu Ala Leu Lys Leu Ala Leu Lys Ala Leu Lys Ala Ala Leu
1               5                   10                  15

Lys Leu Ala
```

<210> SEQ ID NO 21
<211> LENGTH: 18
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 21

```
Leu Leu Ile Ile Leu Arg Arg Arg Ile Arg Lys Gln Ala Lys Ala
1               5                   10                  15

His Ser Lys
```

<210> SEQ ID NO 22
<211> LENGTH: 4
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 22

```
Arg Arg Arg Arg
1
```

<210> SEQ ID NO 23
<211> LENGTH: 5
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 23

```
Arg Arg Arg Arg Arg
1               5
```

<210> SEQ ID NO 24
<211> LENGTH: 6
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 24

Arg Arg Arg Arg Arg Arg
1               5

<210> SEQ ID NO 25
<211> LENGTH: 7
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 25

Arg Arg Arg Arg Arg Arg Arg
1               5

<210> SEQ ID NO 26
<211> LENGTH: 8
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 26

Arg Arg Arg Arg Arg Arg Arg Arg
1               5

<210> SEQ ID NO 27
<211> LENGTH: 9
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 27

Arg Arg Arg Arg Arg Arg Arg Arg Arg
1               5

<210> SEQ ID NO 28
<211> LENGTH: 10
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 28

Arg Arg Arg Arg Arg Arg Arg Arg Arg Arg
1               5                   10

<210> SEQ ID NO 29
<211> LENGTH: 11
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 29

Arg Arg Arg Arg Arg Arg Arg Arg Arg Arg Arg
1               5                   10

```
<210> SEQ ID NO 30
<211> LENGTH: 12
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 30

Arg Arg Arg Arg Arg Arg Arg Arg Arg Arg Arg Arg
1               5                   10

<210> SEQ ID NO 31
<211> LENGTH: 13
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 31

Arg Arg Arg Arg Arg Arg Arg Arg Arg Arg Arg Arg Arg
1               5                   10

<210> SEQ ID NO 32
<211> LENGTH: 14
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 32

Arg Arg Arg Arg Arg Arg Arg Arg Arg Arg Arg Arg Arg Arg
1               5                   10

<210> SEQ ID NO 33
<211> LENGTH: 15
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 33

Arg Arg Arg Arg Arg Arg Arg Arg Arg Arg Arg Arg Arg Arg Arg
1               5                   10                  15

<210> SEQ ID NO 34
<211> LENGTH: 16
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 34

Arg Arg Arg Arg Arg Arg Arg Arg Arg Arg Arg Arg Arg Arg Arg
1               5                   10                  15

Arg

<210> SEQ ID NO 35
<211> LENGTH: 17
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 35

Arg Arg Arg Arg Arg Arg Arg Arg Arg Arg Arg Arg Arg Arg Arg
1               5                   10                  15
```

Arg Arg

<210> SEQ ID NO 36
<211> LENGTH: 9
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 36

Arg Lys Lys Arg Arg Gln Arg Arg Arg
1               5

<210> SEQ ID NO 37
<211> LENGTH: 21
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 37

Thr Arg Ser Ser Arg Ala Gly Leu Gln Phe Pro Val Gly Arg Val
1               5                   10                  15

His Arg Leu Leu Arg Lys
            20

<210> SEQ ID NO 38
<211> LENGTH: 26
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 38

Gly Trp Thr Leu Asn Ser Ala Gly Tyr Leu Leu Gly Lys Ile Asn
1               5                   10                  15

Lys Ala Leu Ala Ala Leu Ala Lys Lys Ile Leu
            20                  25

<210> SEQ ID NO 39
<211> LENGTH: 16
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 39

Arg Gln Ile Lys Ile Trp Phe Gln Asn Arg Arg Met Lys Trp Lys
1               5                   10                  15

Lys

<210> SEQ ID NO 40
<211> LENGTH: 21
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 40

Lys Glu Thr Trp Trp Glu Thr Trp Trp Thr Glu Trp Ser Gln Pro
1               5                   10                  15

Lys Lys Lys Arg Lys Val
            20

```
<210> SEQ ID NO 41
<211> LENGTH: 18
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 41

Arg Gly Gly Arg Leu Ser Tyr Ser Arg Arg Phe Ser Thr Ser
1               5                   10                  15

Thr Gly Arg

<210> SEQ ID NO 42
<211> LENGTH: 12
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 42

Thr Ser Pro Leu Asn Ile His Asn Gly Gln Lys Leu
1               5                   10

<210> SEQ ID NO 43
<211> LENGTH: 21
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 43

Ala Gly Tyr Leu Leu Gly Lys Ile Asn Leu Lys Ala Leu Ala Ala
1               5                   10                  15

Leu Ala Lys Lys Ile Leu
            20

<210> SEQ ID NO 44
<211> LENGTH: 10
<212> TYPE: PRT
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 44

Lys Phe Phe Lys Phe Phe Lys Phe Phe Lys
1               5                   10

<210> SEQ ID NO 45
<211> LENGTH: 32
<212> TYPE: PRT
<213> ORGANISM: ARTIFICIAL SEQUENCE
<220> FEATURE:
<223> OTHER INFORMATION: PEPTIDE AMINO ACID RESIDUES NOS. 1 TO 15 BIND
      TO HDM-2. PEPTIDE AMINO ACID RESIDUES NOS. 16 TO 32 HAVE A MRP
      FUNCTION.

<400> SEQUENCE: 45

Pro Pro Leu Ser Gln Glu Thr Phe Ser Asp Leu Trp Lys Leu Leu
1               5                   10                  15

Lys Lys Trp Lys Met Arg Arg Asn Gln Phe Trp Val Lys Val Gln
                20                  25                  30

Arg Gly

<210> SEQ ID NO 46
<211> LENGTH: 27
```

```
<212> TYPE: PRT
<213> ORGANISM: ARTIFICIAL SEQUENCE
<220> FEATURE:
<223> OTHER INFORMATION: PEPTIDE AMINO ACID RESIDUES NOS. 6 TO 15 BIND
      TO HDM-2. PEPTIDE AMINO ACID RESIDUES NOS. 16 TO 32 HAVE A MRP
      FUNCTION. USING SEQUENCE NUMBERING FOR PNC-27.

<400> SEQUENCE: 46

Glu Thr Phe Ser Asp Leu Trp Lys Leu Leu Lys Lys Trp Lys Met
1               5                   10                  15

Arg Arg Asn Gln Phe Trp Val Lys Val Gln Arg Gly
            20                  25

<210> SEQ ID NO 47
<211> LENGTH: 26
<212> TYPE: PRT
<213> ORGANISM: ARTIFICIAL SEQUENCE
<220> FEATURE:
<223> OTHER INFORMATION: PEPTIDE AMINO ACID RESIDUES NOS. 6 TO 15 BIND
      TO HDM-2. PEPTIDE AMINO ACID RESIDUES NOS. 16 TO 32 HAVE A MRP
      FUNCTION. USING SEQUENCE NUMBERING FOR PNC-27.

<400> SEQUENCE: 47

Pro Pro Leu Ser Gln Glu Thr Phe Ser Lys Lys Trp Lys Met Arg
1               5                   10                  15

Arg Asn Gln Phe Trp Val Lys Val Gln Arg Gly
            20                  25

<210> SEQ ID NO 48
<211> LENGTH: 9
<212> TYPE: PRT
<213> ORGANISM: ARTIFICIAL SEQUENCE
<220> FEATURE:
<223> OTHER INFORMATION: PEPTIDE MAY BIND TO HDM-2 REPRESENTS A PORTION
      OF SEQ ID NO: 1

<400> SEQUENCE: 48

Pro Pro Leu Ser Gln Glu Thr Phe Ser
1               5

<210> SEQ ID NO 49
<211> LENGTH: 10
<212> TYPE: PRT
<213> ORGANISM: ARTIFICIAL SEQUENCE
<220> FEATURE:
<223> OTHER INFORMATION: PEPTIDE MAY BIND TO HDM-2 AND REPRESENTS A
      PORTION OF SEQ ID NO: 1

<400> SEQUENCE: 49

Glu Thr Phe Ser Asp Leu Trp Lys Leu Leu
1               5                   10

<210> SEQ ID NO 50
<211> LENGTH: 10
<212> TYPE: PRT
<213> ORGANISM: ARTIFICIAL SEQUENCE
<220> FEATURE:
<223> OTHER INFORMATION: CONTROL PEPTIDE PNC-29 ALSO KNOWN BY NAME X-13
      IS DERIVED FROM P450 ENZYME AND DOES NOT BIND TO HDM-2.

<400> SEQUENCE: 50

Glu Thr Phe Ser Asp Leu Trp Lys Leu Leu
1               5                   10

<210> SEQ ID NO 51
<211> LENGTH: 13
<212> TYPE: PRT
```

```
<213> ORGANISM: ARTIFICIAL SEQUENCE
<220> FEATURE:
<223> OTHER INFORMATION: PEPTIDE IS AN MRP (MEMBRANE RESIDENT PEPTIDE).

<400> SEQUENCE: 51

Gly Arg Arg Arg Arg Arg Arg Arg Arg Arg Pro Pro Gln
1               5                   10
```